(12) United States Patent
Sackstein

(10) Patent No.: US 10,471,103 B2
(45) Date of Patent: Nov. 12, 2019

(54) METHODS TO IMPROVE CELL THERAPY

(71) Applicant: The Brigham and Women's Hospital, Inc., Boston, MA (US)

(72) Inventor: Robert Sackstein, Sudbury, MA (US)

(73) Assignee: THE BRIGHAM AND WOMEN'S HOSPITAL, INC., Boston, MA (US)

(*) Notice: Subject to any disclaimer, the term of this patent is extended or adjusted under 35 U.S.C. 154(b) by 493 days.

(21) Appl. No.: 14/982,863

(22) Filed: Dec. 29, 2015

(65) Prior Publication Data

US 2016/0184367 A1    Jun. 30, 2016

Related U.S. Application Data

(60) Provisional application No. 62/101,863, filed on Jan. 9, 2015, provisional application No. 62/098,048, filed on Dec. 30, 2014.

(51) Int. Cl.
| | |
|---|---|
| A61K 35/30 | (2015.01) |
| A61K 35/14 | (2015.01) |
| A61K 35/28 | (2015.01) |
| A61K 35/32 | (2015.01) |
| A61K 35/33 | (2015.01) |
| A61K 35/34 | (2015.01) |
| A61K 35/35 | (2015.01) |
| A61K 35/37 | (2015.01) |
| A61K 35/407 | (2015.01) |
| A61K 35/42 | (2015.01) |
| C12N 5/00 | (2006.01) |
| A61K 35/12 | (2015.01) |

(52) U.S. Cl.
CPC .............. *A61K 35/30* (2013.01); *A61K 35/14* (2013.01); *A61K 35/28* (2013.01); *A61K 35/32* (2013.01); *A61K 35/33* (2013.01); *A61K 35/34* (2013.01); *A61K 35/35* (2013.01); *A61K 35/37* (2013.01); *A61K 35/407* (2013.01); *A61K 35/42* (2013.01); *C12N 5/0006* (2013.01); *A61K 2035/124* (2013.01); *C12N 2501/724* (2013.01)

(58) Field of Classification Search
None
See application file for complete search history.

(56) References Cited

U.S. PATENT DOCUMENTS

| | | | | |
|---|---|---|---|---|
| 7,875,585 | B2* | 1/2011 | Sackstein | C07K 14/70585 424/134.1 |
| 7,998,740 | B2* | 8/2011 | Sackstein | A61K 38/1709 435/375 |
| 2014/0161782 | A1 | 6/2014 | Wolpe et al. | |

FOREIGN PATENT DOCUMENTS

| | | |
|---|---|---|
| WO | 2006068720 | 6/2006 |
| WO | 2007005180 | 1/2007 |
| WO | 2007143204 | 12/2007 |
| WO | 2008011094 | 1/2008 |

OTHER PUBLICATIONS

Richardson, Sarah J., et al. "Immunopathology of the human pancreas in type-I diabetes." Seminars in immunopathology. vol. 33. No. 1. Springer-Verlag, 2011. (Year: 2011).*
Sackstein, R., et al., Ex vivo glycan engineering of CD44 programs human multipotent mesenchymal stromal cell trafficking to bone, Nature Medicine, 2008, 14(2): 181-187 Jan. 13, 2008.
Patent Cooperation Treaty, International Search Report issued for PCT/US2015/067873, dated Mar. 22, 2016, 6 pages Mar. 22, 2016.
Sackstein, R., Glycoengineering of HCELL, the Human Bone Marrow Homing Receptor: Sweetly Programming Cell Migration, Annals of Biomedical Engineering, 2011, 40(4): 766-776 Nov. 9, 2011.
Sackstein, R., Engineering cellular trafficking via glycosyltransferase-programmed stereosubstitution, Annals of the New York Academy of Sciences, 2012, 1253(1): 193-200 Apr. 21, 2012.
Merzaban et al., Cell surface glycan engineering of neural stem cells augments neurotropism and improves recovery in a murine model of multiple sclerosis, Glycobiology, 2015, 25(12): 1392-1409 Jul. 7, 2015.
Abdi et al., HCELL Expression on Murine MSC Licenses Pancreatotropism and Confers Durable Reversal of Autoimmune Diabetes in NOD Mice, Stem Cells, 2015, 33(5): 1523-1531 May 23, 2015.
Silvescu et al., G-CSF Induces membrane Expression of a Myeloperoxidase Glycovariant that Operats as an E-Selectin Ligand on Human Myeloid Cells, PNAS, 2014, 111(29): 10696-10701 Jul. 22, 2014.
EP Office Action for Application 15831197.7 dated Apr. 24, 2018.

\* cited by examiner

*Primary Examiner* — Robert J Yamasaki
(74) *Attorney, Agent, or Firm* — Bryan Cave Leighton Paisner LLP

(57) ABSTRACT

Methods of treatment are provided herein, including administration of a population cells modified to enforce expression of an E-selectin and/or an L-selectin ligand, the modified cell population having a cell viability of at least 70% after a treatment to enforce such expression.

5 Claims, 55 Drawing Sheets
(37 of 55 Drawing Sheet(s) Filed in Color)

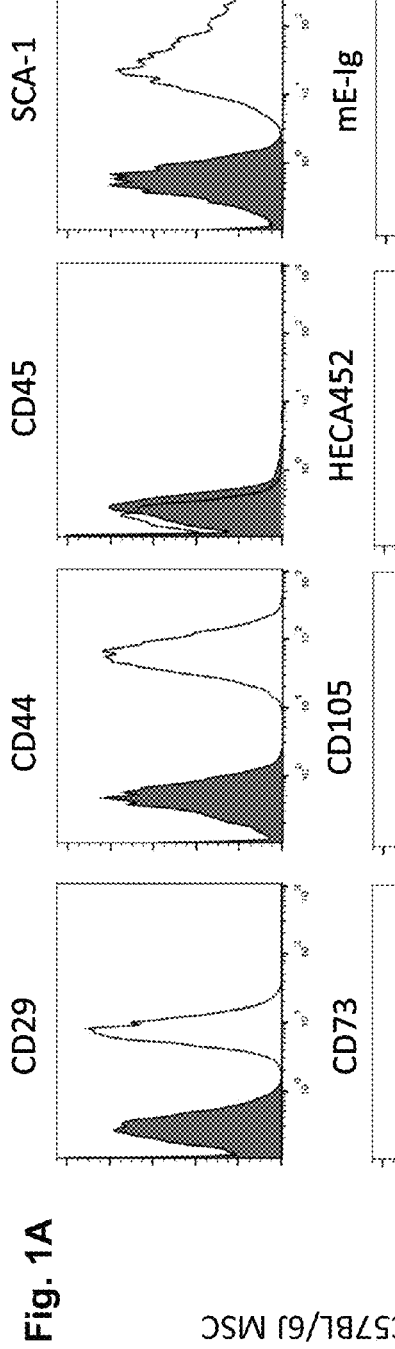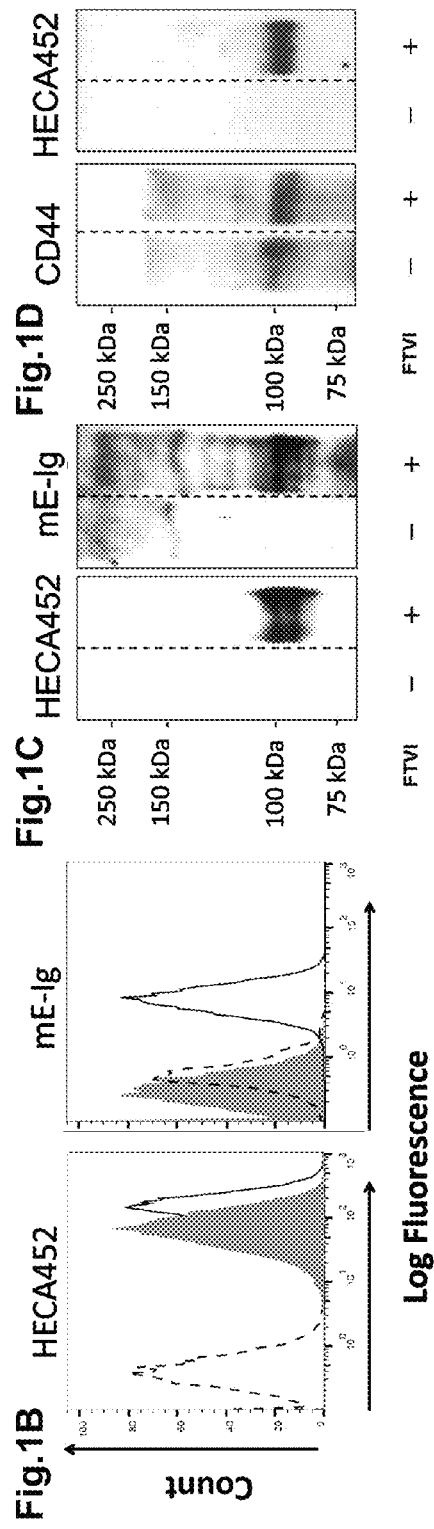

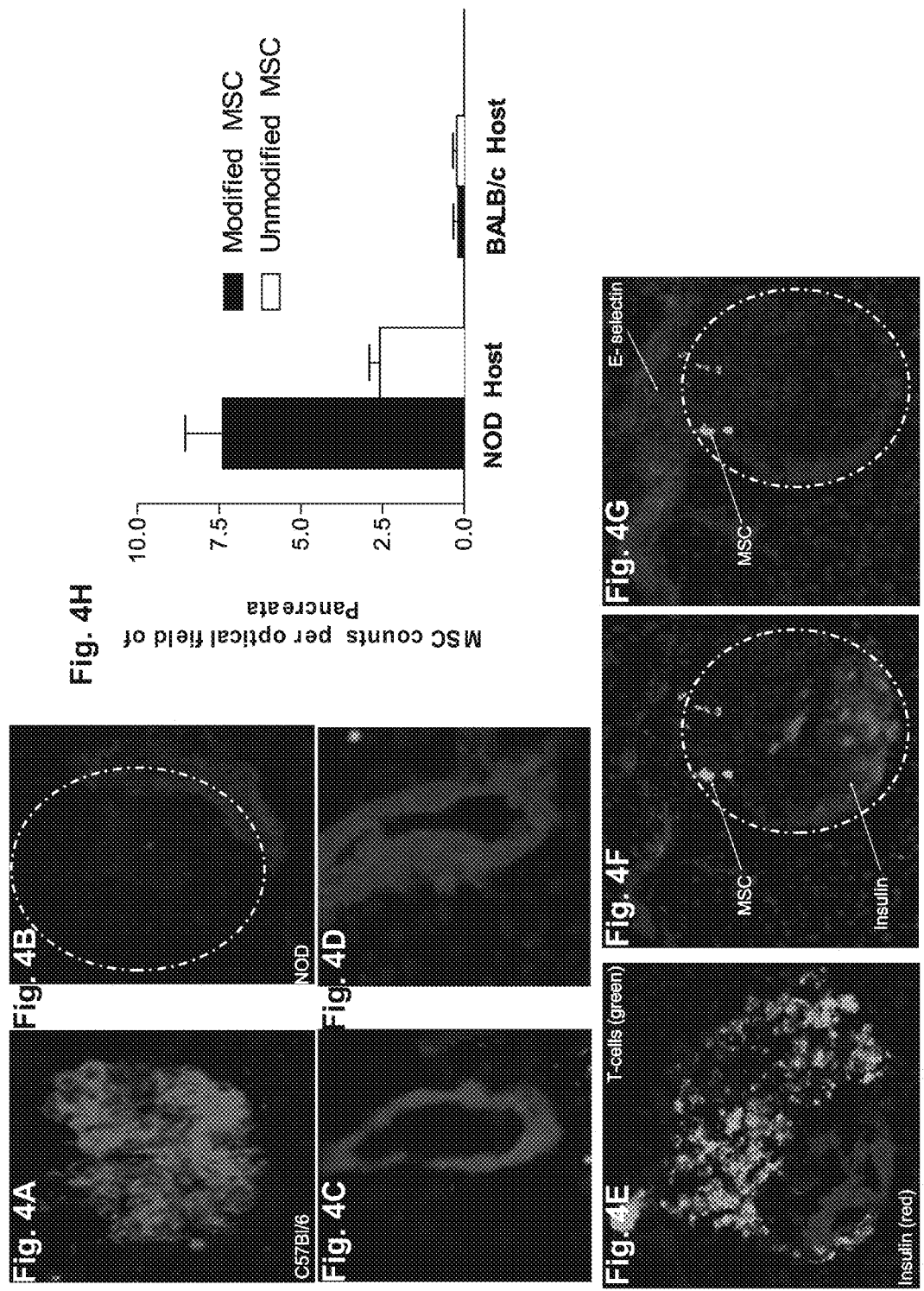

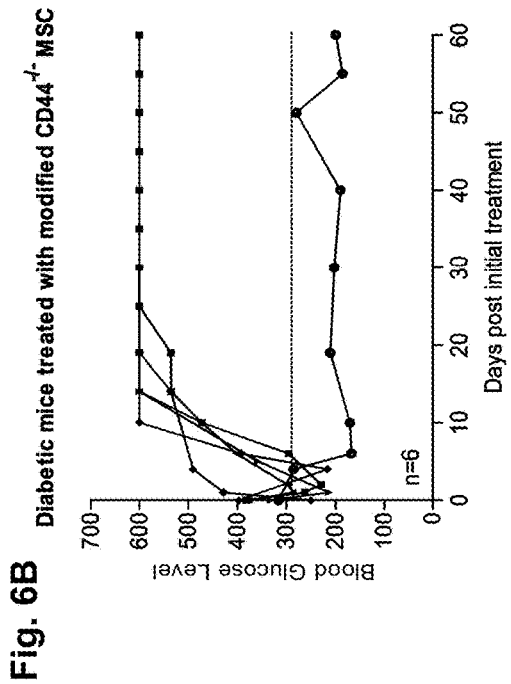
Fig. 6A Diabetic NOD mice treated with Unmodified CD44⁻/⁻ MSC
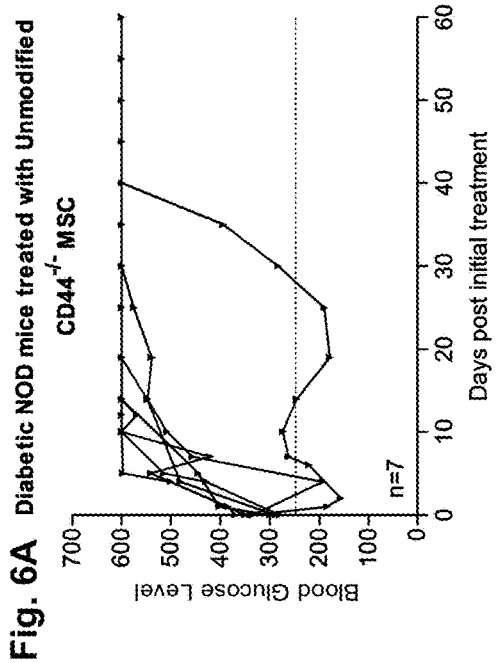
Fig. 6B Diabetic mice treated with modified CD44⁻/⁻ MSC
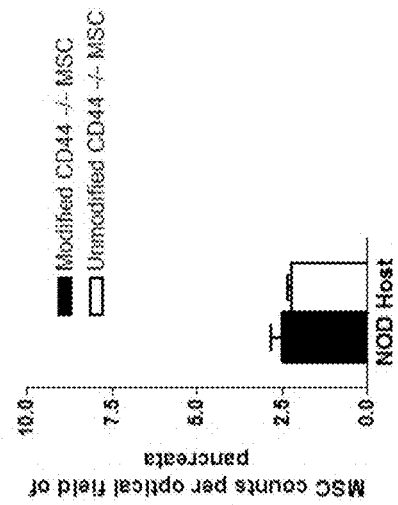
Fig. 6C
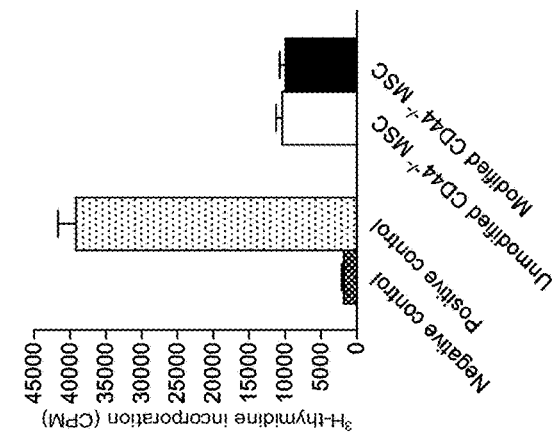
Fig. 6D

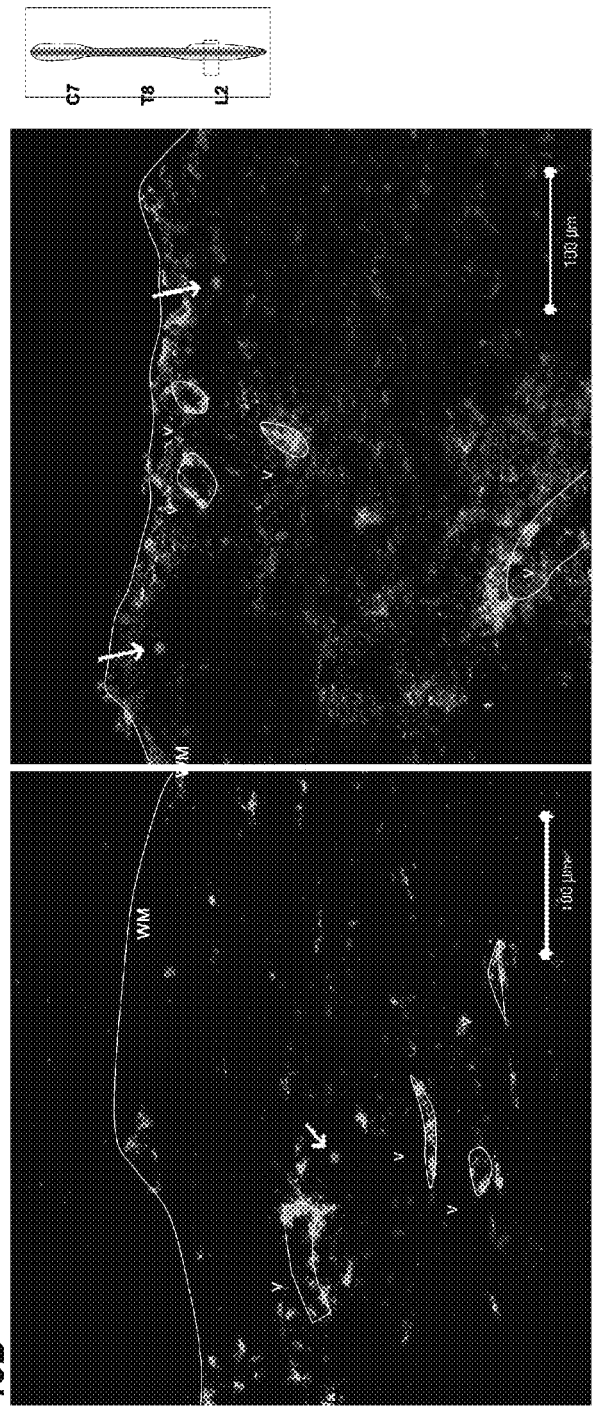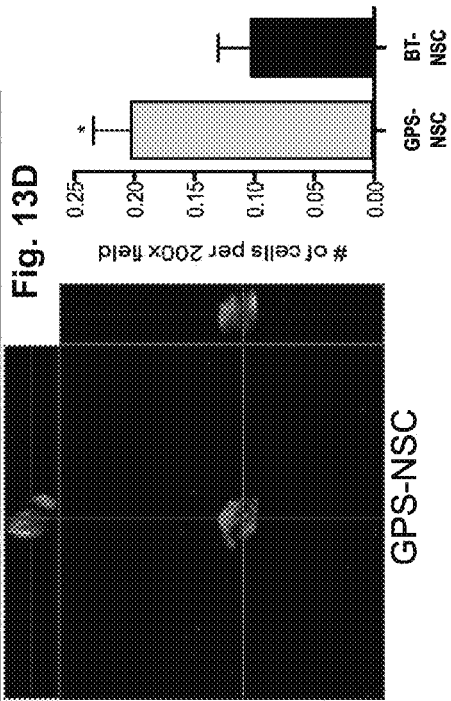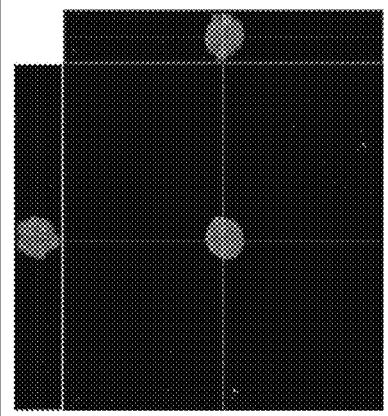

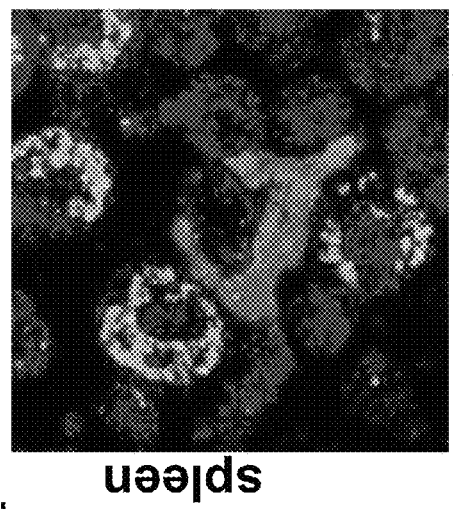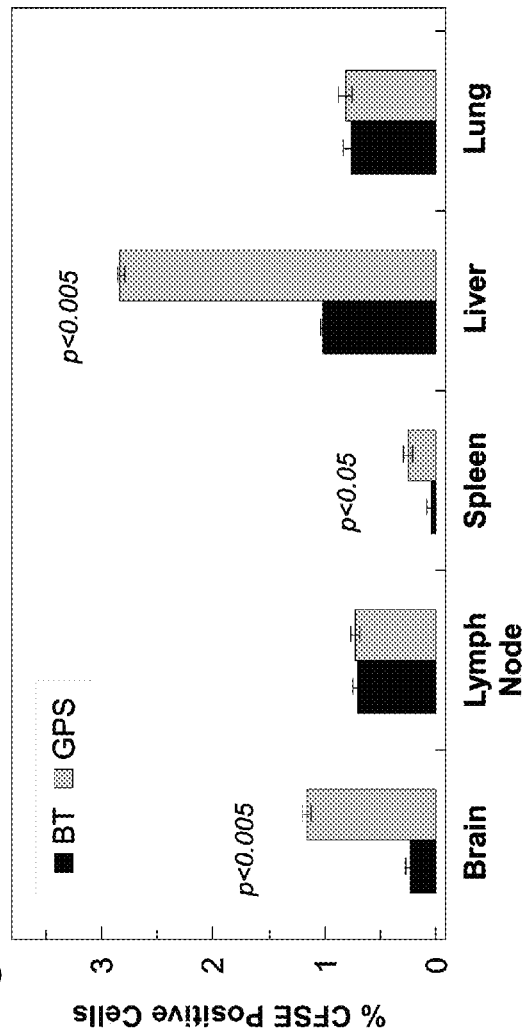
Fig. 13E
Fig. 13F

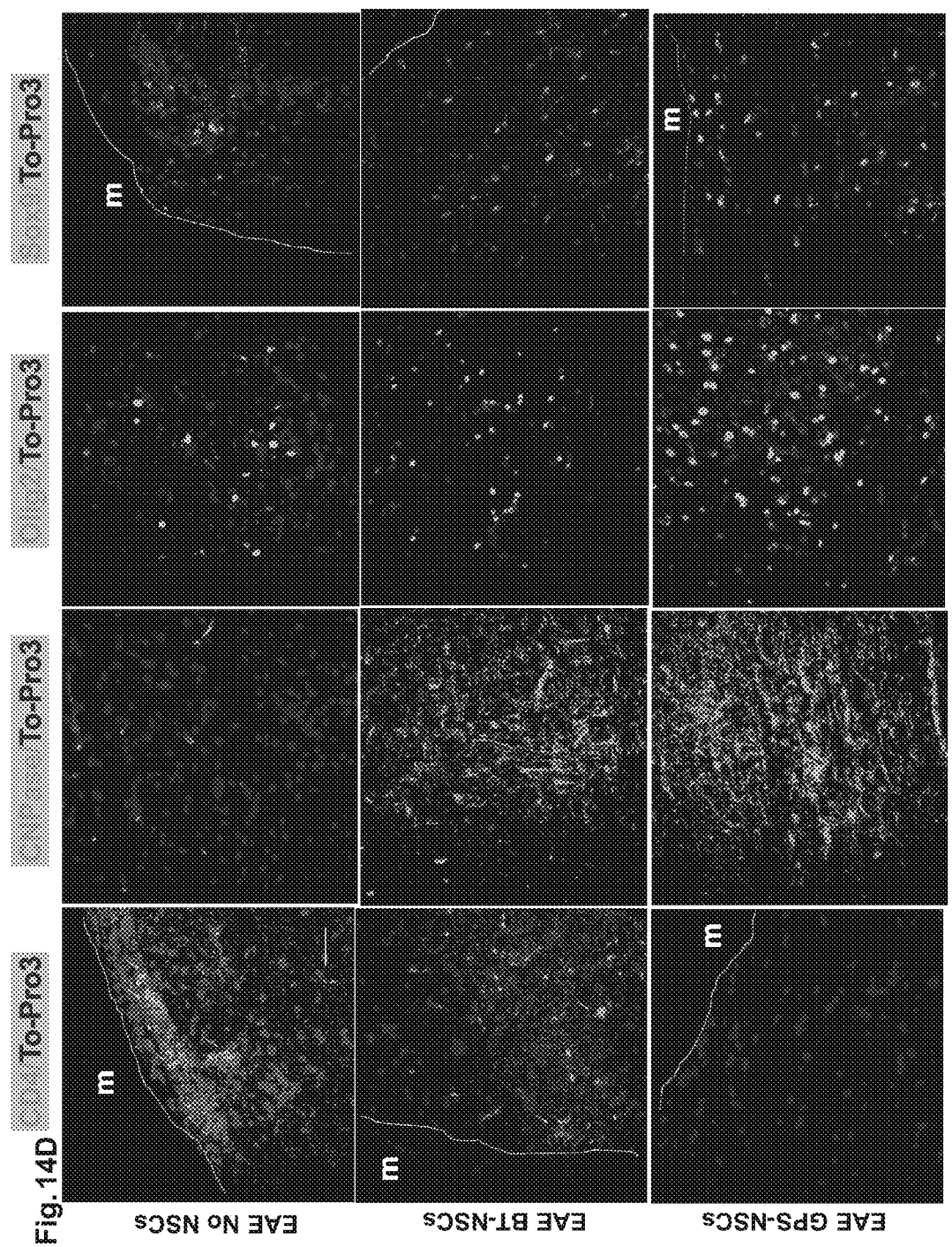

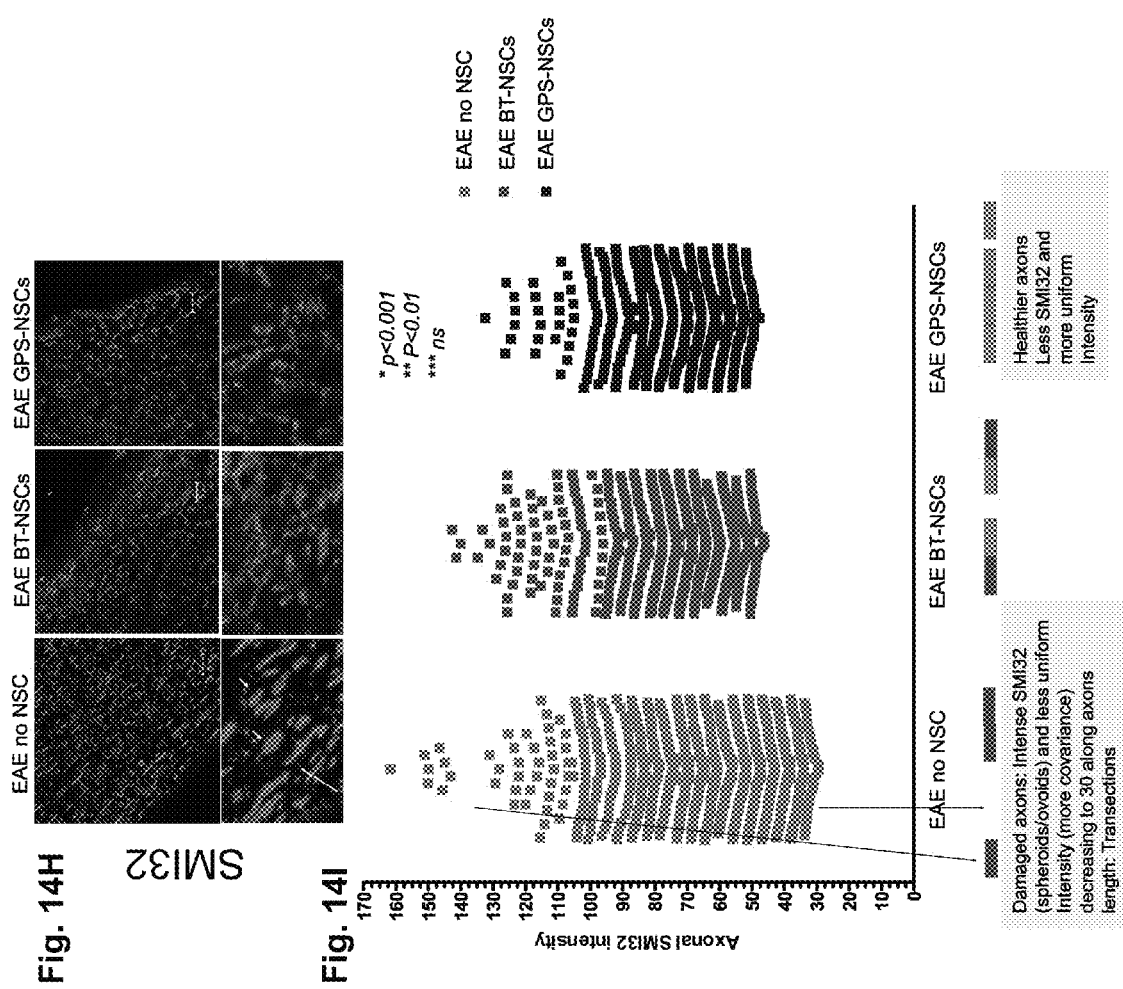

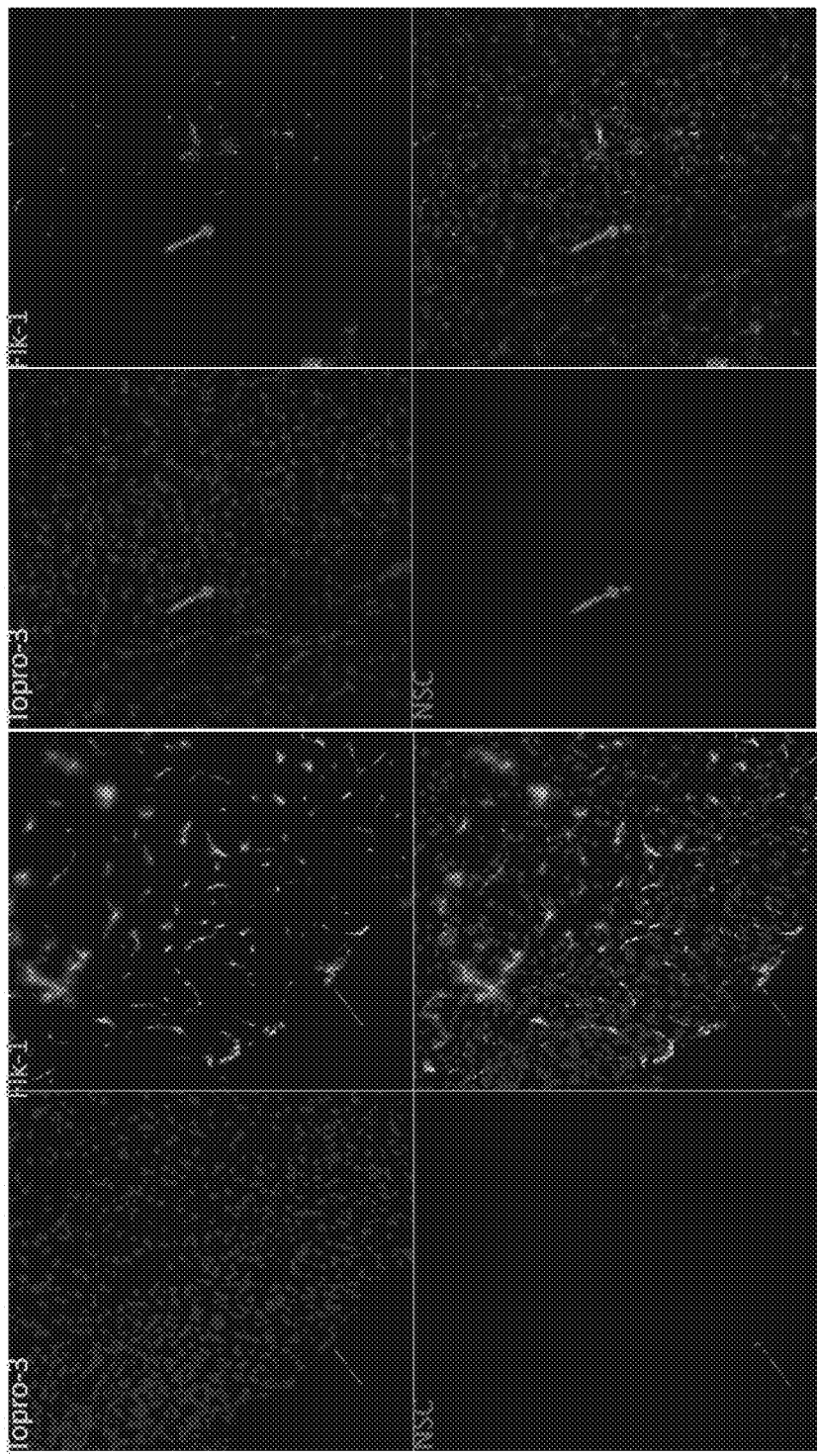
Fig. 20A Day 17

HECA452 reactivity (sLex expression) on Adipose-derived MSCs (A-MSCs) from Lean Subjects (LA-AMCs) and Obese subjects (OA-MSCs) after FTVII (FT7) treatment

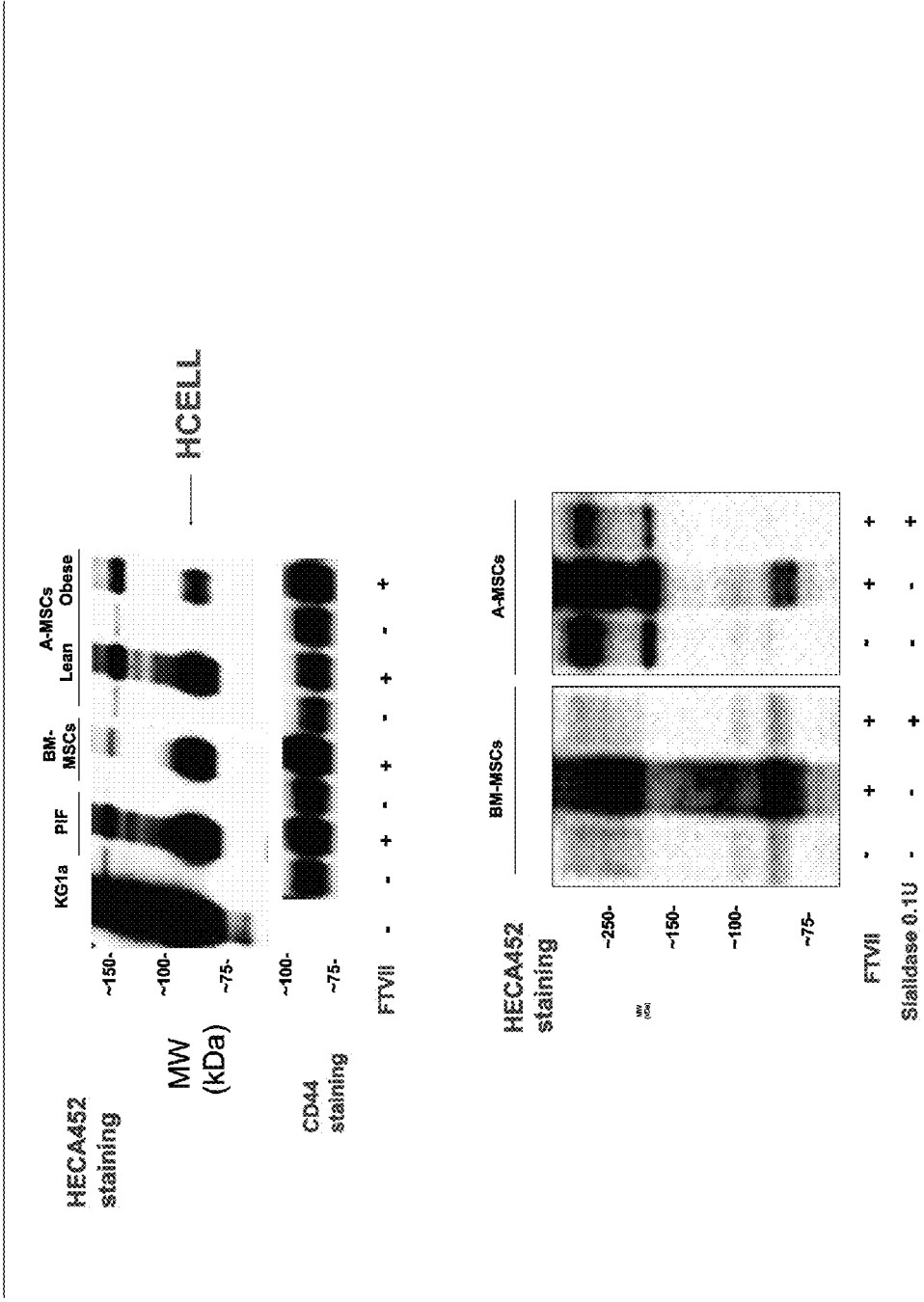
Fig. 25 Biochemical analysis of human Bone Marrow-derived (BM-MSCs) and Adipose-derived (A-MSCs) MSCs after FTVII treatment

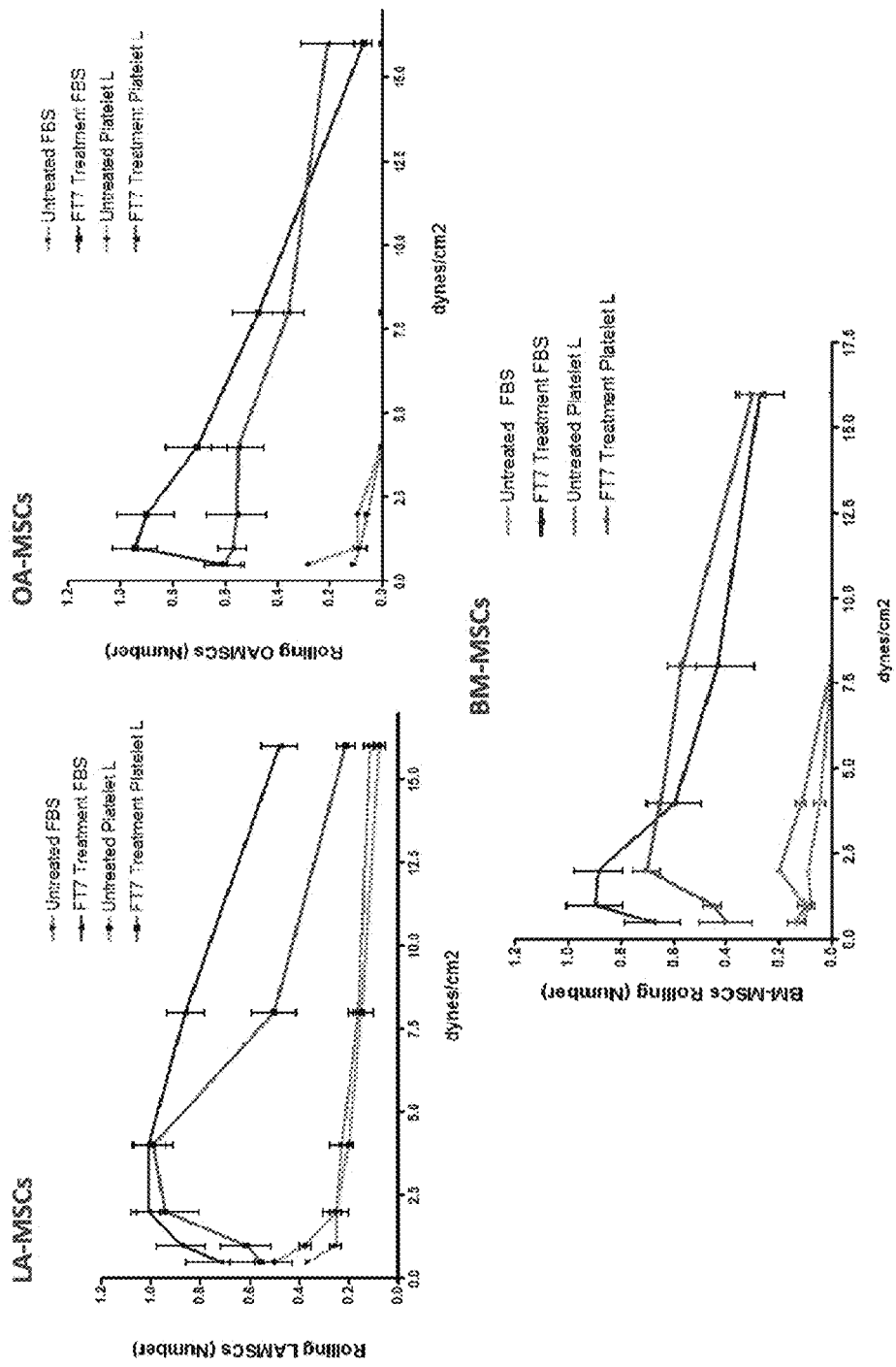
Fig. 26 E-selectin binding (rolling capacity on TNF-stimulated HUVEC) of Lean (LA-MSCs) and Obese (OA-MSCs) adipose-derived MSCs compared to bone marrow-derived MSCs (BM-MSCs) after FTVII (FT7) treatment ; MSCs cultured with either fetal bovine serum (FBS) or Platelet lysate (Platelet L)

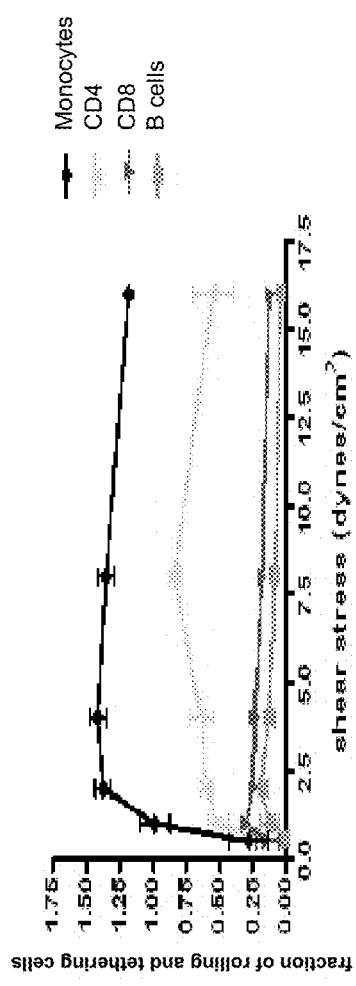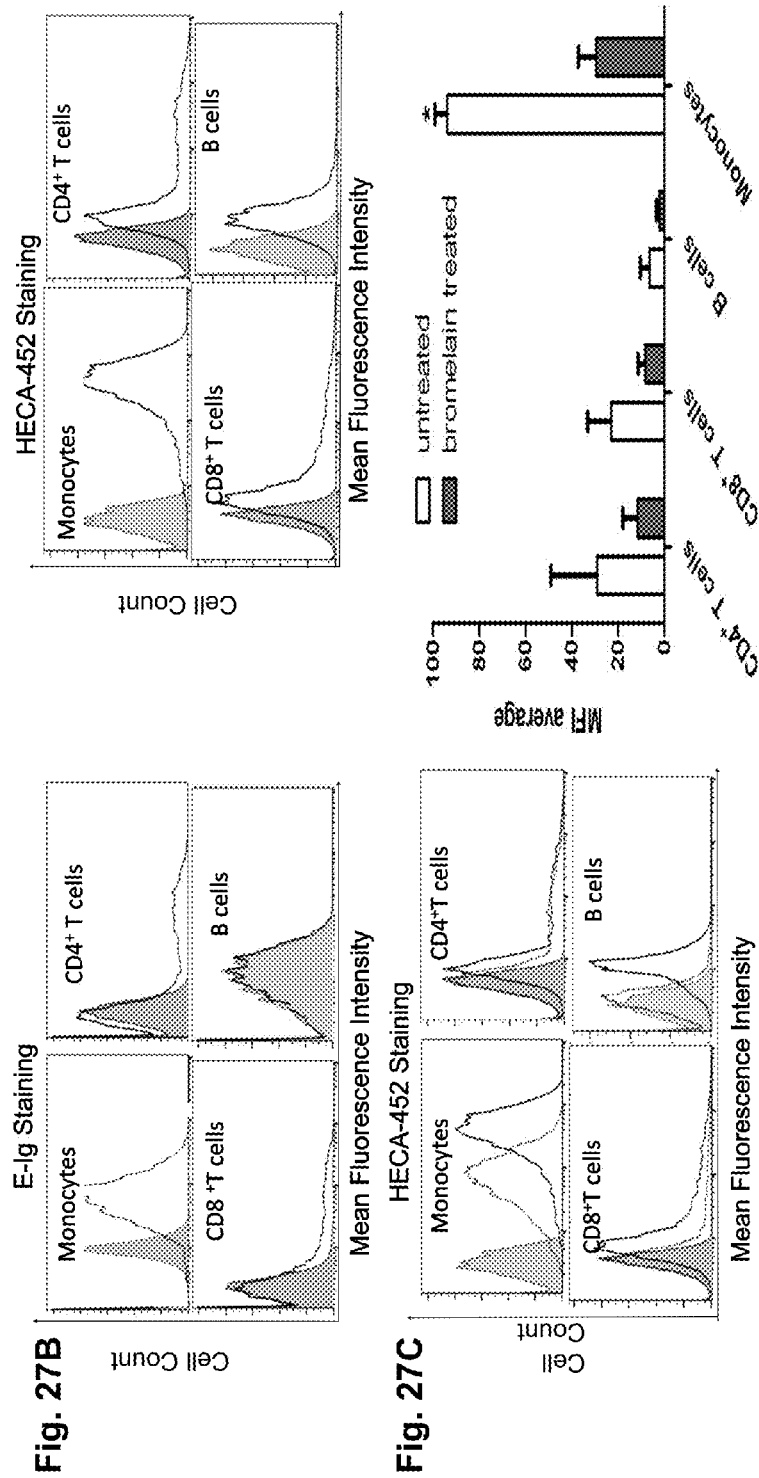
Fig. 27A
Fig. 27B
Fig. 27C

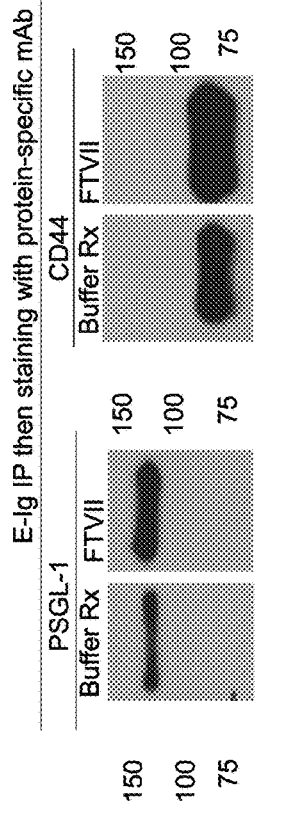
Fig. 28A
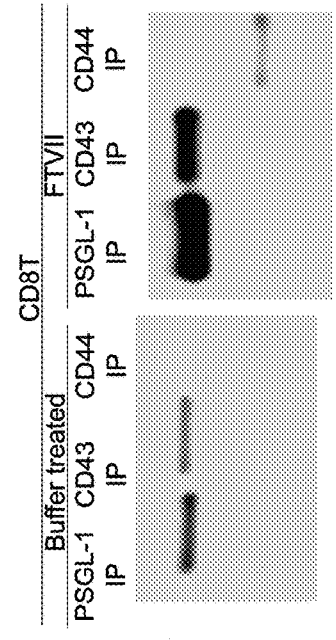
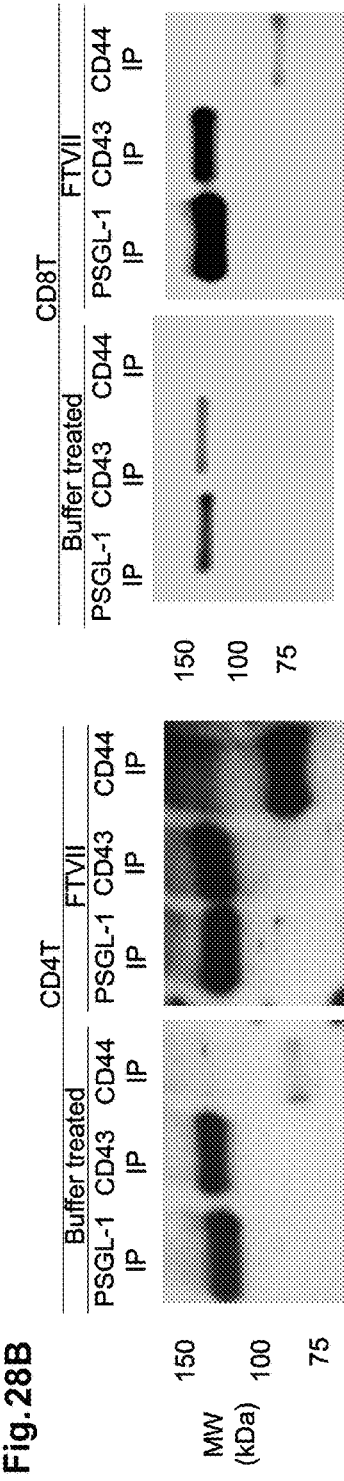
Fig. 28B
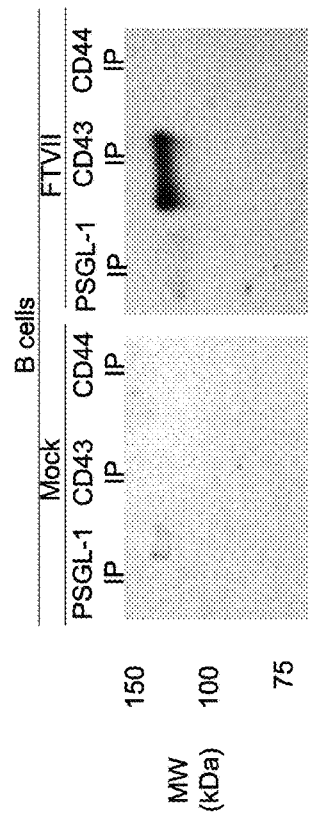

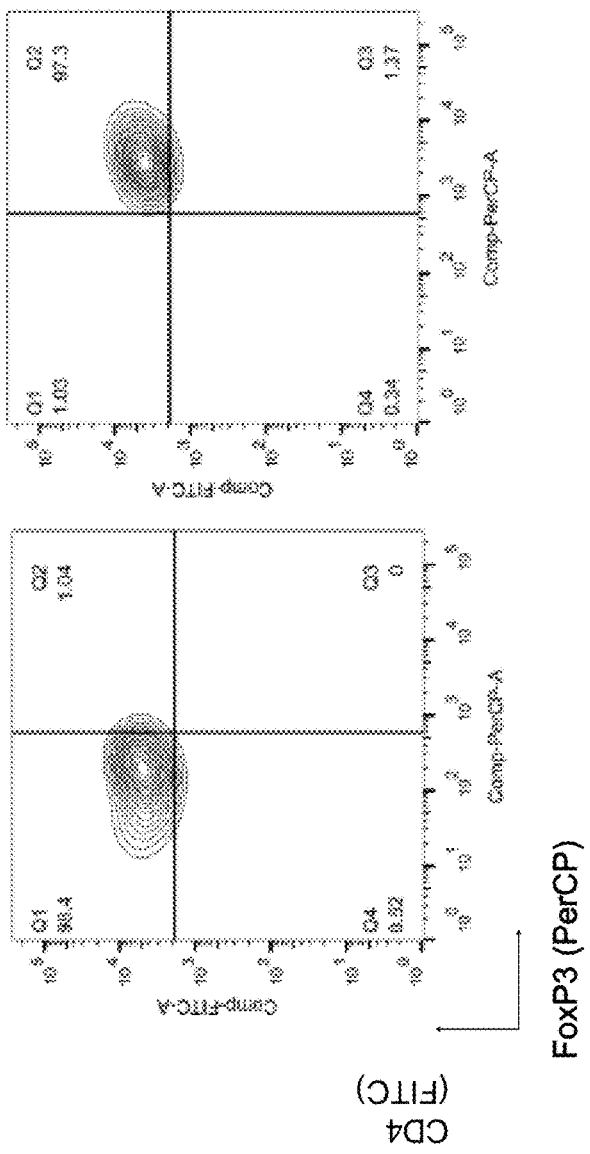

Flow cytometry staining of sLex (HECA452 mAb) of buffer treated and exofucosylated Tregs

METHODS TO IMPROVE CELL THERAPY

This disclosure was made with government support under grants PO1 HL107146 (NHLBI Program of Excellence in Glycosciences), RO1 HL73714, and RO1 HL60528, awarded by National Institutes of Health. The government has certain rights in the disclosure.

This disclosure relates to compositions and methods for modifying the cell surface and the improved efficiency and applicability of such modified cells in cell-based treatment of inflammatory conditions, tissue injury/damage, and cancer.

The success of cell-based therapeutics (also known as "adoptive cellular therapeutics") depends on getting the relevant cells to the site(s) where they are needed in sufficient amount(s) to achieve intended biologic effect(s). Delivery of cells for clinical indications can be achieved by direct (local) injection into involved tissue(s), by intravascular administration (e.g., systemically or by catheter-based delivery to a particular vascular bed), or by application/placement of cells directly onto the affected area (e.g., for skin ulcers, burns, etc.). In all forms of cell administration, it would be advantageous for administered cells to possess membrane molecules that would promote lodgement of the cell within the administered site precisely within tissue microenvironments that are critical to achieve intended effect, e.g., control of inflammation, tissue repair, elimination of rejection, eradication of cancer, etc. One such microenvironmental site are the "perivascular areas" present in and around microvessels within the injured tissue, as it is well known that integrity of the microvasculature, and production of new microvessels "angiogenesis"), is a critical prerequisite to tissue regeneration/repair. Indeed, at all sites of tissue injury, inflammation, and cancer, endothelial cells within the microvessels of affected tissue(s) display a characteristic set of adhesion molecules that serve a key role in recruitment of circulating (blood-borne) cells to the target site. These endothelial molecules are upregulated by inflammatory cytokines such as tumor necrosis factor (TNF) and interleukin 1 (IL-1), and, in humans include the molecule E-selectin, and, in mouse, the molecules E-selectin and P-selectin, which are lectins belonging to a family of adhesion molecules known as "selectins" (to be described in more detail below). In addition, leukocytes that have been recruited to any inflammatory site (including cancer) or to a site of tissue injury/damage display L-selectin, the "leukocyte" selectin, and, therefore, expression of ligands for L-selectin on administered cells would promote lodgement of such cells to regions of leukocyte infiltrates within the affected tissue(s).

At first glance, direct delivery might seem to be the most efficient approach to cell administration especially considering that a concentrated bolus of cells could be applied to an affected area. However, there are situations where local injection may actually be counterproductive to intended therapeutic effects, and, moreover, local injection is practical for only certain anatomic locations: (1) By introducing pertinent cells in media suspension under hydrostatic pressure, the injection procedure could harm the delivered cells and, furthermore, could further compromise tissue integrity and disrupt incipient tissue repair and/or host defense processes, thereby exacerbating the inflammatory condition or counteracting appropriate immune reactions in situ; (2) By virtue of being an invasive method, the injection needle/device (and the suspension solution) could induce target tissue damage and/or instigate collateral tissue damage; (3) Direct injection is most feasible for organs/tissues with well-defined anatomic boundaries (e.g., the heart), and is impractical for tissues without extensive connective tissue support (e.g., the lung); (4) The injection procedure could be technologically demanding and labor-intensive, requiring use of sophisticated delivery systems with substantial imaging support, especially for relatively inaccessible and/or fragile organs/tissues (e.g., the central nervous system); (5) Most importantly, many degenerative and inflammatory conditions are widely distributed and multifocal in nature (e.g., osteoporosis, inflammatory bowel disease, multiple sclerosis, etc.), and thus direct injection is neither practical nor effective. Thus, though there are clinical conditions/situations in which local injection is feasible, the vascular route of administration is mandated for all generalized "systemic" disorders, as well as for any tissue with problematic access and/or anatomy not amenable to local injection (e.g., the pancreas in diabetes, the lung in chronic obstructive pulmonary disease). The capacity to administer cells repeatedly with minimal effort is another important practical advantage of systemic infusion. Therefore, creation of methodologies to optimize the expression/activity of molecular effectors directing both the adhesion/lodgement of directly injected cells within the inflammatory milieu and the physiologic migration of intravascularly administered cells to the affected site(s) is key to achieving the tremendous promise of all cell-based therapeutics.

The capacity to direct migration of blood-borne cells to a predetermined location ("homing") has profound implications for a variety of physiologic and pathologic processes. Recruitment of circulating cells to a specific anatomic site is initiated by discrete adhesive interactions between cells in flow and vascular endothelium at the target tissue(s). The molecules that mediate these contacts are called "homing receptors," and, as defined historically, these structures pilot tropism of cells in blood to the respective target tissue. Historically, three "tissue-specific homing receptors" were described: L-selectin for peripheral lymph nodes, $\alpha_4\beta_7$ (LPAM-1) for intestines and gut-associated lymphoid tissue, and a specialized glycoform of the molecule P-selectin Glycoprotein Ligand-1 (PSGL-1) known, specifically, as the "Cutaneous Lymphocyte Antigen" (CLA) that promotes cell migration to skin (R. Sackstein, Curr Opin Hematol 12, 444 (2005)). Notably, apart from these tissues, it had been recognized for several decades that circulating cells, especially hematopoietic stem cells (HSCs), navigate effectively to bone marrow (T. Lapidot, A. Dar, O. Kollet, Blood 106, 1901 (2005)), and several studies pointed to a role for selectins, predominantly E-selectin binding to HSC E-selectin ligands, in mediating recruitment of HSCs to marrow.

From a biophysical perspective, a homing receptor functions as a molecular brake, effecting initial tethering then sustained rolling contacts of cells in blood flow onto the vascular endothelium at velocities below that of the prevailing bloodstream (Step 1) (R. Sackstein, Curr Opin Hematol 12, 444 (2005)). Thereafter, a cascade of events ensue, typically potentiated by chemokines, resulting in activation of integrin adhesiveness (Step 2), firm adherence (Step 3) and endothelial transmigration (Step 4) (T. A. Springer, Cell 76, 301 (1994)). This "multi-step paradigm" holds that tissue-specific migration is regulated by a discrete combination of homing receptor and chemokine receptor expression on a given circulating cell, allowing for recognition of a pertinent "traffic signal" displayed by the relevant vascular adhesive ligands and chemokines expressed within target endothelium in an organ-specific manner. Following engagement of homing receptor(s) directing trafficking of cells to bone marrow, several lines of evidence indicate that one chemokine in particular, SDF-1 (CXCL12), plays an essential role in Step 2-mediated recruitment of cells to this site (T. Lapidot, A. Dar, O. Kollet, Blood 106, 1901 (2005); A. Peled et al., Science 283, 845 (1999); D. A. Sipkins et al., Nature 435, 969 (2005)). However, expression of SDF-1 is not limited to the marrow, and this chemokine is typically expressed at all sites of tissue injury/inflammation (R. Sackstein, Immunol. Rev. 230: 140-163 (2009)).

The most efficient effectors of Step 1 rolling interactions are the selectins (E-, P- and L-selectin) and their ligands (R. Sackstein, Curr Opin Hematol 12, 444 (2005)). As the name implies, selectins are lectins that bind to specialized carbohydrate determinants, consisting of sialofucosylations containing an $\alpha(2,3)$-linked sialic acid substitution(s) and an $\alpha(1,3)$-linked fucose modification(s) prototypically displayed as the tetrasaccharide sialyl Lewis X (sLe$^x$; Neu5Ac$\alpha$2-3Gal$\beta$1-4[Fuc$\alpha$1-3]GlcNAc$\beta$1-)) (R. Sackstein, Curr Opin Hematol 12, 444 (2005); M. J. Polley et al., Proc Natl Acad Sci USA 88, 6224 (1991)). The sLex glycan is recognized by a variety of monoclonal antibodies (mAbs), including the mAb known as "HECA452." E- and P-selectin are expressed on vascular endothelium (P-selectin also on platelets), and L-selectin is expressed on circulating leukocytes (R. Sackstein, Curr Opin Hematol 12, 444 (2005)). E- and P-selectin are typically inducible endothelial membrane molecules that are prominently expressed only at sites of tissue injury and inflammation, where their expression is generated in response to inflammatory cytokines. However, the microvasculature of bone marrow and skin constitutively expresses these selectins, and they play a key role in steady-state recruitment of blood-borne cells to these sites (R Sackstein J Invest. Dermatology, 122:1061-1069 (2004)). Importantly, within all inflammatory sites and sites of tissue injury/damage in primates (but not rodents), E-selectin is the principal vascular selectin mediating cell recruitment, as the promoter element responsive to the inflammatory cytokines TNF and IL-1 has been deleted from the P-selectin gene. Thus, at all inflammatory sites of humans, vascular E-selectin expression is more pronounced than that of P-selectin (R. Sackstein, Immunol. Rev. 230: 140-163 (2009)).

Two principal ligands for E-selectin have been identified on human hematopoietic stem/progenitor cells (HSPC), the highly sialofucosylated CLA glycoform of PSGL-1 (Z. Laszik et al., Blood 88, 3010 (1996), R. Sackstein, Immunol. Rev. 230: 140-163 (2009)) and a specialized sialofucosylated CD44 glycoform known as Hematopoietic Cell E-/L-selectin Ligand (HCELL) (C. J. Dimitroff, J. Y. Lee, S. Rafii, R. C. Fuhlbrigge, R. Sackstein, J Cell Biol 153, 1277 (2001); C. J. Dimitroff, J. Y. Lee, R. C. Fuhlbrigge, R. Sackstein, Proc Natl Acad Sci US A 97, 13841 (2000)). CD44 is a rather ubiquitous cell membrane protein, but the HCELL phenotype is found predominantly on human HSPCs. In contrast to HCELL's restricted distribution, CLA/PSGL-1 is widely expressed among hematopoietic progenitors and more mature myeloid and lymphoid cells within the marrow (Z. Laszik et al., Blood 88, 3010 (1996), R. Sackstein, Immunol. Rev. 230: 140-163 (2009)). HCELL is operationally defined as CD44 that binds to E-selectin and L-selectin under shear conditions, and is identified by Western blot analysis of cell lysates as a CD44 glycoform reactive with E-selectin-Ig chimera (E-Ig) and with mAb HECA452, which recognizes sialyl Lewis X (and, in addition to sLex, HECA452 recognizes the tetrasaccharide isomer of sLex known as a "sialylated Lewis a" (sLea) in which fucose is attached in $\alpha(1,4)$-linkage to N-acetylglucosamine within a type 1 lactosamine backbone). In addition to CLA and HCELL, human leukocytes and HSPCs can also express a CD43 glycoform known as "CD43-E" which can serve as an E-selectin ligand (Fuhlbrigge et al Blood 107:1421-1426 (2006), Merzaban et al Blood 118:1774-1783 (2011)), and, in mouse leukocytes, another E-selectin ligand known as E-selectin Ligand-1 (ESL-1) has been described (Merzaban et al Blood 118:1774-1783 (2011)). In all glycoprotein selectin ligands (e.g., CD43-E, CLA, and HCELL) binding to E-selectin (and, also, to L-selectin and P-selectin) is critically dependent on $\alpha(2,3)$-sialic acid and $\alpha(1,3)$-fucose modifications (C. J. Dimitroff, J. Y. Lee, S. Rafii, R. C. Fuhlbrigge, R. Sackstein, J Cell Biol 153, 1277 (2001); C. J. Dimitroff, J. Y. Lee, R. C. Fuhlbrigge, R. Sackstein, Proc Natl Acad Sci US A 97, 13841 (2000); R. Sackstein, C. J. Dimitroff, Blood 96, 2765 (2000); C. J. Dimitroff, J. Y. Lee, K. S. Schor, B. M. Sandmaier, R. Sackstein, J Biol Chem 276, 47623 (2001)). On human HSPCs, HCELL displays the pertinent sialofucosylated selectin binding determinants on N-glycans (C. J. Dimitroff, J. Y. Lee, S. Rafii, R. C. Fuhlbrigge, R. Sackstein, J Cell Biol 153, 1277 (2001); R. Sackstein, C. J. Dimitroff, Blood 96, 2765 (2000)). In vitro assays of E- and L-selectin binding under hemodynamic shear stress indicate that HCELL is the most potent ligand for these molecules expressed on any human cell (C. J. Dimitroff, J. Y. Lee, S. Rafii, R. C. Fuhlbrigge, R. Sackstein, J Cell Biol 153, 1277 (2001); C. J. Dimitroff, J. Y. Lee, K. S. Schor, B. M. Sandmaier, R. Sackstein, J Biol Chem 276, 47623 (2001)). Importantly, though E-selectin is constitutively expressed on microvascular endothelium of the marrow and skin, this molecule is prominently expressed on endothelial beds at all sites of inflammation—both acute and chronic types—regardless of whether it is induced by direct tissue injury (e.g., burns, trauma, decubitus ulcers, etc.), ischemic/vascular events (e.g., myocardial infarct, stroke, shock, hemorrhage, coagulopathy, etc.), infections (e.g., cellulitis, pneumonia, meningitis, SIRS, etc.), neoplasia (e.g., breast cancer, lung cancer, lymphoma, etc.), immunologic/autoimmune conditions (e.g., graft vs. host disease, multiple sclerosis, diabetes, inflammatory bowel disease, lupus erythematosus, rheumatoid arthritis, psoriasis, etc.), degenerative diseases (e.g., osteoporosis, osteoarthritis, Alzheimer's disease, etc.), congenital/genetic diseases (e.g., muscular dystrophies, lysosomal storage diseases, Huntington's disease, etc.), adverse drug effects (e.g., drug-induced hepatitis, drug-induced cardiac injury, etc.), toxic injuries (e.g., radiation exposure(s), chemical exposure(s), alcoholic hepatitis, alcoholic pancreatitis, alcoholic cardiomyopathy, cocaine cardiomyopathy, etc.), metabolic derangements (e.g., uremic pericarditis, metabolic acidosis, etc.), iatrogenic conditions (e.g., radiation-induced tissue injury, surgery-related complications, etc.), and/or idiopathic processes (e.g., amyotrophic lateral sclerosis, Parsonnage-Turner Syndrome, etc.).

Among the various aspects of the present disclosure is the provision of methods for the treatment of a disease, disorder or medical condition having E-selectin expression on vascular endothelial cells and/or leukocyte infiltrates within affected tissue(s). E-selectin binds to sialylated, fucosylated carbohydrates (e.g., members of the sialylated Lewis X and Lewis A families) present natively on the surface of certain leukocytes and hematopoietic stem/progenitor cells, i.e., myeloid cells (e.g., neutrophils, monocytes, eosinophils, macrophages, etc.), dendritic cells (both lymphoid- and myeloid-derived), lymphocytes (e.g., naïve and memory T cells, naïve and memory B cells, effector T cells, regulatory T cells, natural killer cells (NK cells), etc.), hematopoietic progenitor cells, and hematopoietic stem cells. These cell types are thus found at acute and chronic inflammatory sites, recruited by vascular E-selectin to such inflammatory sites. Leukocytes and HSPCs characteristically display L-selectin. L-selectin, itself, binds to sialylated, fucosylated carbohydrates such as sLex. Thus, inflammatory sites have cells that express E-selectin (on endothelial cells) and L-selectin (on infiltrating leukocytes and HSPCs).

The ability to achieve intended outcome(s) of cell-based therapeutics is critically dependent on delivery of administered cells to sites where they are needed, and, also, to the localization of the administered cells within specific tissue microenvironments. Accordingly, there is a need in the art for methods to enhance vascular delivery of administered cells to sites of tissue injury/damage, to sites of inflammation, to sites of cancer, and to sites of infection. There is also a need in the art to enhance lodgement/colonization of the administered cells within the affected tissue. Briefly, therefore, the present disclosure is directed to methods of treating a disease, disorder or medical condition manifesting as inflamed and/or damaged tissue and/or cancer in a subject, the methods comprising administering to the subject a cell population that expresses an E-selectin ligand and/or an L-selectin ligand at a level that exceeds that of a native population of the cells. The administration occurs coincident with expression of E-selectin on endothelial cells within the target tissue (e.g., inflamed and/or damaged tissue, cancerous tissue) and/or coincident with accumulation of leukocytes (e.g., leukocytic infiltrates) within the target tissue. The administration may be by direct injection within the target tissue and/or via the vasculature and/or via other means as described in further detail below.

The present disclosure is further directed to a method for the treatment of inflammation with a viable population of cells that express an E-selectin and/or L-selectin ligand. The viable cell population expresses an E-selectin ligand and/or an L-selectin ligand at a level that exceeds the level of expression of a native population of the cells. The administration occurs coincident with expression of E-selectin on endothelial cells within the target tissue (e.g., inflamed and/or damaged tissue, cancerous tissue) and/or coincident with accumulation of leukocytes (e.g., leukocytic infiltrates) within the target tissue. The administration may be by direct injection into the target tissue and/or via the vasculature (and/or via other means as described in further detail below) and treatment of the disease, disorder or medical condition need not be accompanied by long-term engraftment of the administered cells (i.e., treatment could be achieved either with transient colonization or with long-term persistence/longevity of administered cells at the treatment site or with proliferation of administered cells at the treatment site or with differentiation and/or maturation of administered cells at the treatment site).

The present disclosure is further directed to a viable population of cells that express an E-selectin and/or L-selectin ligand for use in the manufacture of a medicament for treating inflammation in a subject. The viable cell population expresses an E-selectin ligand and/or an L-selectin ligand at a level that exceeds the level of expression of a native population of the cells. The administration occurs coincident with expression of E-selectin on endothelial cells within the target tissue (e.g., inflamed and/or damaged tissue, cancerous tissue) and/or coincident with accumulation of leukocytes (e.g., leukocytic infiltrates) within the target tissue. The administration may be by direct injection into the target tissue and/or via the vasculature and/or via other means as described in further detail below.

The present disclosure is further directed to a viable population of cells that express an E-selectin ligand and/or an L-selectin ligand for use in the manufacture of a medicament for the treatment of a tumor/malignant disease, the treatment comprising administering to the subject the population of cells that express an E-selectin ligand and/or an L-selectin ligand, wherein the population expresses the E-selectin ligand and/or L-selectin ligand at a level that exceeds the level of expression of a native population of the cells, wherein said treatment comprises administering the population coincident with E-selectin expression on endothelial cells within the tumor/malignant tissue and/or coincident with accumulation of leukocytes within the tumor/malignant tissue.

The present disclosure is further directed to a viable population of cells that express an E-selectin ligand and/or an L-selectin ligand for use in the manufacture of a medicament for the treatment of a diseased state manifesting inflammation, the treatment comprising administering to the subject the population of cells that express an E-selectin ligand and/or an L-selectin ligand, wherein the population expresses the E-selectin ligand and/or L-selectin ligand at a level that exceeds the level of expression of a native population of the cells, wherein said treatment comprises administering the population coincident with the onset of E-selectin expression on endothelial cells within the tumor/malignant tissue and/or coincident with accumulation of leukocytes within the tumor/malignant tissue.

Other methods involving the administration (e.g., via the vasculature and/or via direct injection into tissue and/or via other means) described herein include, for example, method of enhancing cell delivery and colonization in an inflamed and/or damaged tissue or site of cancer in a subject (collectively, a "target" tissue), methods of enhancing cell delivery into a target tissue of a subject and/or enhancing tissue colonization in the target tissue of the subject, methods of improving cellular delivery to a target tissue in a subject, methods of enhancing cell delivery and colonization into a target tissue of a subject, method of enhancing homing and engraftment of a cell population within a target tissue in a subject, methods of treating an inflammatory condition in a subject, methods of enhancing tissue repair/regeneration in a subject, and methods of treating tumor/malignant disease in a subject.

In general, any of a variety of inflammatory conditions (e.g., acute and/or chronic) and/or damaged tissue may be treated in accordance with the methods described herein, including, but not limited to those initiated by direct tissue injury (e.g., burns, trauma, decubitus ulcers, etc.), ischemic/vascular events (e.g., myocardial infarct, stroke, shock, hemorrhage, coagulopathy, etc.), infections (e.g., cellulitis, pneumonia, meningitis, SIRS, etc.), neoplasia (e.g., breast cancer, lung cancer, lymphoma, etc.), immunologic/autoimmune conditions (e.g., graft vs. host disease, multiple sclerosis, diabetes, inflammatory bowel disease, lupus erythematosus, rheumatoid arthritis, psoriasis, etc.), degenerative diseases (e.g., osteoporosis, osteoarthritis, Alzheimer's disease, etc.), congenital/genetic diseases (e.g., epidermolysis bullosa, osteogenesis imperfecta, muscular dystrophies, lysosomal storage diseases, Huntington's disease, etc.), adverse drug effects (e.g., drug-induced hepatitis, drug-induced cardiac injury, etc.), toxic injuries (e.g., radiation exposure(s), chemical exposure(s), alcoholic hepatitis, alcoholic pancreatitis, alcoholic cardiomyopathy, cocaine cardiomyopathy, etc.), metabolic derangements (e.g., uremic pericarditis, metabolic acidosis, etc.), iatrogenic conditions (e.g., radiation-induced tissue injury, surgery-related complications, etc.), and/or idiopathic processes (e.g., amyotrophic lateral sclerosis, Parsonnage-Turner Syndrome, etc.).

In certain embodiments, for example, the E-selectin ligand and/or L-selectin ligand expressed by the cell population is selected from one or more of Hematopoietic Cell E-/L-selectin Ligand (HCELL), Neural Cell Adhesion Molecule E-selectin Ligand (NCAM-E), CD43E, and CLA. In one embodiment, the E-selectin ligand is Hematopoietic Cell E-/L-selectin Ligand (HCELL) and/or Neural Cell Adhesion Molecule E-selectin Ligand (NCAM-E). In another embodiment, the E-selectin ligand is HCELL. In another embodiment, the E-selectin ligand is NCAM-E. In another embodiment, the L-selectin ligand is HCELL. Notably, since E-selectin is expressed within endothelial beds of the affected tissue and leukocytes characteristically express L-selectin, expression of HCELL, a potent E-selectin and L-selectin ligand, would serve to promote tissue lodgement expressly within the microenvironments of most intense immunoreactivity/tissue damage.

As discussed elsewhere herein in greater detail, a variety of methods may be utilized to prepare the population of cells for administration to the subject. In one embodiment, the population is prepared by contacting the cell or a population of cells with glycosyltransferase together with appropriate donor nucleotide sugar. For example, glycan engineering may be used to sialofucosylate CD44 to enforce the expression of Hematopoietic Cell E-selectin Ligand (HCELL), by glycosyltransferase-enforced expression of fucose residues (fucosylation), sialic acid residues (sialylation), or both (sialofucosylation). Alternatively, glycosyltransferases such as a fucosyltransferase may be used to transfer intact glycan structures such as sialyl-Lewis$^x$ or sialyl-Lewis$^a$ to cell surfaces. In addition, non-enzymatic methods may be used to covalently or non-covalently bind E-selectin and/or L-selectin ligands to cell surfaces. For example, aptamers, sLex (sialyl-Lewis$^X$), glycomimetics and/or peptidomimetics of sLex glycans, sLea (sialyl-Lewis$^a$), glycomimetics and/or peptidomimetics of sLea glycans, and other moieties that bind E-selectin and/or L-selectin may be non-covalently bound to cell surfaces using biotin-streptavidin pairs or covalently bound to the cell surfaces; whether covalent or non-covalent, the binding may be direct or via a linker. By way of further example, phage display particles or antibodies that bind E-selectin and/or L-selectin may be covalently or non-covalently bound to the cell surface, in each case mediating adherence of treated cells to E-selectin and/or L-selectin.

In general, and independent of the manner of preparing the cell population, the manner of preparation provides a modified cell population having a viability of at least 70% at 24 hours from the time of modification. In one such embodiment, the modified cell population has a viability of at least 80% at 24 hours from the time of the modification. In some embodiments, the modified cell population has a viability of at least 85% at 24 hours from the time of the modification. In some embodiments, the modified cell population has a viability of at least 90% at 24 hours from the time of the modification. Viability may be determined by methods known in the art such as trypan blue exclusion, or by dual color flow cytometry assessment for propidium iodide and Annexin V staining. Preferably, the phenotype of the cells (other than the cell surface modification) is preserved after treatment. By preserved phenotype it is meant the cell maintains its native function and/or activity. For example, if the cell is a stem cell it retains its regenerative potency, e.g., its totipotency or its pluripotency or its multipotency or its unipotency.

The modified cell populations are viable (i.e., have a viability of at least 70% at 24 hours from the time of modification as described above) and have enhanced binding to E-selectin and/or L-selectin relative a native population of the cells. The administration of cells may be via the vasculature and/or by direct injection into the tissue (and/or by other means as described in detail below). In one embodiment, the modified cell population is administered at a time coincident with the onset of inflammation or the infiltration of leukocytes into tissue. In another embodiment, the modified cell population is administered just prior to the onset of inflammation or the infiltration of leukocytes into the tissue.

In cases where cells undergo glycan engineering to enforce sLex expression or undergo decoration with sLex structures (e.g., via avidin-spreptavidin techniques), measurement of increased sLex expression on treated cells can be performed by fluorescence staining with mAb HECA452 or any other mAb which recognizes sLex determinants, followed by flow cytometry to detect cell fluorescence intensity. The predetermined fluorescence threshold of the modified cell population is determined by first analyzing a sample of native (untreated) cells. Increases in sLex of treated cells is defined as increase percentage of marker-positive cells (e.g., HECA452-reactive cells) of greater than 10% compared to native population of cells and/or by a 10% increase in mean channel fluorescence intensity over that of the baseline (untreated) cell population. For detecting whether the treated cell population has increased binding to E-selectin, binding to E-selectin can be assessed using either parallel plate flow chamber studies under shear stress conditions as described herein or via staining with E-selectin-Ig chimera and assessment of fluorescence intensity by flow cytometry. The control (baseline) sample of cells is assayed using the functional E-selectin binding assay described elsewhere herein, or by another generally accepted E-selectin fluorescence binding assay known in the art. E-selectin binding fluorescence levels are measured for the control (baseline) population sample. Enhanced binding to E-selectin is defined as treated cells having increased adherence to E-selectin in an E-selectin-specific binding assay. In one embodiment, enhanced binding to E-selectin can be defined by a fluorescence shift in an E-selectin binding assay using fluorochrome-conjugated reagents, e.g., binding to E-selectin-Ig chimera as assessed by flow cytometry, in which the number of cells within the population that possess E-selectin binding increases by at least 10% more than that of the base-line binding (i.e., increase of 10% in marker-positive population) and/or is at least 10% greater in mean channel fluorescence than a predetermined fluorescence threshold (associated with the native cell population). In another embodiment, the percentage of cells that possess increased E-selectin reactivity is increased by 25% and/or the modified population exceeds the predetermined fluorescence threshold by 25%. In another embodiment, the modified population exceeds the baseline reactivity and/or predetermined fluorescence threshold by 50%. In another embodiment, the percentage of cells that possess increased E-selectin reactivity is increased by 75% over that of the baseline population of E-selectin-binding cells and/or the modified population exceeds the predetermined fluorescence threshold by 75%. In another embodiment, at least 90% of the cells in the modified population exceed the baseline E-selectin-binding population and/or the predetermined fluorescence threshold. In another embodiment, at least 95% of the cells in the modified population exceed the baseline E-selectin-binding population and/or the predetermined fluorescence threshold.

Enhanced binding to L-selectin may be determined by an increase in binding to L-selectin using a functional L-selectin binding assay with high specificity such as a parallel plate flow chamber under dynamic shear stress conditions or a Stamper-Woodruff Assay, wherein the cell treatment increases the percentage of cells supporting L-selectin-mediated adherence. In the case of parallel plate assays, the treated cell population displays at least a 10% increase in tethering/rolling adhesive interactions to L-selectin (affixed and displayed on the chamber plastic or glass support surface) compared to that of baseline (untreated cells). In the case of the Stamper-Woodruff assay, increased L-selectin lymphocyte adherence is defined by at least a 10% increase in treated cell binding to L-selectin+ lymphocytes under a rotatory shear of 80 rpm; baseline cell binding is assessed on the untreated (control population), and directly compared to that in the treated cell population.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other objects and features will be in part apparent and in part pointed out hereinafter.

BRIEF DESCRIPTION OF THE DRAWINGS

The patent or application file contains at least on drawing executed in color. Copies of this patent or patent application with color drawings(s) will be provided by the Office upon request and payment of the necessary fee.

FIGS. 1A-1D. Effects of Exofucosylation (FTVI treatment) on E-selectin ligand expression by mouse mesenchymal stem cells (MSCs). (FIG. 1A) MSCs derived from C57BL/6 marrow lack expression of CD45 and express characteristic mouse MSC markers Sca-1, CD29, CD44, CD73 and CD105. MSCs natively lack reactivity with mAb HECA452 and with E-selectin-Ig chimera (mE-Ig) (istoype=red color and antibody=blue color). (FIG. 1B) Fucosyltransferase VI (FTVI)-modified MSC (solid line) stained positive for mAbs HECA452 and were reactive with mE-Ig. Digestion of FTVI-modified MSCs with bromelain and proteinase K (shaded histogram) significantly reduced murine E-selectin-Ig chimera (mE-Ig) reactivity, but not HECA452 staining, indicating that bromelain-sensitive glycoproteins serve as the principal E-selectin ligand(s) on glycan-modified FTVI-treated) MSCs. Dashed line represents staining controls (isotype control for HECA452 staining and calcium chelation with EDTA for mE-Ig staining). (FIG. 1C) Western blot analysis of HECA452 (left) and mE-Ig (right) reactivity of cell lysates of unmodified MSCs (−) and FTVI-modified MSCs (+). FTVI modification induced HECA452- and mE-Ig-reactive moieties predominantly on a doublet glycoprotein band of ~100 kDa. (FIG. 1D) CD44 was immunoprecipitated from equivalent amounts of cell lysate from FTVI-modified (+) or unmodified (−) MSCs. Immunoprecipitates were then electrophoresed and blotted with CD44 (mAbs KM114 and IM7; left) and HECA452 (right).

(FIG. 3A) Hyperglycemic NOD injected with PBS (untreated control) showed no reversal of hyperglycemia (glucose levels above 600 mg glucose/dL). As compared to infusion of unmodified MSCs (FIG. 3B), infusion of FTVI-modified MSCs (FIG. 3C) resulted in a marked increase in number of mice with reversion to normoglycemia and in the durability of diabetes reversal. Arrows in X-axis denote days of MSC infusion.

FIGS. 4A-4H. Immunofluorescence staining of islets to assess expression of E-selectin and localization of MSCs in the pancreas. FIGS. 4A-4B: Pancreatic islets of (FIG. 4A) diabetic-resistant BALB/c mice and (FIG. 4B) NOD mice were stained for expression of insulin (green) and E-selectin (red). Islets are demarcated by dashed line. Compared to BALB/c (FIG. 4A), NOD mice (FIG. 4B) show diminished insulin production due to insulitis. In FIGS. 4C-4G, cryostat sections of pancreas from MSC-treated NOD mice stained with DAPI (blue). FIGS. 4C-4D: Staining of sequential sections of NOD pancreas demonstrates co-localization of endothelial marker CD31 (FIG. 4C) and E-selectin (FIG. 4D), confirming the presence of E-selectin on peri-islet endothelial cells. FIG. 4E: Co-staining of NOD islet with DAPI (blue), T-cell marker CD3 (green) and insulin (red) (FIG. 4E) reveals characteristic T-cell infiltration at the margins of the islet. FIGS. 4F-4G: Immunofluorescence images of a cryostat section stained for infiltrating MSC (visualized with FITC-conjugated anti-sLex mAb HECA452; green), islet (FIG. 4F) (visualized by APC-conjugated anti-insulin mAb; red) and E-selectin-expressing microvessel (FIG. 4G) (visualized with PE-conjugated anti-E-selectin mAb; red). Staining identifies HECA452+MSCs in zones of insulitis, in proximity to E-selectin-expressing microvessels in the peri-islet area and clustered within areas of lymphocytic infiltrates (i.e., cells which characteristically express L-selectin). FIG. 4H: Pancreatic infiltration of intravenously administered MSCs into NOD and BALB/c hosts. Accumulation of FTVI-modified MSCs into pancreata of NOD mice is 3-fold higher compared to that of unmodified MSCs (p<0.01), whereas no difference in pancreatic infiltrates is observed in BALB/c host (n=3 mice per group; minimum 30 fields counted per group at 60× magnification).

(FIG. 5A) Similar levels of hGH was detected in the serum of NOD mice at different time points following injection with pHRST-hGH-transduced FTVI-modified or unmodified MSCs. (FIG. 5B) FTVI-modified and unmodified MSCs equally suppress proliferation of NOD CD4+ T cells stimulated with CD3/CD28, indicating that glycan-modification does not increase MSC capacity to suppress lymphocyte proliferation.

FIGS. 6A-6D. Lack of CD44 expression abrogates the anti-diabetic effect of systemically administered FTVI-modified MSC. (FIG. 6A) As compared to unmodified wild type MSC (FIG. 3B), administration of CD44-deficient MSCs shows modest anti-diabetic effect. Only 1 NOD mouse (out of 7) receiving unmodified CD44 KO MSCs showed reversal of hyperglycemia which was transient (diabetes recurrence at ~day 30), and 6 out of 7 diabetic NOD mice remained hyperglycemic. (FIG. 6B) As compared to results in mice receiving FTVI-modified wild-type MSCs (FIG. 3C), administration of FTVI-modified CD44 KO MSCs conferred minimal anti-diabetic effects, with only 1 out of 6 NOD mice showing reversal of hyperglycemia. (FIG. 6C) Accumulation of MSCs in NOD pancreata was no different in mice receiving FTVI-modified CD44 KO MSCs (white bar) compared to mice receiving unmodified CD44 KO MSCs (black bar) (p<0.01), and in each case was similar to that receiving unmodified MSC (FIG. 4H). MSC infiltrates were quantified at ×60 magnification. (FIG. 6D) Both FTVI-modified and unmodified CD44 KO MSCs possess immunosuppressive capacity, similarly dampening T cell proliferation in the CD3/CD28 T cell stimulation assay.

(FIG. 9A) Flow cytometric analysis of HECA452, KM93, CSLEX-1, E-selectin ligand (binding to E-selectin-Ig chimera (E-Ig)), and P-selectin ligand (P-selectin-Ig chimera (P-Ig)) expression on NSCs. The corresponding isotype controls showed overlapping signals for each antibody surveyed i.e. RatIgM (for HECA-452; MFI: 1.9); Mouse IgM (for KM93 and CSLEX-1; MFI: 2.7), and human $IgG_1$ (for E-Ig and P-Ig; MFI: 3.5). A histogram plot representing a typical E-Ig binding profile illustrates that over 99% of the cells consistently express E-Ig binding following glycosyltransferase-programmed stereosubstitution (GPS) via cell surface treatment with Fucosyltransferase VI. (FIG. 9B) Flow cytometric analysis of CD43 (S7 and 1B11), PSGL-1 (2PH1, 4RA10), CD44 (IM7, KM114), NCAM, PSA, CD49d, CD49e, CD29, LPAM-1, CD11a, CD18, and CXCR4. Dotted line is isotype control, black line is specific antibody. All results displayed are representative of n=5 flow cytometry experiments performed on NSCs.

(FIG. 10A) Flow cytometric analysis of HECA452, CD15, KM93, CSLEX1, E-Ig and P-Ig reactivity on BT-NSCs (black bars) and GPS-NSCs (grey bars). The corresponding isotype controls for each antibody surveyed were: Rat IgM (for HECA-452; MFI: 1.8); Mouse IgM (for CD15, KM93, and CSLEX-1; MFI: 1.9), and human $IgG_1$ (for E-Ig and P-Ig; MFI: 3.2). Results displayed are representative of five separate experiments. (FIG. 10B) Flow cytometric analysis of HECA452 reactivity of GPS-NSCs undigested (black bars) or digested with bromelain (grey bars) prior to GPS treatment. Values are means±SEM. (n=3 for each group). (FIG. 10C) Flow cytometric analysis of HECA452 reactivity of GPS-NSCs undigested (black bars) or digested with phospholipase C (PI-PLC) to cleave GPI anchors (grey bars). Values are means±SEM. (n=3 for each group).

(FIG. 11A) CD44 was immunoprecipitated (with IM7 and KM114 mAb to CD44) from equivalent amounts of cell lysates from GPS-treated (GPS) or buffer-treated (BT) NSCs. Western blot analysis was performed on immunoprecipitates of NSCs and supernatants (SN) from the immunoprecipitates, which were electrophoresed and blotted with HECA452, E-Ig, and CD44. (FIG. 11B) N-CAM was immunoprecipitated (with N-CAM 13) from equivalent amounts of cell lysates from GPS-treated (+) or buffer-treated (−) NSCs lysates that had been either treated with PNGaseF (+) or not (−) Immunoprecipitates were then electrophoresed and blotted with E-Ig and N-CAM. Staining with E-Ig was performed in the presence of $Ca^{2+}$. (FIG. 11C) NSCs were treated with GPS on Day 0 and cultured for another 3 days in normal growth media. Every 24 hours aliquots of cells were removed and assayed for E-selectin ligand activity by flow cytometry. See also FIGS. 11A-11C, 12A-12B, 13A-13F.

(FIG. 12A) BT-NSCs or GPS-NSCs were perfused over IL-1β and TNF-α stimulated HUVECs at 1.0 $dyn/cm^2$. NSC accumulation was then determined at shear stresses of 1, 2, 4, 8, 16, 25 and 32 $dyn/cm^2$. GPS-NSCs show rolling adhesive interactions on HUVECs at a shear stress of up to 32 $dyn/cm^2$. To control for the specificity of binding of GPS-NSCs, EDTA was added to the assay buffer (EDTA group), or stimulated HUVECs were pretreated with a function blocking mAb to E-selectin (anti-E-Sel group) before use in adhesion assays. Values are means±SEM. (n=4 for each group). P 0.001 for comparisons of GPS-NSCs to all other groups at all shear stress levels. (FIG. 12B) Adhesion bar graph for blot rolling assay (rolling cells/$mm^2$) for CHO-E cells perfused over SDS-PAGE immunoblots of HECA-452-reactive membrane glycoproteins of NSCs at 0.6 $dyne/cm^2$. Immunoprecipitates of CD44/HCELL and panNCAM from both BT-NSC (black bars) and GPS-NSCs (grey bars) were resolved by SDS-PAGE and blotted for HECA-452 prior to performing the assay. To control for the specificity of CHO-E binding to membrane glycoproteins, EDTA was added to the buffer containing the CHO-E cells before use in adhesion assays; no cells bound under this condition (data not shown). Results presented are representative of multiple runs (n=4) on HECA-452 blots of multiple (n=3) membrane preparations of NSCs.

FIGS. 13A-13F: GPS-NSCs exhibit improved homing in an EAE model in vivo. (FIGS. 13A-13D) GPS-NSCs migrate to the CNS parenchyma more efficiently than BT-NSCs. $1×10^6$ GPS-NSCs or BT-NSCs were labeled with PKH26 dye and were injected intravenously to MOG-induced EAE mice on day 9 and day 13 post-immunization (PI). (FIG. 13A) Analysis of the forebrain of EAE mice (on day 17 PI) that either received BT-NSCs or GPS-NSCs, revealed that lower numbers of PKH26-positive cells are seen in animals injected with BT-NSCs compared to GPS-NSCs. The yellow arrowheads indicate NSCs and the white arrows indicate infiltrates. The white dashed line indicates Meningeal borders. FIGS. 20A-20B show further analysis of these sections to confirm that the NSCs (PKH26; red) are located outside of Flk-1 vessels (green) and that they are SOX-2 positive (green). (FIG. 13B) Lumbar-sacral spinal cords (insert) were harvested on day 17 PI. At day 17 PI, more GPS-NSCs migrated out of the blood vessels into the spinal cord parenchyma than BT-NSCs. Blood vessels were visualized by Flk-1 (VEGFR2; green) staining. The edge of the spinal cord parenchyma is highlighted with a white dotted line. NSCs labeled with PKH26 dye are shown in red and nuclei counterstained with TO-PRO-3 are blue. WM, white matter. V, blood vessels. (FIG. 13C) The insets show a 3-dimentional view of the migrated NSCs indicated by the arrows in FIG. 13A. (FIG. 13D) Quantification of numbers of BT-NSCs and GPS-NSCs per 200× migrating per spinal cord area at day 17 PI were determined. A significant increase in the numbers of migrating GPS-NSCs over BT-NSCs was evident, * p<0.05. (FIG. 13E) Quantification of biodistribution of NSCs. GPS-NSCs (grey bars) or BT-NSCs (black bars) were labeled with CFDA-SE and injected intravenously into MOG-treated C57BL6 mice on day 9 and day 13 post-immunization. Brain, lymph nodes, spleen, liver and lung were analyzed 16 hours after the last injection to determine the percentage of CFSE positive cells present within a defined gate representing NSCs. Non-EAE mice that received GPS-NSCs or BT-NSCs were used to standardize the signals observed in each tissue tested. Mice that did not receive cells were used to determine the background signal. Error bars represent the standard error of the mean. Data are representative of 2 separate experiments where 10 mice per group were tested. (FIG. 13F) In vivo confocal demonstration that exofucosylated NSCs are found in close contact with CD4 T cells in the spleen in vivo (NSCs are labeled pink and CD4 T cells in green); this co-localization of NSCs and lymphocytes would be engendered by NSC HCELL binding to lymphocyte L-selectin.

FIGS. 14A-14I: GPS-NSCs contribute to significant amelioration of EAE symptoms through enhanced neuroprotection. (FIG. 14A) The EAE clinical scores in C57BL/6 mice immunized with MOG 35-55 on Day 0 and subsequently injected with 1×10$^6$ GFP-labeled buffer-treated NSCs (BT-NSC; filled red triangles; n=30), GPS-treated NSCs (GPS-NSC; filled green circles; n=30) or sham-treated mice (No NSC; filled black circles; n=30) on day 9 and day 13 after immunization were determined. Mice that received GPS-NSCs displayed a pronounced clinical improvement compared with sham-treated mice (p=0.0001) and mice injected i.v. with BT-NSCs (p=0.006). (FIG. 14B) The cumulative burden of disease was assessed by performing a linear regression analysis comparing the slope of the curves in (FIG. 14A). These data highlight GPS-NSCs (green dotted line) significantly improve the clinical scores above that of BT-NSCs (red line). Mice receiving either GPS-NSCs or BT-NSCs displayed significantly improved clinical scores compared to mice that did not receive NSCs (No NSCs; black line). These data also suggest that BT-HSPCs (blue line) and GPS-HSPCs (purple line) worsen disease (see FIG. 21C). (FIG. 14C) Neuropathology at day 30 PI of the brain from EAE mice injected with NSCs was analyzed by staining with anti-CD11b mAb (green) and the nuclear label To-Pro3 (blue). GPS-NSC injection leads to significantly less injury per brain section as measured by numeration of CD11 b macrophage/microglia from 20 different sections of 3 different spinal cords. Bar graphs depict the numeration of CD11 b macrophage/microglia in spinal cord sections per high power field (HPF) from EAE mice that received No NSC, BT-NSC, or GPS-NSC and also the numeration of infiltrates per HPF were calculated based on To-Pro3 staining. White boxes correspond to higher magnification images. Yellow arrowheads correspond to activated microglia and white arrows correspond to infiltrates in the meninges (m). Note that the microglia in the No NSC samples are more activated than those found in the BT-NSC and GPS-NSC samples. Also the size of the infiltrates in the meninges is larger in the No NSC samples than in the BT-NSC samples. Scale bars, 100 µm for top panels. Scale bars, 50 µm for bottom panels. (FIG. 14D) Neuropathology of the brain from EAE mice injected with NSCs was analyzed by staining 20 different sections of 3 separate brains from mice that either received no NSCs (EAE No NSCs), BT-NSC (EAE BT-NSCs), or GPS-NSC (EAE GPS-NSCs) with CD4 (to measure T cell infiltrations), CNPase (to quantify remyelinating cells), Olig-2 (to measure oligodendroglial differentiation) or SOX-9 (to measure multipotency of neural precursors) (green) and To-Pro3 (blue). GPS-NSC injection lead to significantly less T cell infiltrations, enhanced remyelination, higher numbers of oligodendroglia, and preservation of progenitor numbers. (FIG. 14E) Bar graphs depict the numeration of CD4 T, CNPase, Olig2, SOX-9 cells in brain sections per high power field (HPF) from EAE mice that received No NSC, BT-NSC, or GPS-NSC (as outlined in (FIG. 14D)), indicating that animals that received GPS-NSCs display enhanced neuroprotection of progenitor cells. (FIGS. 14F-14I) GPS-NSC and BT-NSC injection leads to increased axonal regeneration and axonal protection compared to No NSC control as measured by increased GAP-43 (green; p<0.001) staining (FIG. 14F) and by decreased staining with the monoclonal antibody SMI32 (red; p<0.001) (FIG. 14H) as assessed by quantitative confocal imaging of GAP43 pixel intensity in more than 500 individual measurements. To-Pro3 staining dye was used to detect cell nuclei (blue). (FIGS. 14G-14H) Based on quantitative confocal imaging of more than 500 individual measurements of pixel intensity (Imitola, J., Cote, D., et al. 2011) graphical representation of GAP-43 (FIG. 14G) and SMI32 (FIG. 14I) was determined; note that SMI32 patterns (FIG. 14I) demonstrated axonal ovoids in animals with EAE but reduction in animals injected with NSCs (FIG. 14I) and SMI32 pixel intensity showed a gradual correction of axonal integrity in animals with GPS-NSCs. There is a reduction of axonal ovoid and axonal fragments compared to controls and BT-NSCs as depicted in the cartoon below (FIG. 14I) Scale bar, 100 µm except for SMI32 staining where scale bar, 50 µm.

(FIG. 16A) Flow cytometric analysis of CD15, CSLEX-1, HECA452, and E-selectin ligand (E-Ig binding), expression on human NSCs either treated with GPS (grey bars) or buffer-treated (BT; black bars). The mean fluorescence intensity is shown for each antibody measured. (FIG. 16B) Flow cytometric analysis of CD44, PSGL-1, NCAM, and CD43. (FIG. 16C) Western blot analysis of E-Ig reactivity of NSC lysates from mouse and human sources. CD44 and NCAM were immunoprecipitated from equivalent amounts of cell lysates from GPS-treated (+) or buffer-treated (−) mouse NSCs or human NSCs. Immunoprecipitates were then electrophoresed and blotted with E-Ig. Staining of GPS-treated NSCs with E-Ig was performed in the presence of $Ca^{2+}$.

(FIG. 18D) GFAP+ astrocytes and NG2+ oligodendrocytes are shown in red and To-Pro3 is used to stain nuclei of neural stem cells treated in vitro with control buffer (BT) or FTVI (GPS). Scale bar, 50 μm. These figures are related to FIGS. 11A-11C.

(FIG. 19C) $1 \times 10^6$ BT-NSCs or GPS-NSCs were treated for 24 h with or without inflammatory cytokines (10 ng/mL IFN-Y and 15 ng/mL TNF-α) and with or without E-Ig (5 ng/mL) prior to RNA extraction and cDNA synthesis. Real-time RT-PCR revealed the fold change in gene expression (related to BT or GPS-NSCs alone) calculated using $2^{-\Delta\Delta CT}$ method and the relative expression of LIF mRNA was assayed relative to GAPDH housekeeping gene. Values are means±SEM (n=4 experiments). These figures are related to FIGS. 11A-11C.

FIGS. 20A-20B: GPS-NSCs migrate to the CNS parenchyma more efficiently than BT-NSCs. $1 \times 10^6$ GPS-NSCs or BT-NSCs were labeled with PKH26 dye and were injected intravenously to MOG-induced EAE mice on day 9 and day 13 post-immunization (PI). Brains were harvested on day 17 PI and snap-frozen before 20 μm sections were prepared and stained with antibodies: anti-Flk-1 (VEGFR2; green) or anti-SOX-2 (red) to reveal blood vessels and the position of the NSCs respectively. (FIG. 20A) BT NSCs are primarily localized with FLK-1+ endothelial cells whereas GPS-NSCs are found in the parenchyma as they have crossed the endothelium. These NSCs express sox-2, a marker for neural stem cells (FIG. 20B). These figures are related to FIGS. 13A-13F.

(FIG. 21A) Flow cytometric analysis of E-Ig reactivity on BT- and GPS-mouse hematopoietic stem/progenitor cells (HSPC; Lineage$^{neg}$C-kit$^{pos}$). The mean fluorescence intensity is shown above each histogram for the hIgG$_1$ isotype control, E-Ig reactivity on BT-HSPC and E-Ig reactivity on GPS-HSPC. These cells were used for in vivo EAE experiments as a control. (FIG. 21B) The EAE clinical scores in C57BL/6 mice immunized with MOG 35-55 on Day 0 and subsequently injected with $1 \times 10^6$ buffer-treated HSPC (BT-HSPC; open blue diamonds; n=30), GPS-treated HSPC (GPS-HSPC; open purple diamonds; n=30) or sham-treated mice (No NSC; filled black circles; n=30) on day 9 and day 13 after immunization were determined. No significant improvement in the clinical scores was evident in mice receiving either BT- or GPS-HSPC. (FIG. 21C) The cumulative burden of disease was assessed by performing a linear regression analysis comparing the slope of the curves in (21B). These figures are related to FIGS. 14A-14H.

FIG. 25. Western blot analysis of cell lysates of adipose-derived MSCs. Lysates of MSCs from bone marrow (BM- MSCs) and from lean and obese adipose tissue (A-MSCs) were exofucosylated with FTVII (+) or treated with buffer alone (−), then were subjected to SDS-PAGE and blotted with HECA452 or with anti-human CD44 mAb. Lysates of the hematopoietic cell line KG1a (control) and the fibroblast cell line PIF were co-electrophoresed and blotted. KG1a cells express HCELL (HECA-452-reactive CD44 at mw of ~80 kDa). As shown in the figure, FTVII treatment results in enforced expression of HCELL (HECA452-reactive CD44) on PIF cells and on MSCs derived from adipose tissue of lean and obese subjects (upper panel); staining for expression of CD44 in each lysate is shown below the HECA452 blot. Expression of HCELL (~80 kDa HECA452-reactive band) is abrogated following sialidase treatment of cells (lower panel), consistent with sialidase sensitivity of HCELL expression (i.e., elimination of sLex). Note that HCELL may appear as a doublet at ~80 kDa (see profile of FTVII-treated A-MSC in lower panel), which reflects variable glycosylation of the core CD44 glycoprotein that does not affect E-selectin or L-selectin ligand activity of the HCELL molecule.

FIG. 26. Results of parallel plate flow chamber studies of MSCs perfused over TNF-stimulated human umbilical vein endothelial cells (HUVEC). As measured under defined hemodynamic shear conditions (dynes/cm$^2$, shown on x-axis), α(1,3)-exofucosylation (FTVII treatment) of A-MSCs derived from lean subjects (LA-MSCs) and from obese subjects (OA-MSCs) confers potent E-selectin binding on E-selectin displayed on TNF-stimulated HUVEC; the E-selectin ligand activity of FTVII-treated (HCELL+) adipose-derived MSCs is equivalent to that of FTVII-treated (HCELL+) bone marrow-derived MSCs (BM-MSCs; lower panel). Untreated MSCs have no significant binding interactions on HUVEC at any of the shear stress levels.

FIGS. 27A-27C. Analysis of effects of α(1,3)-exofucosylation on E-selectin binding of various leukocytes. (FIG. 27A) Parallel plate flow chamber analysis of tethering and rolling interactions of native peripheral blood leukocytes with endothelial E-selectin (expressed on TNF-stimulated human umbilical vein endothelial cells (HUVEC)). Monocytes, CD4 T cells, CD8 T cells and B cells were freshly isolated and then perfused over TNF-simulated HUVECs TNF induces HUVEC to express E-selectin) at a flow rate ranging from 0.5-16 dynes/cm$^2$ and cell rolling was observed and recorded for video analysis. Monocytes and CD4 T cells show rolling adhesive interactions on TNF-activated HUVEC at a shear stress up to 16 dynes/cm$^2$, whereas CD8 and B cells show minimal adhesive shear-resistant adhesive interactions. Note that monocytes cell rolling was 3-fold greater than CD4 T cells. Values are means±SEM for a minimum of 3 independent experiments. (FIG. 27B) Representative flow cytometric histograms of staining with E-selectin-Ig chimera ("E-Ig", a probe for E-selectin ligands (from R&D Systems)) (left) and mAb HECA452 (right) of monocytes, CD4 and CD8 T cells, and B cells. Filled curves represent isotype control (or, for E-Ig staining, E-selectin binding in the absence of input Ca$^{2+}$) and open curves show specific reactivity (for E-Ig, binding in presence of input Ca$^{2+}$). (FIG. 27C) Untreated (solid black line) or protease (bromelain) treated (dotted line) cells were stained with HECA452 mAb and analyzed by flow cytometry. Protease (bromelain) treatment (dotted line) markedly decreases HECA452 staining of monocytes, CD4 T cells, CD8 T cells, and B cells, showing that glycoproteins are the principal carriers of sLex determinants on these cells.

FIGS. 28A-28C. Functional E-selectin ligand expression on monocytes and lymphocytes is increased by α(1,3)-exofucosylation treatment. (FIG. 28A) Human monocytes were FTVII-treated or buffer treated (mock) and subjected to immunoprecipitation with E-selectin-Ig chimera ("E-Ig", a probe for E-selectin ligands (from R&D Systems)) followed by SDS-PAGE and blotted with HECA-452, anti-CD43, anti-CD44 and anti-PSGL-1 mAbs, respectively. Note increased immunoprecipitation with E-Ig following FTVII treatment of monocytes, prominently on CD44 (i.e., creation of HCELL) and CD43 (creation of CD43-E-selectin ligand ("CD43-E"). (FIG. 28B) Western blot analysis of sequential immunoprecipitation of PSGL-1, CD43 and CD44 from lysates of CD4 T cells, CD8 T cells and B cells, followed by staining with E-Ig. (FIG. 28C) Parallel plate flow chamber analysis of tethering and rolling interactions of untreated ("unt") and FTVII-treated α(1,3)-exofucosylation; "FT7") of monocytes, CD4 and CD8T cells, and B cells on TNF-α activated HUVEC (which express E-selectin). FTVII treatment ("FT7") markedly augments E-selectin-mediated adherence of flowing cells to HUVEC under all shear stress levels tested.

(FIG. 29A) Representative flow cytometric histograms of HECA-452 mAb and E-Ig reactivity staining of mo-DCs. Grey lines represent isotype control or, for E-Ig, staining in the absence of Ca2+, whereas dotted black line represents PA-S mo-DCs and solid black lines are CD14-S mo-DCs. (FIG. 29B) Western blot analysis of E-selectin staining of CD14-S and PA-S mo-DC lysates. Whole cell lysates equivalent to 2×10$^6$ mo-DCs were resolved on a SDS-PAGE gel and immunoblotted. MW markers are along Y-axis (in kDa). Mo-DCs cultured on CD14 beads (CD14-S Mo-DCs) have higher HCELL expression (~80 kDa band) than those cultured on plastic (PA Mo-DCs). (FIG. 29C) Western blot analysis of CD44 immunoprecipitated from cell lysates of CD14-S and PA-S mo-DCs. CD44 immunoprecipitates (CD44 IP) were then blotted and stained with E-Ig chimera or anti-CD44 mAb. MW markers are as noted along Y-axis (in kDa). Note pronounced HCELL expression on CD14-S mo-DCs.

(FIG. 30A) Western blot analysis comparing E-selectin binding (E-Ig) of lysates of 2×10$^6$ of KG1a cells and of mo-DCs. (FIG. 30B) Western blot analysis of E-Ig reactivity of mo-DC that were buffer treated (−) or FTVI-treated (+). FTVI treatment induces E-Ig binding at ~80 kDa, indicating enforced expression of HCELL. (FIG. 30C) Transendothelial migration (TEM) assay of buffer treated (BT) and FTVI-treated mo-DCs under shear flow conditions (2 dynes/cm$^2$) on TNF-α-stimulated HUVEC. The TEM value is the fold-increase in migration of cells on TNF-α-stimulated HUVEC compared with cells transmigrated on untreated HUVECs (which was minimal). TEM was analyzed under different conditions: HUVEC preincubated with function blocking anti-E-selectin mAb clone 68-5H11, mo-DC pre-incubated with function blocking anti-VLA-4 mAb HP2/1 or isotype mAb, and mo-DC treated with sialidase or pertussis toxin (PTX). As shown, exofucosylated DCs have higher TEM than untreated cells; TEM is abrogated by function-blocking antibodies to E-selectin and VLA-4, and by sialidase or PTX treatment of cells. (FIG. 30D) Analysis of the number of tethering and rolling mo-DCs (per cm$^2$ of endothelial surface area) and number of firmly adhering cells (per cm$^2$ of endothelial surface area) in the TEM assay. Note higher tethering/rolling interactions with exofucosylated DCs. (FIG. 30E) Average rolling velocity of buffer treated (BT) and FTVI-treated mo-DCs in the TEM assay. The cell number was counted at 2.0 dyne/cm2 shear stress (i.e., perfused over TNF-α-stimulated HUVEC, at 2.0 dyne/cm2 shear stress). Values are means±SD (n=3). Statistical significant differences (p<0.05) are indicated by brackets and asterisks. The slower rolling of FTVI-treated DCs is indicative of higher efficiency of DC binding interactions to endothelial E-selectin under hemodynamic shear conditions.

FIG. 31. Expression of FoxP3 on regulatory T cells generated by ex vivo expansion of human CD4+ cells in presence of antibodies to CD3 and CD28, and IL-2 supplementation. Dual color flow cytometry histograms showing expression of CD4 and FoxP3 on cultured CD4+/CD127-low T cells; high FoxP3 staining indicates that all culture-expanded cells are Tregs.

EMBODIMENTS

Figure 2:
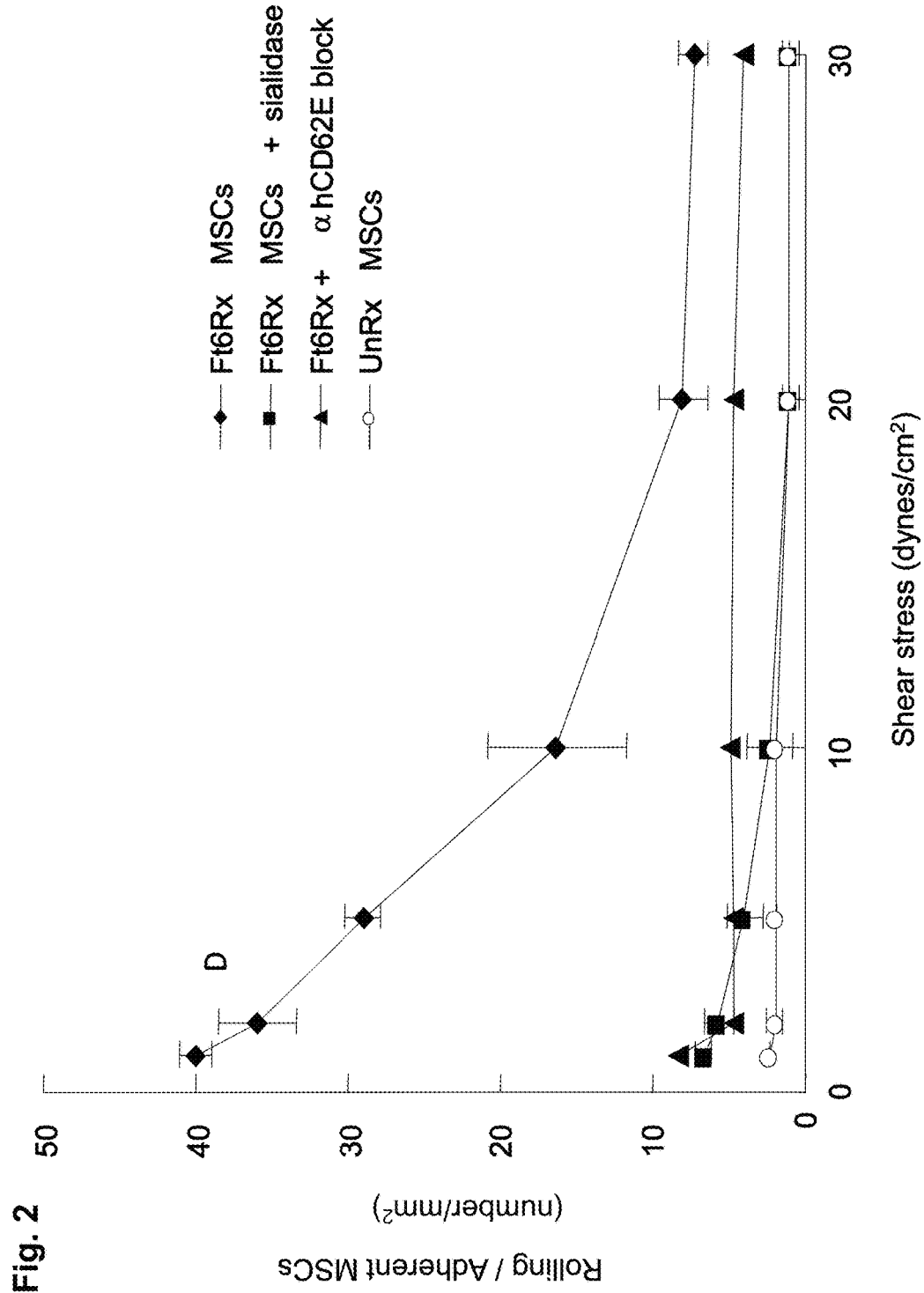
FIG. 2. Parallel plate flow chamber assay of FTVI-modified and unmodified wild type MSC adherence to TNF-α treated human umbilical vein endothelial cells (HUVEC). FTVI modification markedly improved MSC adhesion to HUVEC at 0.5 dynes/cm$^2$, with binding evident at shear stress in excess of 20 dynes/cm$^2$ Treatment of HUVEC with anti-E-selectin (anti-CD62E) function-blocking mAb reduced rolling adhesive interactions of FTVI-modified MSCs to levels similar to that of unmodified MSCs. Similarly, removal of sLex determinants by sialidase treatment of FTVI-modified MSCs reduced adhesion to levels equivalent to unmodified MSCs.

The present disclosure is directed to methods of treating a disease, disorder, or medical condition manifesting as inflamed and/or damaged tissue or cancer in a subject. The methods involve the administration, to a subject in need of tissue repair/regeneration or cancer treatment, of a cell population that expresses an E-selectin ligand and/or an L-selectin ligand at levels that exceeds the level of E-selectin and/or L-selectin binding of a native population of the cells. The composition of cells is disposed in a pharmaceutically-acceptable solution, suspension, carrier or vehicle for administration to a subject or for storage (e.g., cryopreserved) prior to administration to a subject.

Administration of cell populations described herein for therapeutic indications can be achieved in a variety of ways, in each case as clinically warranted/indicated, using a variety of anatomic access devices, a variety of administration devices, and a variety of anatomic approaches, with or without support of anatomic imaging modalities (e.g., radiologic, MRI, ultrasound, etc.) or mapping technologies (e.g., epiphysiologic mapping procedures, electromyographic procedures, electrodiagnostic procedures, etc.). Cells can be administered systemically, via either peripheral vascular access (e.g., intravenous placement, peripheral venous access devices, etc.) or central vascular access (e.g., central venous catheter/devices, arterial access devices/approaches, etc.). Cells can be delivered intravascularly into anatomic feeder vessels of an intended tissue site using catheter-based approaches or other vascular access devices (e.g., cardiac catheterization, etc.) that will deliver a vascular bolus of cells to the intended site. Cells can be introduced into the spinal canal and/or intraventricularly intrathecally, into the subarachnoid space to distribute within cerebrospinal fluid and/or within the ventricles). Cells can be administered directly into body cavities or anatomic compartments by either catheter-based approaches or direct injection (e.g., intraperitoneal, intrapleural, intrapericardial, intravesicularly (e.g., into bladder, into gall bladder, into bone marrow, into biliary system (including biliary duct and pancreatic duct network), intraurethrally, via renal pelvis/intraureteral approaches, intravaginally, etc.)). Cells can be introduced by direct local tissue injection, using either intravascular approaches (e.g., endomyocardial injection), or percutaneous approaches, or via surgical exposure/approaches to the tissue, or via laparoscopic/thoracoscopic/endoscopic/colonoscopic approaches, or directly into anatomically accessible tissue sites and/or guided by imaging techniques (e.g., intra-articular, into spinal discs and other cartilage, into bones, into muscles, into skin, into connective tissues, and into relevant tissues/organs such as central nervous system, peripheral nervous system, heart, liver, kidneys, spleen, etc.). Cells can also be placed directly onto relevant tissue surfaces/sites (e.g., placement onto tissue directly, onto ulcers, onto burn surfaces, onto serosal or mucosal surfaces, onto epicardium, etc.). Cells can also administered into tissue or structural support devices (e.g., tissue scaffold devices and/or embedded within scaffolds placed into tissues, etc.), and/or administered in gels, and/or administered together with enhancing agents (e.g., admixed with supportive cells, cytokines, growth factors, resolvins, anti-inflammatory agents, etc.).

The cell population is administered to the subject during a period of (i.e., coincident with) induced expression (and, preferably, coincident with the onset of induced expression) of E-selectin on vascular endothelium within one or more tissues of the subject. The enforced expression of E-selectin ligands on the surface of administered cells will aid in revascularization, in host defense (e.g., against infection or cancer) and/or in tissue repair/regeneration and/or mediate immunomodulatory processes that will dampen inflammation and/or prevent inflammation. The expression of ligands for E-selectin guides delivery of intravascularly administered cells to sites of inflammation by mediating binding of blood-borne cells to vascular E-selectin expressed on endothelial cells at sites of inflammation. Moreover, whether cells are administered systemically, intravascularly, into the spinal canal and/or intraventricularly intrathecally, into the subarachnoid space to distribute within cerebrospinal fluid), directly into body cavities or compartments, by direct local tissue injection, or by placement onto relevant tissue surfaces/sites, the expression of ligands for E-selectin and/or L-selectin on administered cells promotes lodgement of cells within the affected tissue milieu, in apposition to cells bearing E-selectin (i.e., endothelial cells) and/or L-selectin (i.e., leukocytes), respectively, within the target site. Thus, the spatial distribution and localization of administered cells within the target tissue is modulated by the expression of E-selectin and/or L-selectin ligands on administered cells.

Particularly, the colonization of a desired cell type at a site of inflammation occurs as a result of the enforced expression of cell surface E-selectin ligands on the administered cells, such that the administered cells have augmented binding to E-selectin, thereby promoting the systemic delivery of the desired cells and/or the lodgement of cells when injected directly into the affected site. For example, the enforced expression of E-selectin ligands (e.g., HCELL, CD43-E, CLA/PSLG-1, ESL-1, NCAM-E, etc.) is advantageously capable of anchoring directly injected cells within E-selectin-expressing vessels at sites of inflammation, tissue injury, or cancer. Thus, the present methods augment efficiency in the delivery of relevant cells at or to a site of inflammation, tissue injury, or cancer, including, for example, the capacity to deliver tissue-reparative stem cells, to deliver immunomodulatory cells (e.g., mesenchymal stem cells, T-regulatory cells, NK-cells, dendritic cells, etc.), and the capacity to deliver immune effector cells to combat the inciting inflammatory process or cancer (e.g., in the case of infection or malignancy, delivery of pathogen-specific immune effector T cells cells or cancer-specific cytotoxic T cells or NK cells, respectively); such immunologic cells (regulatory T-cells, NK cells, cytotoxic T-cells, dendritic cells, etc.) may be antigen-pulsed, tumor cell pulsed, virus pulsed, and other means to create antigen specificity. Similarly, the enforced expression of L-selectin ligands (e.g., HCELL, PSGL-1, etc.) is advantageously capable of anchoring directly injected cells within L-selectin-expressing cells infiltrating sites of inflammation, tissue injury, or cancer.

The enhanced expression of an E-selectin ligand on the cell surface will drive vascular homing of cells to any site where E-selectin is expressed. In various embodiments, the cell population expresses Hematopoietic Cell E-/L-selectin Ligand (HCELL) and/or Neural Cell Adhesion Molecule E-selectin Ligand (NCAM-E). Other E-selectin ligands that may be expressed by cells include, for example, CD43-E, ESL-1, PSGL-1 and the CLA glycoform of PSGL-1. For example, since CD44 is a ubiquitously expressed cell membrane protein and is displayed on stem/progenitor cell populations of both "adult" and embryonic types, the capacity to modify glycosylation of this protein by ex vivo glycan engineering to create the HCELL (CD44 glycoform) phenotype will drive migration of injected (e.g., intravascularly) (adoptively transferred) cells in vivo to marrow or to any tissue/organ site where E-selectin is expressed. Thus, the modified cells can be used in therapeutic settings to achieve targeted cell migration in a variety of physiologic and pathologic processes, including, for example, bone diseases, immune diseases, infectious diseases, and cancer therapeutics, to name just a few conditions.

It has also been discovered that the disease, disorder, or medical condition having associated inflammation can be treated using the instant methods even in the absence of differentiation of the cell population in the subject. That is, there are trophic effects of administered cells at the site of inflammation without persistent engraftment and/or repopulation of the administered cells, irrespective of the type of tissue involved. These trophic effects include release of cytokines/growth factors that promote revascularization (e.g., VEGF), that promote tissue repair (e.g., TGF-β), that are immunomodulatory (e.g., IL-10), that stimulate growth/proliferation of tissue-resident progenitors (e.g., SCF, LIF, etc) and many other tissue-reparative processes (e.g., mitochondria delivery to cells). In addition, administered cells (e.g., Tregs, MSCs, dendritic cells, etc.) may have potent immunomodulatory properties, including direct suppression of activated lymphocytes (e.g., via expression of PDL-1).

As exemplified by FIGS. 4A-4H, and as described in greater detail in the examples, cell populations modified to have enhanced E-selectin and/or L-selectin binding activity relative to native populations of the cell type have increased capacity to home, infiltrate and colonize tissue in the vicinity of E-selectin-expressing vasculature. Additionally, in one embodiment such cells lodge into sites of inflammation via binding to E-selectin on endothelial cells or lodge into sites of infiltrating leukocytes within the inflammatory site (e.g., see FIGS. 4F-4G). Further, beneficial effects (e.g., amelioration of the disease) may be realized by parenteral delivery or by direct injection into the site of inflammation or the site of infiltrating leukocytes even in the absence of differentiation of the cells (or long-term engraftment) after administered cell lodgement within the site (i.e., transient engraftment may be sufficient to deliver intended biologic effect (s)).

In certain embodiments, the methods for glycan-engineering described in U.S. Pat. No. 8,084,236 for the enforcement of HCELL expression in viable cell populations, discussed in detail below, can induce higher amounts of expression of E-selectin ligands on such cells to promote their vascular delivery to sites of inflammation, and can induce higher amounts of E-selectin ligands and L-selectin ligands that can promote lodgement of cells within the affected tissue milieu.

Treatment of the subject refers to reducing or eliminating in an individual a clinical symptom of a disease, disorder, or medical condition having associated inflammation or delaying or preventing in an individual the onset of a clinical symptom of such disease, disorder, or medical condition. For example, treating can mean reducing a symptom of a condition characterized by an acute and/or chronic inflammation by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with acute and chronic inflammation are well known and can be determined by a person of ordinary skill in the art by taking into account factors, including, without limitation, the location of the acute and/or chronic inflammation, the cause of the acute and/or chronic inflammation, the severity of the acute and/or chronic inflammation, and/or the tissue or organ affected by the acute and/or chronic inflammation. Those of skill in the art will know the appropriate symptoms or indicators associated with a specific type of acute and/or chronic inflammation and will know how to determine if an individual is a candidate for treatment as disclosed herein.

Subjects that may be treated in accordance with the methods described herein includes any mammal (e.g., a human), such as a mammal that can be susceptible to a disease. Examples include, for instance, a human, a non-human primate, a cow, a horse, a pig, a sheep, a goat, a dog, a cat, or a rodent such as a mouse, a rat, a hamster, or a guinea pig. A subject can be a subject diagnosed with a disease, disorder, or medical condition having associated inflammation or otherwise known to have a disease, disorder, or medical condition the result or symptom of which is acute and/or chronic inflammation. In some embodiments, a subject can be diagnosed as, or known to be, at risk of developing a disease, disorder, or medical condition having associated inflammation. In certain embodiments, a subject can be selected for treatment on the basis of a known disease, disorder, or medical condition in the subject the result or symptom of which is an acute and/or chronic inflammation. In some embodiments, a subject can be selected for treatment on the basis of a suspected disease, disorder, or medical condition having associated inflammation in the subject. In some embodiments, the disease, disorder, or medical condition can be diagnosed by detecting a mutation or other abnormality in a biological sample (e.g., urine, sputum, whole blood, serum, stool, etc., or any combination thereof. Accordingly, a modified cell population can be administered to a subject based, at least in part, on the fact that a mutation, symptom, or other abnormality is detected in at least one sample (e.g., biopsy sample or any other biological sample) obtained from the subject. In some embodiments, diabetes, multiple sclerosis, or cancer (for example) cannot have been detected or located in the subject, but the presence of a mutation, symptom, or other abnormality associated with diabetes, multiple sclerosis, or cancer in at least one biological sample can be sufficient to administer modified cells to the subject in accordance with the methods described herein. In some embodiments, the composition can be administered to prevent the development of a disease, disorder, or medical condition such as diabetes, multiple sclerosis, or cancer. However, in some embodiments, the presence of an existing disease, disorder, or medical condition can be suspected, but not yet identified, and a composition of the disclosure can be administered to prevent further growth or development of the disease, disorder, or medical condition. The administered cells can be derived from autologous sources (i.e., derived from the host itself), syngeneic sources (derived from an identical twin), or allogeneic sources (derived from non-genetically identical donor).

Timing of Administration

As noted above, the cell population is administered to the subject coincident with induced expression (and preferably coincident with the onset of induced expression) of E-selectin by endothelial cells of the subject, or just prior to expected increased E-selectin expression within an affected tissue (i.e., as prophylaxis prior to or coincident with delivery of E-selectin-inducing inflammatory stimulus (e.g., radiation therapy)) or in anticipation of a reaction to a pathogen or disease process with subsequent upregulation of vascular E-selectin expression (e.g., following exposure to or endogenous reactivation of an infectious agent, prior to overt flare of autoimmune disease, prior to elaboration of graft-versus-host disease (GVHD), etc.)). Accordingly, the treatment methods described herein may be implemented, for example, when the subject (e.g., a human patient) presents to his/her physician or healthcare provider with one or more symptoms of inflammation or anticipated inflammatory flare. For a subject with diabetes, for example, such initial symptoms may include polyuria, nocturia, weight loss/gain, and/or lack of satiety, at which time (and prior to the onset of diabetic ketoacidosis) the subject may be administered the modified cells in accordance with the disclosure. For a subject with multiple sclerosis, for example, such initial symptoms may include transient sensory perturbations (e.g., numbness, tingling) and/or fasciculations (twitching) and/or muscular weakness episodes.

In general, the temporal aspects of the administration of the modified cells may depend for example, on the particular modified cells, or the nature of the disease, disorder, or medical condition (and associated inflammation, tissue injury, or cancer) being treated. Other considerations may include the severity of the disease, disorder, or medical condition; activity of the specific cells or cell fragments and modifications employed; the specific composition employed; the age, body weight, general health, sex and diet of the subject; the time of administration, route of administration, and rate of excretion; the duration of the treatment; drugs used in combination or coincidental with the treatment regime; and like factors.

Accordingly, administration of the modified cells can occur as a single event or over a time course of treatment. For example, the modified cells can be administered hourly (e.g., every hour, every two hours, every three hours, every four hours, every five hours, every six hours, and so on), daily, weekly, bi-weekly, bi-monthly or monthly. For treatment of acute conditions, for example, the time course of treatment may be at least several hours, days, or weeks. Certain conditions could extend treatment from several days to several weeks, months, or years. For example, treatment could extend over one week, two weeks, or three weeks, or longer (e.g., one to several months). For more chronic conditions, treatment could extend from several weeks to several months, a year or more, or the lifetime of the patient in need of such treatment. Alternatively, the compounds and agents can be administered hourly, daily, weekly, bi-weekly, bi-monthly, or monthly, for a period of several weeks, months, years, or over the lifetime of the patient as a prophylactic or as a therapeutic measure.

It will also be understood that the frequency of doses may be increased or decreased based upon the nature and severity of the disease, disorder, or medical condition (and associated inflammation) and/or the stage of the disease, disorder, or medical condition in the subject. For example, depending on these and other factors, less frequent administration may be desirable at the beginning of the treatment and more frequent administration may be desirable at or near end-stage, or vice versa. The various targets and symptoms may also be tracked (e.g., insulin levels in a diabetic subject) and the administration and dose amount may be tailored accordingly.

If desired, the cells can be divided into multiple doses for purposes of administration; consequently, single dose compositions may contain such amounts or submultiples thereof to make up the dose.

Indications

The present disclosure is directed to the treatment of a disease, disorder, or medical condition wherein E-selectin is expressed in endothelial beds of the affected tissue(s) and/or L-selectin-expressing leukocytes have infiltrated/accumulated in the affected tissue(s). As discussed above, E-selectin and L-selectin each bind to sialylated, fucosylated carbohydrates, and enforced expression of these sialofucosylated glycan structures on the cell surface serves to program binding to these selectins. Accordingly, the disclosure describes methods to enhance homing to target tissue(s) by augmenting the expression of E-selectin ligands on administered cells; additionally, in describing methods to enhance expression of potent E-selectin and L-selectin ligands (such as HCELL) on administered cells to promote adherence to E-selectin on vascular endothelial cells and/or of L-selectin on tissue-infiltrating leukocytes within affected tissue(s), the disclosure provides a means to augment colonization/lodgement of the cells within relevant tissue microenvironments where biologic effects are intended. In general, the methods described herein have utility in improving the outcome of any cell-based therapeutic approach, be it in immunotherapy applications (e.g., administration of culture-expanded antigen-specific T cells and/or culture expanded NK cells for cancer or infectious disease applications, administration of culture-expanded chimeric antigen receptor (CAR) T cells, administration of antigen-pulsed dendritic cells, etc.), immunomodulatory/immunosuppressive therapeutic applications (e.g., administration of culture-expanded regulatory T cells (Tregs), administration of antigen-pulsed dendritic cells, administration of mesenchymal stem cells, administration of culture-expanded NKT cells, etc.), or tissue repair/regenerative medicine applications (e.g., use of stem and/or progenitor cells or other tissue-reparative cells for tissue regeneration/restoration; use of culture-expanded stem cells and/or culture-expanded progenitor cells for tissue regeneration/restoration). Within utility in regenerative medicine applications, it is understood that administered cells may themselves contribute to regenerate the target tissue by way of long-term engraftment (with attendant proliferation/differentiation) yielding tissue-specific cells (e.g., such as in transplantation of hematopoietic stem cells for blood cell production) and/or may deliver a tissue restorative/reparative effect without long-term engraftment or differentiation into tissue-resident cells (e.g., via delivery of trophic effects that stimulate resident stem/progenitors to repair the injured tissue(s) and/or by dampening inflammatory processes that promote injury and impede repair). All applications for all indications described herein can be used alone or in combination with enhancing agents (e.g., growth factors, tissue scaffolds, etc.).

Any and all diseases, disorders, or medical conditions having associated inflammation (e.g., acute and/or chronic), tissue injury/damage or neoplastic conditions may be treated in accordance with the methods described herein, including, but not limited to those initiated by direct tissue injury (e.g., burns, trauma, bone fracture, bone deformities, decubitus ulcers, etc.), ischemic/vascular events (e.g., myocardial infarct, stroke, shock, hemorrhage, coagulopathy, etc.), infections (e.g., cellulitis, pneumonia, meningitis, cystitis, sepsis, SIRS, etc.), neoplasia (e.g., breast cancer, lung cancer, prostate cancer, renal cell cancer, lymphoma, leukemia, etc.), immunologic/autoimmune conditions (e.g., acute or chronic GVHD, multiple sclerosis, diabetes, inflammatory bowel disease (e.g., Crohn's disease, ulcerative colitis), rheumatoid arthritis, psoriasis, etc.), degenerative diseases (e.g., osteoporosis, osteoarthritis, spinal disc degeneration, Alzheimer's disease, atherosclerosis, etc.), congenital/genetic diseases (e.g., epidermolysis bullosa, osteogenesis imperfecta, muscular dystrophies, lysosomal storage diseases, Huntington's disease, etc.), adverse drug effects (e.g., chemotherapy-induced tissue/organ toxicity, radiotherapy toxicity, drug-induced hepatitis, drug-induced cardiac injury, etc.), toxic injuries (e.g., radiation exposure(s), chemical exposure(s), alcoholic hepatitis, alcoholic pancreatitis, alcoholic cardiomyopathy, cocaine cardiomyopathy, etc.), metabolic derangements (e.g., uremic pericarditis, metabolic acidosis, etc.), iatrogenic conditions (e.g., radiation-induced tissue injury, surgery-related complications, etc.), and/or idiopathic processes (e.g., amyotrophic lateral sclerosis, Parsonnage-Turner Syndrome, etc.).

Other general and specific diseases, disorders, or medical condition that may be treated in accordance with the methods described herein include, but are not limited to:

Acute Leukemias, e.g., Acute Biphenotypic Leukemia, Acute Lymphocytic Leukemia (ALL), Acute Myelogenous Leukemia (AML), and Acute Undifferentiated Leukemia;

Myelodysplastic Syndromes, e.g., Amyloidosis Chronic Myelomonocytic Leukemia (CMML), Refractory Anemia (RA), Refractory Anemia with Excess Blasts (RAEB), Refractory Anemia with Excess Blasts in Transformation (RAEB-T), and Refractory Anemia with Ringed Sideroblasts (RARS);

Myeloproliferative Disorders, e.g., Acute Myelofibrosis, Agnogenic Myeloid Metaplasia (Myelofibrosis), Essential Thrombocythemia, chronic myelogenous leukemia, and Polycythemia Vera;

Phagocyte Disorders, e.g., Chediak-Higashi Syndrome, Chronic Granulomatous Disease, Leukocyte adhesion deficiencies, myeloperoxidase deficiency, Neutrophil Actin Deficiency, and Reticular Dysgenesis;

Lysosomal Storage Diseases, e.g., Adrenoleukodystrophy, Alpha Mannosidosis, Gaucher's Disease, Hunter's Syndrome (MPS-II), Hurler's Syndrome (MPS-IH), Krabbe Disease, Maroteaux-Lamy Syndrome (MPS-VI), Metachromatic Leukodystrophy, Morquio Syndrome (MPS-IV), Mucolipidosis II (I-cell Disease), Mucopolysaccharidoses (MPS), Niemann-Pick Disease, Sanfilippo Syndrome (MPS-III), Scheie Syndrome (MPS-IS), Sly Syndrome, Beta-Glucuronidase Deficiency (MPS-VII), and Wolman Disease;

Inherited Erythrocyte Abnormalities, e.g., Beta Thalassemia, Blackfan-Diamond Anemia, Pure Red Cell Aplasia, and Sickle Cell Disease;

Inherited Platelet Abnormalities, e.g., Amegakaryocytosis/Congenital Thrombocytopenia, Gray platelet syndrome;

Solid organ malignancies, e.g., Brain Tumors, Ewing Sarcoma, Neuroblastoma, Ovarian Cancer, Renal Cell Carcinoma, Lung Cancers, Breast cancers, Gastric cancers, Esophageal cancers, Skin cancers, Oral cancers, Endocrine cancers, Liver cancers, Biliary system cancers, Pancreatic cancer, Prostate Cancer, and Testicular Cancer;

Other Applications, e.g., Bone Marrow Transplants, Heart Disease (myocardial infarction), Liver Disease, Muscular Dystrophy, Alzheimer's Disease, Parkinson's Disease, Spinal Cord Injury, Spinal disc disease/degeneration, Bone disease, Bone fracture, Stroke, Peripheral Vascular Disease, Head trauma, Bullous diseases, Mitochondrial diseases, Ex vivo and In vivo expanded stem and progenitor cell populations, In vitro fertilization application and enhancement, Hematopoietic Rescue Situations (Intense Chemo/Radiation), Stem cells and progenitor cells derived from various tissues sources, Application in humans and animals, and Limb regeneration, reconstructive surgical procedures/indications, alone or in combination with enhancing agents;

Chronic Leukemias, e.g., Chronic Lymphocytic Leukemia (CLL), Chronic Myelogenous Leukemia (CML), Juvenile Chronic Myelogenous Leukemia (JCML), and Juvenile Myelomonocytic Leukemia (JMML), Stem Cell Disorders, e.g., Aplastic Anemia (Severe), Congenital Cytopenia, Dyskeratosis Congenita, Fanconi Anemia, and Paroxysmal Nocturnal Hemoglobinuria (PNH);

Lymphoproliferative Disorders, e.g., Hodgkin's Disease, Non-Hodgkin's Lymphomas, and Prolymphocytic Leukemia;

Histiocytic Disorders, e.g., Familial Erythrophagocytic Lymphohistiocytosis, Hemophagocytosis, Hemophagocytic Lymphohistiocytosis, Histiocytosis-X, and Langerhans' Cell Histiocytosis;

Congenital (Inherited) Immune System Disorders, e.g., Absence of T and B Cells, Absence of T Cells, Normal B Cell SCID, Ataxia-Telangiectasia, Bare Lymphocyte Syndrome, Common Variable Immunodeficiency, DiGeorge Syndrome, Kostmann Syndrome, Leukocyte Adhesion Deficiency, Omenn's Syndrome, Severe Combined Immunodeficiency (SCID), SCID with Adenosine Deaminase Deficiency, Wiskott-Aldrich Syndrome, and X-Linked Lymphoproliferative Disorder;

Other Inherited Disorders, e.g., Cartilage-Hair Hypoplasia, Ceroid Lipofuscinosis, Congenital Erythropoietic Porphyria, Familial Mediterranean Fever, Glanzmann Thrombasthenia, Lesch-Nyhan Syndrome, Osteopetrosis, and Sandhoff Disease;

Plasma Cell Disorders, e.g., Multiple Myeloma, Plasma Cell Leukemia, and Waldenstrom's Macroglobulinemia; and Autoimmune Diseases, e.g., Multiple Sclerosis, Rheumatoid Arthritis, Systemic Lupus Erythematosus, Scleroderma, Ankylosing spondylitis, Diabetes Mellitus, and Inflammatory Bowel Diseases.

Articular and skeletal diseases/conditions, e.g., disc degeneration, synovial disease, cartilage degeneration, cartilage trauma, cartilage tears, arthritis, bone fractures, bone deformities, bone reconstruction, osteogenesis imperfecta, congenital bone diseases/conditions, genetic bone diseases/conditions, osteoporosis. Osteopetrosis, hypophosphatasia, metabolic bone disease, etc.

Skin/soft tissue diseases and conditions such as bullous diseases, psoriasis, eczema, epidermolysis bullosa, ulcerative skin conditions, soft tissue deformities (including post-surgical skin and soft tissue deformities), plastic surgery/reconstructive surgery indications, etc.

In general, associated inflammation symptoms that include, without limitation, fever, pain, edema, hyperemia, erythema, bruising, tenderness, stiffness, swollenness, chills, respiratory distress, hypotension, hypertension, stuffy nose, stuffy head, breathing problems, fluid retention, blood clots, loss of appetite, weight loss, polyuria, nocturia, anuria, dyspnea, dyspnea on exertion, muscle weakness, sensory changes, increased heart rate, decreased heart rate, arrythmias, polydipsia, formation of granulomas, fibrinous, pus, non-viscous serous fluid, or ulcers. The actual symptoms associated with an acute and/or chronic inflammation are well known and can be determined by a person of ordinary skill in the art by taking into account factors, including, without limitation, the location of the inflammation, the cause of the inflammation, the severity of the inflammation, the tissue or organ affected, and the associated disorder.

Specific patterns of acute and/or chronic inflammation are seen during particular situations that arise in the body, such as when inflammation occurs on an epithelial surface, or pyogenic bacteria are involved. For example, granulomatous inflammation is an inflammation resulting from the formation of granulomas arising from a limited but diverse number of diseases, include, without limitation, tuberculosis, leprosy, sarcoidosis, and syphilis. Purulent inflammation is an inflammation resulting in large amount of pus, which consists of neutrophils, dead cells, and fluid. Infection by pyogenic bacteria such as staphylococci is characteristic of this kind of inflammation. Serous inflammation is an inflammation resulting from copious effusion of non-viscous serous fluid, commonly produced by mesothelial cells of serous membranes, but may be derived from blood plasma. Skin blisters exemplify this pattern of inflammation. Ulcerative inflammation is an inflammation resulting from the necrotic loss of tissue from the epithelial surface, exposing lower layers and forming an ulcer.

An acute and/or chronic inflammation symptom can be associated with a large, unrelated group of disorders which underlay a variety of diseases and disorders. The immune system is often involved with acute and/or chronic inflammatory disorders, demonstrated in both allergic reactions, arthritic conditions, and some myopathies, with many immune system disorders resulting in abnormal inflammation. Non-immune diseases with etiological origins in acute and/or chronic inflammatory processes include cancer, atherosclerosis, and ischaemic heart disease. Non-limiting examples of disorders exhibiting acute and/or chronic inflammation as a symptom include, without limitation, acne, acid reflux/heartburn, age related macular degeneration (AMD), allergy, allergic rhinitis, Alzheimer's disease, amyotrophic lateral sclerosis, anemia, appendicitis, arteritis, arthritis, asthma, atherosclerosis, autoimmune disorders, balanitis, blepharitis, bronchiolitis, bronchitis, a bullous pemphigoid, burn, bursitis, cancer, cardiac arrest, carditis, celiac disease, cellulitis, cervicitis, cholangitis, cholecystitis, chorioamnionitis, chronic obstructive pulmonary disease (COPD) (and/or acute exacerbations thereof), cirrhosis, colitis, congestive heart failure, conjunctivitis, drug-induced tissue injury (e.g., cyclophosphamide-induced cystitis), cystic fibrosis, cystitis, common cold, dacryoadenitis, decubitus ulcers, dementia, dermatitis, dermatomyositis, diabetes, diabetic neuropathy, diabetic retinopathy, diabetic nephropathy, diabetic ulcer, digestive system disease, eczema, emphysema, encephalitis, endocarditis, endocrinopathies, endometritis, enteritis, enterocolitis, epicondylitis, epididymitis, fasciitis, fibromyalgia, fibrosis, fibrositis, gastritis, gastroenteritis, gingivitis, glomerulonephritis, glossitis, heart disease, heart valve dysfunction, hepatitis, hidradenitis suppurativa, Huntington's disease, hyperlipidemic pancreatitis, hypertension, ileitis, infection, inflammatory bowel disease, inflammatory cardiomegaly, inflammatory neuropathy, insulin resistance, interstitial cystitis, interstitial nephritis, iritis, ischemia, ischemic heart disease, keratitis, keratoconjunctivitis, laryngitis, lupus nephritis, macular degeneration, mastitis, mastoiditis, meningitis, metabolic syndrome (syndrome X), a migraine, mucositis, multiple sclerosis, myelitis, myocarditis, myositis, nephritis, neuronitis, non-alcoholic steatohepatitis, obesity, omphalitis, oophoritis, orchitis, osteochondritis, osteopenia, osteomyelitis, osteoporosis, osteitis, otitis, pancreatitis, Parkinson's disease, parotitis, pelvic inflammatory disease, pemphigus vularis, pericarditis, peritonitis, pharyngitis, phlebitis, pleuritis, pneumonitis, polycystic nephritis, proctitis, prostatitis, psoriasis, pulpitis, pyelonephritis, pylephlebitis, radiation-induced injury, renal failure, reperfusion injury, retinitis, rheumatic fever, rhinitis, salpingitis, sarcoidosis, sialadenitis, sinusitis, spastic colon, stasis dermatitis, stenosis, stomatitis, stroke, surgical complication, synovitis, tendonitis, tendinosis, tenosynovitis, thrombophlebitis, thyroiditis, tonsillitis, trauma, traumatic brain injury, transplant rejection, trigonitis, tuberculosis, tumor, ulcers, urethritis, ursitis, uveitis, vaginitis, vasculitis, and vulvitis.

General categories of diseases, disorders, and trauma that can result in or otherwise cause acute and/or chronic inflammation include, but are not limited to genetic diseases, neoplasias, direct tissue injury, autoimmune diseases, infectious diseases, vascular diseases/complications (e.g., ischemia/reperfusion injury), iatrogenic causes (e.g. drug adverse effects, radiation injury, etc.), and allergic manifestations.

In one embodiment, an acute and/or chronic inflammation comprises a tissue inflammation. In general, tissue inflammation is an acute and/or chronic inflammation that is confined to a particular tissue or organ. Thus, for example, a tissue inflammation may comprise a skin inflammation, a muscle inflammation, a tendon inflammation, a ligament inflammation, a bone inflammation, a cartilage/joint inflammation, a lung inflammation, a heart inflammation, a liver inflammation, a gall bladder inflammation, a pancreatic inflammation, a kidney inflammation, a bladder inflammation, an gum inflammation, an esophageal inflammation, a stomach inflammation, an intestinal inflammation, an anal inflammation, a rectal inflammation, a vessel inflammation, a vaginal inflammation, a uterine inflammation, a testicular inflammation, a penile inflammation, a vulvar inflammation, a neuron inflammation, an oral inflammation, an ocular inflammation, an aural inflammation, a brain inflammation, a ventricular/meningial inflammation and/or inflammation involving central or peripheral nervous system cells/elements.

In another embodiment, an acute and/or chronic inflammation comprises a systemic inflammation. Although the processes involved are similar if not identical to tissue inflammation, systemic inflammation is not confined to a particular tissue but rather involves multiple sites within the body, involving the epithelium, endothelium, nervous tissues, serosal surfaces and organ systems. When it is due to infection, the term sepsis can be used, with bacteremia being applied specifically for bacterial sepsis and viremia specifically to viral sepsis. Vasodilation and organ dysfunction are serious problems associated with widespread infection that may lead to septic shock and death.

In another embodiment, an acute and/or chronic inflammation is induced by an arthritis. Arthritis includes a group of conditions involving damage to the joints of the body due to the inflammation of the synovium including, for example, osteoarthritis, rheumatoid arthritis, juvenile idiopathic arthritis, spondyloarthropathies like ankylosing spondylitis, reactive arthritis (Reiter's syndrome), psoriatic arthritis, enteropathic arthritis associated with inflammatory bowel disease, Whipple disease and Behcet disease, septic arthritis, gout (also commonly referred to as gouty arthritis, crystal synovitis, metabolic arthritis), pseudogout (calcium pyrophosphate deposition disease), and Still's disease. Arthritis can affect a single joint (monoarthritis), two to four joints (oligoarthritis) or five or more joints (polyarthritis) and can be either an auto-immune disease or a non-autoimmune disease.

In another embodiment, an acute and/or chronic inflammation is induced by an autoimmune disorder. Autoimmune diseases can be broadly divided into systemic and organ-specific autoimmune disorders, depending on the principal clinico-pathologic features of each disease. Systemic autoimmune diseases include, for example, systemic lupus erythematosus (SLE), Sjogren's syndrome, Scleroderma, rheumatoid arthritis and polymyositis. Local autoimmune diseases may be endocrinologic (Diabetes Mellitus Type 1, Hashimoto's thyroiditis, Addison's disease, etc.), dermatologic (pemphigus vulgaris), hematologic (autoimmune haemolytic anemia), neural (multiple sclerosis) or can involve virtually any circumscribed mass of body tissue. Types of autoimmune disorders include, without limitation, acute disseminated encephalomyelitis (ADEM), Addison's disease, an allergy or sensitivity, amyotrophic lateral sclerosis (ALS), anti-phospholipid antibody syndrome (APS), arthritis, autoimmune hemolytic anemia, autoimmune hepatitis, autoimmune inner ear disease, autoimmune pancreatitis, bullous pemphigoid, celiac disease, Chagas disease, chronic obstructive pulmonary disease (COPD) (including acute exacerbations thereof), diabetes mellitus type 1 (IDDM), endometriosis, fibromyalgia, Goodpasture's syndrome, Graves' disease, Guillain-Barre syndrome (GBS), Hashimoto's thyroiditis, hidradenitis suppurativa, idiopathic thrombocytopenic purpura, inflammatory bowel disease (IBD), interstitial cystitis, lupus (including discoid lupus erythematosus, drug-induced lupus erythematosus. lupus nephritis, neonatal lupus, subacute cutaneous lupus erythematosus and systemic lupus erythematosus), morphea, multiple sclerosis (MS), myasthenia gravis, myopathies, narcolepsy, neuromyotonia, pemphigus vulgaris, pernicious anaemia, primary biliary cirrhosis, recurrent disseminated encephalomyelitis (multiphasic disseminated encephalomyelitis), rheumatic fever, schizophrenia, scleroderma, Sjogren's syndrome, tenosynovitis, vasculitis, and vitiligo. In one particular embodiment, the acute and/or chronic inflammation results from or is otherwise caused by diabetes in the subject. In another particular embodiment, the acute and/or chronic inflammation results from or is otherwise caused by multiple sclerosis in the subject.

In another embodiment, an acute and/or chronic inflammation is induced by a myopathy. In general, myopathies are caused when the immune system inappropriately attacks components of the muscle, leading to inflammation in the muscle. A myopathy includes, for example, an inflammatory myopathy and an auto-immune myopathy. Myopathies include, for example, dermatomyositis, inclusion body myositis, and polymyositis.

In another embodiment, an acute and/or chronic inflammation is induced by a vasculitis. Vasculitis is a varied group of disorders featuring inflammation of a vessel wall including lymphatic vessels and blood vessels like veins (phlebitis), arteries (arteritis) and capillaries due to leukocyte migration and resultant damage. The inflammation may affect any size blood vessel, anywhere in the body. It may affect either arteries and/or veins. The inflammation may be focal, meaning that it affects a single location within a vessel, or it may be widespread, with areas of inflammation scattered throughout a particular organ or tissue, or even affecting more than one organ system in the body. Vasculitis include, without limitation, Buerger's disease (thromboangiitis obliterans), cerebral vasculitis (central nervous system vasculitis), ANCA-associated vasculitis, Churg-Strauss arteritis, cryoglobulinemia, essential cryoglobulinemic vasculitis, giant cell (temporal) arteritis, Golfer's vasculitis, Henoch-Schonlein purpura, hypersensitivity vasculitis (allergic vasculitis), Kawasaki disease, microscopic polyarteritis/polyangiitis, polyarteritis nodosa, polymyalgia rheumatica (PMR), rheumatoid vasculitis, Takayasu arteritis, Wegener's granulomatosis, and vasculitis secondary to connective tissue disorders like systemic lupus erythematosus (SLE), rheumatoid arthritis (RA), relapsing polychondritis, Behcet's disease, or other connective tissue disorders, vasculitis secondary to viral infection.

In another embodiment, an acute and/or chronic inflammation is induced by a skin disorder. Skin disorders include, for example, an acne, including acne vulgaris, a bullous phemigoid, a dermatitis, including atopic dermatitis and acute and/or chronic actinic dermatitis, an eczema-like atopic eczema, contact eczema, xerotic eczema, seborrhoeic dermatitis, dyshidrosis, discoid eczema, venous eczema, dermatitis, dermatitis herpetiformis, neurodermatitis, and autoeczematization, and stasis dermatitis, diabetic skin complications, hidradenitis suppurativa, lichen planus, psoriasis including plaqure psoriasis, nail psoriasis, guttate psoriasis, scalp psoriasis, inverse psoriasis, pustular psoriasis, erythrodermis psoriasis, and psoriatic arthritis, rosacea and scleroderma including morphea, ulcers.

In another embodiment, an acute and/or chronic inflammation is induced by a gastrointestinal disorder. A gastrointestinal disorder includes, for example, irritable bowel disease (IBD), an inflammatory bowel disease including Crohn's disease and an ulcerative colitis like ulcerative proctitis, left-sided colitis, pancolitis, and fulminant colitis.

In another embodiment, an acute and/or chronic inflammation is induced by a cardiovascular disease. When LDL cholesterol becomes embedded in arterial walls, it can invoke an immune response. Acute and/or chronic inflammation eventually can damage the arteries, which can cause them to burst. In general, cardiovascular disease is any of a number of specific diseases that affect the heart itself and/or the blood vessel system, especially the veins and arteries leading to and from the heart. There are over 60 types of cardiovascular disorders including, for example, a hypertension, endocarditis, myocarditis, heart valve dysfunction, congestive heart failure, myocardial infarction, a diabetic cardiac conditions, blood vessel inflammation like arteritis, phlebitis, vasculitis; arterial occlusive disease like arteriosclerosis and stenosis, inflammatory cardiomegaly, a peripheral arterial disease; an aneurysm; an embolism; a dissection; a pseudoaneurysm; a vascular malformation; a vascular nevus; a thrombosis; a thrombophlebitis; a varicose veins; a stroke. Symptoms of a cardiovascular disorder affecting the heart include, without limitation, chest pain or chest discomfort (angina), pain in one or both arms, the left shoulder, neck, jaw, or back, shortness of breath, dizziness, faster heartbeats, nausea, abnormal heartbeats, feeling fatigued. Symptoms of a cardiovascular disorder affecting the brain include, without limitation, sudden numbness or weakness of the face, arm, or leg, especially on one side of the body, sudden confusion or trouble speaking or understanding speech, sudden trouble seeing in one or both eyes, sudden dizziness, difficulty walking, or loss of balance or coordination, sudden severe headache with no known cause. Symptoms of a cardiovascular disorder affecting the legs, pelvis and/or arm include, without limitation, claudication, which is a pain, ache, or cramp in the muscles, and cold or numb feeling in the feet or toes, especially at night.

In another embodiment, an acute and/or chronic inflammation is induced by a cancer. In general, inflammation orchestrates the microenvironment around tumors, contributing to proliferation, survival and migration. For example, fibrinous inflammation results from a large increase in vascular permeability which allows fibrin to pass through the blood vessels. If an appropriate procoagulative stimulus is present, such as cancer cells, a fibrinous exudate is deposited. This is commonly seen in serous cavities, where the conversion of fibrinous exudate into a scar can occur between serous membranes, limiting their function. In another example, a cancer is an inflammatory cancer like a NF-κB-driven inflammatory cancer.

In another embodiment, an acute and/or chronic inflammation is a pharmacologically-induced inflammation. Certain drugs or exogenic chemical compounds, including deficiencies in key vitamins and minerals, are known to effect inflammation. For example, Vitamin A deficiency causes an increase in an inflammatory response, Vitamin C deficiency causes connective tissue disease, and Vitamin D deficiency leads to osteoporosis. Certain pharmacologic agents can induce inflammatory complications, e.g., drug-induced hepatitis. Certain illicit drugs such as cocaine and ecstasy may exert some of their detrimental effects by activating transcription factors intimately involved with inflammation (e.g., NF-κB). Radiation therapy can induce pulmonary toxicity, burns, myocarditis, mucositis, and other tissue injuries depending on site of exposure and dose.

In another embodiment, an acute and/or chronic inflammation is induced by an infection. An infectious organism can escape the confines of the immediate tissue via the circulatory system or lymphatic system, where it may spread to other parts of the body. If an organism is not contained by the actions of acute inflammation it may gain access to the lymphatic system via nearby lymph vessels. An infection of the lymph vessels is known as lymphangitis, and infection of a lymph node is known as lymphadenitis. A pathogen can gain access to the bloodstream through lymphatic drainage into the circulatory system. Infections include, without limitation, bacterial cystitis, bacterial encephalitis, pandemic influenza, viral encephalitis, and viral hepatitis (A, B and C).

In another embodiment, an acute and/or chronic inflammation is induced by a tissue or organ injury. Tissue or organ injuries include, without limitation, a burn, a laceration, a wound, a puncture, or a trauma.

In another embodiment, an acute and/or chronic inflammation is induced by a transplant rejection. Transplant rejection occurs when a transplanted organ or tissue is not accepted by the body of the transplant recipient because the immune system of the recipient attacks the transplanted organ or tissue. An adaptive immune response, transplant rejection is mediated through both T-cell-mediated and humoral immune (antibodies) mechanisms. A transplant rejection can be classified as a hyperacute rejection, an acute rejection, or a chronic rejection. Acute and/or chronic rejection of a transplanted organ or tissue is where the rejection is due to a poorly understood acute and/or chronic inflammatory and immune response against the transplanted tissue. Also included as transplant rejection is graft-versus-host disease (GVHD), either acute or chronic GVHD. GVHD is a common complication of allogeneic bone marrow transplantation in which functional immune cells in the transplanted marrow recognize the recipient as "foreign" and mount an immunologic attack. It can also take place in a blood transfusion under certain circumstances. GVHD is divided into acute and chronic forms. Acute and chronic GVHD appear to involve different immune cell subsets, different cytokine profiles, somewhat different host targets, and respond differently to treatment. In another embodiment, an acute and/or chronic inflammation is induced by a Th1-mediated inflammatory disease. In a well-functioning immune system, an immune response should result in a well-balanced pro-inflammatory Th1 response and anti-inflammatory Th2 response that is suited to address the immune challenge. Generally speaking, once a pro-inflammatory Th1 response is initiated, the body relies on the anti-inflammatory response invoked by a Th2 response to counteract this Th1 response. This counteractive response includes the release of Th2 type cytokines such as, e.g., IL-4, IL-5, and IL-13 which are associated with the promotion of IgE and eosinophilic responses in atopy, and also IL-10, which has an anti-inflammatory response. A Th1-mediated inflammatory disease involves an excessive pro-inflammatory response produced by Th1 cells that leads to acute and/or chronic inflammation. The Th1-mediated disease may be virally, bacterially or chemically (e.g., environmentally) induced. For example, a virus causing the Th1-mediated disease may cause a chronic or acute infection, which may cause a respiratory disorder or influenza.

In another embodiment, an acute and/or chronic inflammation comprises an acute and/or chronic neurogenic inflammation. Acute and/or chronic neurogenic inflammation refers to an inflammatory response initiated and/or maintained through the release of inflammatory molecules like SP or CGRP which released from peripheral sensory nerve terminals (i.e., an efferent function, in contrast to the normal afferent signaling to the spinal cord in these nerves). Acute and/or chronic neurogenic inflammation includes both primary inflammation and secondary neurogenic inflammation. Primary neurogenic inflammation refers to tissue inflammation (inflammatory symptoms) that is initiated by, or results from, the release of substances from primary sensory nerve terminals (such as C and A-delta fibers). Secondary neurogenic inflammation refers to tissue inflammation initiated by non-neuronal sources (e.g., extravasation from vascular bed or tissue interstitium-derived, such as from mast cells or immune cells) of inflammatory mediators, such as peptides or cytokines, stimulating sensory nerve terminals and causing a release of inflammatory mediators from the nerves. The net effect of both forms (primary and secondary) of acute and/or chronic neurogenic inflammation is to have an inflammatory state that is maintained by the sensitization of the peripheral sensory nerve fibers. The physiological consequence of the resulting acute and/or chronic neurogenic inflammation depends on the tissue in question, producing, such as, e.g., cutaneous pain (allodynia, hyperalgesia), joint pain and/or arthritis, visceral pain and dysfunction, pulmonary dysfunction (asthma, COPD), and bladder dysfunction (pain, overactive bladder).

Routes of Administration

The cell population expressing an E-selectin and/or L-selectin ligand can be administered to subjects in accordance with a number of suitable routes of administration. Exemplary methods can include vascular injection, for example intravenous (i.v.) injection, or direct implantation of cells into a target site in a subject.

Other methods of delivery can include intratracheal delivery, intrathecal delivery, intraosseous delivery, pulmonary delivery, buccal delivery, aerosol delivery, inhalational delivery, and oral delivery. Still other methods can include intraarterial delivery, intracerebral delivery, intraintestinal delivery, intracardiac delivery, subcutaneous delivery, intramuscular delivery, intraorbital delivery, intracapsular delivery, intraspinal delivery, intraperitoneal delivery, intrasternal delivery, intravesical delivery, intralymphatic delivery, intracavital delivery, vaginal delivery, rectal delivery, transurethral delivery, intradermal delivery, intraocular delivery, aural delivery, intramammary delivery, orthotopic delivery, intratracheal delivery, intralesional delivery, percutaneous delivery, endoscopical delivery, transmucosal delivery, sublingual delivery, and direct application on body surfaces (e.g., directly onto skin surface).

Cells can be inserted into a delivery device which facilitates introduction by injection or implantation into the subjects. Such delivery devices can include tubes, e.g., catheters, for injecting cells and fluids into the body of a recipient subject. Such delivery devices may also include endoscopic delivery devices and methods. Preferably, the tubes additionally have a needle, e.g., a syringe, through which the cells of the disclosure can be introduced into the subject at a desired location.

The cells can be delivered subsequent to manipulations/procedures to enhance E-selectin and/or L-selectin binding activity, or, in some embodiments, cryopreserved and then thawed prior to administration to a subject. The cells can be prepared for delivery in a variety of different forms. For example, the cells can be suspended in a solution or gel or embedded in a support matrix when contained in such a delivery device. Cells can be mixed with a pharmaceutically acceptable carrier or diluent in which the cells of the disclosure remain viable. Pharmaceutically acceptable carriers and diluents include saline, aqueous buffer solutions, solvents and/or dispersion media. The use of such carriers and diluents is well known in the art. The solution is preferably sterile and fluid. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions can be prepared by incorporating cells as described herein in a pharmaceutically acceptable carrier or diluent and, as required, other ingredients, followed by filtered sterilization.

Intravascular delivery via needles or vascular-assisted devices (e.g., catheter-based) injection techniques for cell administration can also be used to achieve distribution through the entire vasculature, or to the vasculature of a particular organ, such as for example liver, or kidney or any other organ. This includes non-specific targeting of the vasculature. Alternatively, any organ can be targeted by selecting a specific injection site, such as e.g., a liver portal vein. Alternatively, the injection can be performed systemically into any vein in the body. This method is useful for enhancing stem cell numbers in aging patients. In addition, the cells can function to populate vacant stem cell niches or create new stem cells to replenish the organ, thus improving organ function. For example, cells can take up pericyte locations within the vasculature.

In some embodiments, the cells are introduced into the subject as part of a cell aggregate (e.g., a pancreatic islet), tissue, or organ, e.g., as part of an organ transplant method.

Delivery of cells can also be used to target sites of active angiogenesis. For example, delivery of endothelial progenitor cells or mesenchymal stem or progenitor cells can enhance the angiogenic response at a wound site. Targeting of angiogenesis can also be useful for using cells as a vehicle to target drugs to tumors.

Modified Cells and Methods for their Preparation

Due, at least in part, to their increased homing capabilities, certain E- and/or L-selectin expressing cells are useful in the methods described herein. By way of example, cells can improve engraftment of stem cells such as HSPCs in clinical transplantation, for use of MSC in cell-based therapy (e.g., for bone diseases) or directing migration and infiltration of progenitor/stem cells at injured/damaged tissue(s) for regenerative therapeutics in accordance with the methods described herein.

Accordingly, the cells used in the methods described herein express an E-selectin ligand and/or an L-selectin ligand. Thus, for example, after modification, the cell binds E-selectin and/or L-selectin. In various embodiments, the modified cell can bind P-selectin. In one particular embodiment, after modification the cells express the sialofucosylated CD44 glycoform known as Hematopoietic Cell E-/L-selectin Ligand (HCELL). In another particular embodiment, after modification the cells express Neural Cell Adhesion Molecule E-selectin Ligand (NCAM-E). In certain embodiments, after modification the cells express both HCELL and NCAM-E. In certain embodiments the cells express HCELL and/or CD43-E and/or CLA. After modification, the cell is capable of homing in vivo to the bone marrow and or sites of inflammation.

In certain embodiments, the cells used in the methods described herein express an L-selectin ligand. In one particular embodiment, after modification the cells express the potent L-selectin ligand known as Hematopoietic Cell E-/L-selectin Ligand (HCELL), sialofucosylated CD44 glycoform. In another embodiment, the cells express increased amounts of the L-selectin ligands HCELL and/or PSGL-1, or the E-selectin ligands HCELL, CLA, CD43-E, NCAM-E, or ESL-1. Such cells may lodge into sites of inflammation via binding to E-selectin on endothelial cells or via binding to L-selectin expressed on infiltrating leukocytes within the inflammatory site.

For ex vivo custom engineering of live cell surface glycans using glycosyltransferases, it is imperative that the treated cells remain viable and phenotypically conserved following treatment(s). Previously, divalent metal co-factors such as manganese had been deemed critical for enzymatic activity for $\alpha(1,3)$-fucosyltransferases, with use of such co-factors at levels that were overtly cytotoxic (e.g., 10 mM $Mn^{++}$). However, it is now known that these glycosyltransferases possess enzymatic activity in the absence of, or in presence of, relatively small amounts of, divalent metal co-factors (e.g., divalent cations such as manganese, magnesium, calcium, zinc, cobalt or nickel). Moreover, these enzymes can be stored in absence of stabilizers such as glycerol which can themselves be toxic to cells. Certain glycosyltransferase compositions described in U.S. Pat. No. 7,875,585 are particularly useful in modification of glycans on live cells, which cells and/or particles or fragments thereof can then be used in the treatment methods described herein. In applications utilizing stem cells, it is also important to analyze whether differentiation along characteristic lineages is affected by enzymatic treatment.

Various methods can be utilized for preparing cells that bind E-selectin and/or L-selectin.

For example, U.S. Pat. Nos. 7,875,585 and 8,084,236, provide compositions and methods for ex vivo modification of cell surface glycans on a viable cell, the latter of which may in turn be utilized in methods of treatment of acute or chronic inflammation as described herein. The compositions include a purified glycosyltransferase polypeptide and a physiologically acceptable solution, for use together with appropriate donor nucleotide sugars in reaction buffers and reaction conditions specifically formulated to retain cell viability. In certain preferred embodiments, the physiologically acceptable solution is free or substantially free of divalent metal co-factors, to such extent that cell viability is not compromised. In these and other preferred embodiments, the composition is also free or substantially free of stabilizer compounds such as for example, glycerol. Glycosyltransferase include for example, fucosyltransferase, galactosyltransferase, sialytransferase and N-acetylglucosaminyltransferase. In one embodiment, the fucosyltransferase is an alpha 1,3 fucosyltransferase such as an alpha 1,3 fucosyltransferase III, alpha 1,3 fucosyltransferase IV, an alpha 1,3 fucosyltransferase V, an alpha 1,3 fucosyltransferase VI, an alpha 1,3 fucosyltransferase VII or an alpha 1,3 fucosyltransferase IX. The sialyltransferase can be ST3GalIII, ST3GalIV, or ST3GalVI.

Glycans are modified on the surface of a cell by contacting a population of cells with one or more glycosyltransferase compositions described above. The cells are contacted with the glycosyltransferase composition together with appropriate nucleotide sugar donor (e.g., GDP-fucose, CMP-sialic acid) under conditions in which the glycosyltransferase has enzymatic activity. Glycan modification according to this method results in cells that have at least 70%, 75%, 80%, 85%, 90%, 95%, 96%, 97%, 98%, 99% or more viability at 24 hours or more after treatment. In one embodiment, for example, the cells have at least 70% viability at 48 hours after treatment. In one such embodiment, for example, the cells have at least 75% viability at 48 hours after treatment. In one embodiment, for example, the cells have at least 80% viability at 48 hours after treatment. In addition, the phenotype of the cells (other than the glycan modification) is preferably preserved after treatment. By preserved phenotype it is meant the cell maintains its native function and/or activity. For example, if the cell is a stem cell it retains its potency, i.e., its relevant totipotency or pluripotency or multipotency or unipotency, as would be characteristic of that particular stem cell type.

Another method of modifying cells for use in the treatment methods described herein can be found in U.S. Patent Application Pub. No. 2013/0040837. In accordance with the methods described therein, nucleic acids (e.g., an aptamer) that specifically bind to a non-nucleic acid target may be immobilized onto the cell membrane. The aptamers can be selected for a specific target, such as those capable of binding to particular proteins. Thus, for example, aptamers that bind to cell surface receptors/cell adhesion molecules (e.g., E-selectin, L-selectin) may be immobilized onto the surface of the cell to improve cell targeting. The aptamers may be conjugated to the cell surface using a three step modification process that includes (i) treatment of cells (in a suspension after trypsinization) with sulfonated biotinyl-N-hydroxy-succinimide (NHS-biotin) to introduce biotin groups on the cell surface, (ii) complexing with streptavidin, and (iii) coupling with biotinylated aptamers. Using this approach, Karp et al. reported in US 2013/0040837 that typically ~21,000 molecules were attached per cell using this procedure and that the site density of aptamers on the cell surface could be readily tuned by adjusting the aptamer concentration used in the conjugation.

Expression of selectin binding may also be induced by covalent addition of sLex or sLea moieties or other oligosaccharide complexes that bind selectins. For example, as described more fully and as exemplified by Karp et al. in US2011/0206740, biotin-streptavidin conjugation was utilized to chemically incorporate the sialyl-Lewis$^x$ moiety onto the cell surface. More specifically, the free amine groups present on the surface of the cells were allowed to react with N-hydroxy-succinimide group of biotinyl-N-hydroxy-succinimide to biotinylate the cell surface. This step was subsequently followed by reacting the biotin moiety of the cell surface with a streptavidin molecule. The strong interaction between biotin and streptavidin allows the streptavidin molecule to be immobilized on the cell surface. The streptavidin is then reacted with biotinylated SLeX (Sialyl-Lex-PAA-Biotin) to introduce SLeX on the cell surface.

In an alternative approach to glycan engineering of cell surfaces, a fucosyltransferase is used incorporate an en bloc assembly of an sLex or sLea glycan onto a cell surface as described, for example, by Srivastava et al., J. Biol. Chem. 1992, 267:22356-22361. More specifically, Srivastava et al. reported that a partially purified Le-FucT from human milk, which normally used GDP-fucose as the donor for the transfer of a single fucose residue will also transfer a fucose residue substituted on C-6 by a very large sterically demanding structure. Accordingly, the fucosyltransferase could be used to transfer a glycan such as such as sialyl-Lewis$^x$ to increase the level of expression of E-selectin ligand and/or an L-selectin ligand on the surface of a population cells that is greater than the level of expression for a native population of such cells.

In another embodiment, a variety of bifunctional chemical linkers can be used to covalently attach sLex or sLea glycans, or glycomimetics of sLex or sLea, or peptidomimetics of sLex or sLea (e.g., as could be generated by phage display technology). Similarly, mAb or mAb fragments thereof that bind to E-selectin and/or L-selectin could be conjugated to the cell surface to enhance binding to E-selectin and/or L-selectin, respectively.

In addition to the foregoing, any other methods of modifying a cell or cells to express an E-selectin ligand and/or an L-selectin ligand may be utilized. This includes, for example, the promotion of covalent and/or non-covalent interactions, hydrogen bonding, and/or van der Wals forces between the cell surface and the ligand, phage display product, and the like.

In general, any type of cell can modified and used in the treatment methods described herein. For animal use it is preferable that the cell is of animal origin, while for human use it is preferably that the cell is a human cell; in each case, an autologous cell source could be used, a syngeniec source cell could be used, an allogeneic source cell could be used (including a combination of allogenic donor cells in a given cell product), or a xenogeneic cell source can be utilized. The cell can be a primary cell, e.g., a primary hepatocyte, a primary neuronal cell, a primary myoblast, a primary mesenchymal stem cell, primary progenitor cell, or it can be a cell of an established cell line or of a culture expanded cell (e.g., T cells, dendritic cells, etc). It is not necessary that the cell be capable of undergoing cell division; a terminally differentiated cell can be used in the methods described herein. In this context, the cell can be of any cell type including, but not limited to embryonic stem cells, adult stem cells, induced pluripotent stem cells, blood progenitor cells, tissue progenitor cells, epithelial, endothelial, neuronal, adipose, cardiac, skeletal muscle, fibroblast, immune cells (for example, dendritic cells, monocytes, macrophages, leukocytes (e.g., a lymphocyte such as a B-lymphocyte, a T-lymphocyte, or a subset of T-lymphocytes, such as regulatory lymphocyte ($CD4^+/CD25^+/FOXP3^+$)), a naïve T cell, a central memory T cell, an effector memory T cell, an effector T cell, NK cells, etc.), hepatic, splenic, lung, circulating blood cells, platelets, reproductive cells, gastrointestinal cells, renal cells, bone marrow cells, cardiac cells, endothelial cells, endocrine cells, skin cells, muscle cells, neuronal cells, and pancreatic cells. The cell can be a cell line, a stem cell (e.g., a mesenchymal stem cell, a hematopoietic stem cell, a tissue stem/progenitor cell (for example, a neural stem cell, gastrointestinal stem cell, myocyte stem cell, cardiomyocyte progenitor/stem cell, endothelial progenitor cell, or pulmonary stem cell), an umbilical cord stem cell, or an embryonic stem cell, or a primary cell isolated from any tissue including, but not limited to brain, liver, lung, gut, stomach, fat, muscle, testes, uterus, ovary, skin, spleen, endocrine organ and bone, and the like.

Where the cell is maintained under in vitro conditions, conventional tissue culture conditions and methods can be used, and are known to those of skill in the art. Isolation and culture methods for various cells are well within the knowledge of one skilled in the art.

In addition, both heterogeneous and homogeneous cell populations are contemplated for use with the methods and compositions described herein. In addition, aggregates of cells, cells attached to or encapsulated within particles, cells within injectable delivery vehicles such as hydrogels, and cells attached to transplantable substrates (including scaffolds) or applied into tissue(s) that harbors scaffolds/transplantable substrates are contemplated for use with the methods and compositions described herein. Moreover, cells may be used in combination with tissue proliferative/enhancing agents and/or anti-inflammatory agents (e.g., growth factors, cytokines, prostaglandins, trophic agents, Resolvins, NSAIDS, steroids, etc.)

The present disclosure further includes the following enumerated embodiments.

Embodiment 1. A method of enhancing cell delivery into a target tissue of a subject and/or enhancing tissue colonization in the target tissue of the subject, the method comprising: administering to the subject a population of cells that express an E selectin ligand and/or an L-selectin ligand, the population expressing the E selectin ligand and/or L-selectin ligand at a level that exceeds the level of expression of a native population of the cells, wherein said cell administration occurs coincident with E selectin expression on endothelial cells within the target tissue and/or coincident with accumulation of leukocytes within the target tissue.

Embodiment 2. A method of treating a disease, disorder or medical condition manifesting as inflamed and/or damaged tissue in a subject, the method comprising: administering to the subject a population of cells that express an E selectin ligand and/or an L-selectin ligand, the population expressing the E selectin ligand and/or L-selectin ligand at a level that exceeds the level of expression of a native population of the cells, wherein said cell administration occurs coincident with E selectin expression on endothelial cells within the target tissue and/or coincident with accumulation of leukocytes within the target tissue, and wherein said population exhibits enhanced localization and/or colonization within the inflamed and/or damaged tissue relative to a native population of the administered cells.

Embodiment 3. A method of improving cellular delivery to a target tissue in a subject, the method comprising: administering to the subject, via vascular delivery and/or via direct tissue injection (i.e., directly into affected tissue site(s)) and/or intrethecally and/or intracavitary and/or intravesically and/or within anatomic conduits (biliary system, urinary system, etc.) and/or onto tissue (i.e., placement onto affected tissue), a population of cells that express an E selectin ligand and/or an L-selectin ligand, the population expressing the E selectin ligand and/or L-selectin ligand at a level that exceeds the level of expression of a native population of the cells, wherein said cell administration occurs coincident with E selectin expression on endothelial cells within the target tissue and/or coincident with accumulation of leukocytes within the target tissue, and wherein said administered cell population achieves one or more of enhanced homing, colonization, and engraftment relative to a native population of cells.

Embodiment 4. A method of enhancing cell delivery and colonization in an inflamed and/or damaged tissue of a subject, the method comprising: directly injecting into or placing onto/within said inflamed and/or damaged tissue a population of cells that express an E selectin ligand and/or an L-selectin ligand, the population expressing the E selectin ligand and/or L-selectin ligand at a level that exceeds the level of expression of a native population of the cells, wherein said injection/placement occurs coincident with E selectin expression on endothelial cells within the target tissue and/or coincident with accumulation of leukocytes within the target tissue.

Embodiment 5. A method of enhancing cell delivery, colonization and/or engraftment into a target tissue of a subject, the method comprising: administering via the vasculature of the subject a population of cells that express an E selectin ligand and/or an L-selectin ligand, the population expressing the E selectin ligand and/or L-selectin ligand at a level that exceeds the level of expression of a native population of the cells, wherein said administration occurs coincident with E selectin expression on endothelial cells within the target tissue and/or coincident with accumulation of leukocytes within the target tissue.

Embodiment 6. A method of enhancing lodgement, colonization and/or engraftment of a cell population within a target tissue in a subject, the method comprising: directly injecting into the target tissue or placement onto the target tissue a population of cells that express an E selectin ligand and/or an L-selectin ligand, the population expressing the E selectin ligand and/or L-selectin ligand at a level that exceeds the level of expression of a native population of the cells, wherein said injection occurs coincident with E selectin expression on endothelial cells within the target tissue and/or coincident with accumulation of leukocytes within the target tissue, and wherein said population achieves enhanced target tissue colonization relative to a native population of the cells.

Embodiment 7. A method of treating a disease, disorder or medical condition manifesting as inflamed and/or damaged tissue in a subject, the method comprising: administering to the subject a population of cells that express an E selectin ligand and/or an L-selectin ligand, the population expressing the E selectin ligand and/or L-selectin ligand at a level that exceeds the level of expression of a native population of the cells, and wherein said injection occurs coincident with E selectin expression on endothelial cells within the inflamed and/or damaged tissue and/or coincident with accumulation of leukocytes within the inflamed and/or damaged tissue.

Embodiment 8. A method of treating a tumor/malignant disease in a subject, the method comprising: administering to the subject a population of cells that express an E selectin ligand and/or an L-selectin ligand, the population expressing the E selectin ligand and/or L-selectin ligand at a level that exceeds the level of expression of a native population of the cells, wherein said administration occurs coincident with E selectin expression on endothelial cells within tissue(s) harboring tumor/malignant cells and/or coincident with accumulation of leukocytes within the tissue(s) harboring tumor/malignant cells.

Embodiment 9. A population of cells that express an E selectin ligand and/or an L-selectin ligand for use in the manufacture of a medicament for the treatment of a disease, disorder or medical condition manifesting as inflamed and/or damaged tissue in a subject, the treatment comprising administering to the subject the population of cells that express an E selectin ligand and/or an L-selectin ligand, wherein the population expresses the E selectin ligand and/or L-selectin ligand at a level that exceeds the level of expression of a native population of the cells, wherein said treatment comprises administering the population coincident with E selectin expression on endothelial cells within the inflamed and/or damaged tissue and/or coincident with accumulation of leukocytes within the inflamed and/or damaged tissue.

Embodiment 10. A population of cells that express an E selectin ligand and/or an L-selectin ligand for use in the manufacture of a medicament for the treatment of a tumor/malignant disease, the treatment comprising administering to the subject the population of cells that express an E selectin ligand and/or an L-selectin ligand, wherein the population expresses the E selectin ligand and/or L-selectin ligand at a level that exceeds the level of expression of a native population of the cells, wherein said treatment comprises administering the population coincident with E selectin expression on endothelial cells within the tumor/malignant tissue and/or coincident with accumulation of leukocytes within the tumor/malignant tissue.

Embodiment 11. The method or population of any one of Embodiments 1-10, wherein said cell administration occurs coincident with E selectin expression on endothelial cells and infiltrates of leukocytes bearing L-selectin within the target tissue.

Embodiment 12. The method or population of any one of Embodiments 1-11, wherein said administration/injection occurs during infiltration of leukocytes to an/the inflamed and/or damaged tissue.

Embodiment 13. The method or population of any one of Embodiments 1-12, further comprising engraftment of the administered population of cells in a milieu of an/the inflamed and/or damaged tissue.

Embodiment 14. The method or population of any one of Embodiments 1-13, wherein an immunomodulatory effect is achieved by colonization of cells within an/the inflamed and/or damaged tissue.

Embodiment 15. The method or population of any one of Embodiments 1-14, wherein a tissue reparative effect is achieved by colonization of administered cells within an/the inflamed and/or damaged tissue.

Embodiment 16. The method or population of any one of Embodiments 1-15, wherein an enhanced host defense/immune response effect is achieved by delivery and colonization of administered cells within an/the inflamed and/or damaged tissue.

Embodiment 17. The method or population of any one of Embodiments 1-16, wherein an anti-malignancy effect is achieved by colonization of administered cells within a/the tumor/malignant tissue site.

Embodiment 18. The method or population of any one of Embodiments 1-17, wherein said administration/injection comprises one or a series of injections of the cell population.

Embodiment 19. The method or population of cells of any one of Embodiments 1-18, wherein said administration/injection comprises daily, weekly, bi-weekly, monthly, or yearly injections of the cell population.

Embodiment 20. The method or population of cells of any one of Embodiments 1-9, further comprising one or more additional administrations/injection of the cell population upon a decrease in the subject of an immunomodulatory effect of a prior administration/injection.

Embodiment 21. The method or population of cells of any one of Embodiments 1-20, wherein the cell population is administered/injected intravenously.

Embodiment 22. The method or population of cells of any one of Embodiments 1-21, wherein the cell population is administered by direct injection to the inflamed and/or injured tissue.

Embodiment 23. The method or population of cells of any one of Embodiments 1-21, wherein the cell population is placed onto the inflamed tissue and/or injured tissue.

Embodiment 24. The method or population of cells of any one of Embodiments 1-21, wherein the cell population is placed onto an/the inflamed tissue and/or injured tissue.

Embodiment 25. The method or population of cells of any one of Embodiments 1-21, wherein the cell population is utilized in combination with other enhancing agents, anti-inflammatory agents, or with tissue scaffolds/transplantable devices/gels.

Embodiment 26. The method or population of any one of Embodiments 1-25, wherein the population of cells express an E selectin ligand and an L-selectin ligand.

Embodiment 27. The method or population of any one of Embodiments 1-26 wherein the E-selectin ligand and/or L-selectin ligand is selected from one or more of Hematopoietic Cell E-/L-selectin Ligand (HCELL), Neural Cell Adhesion Molecule E-selectin Ligand (NCAM-E), CD43E, CLA, and ESL-1.

Embodiment 28. The method or population of any one of Embodiments 1-27, wherein the E-selectin ligand is Hematopoietic Cell E-/L-selectin Ligand (HCELL) and/or Neural Cell Adhesion Molecule E-selectin Ligand (NCAM-E).

Embodiment 29. The method or population of any one of Embodiments 1-28, wherein the E-selectin ligand is HCELL.

Embodiment 30. The method or population of any one of Embodiments 1-29, wherein the E-selectin ligand is NCAM-E.

Embodiment 31. The method or population of any one of Embodiments 1-30, wherein the L-selectin ligand is HCELL.

Embodiment 32. The method or population of any one of Embodiments 1-31, wherein the cell population comprises one or more of epithelial, endothelial, neuronal, adipose, cardiac, skeletal muscle, fibroblast, and immune cells (for example, dendritic cells, monocytes, macrophages, leukocytes (e.g., a lymphocyte such as a NK cell, a B-lymphocyte, a T-lymphocyte, or a subset of T-lymphocytes, such as regulatory lymphocyte (CD4+/CD25+/FOXP3+)), a cytotoxic lymphocyte, etc.), hepatic, splenic, lung, circulating blood cells, platelets, reproductive cells, gastrointestinal, renal, bone marrow, pancreatic cells, a stem cell (e.g., a mesenchymal stem cell, a hematopoietic stem cell, a tissue stem/progenitor cell (for example, a neural stem cell, myocyte stem cell or pulmonary stem cell), an umbilical cord stem cell, or an embryonic stem cell, or an induced pluripotent stem cell, or a differentiated progenitor derived from an embryonic stem cell or from an induced pluripotent stem cells, or a differentiated progenitor derived from an adult stem cell, or a primary cell isolated from any tissue (e.g., brain, liver, lung, gut, stomach, fat, muscle, testes, uterus, ovary, skin, spleen, endocrine organ and bone), or a culture-expanded progenitor cell population, or a culture-expanded stem cell population, or a culture-expanded primary cell population.

Embodiment 33. The method or population of any one of Embodiments 1-32, wherein the cell population is a mesenchymal stem cell, a hematopoietic stem cell, a tissue stem/progenitor cell, an umbilical cord stem cell, or an embryonic stem cell.

Embodiment 34. The method or population of any one of Embodiments 1-33, wherein the cell population is a leukocyte (e.g., a lymphocyte such as an NK cell, B-lymphocyte, a T-lymphocyte, or a subset of T-lymphocytes, such as regulatory lymphocyte (CD4+/CD25+/FOXP3+)), a cytotoxic T cell, etc.).

Embodiment 35. The method or population of any one of Embodiments 1-34, wherein the disease, disorder or medical condition is one or more of direct tissue injury (e.g., burns, trauma, decubitus ulcers, etc.), ischemic/vascular events (e.g., myocardial infarct, stroke, shock, hemorrhage, coagulopathy, etc.), infections (e.g., cellulitis, pneumonia, meningitis, sepsis, SIRS, etc.), neoplasia (e.g., breast cancer, lung cancer, prostate cancer, lymphoma, leukemia, etc.), immunologic/autoimmune conditions (e.g., graft vs. host disease, multiple sclerosis, diabetes, inflammatory bowel disease, lupus erythematosus, rheumatoid arthritis, psoriasis, etc.), degenerative diseases (e.g., osteoporosis, osteoarthritis, Alzheimer's disease, etc.), congenital/genetic diseases (e.g., epidermolysis bullosa, osteogenesis imperfecta, muscular dystrophies, lysosomal storage diseases, Huntington's disease, etc.), adverse drug effects (e.g., drug-induced hepatitis, drug-induced cardiac injury, etc.), toxic injuries (e.g., radiation exposure(s), chemical exposure(s), alcoholic hepatitis, alcoholic pancreatitis, alcoholic cardiomyopathy, cocaine cardiomyopathy, etc.), metabolic derangements (e.g., uremic pericarditis, metabolic acidosis, etc.), iatrogenic conditions (e.g., radiation-induced tissue injury, surgery-related complications, etc.), and/or idiopathic processes (e.g., amyotrophic lateral sclerosis, Parsonnage-Turner Syndrome, etc.).

Embodiment 36. The method or population of any one of Embodiments 1-35, wherein the disease, disorder or medical condition is diabetes.

Embodiment 37. The method or population of any one of Embodiments 1-36, wherein the disease, disorder or medical condition is multiple sclerosis.

Embodiment 38. The method or population of any one of Embodiments 1-37, wherein the subject is a human, non-human primate, mouse, rat, dog, cat, horse, or cow.

Embodiment 39. The method or population of any one of Embodiments 1-38, wherein the subject is a human patient.

Embodiment 40. The method or population of any one of Embodiments 1-39 wherein the cell population is treated to form a modified cell population having an enforced expression of an E-selectin and/or an L-selectin ligand, and the cell population has a viability of at least 70% at 24 hours after the treatment.

Embodiment 41. The method or population of any one of Embodiments 1-40 wherein the cell population has a viability of at least 80% at 24 hours after the treatment.

Embodiment 42. The method or population of any one of Embodiments 1-40 wherein the cell population has a viability of at least 70% at 48 hours after the treatment.

Embodiment 43. The method or population of any one of Embodiments 1-42 wherein, upon administration to the cell population to a subject, the cell population lodges within a tissue comprising infiltrating leukocytes.

Embodiment 44. The method or population of Embodiment 43 wherein the administration is a direct injection into the tissue or placement onto the tissue.

Embodiment 45. The method or population of Embodiment 43 wherein the administration is vascular.

Embodiment 46. The method or population of any of Embodiments 1-21 or 25-42 wherein the population is administered systemically, via either peripheral vascular access or central vascular access.

Embodiment 47. The method or population of any of Embodiments 1-21 or 25-42 wherein the population is administered intravascularly into anatomic feeder vessels of an intended tissue site using catheter-based approaches or other vascular access devices that will deliver a vascular bolus of cells to the intended site.

Embodiment 48. The method or population of any of Embodiments 1-21 or 25-42 wherein the population is administered by introduction into the spinal canal and/or intraventricularly.

Embodiment 49. The method or population of any of Embodiments 1-21 or 25-42 wherein the population is administered directly into body cavities by either catheter-based approaches or direct injection.

Embodiment 50. The method or population of any of Embodiments 1-21 or 25-42 wherein the population is administered by direct local tissue injection, using either intravascular approaches, or percutaneous approaches, or directly into anatomically accessible tissue sites and/or guided by imaging techniques.

Embodiment 51. The method or population of any of Embodiments 1-21 or 25-42 wherein the population is administered by placement directly onto relevant tissue surfaces/sites.

Embodiment 52. The method or population of any of Embodiments 1-21 or 25-42 wherein the population is administered into scaffolds or embedded within scaffolds placed into tissues, and/or administered in gels, and/or administered together with enhancing agents.

Embodiment 53. The method or population of any of Embodiments 1-21 or 25-42 wherein the population is administered into the cerebrospinal fluid.

Having described the disclosure in detail, it will be apparent that modifications and variations are possible without departing the scope of the disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the disclosure.

Example 1

Figure 24:
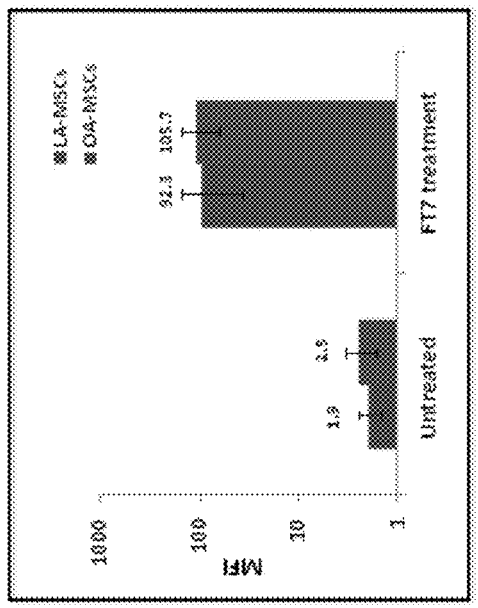
FIG. 24. FTVII treatment of adipose-derived MSCs from lean subjects and from obese subjects results in creation of sLex structures on the cell surface. Bar graphs display flow cytometry results (MFI, mean±SEM) of sLex expression (HECA452-reactivity) following α(1,3)-exofucosylation of adipose-derived MSCs (n=4 samples of MSCs derived from lean and obese subjects).
Figure 28C:
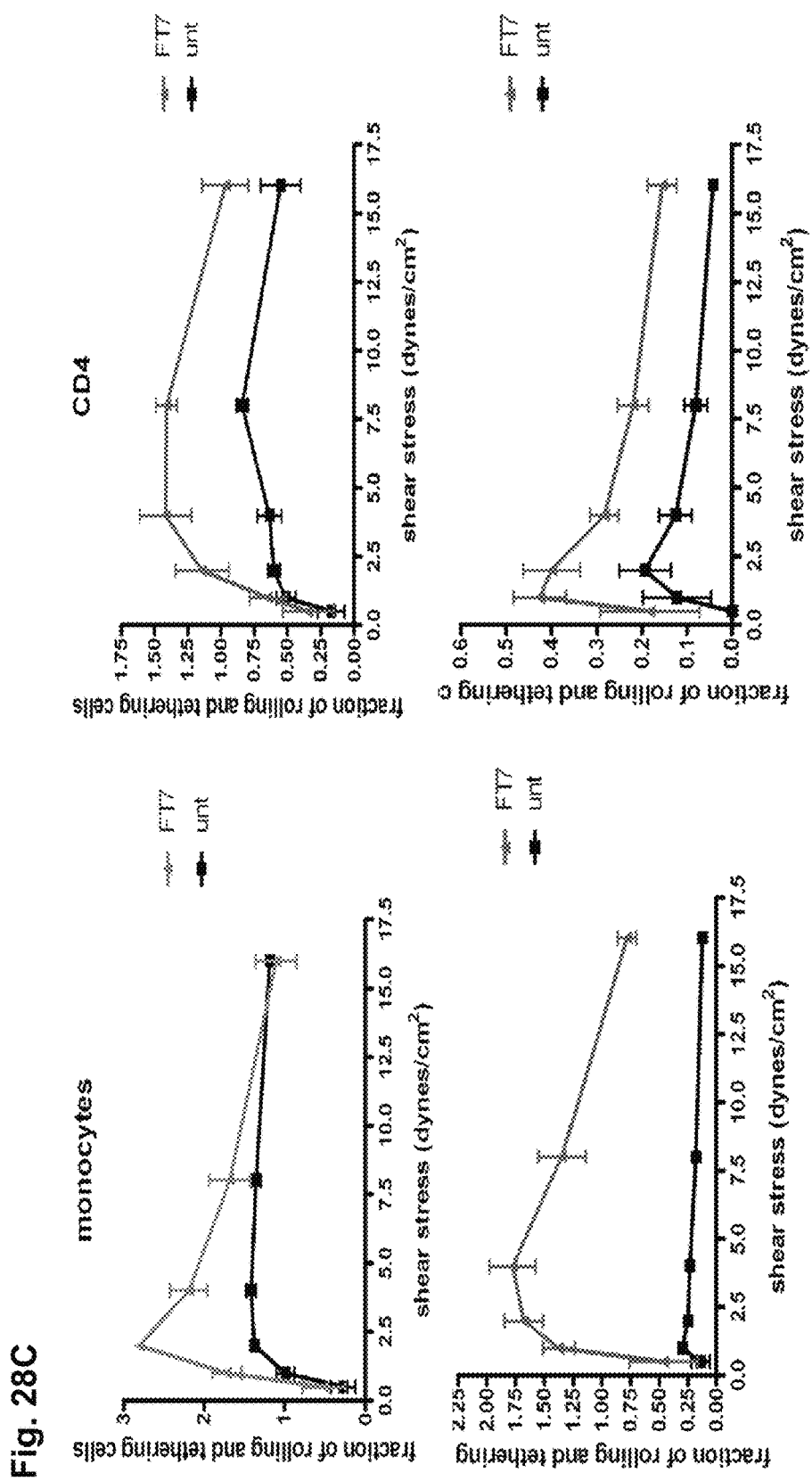
Figure 29A:
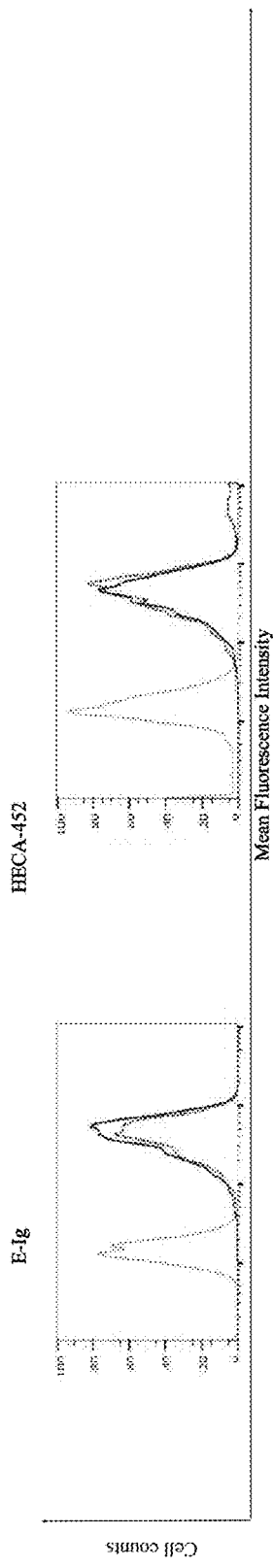
FIGS. 29A-29C: CD44 expressed by monocyte-derived dendritic cells (i.e., cultured following selection of monocytes by CD14 expression (CD14-S mo-DCs)) binds E-selectin.
Figure 29C:
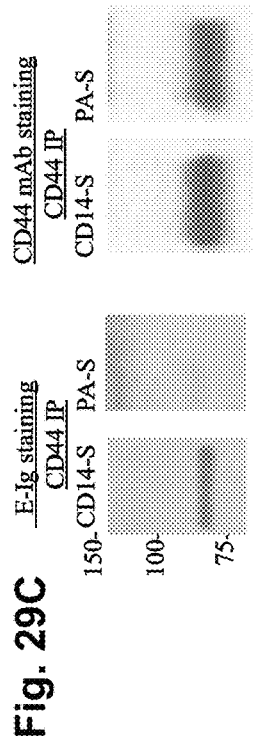
Figure 29B:
Figure 30A:
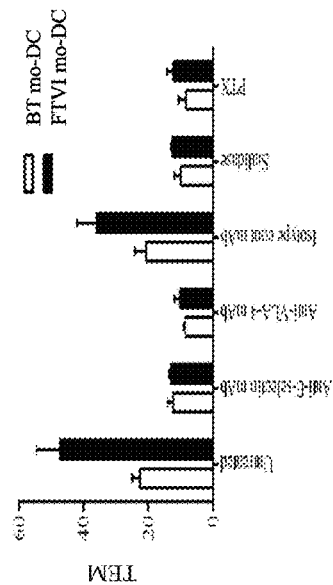
FIGS. 30A-30E. α(1,3)-Exofucosylation of human mo-DCs enforces higher E-selectin ligand activity and endothelial E-selectin expression promotes transendothelial migration (TEM) of exofucosylated DCs.
Figure 30B:
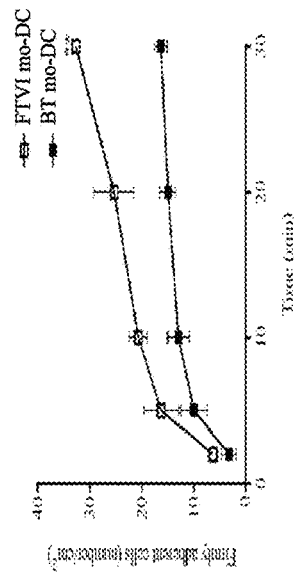
Figure 30C:
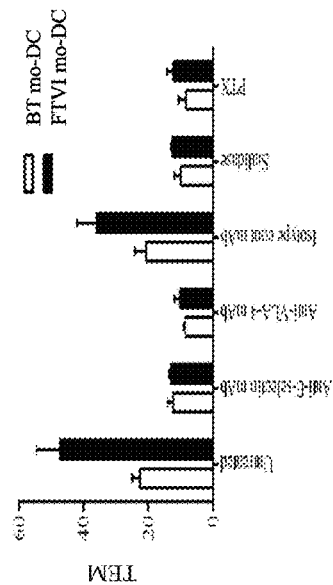
Figure 30D:
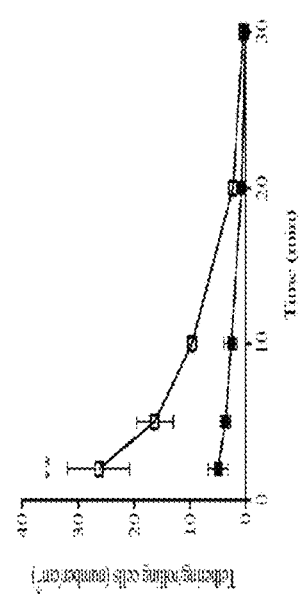
Figure 30E:
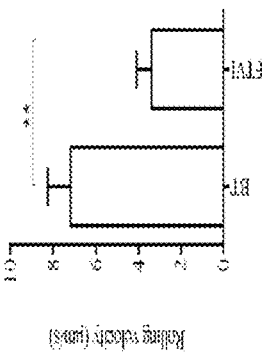
Figure 32:
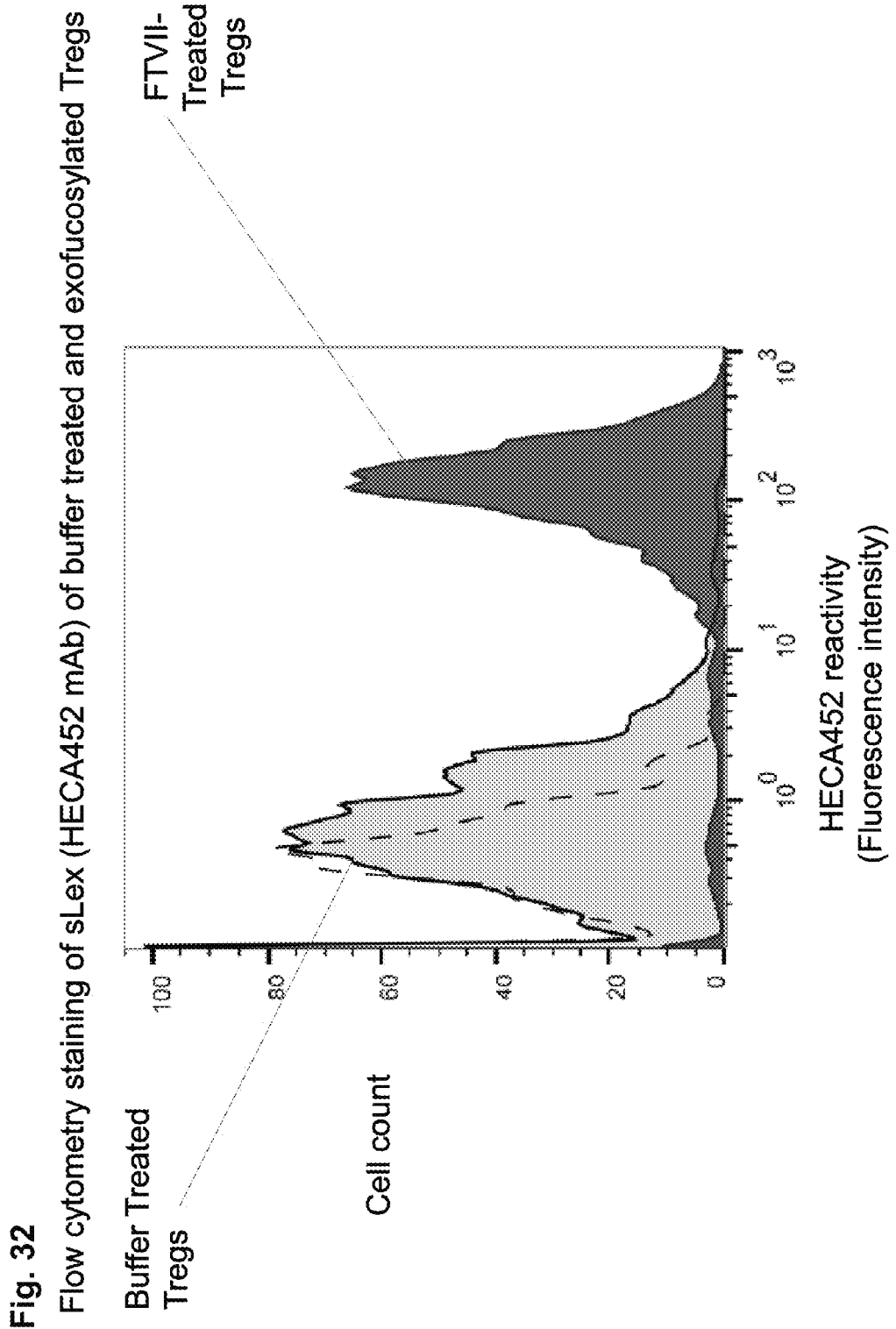
FIG. 32. Flow cytometry profiles of sLex expression (HECA452 staining) of buffer treated (light grey fill) and exofucosylated (FTVII-treated; black fill) Tregs. Note that buffer-treated Tregs have no sLex expression (i.e., profile is similar to isotype control staining (dashed line)), whereas FTVII-treated cells display high levels of sLex.
Figure 33:
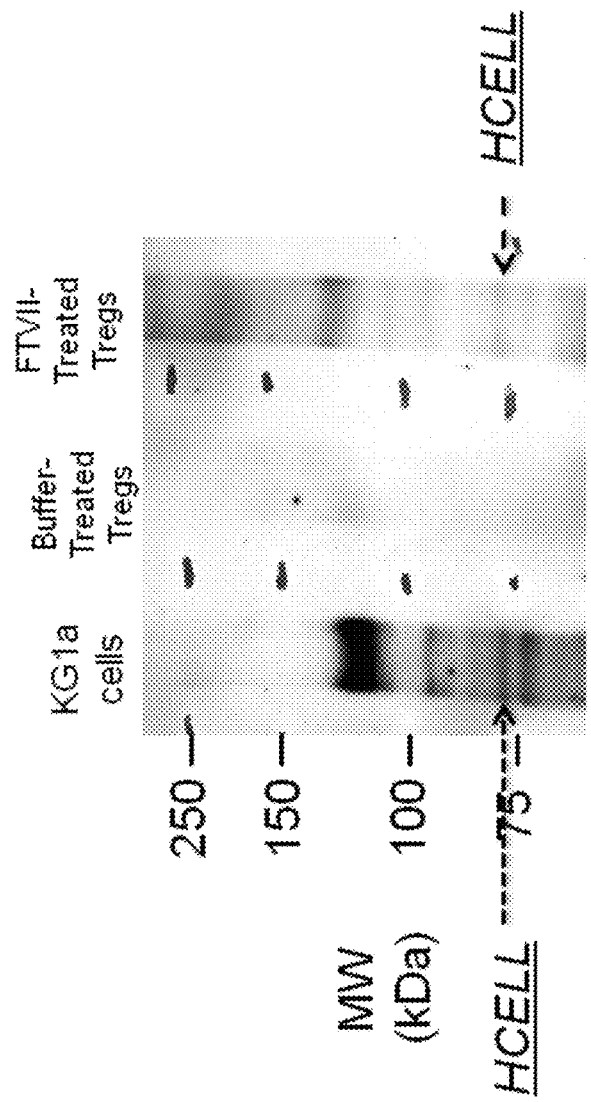
FIG. 33. Western blot analysis of E-Ig staining of FTVII-treated and buffer treated (BT) Tregs compared with the human myeloid leukemia cell line KG1a. Buffer treated T regs have no E-selectin ligands. α(1,3)-Exofucosylation induces expression of several glycoprotein E-selectin ligands on Tregs, including expression of HCELL (~80 kDa band). KG1a cells natively express HCELL.
Figure 34:
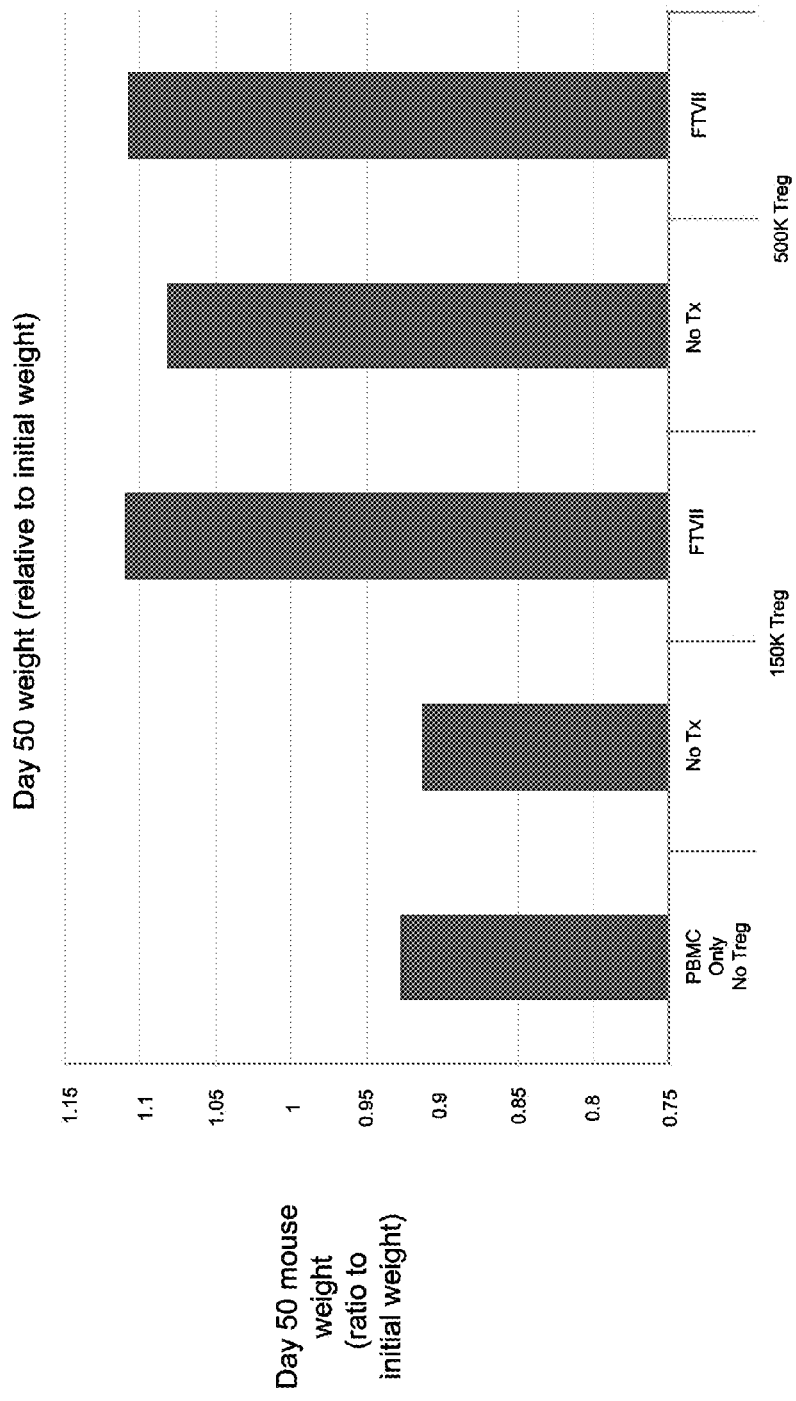
FIG. 34. Titration of regulatory T cell dosing in xenogenic graft versus host disease (GVHD). Xenogeneic GVHD-associated weight loss (measured at day 50 post-injection of PBMCs) is abrogated by intravenous injection of $1.5 \times 10^5$ T regs but not by injection of similar dose of buffer treated Tregs (weight values are mean of N=3 mice). However, injection of $5 \times 10^5$ Tregs prevents GVHD weight loss regardless of α(1,3)-exofucosylation of administered Treg cells (mean of N=3 mice). Thus, α(1,3)-exofucosylation of Tregs increases potency in immunomodulation of GVHD by 3-fold.

Alpha(1,3)-Fucosyltransferase Treatment of Adipose-Derived Mesenchymal Stem Cells Enforces Expression of HCELL Prior studies indicated that bone marrow-derived mesenchymal stem cells (MSCs) can be glycan engineered by α(1,3)-fucosyltransferases to create the potent E- and L-selectin ligand HCELL (R Sackstein et al, Nature Medicine 14:181-187 (2008)). To determine whether HCELL expression can be enforced on MSC derived from non-bone marrow sources, we analyzed the effects of α(1,3)-exofucosylation on adipose-derived mesenchymal stem cells. To this end, adipose tissue was obtained from liposuction material from both lean and obese subjects and mesenchymal stem cells were cultured as described (R Sackstein et al, Nature Medicine 14:181-187 (2008)). Cells were grown at low density (confluence <60%) under both normoxic (21% $O_2$) and hypoxic (<5% $O_2$) conditions in MSC medium supplemented with either FBS (DMEM with 20% FBS and 1% penicillin/streptomycin) or with human platelet lysate (DMEM with 5% human platelet lysate and 1% penicillin/streptomycin). MSCs were passaged when confluence approached 60%, and MSCs were harvested at passages 3-6. MSCs ($20\times10^6$/ml) were then treated with Fucosyltransferase VII (FTVII; prepared by R&D Systems in suspension without divalent cations) at 20 ug/ml or with Fucosyltransferase VI (60 mU/ml (R Sackstein et al, Nature Medicine 14:181-187 (2008))) in each case in Hank's balanced salt solution (HBSS) without divalent cations containing 10 mM HEPES, 0.1% human serum albumin and 1 mM GDP-fucose (Sigma) for 60 min at 37° C., whereas control cells (buffer-treated) were treated in the same buffer without FTVII or without FTVI. Cell viability was assessed routinely by dual laser flow cytometry using propidium iodide and annexin V staining. Cell viability was consistently greater than 80% at 24 hours following α(1,3)-exofucosylation with either FTVI or FTVII. See FIGS. 24-26.

Example 2

Alpha(1,3)-Fucosyltransferase Treatment of Human Blood Leukocytes Induces High Level E-Selectin Ligand Activity on the Cells and Enforces Expression of HCELL The enforced expression of E selectin ligands HCELL and other E-selectin ligands) on surfaces of desired cells (e.g. stem cells, progenitor cells, leukocytes, etc.) would confer heightened capacity of those cells to traffic intravascularly to sites of tissue inflammation/damage and to sites of tumor/cancer infiltrates on the basis of vascular E-selectin expression on endothelial cells within the affected tissue(s). Additionally, once extravasated, the expression of HCELL (or other enforced E-selectin/L-selectin ligands) on the relevant administered cell surface would serve to promote colonization of the administered cells within the target tissue, as administered cells would collect within perivascular areas via E-selectin ligand adherence to E-selectin expressed at endothelial cells, and, additionally, administered cells would also anchor via L-selectin ligand adherence to L-selectin displayed on the surfaces of infiltrating leukocytes within the inflamed/damaged or cancer tissue milieu. As such, enforcing the expression of HCELL and of other E-selectin ligands and/or L-selectin ligands on stem cells/progenitor cells and on specific leukocyte subsets (including, for example, NK cells, CD4 T cells, CD8 T cells, Tregs, monocytes, dendritic cells and granulocytes, as well as relevant leukocytes expanded in culture for therapeutic purposes (e.g., antigen-specific T cells, expanded NK cells, chimeric antigen receptor T cells (CAR T cells), etc.)) could be harnessed in adoptive cell therapeutics (for tissue regeneration/repair and/or for immunotherapy to either augment immunity or to dampen immunity). Thus, critically, enforced expression of HCELL would enable efficient trafficking of intravascularly administered cells to target sites by E-selectin-dependent endothelial interactions yielding recruitment of blood-borne cells, thereafter followed by E-selectin-mediated and L-selectin-mediated lodgement of the extravasated cells with discrete tissue microenvironments. Moreover, similarly, if such cells were injected directly into the affected site(s) of tissue injury/damage or at sites of cancer, enforced expression of HCELL and other E-selectin/L-selectin ligands would promote E-selectin-mediated and L-selectin-mediated lodgement/colonization of the cells within the tissue milieu.

To analyze the molecular targets of cell surface α(1,3)-exofucosylation and the effects of exofucosylation on leukocyte E-selectin and L-selectin ligand activity, studies were performed on primary human peripheral blood leukocytes obtained from citrated whole blood. Leukocytes were separated by immunomagnetic bead sorting (Miltenyi) into monocytes (CD14+ cells), CD4+ lymphocytes, CD8+ lymphocytes, and B cells (CD19+ cells). Cells were treated with Fucosyltransferase VII (FTVII; prepared by R&D Systems in suspension without divalent cations) at 20 ug/ml or with Fucosyltransferase VI (at 60 mU/ml (R Sackstein et al, Nature Medicine 14:181-187 (2008))) in each case in Hank's balanced salt solution (HBSS) without divalent cations containing 10 mM HEPES, 0.1% human serum albumin and 1 mM GDP-fucose (Sigma) for 60 min at 37° C., whereas control cells (buffer-treated) were treated in the same buffer without FTVII or without FTVI. Cell viability was assessed routinely by dual laser flow cytometry using propidium iodide and annexin V staining. Cell viability was consistently greater than 80% at 24 hours following exofucosylation with either FTVI or FTVII. See FIGS. 27A-27C and FIGS. 28A-28C.

Example 3

Alpha(1,3)-Fucosyltransferase Treatment of Primary Cultures of Human Dendritic Cells Induces High Level E-Selectin Ligand Activity on the Cells and Enforces Expression of HCELL To assess the capacity of α(1,3)-exofucosylation to modulate E-selectin and L-selectin ligand activity of human dendritic cells, monocytes were isolated from human peripheral blood mononuclear cells using anti-CD14 coated magnetic beads (Miltenyi Biotech) (CD14-S) or by plastic adherence (PA-S), and then cultured per standard protocols with cytokines IL-4 and GM-CSF for 6 days to induce differentiation into monocyte-derived dendritic cells (mo-DCs). Monocyte purity was evaluated by flow cytometry for expression of CD14, and differentiation and maturation of mo-DCs was evaluated by staining for expression of BDCA-1, HLA-DR, CD80, and CD86 (each from BD Biosciences). Mo-DCs were then treated with Fucosyltransferase VII (FTVII; prepared by R&D Systems in suspension without divalent cations) at 20 ug/ml or with Fucosyltransferase VI (60 mU/ml (R Sackstein et al, Nature Medicine 14:181-187 (2008))) in each case in Hank's balanced salt solution (HBSS) without divalent cations containing 10 mM HEPES, 0.1% human serum albumin and 1 mM GDP-fucose (Sigma) for 60 min at 37 IC, whereas control cells (buffer-treated) were treated in the same buffer without FTVII or without FTVI. Cell viability was assessed routinely by dual laser flow cytometry using propidium iodide and annexin V staining. Cell viability was consistently greater than 80% at 24 hours following exofucosylation with either FTVI or FTVII. See FIGS. 29A-29C and FIGS. 30A-30E.

Example 4

Alpha(1,3)-Fucosyltransferase Treatment of Primary Cultures of Human Regulatory T Cells (Tregs) Induces High Level E-Selectin Ligand Activity on the Cells and Enforces Expression of HCELL; Administration HCELL+ Tregs Suppresses Xenogeneic GVHD Induced by Autologous Cells The ability to enhance delivery of immunomodulatory cells (such as MSCs and Tregs) to sites of inflammation would serve to improve the potential of adoptive cell therapeutics to dampen tissue damage in immunologic diseases (e.g., GVHD, rheumatoid arthritis, etc.) and in exuberant inflammatory responses to infections (e.g., sepsis, fulminant viral hepatitis, etc.). To this end, we investigated the effects of α(1,3)-exofucosylation on the capacity of intravascularly administered primary human Tregs to treat xenogeneic graft-versus-host disease in a human-mouse GVHD model. We sought to assess the capacity of Tregs derived from the autologous lymphocyte source that induced GVHD, as this strategy would be relevant to clinical hematopoietic stem cells transplantation (i.e., Tregs would be expanded from donor hematopoietic/immune cell inoculum, and, therefore, donor Tregs would be used to treat GVHD induced by donor immune cells). To this end, peripheral blood mononuclear cells (PBMCs) were obtained by Ficoll gradient centrifugation of whole blood of a healthy human donor. CD4-high/CD127-low T cells were isolated using a negative selection magnetic immunobead system (Miltenyi) and expanded in culture in the presence of anti-CD3/anti-CD28 mAb supplemented with IL-2 to produce CD4+/FoxP3+/CD25+ cells (Tregs). Unfractionated PBMCs from the same donor subject were injected IP ($10^7$ cells/mouse) into NSG host mice intraperitoneally. Fourteen days after injection (accordingly, day 14 of Treg expansion) the expanded Treg cells were collected and then treated with Fucosyltransferase VII (FTVII; prepared by R&D Systems in suspension without divalent cations) at 20 ug/ml or with Fucosyltransferase VI (60 mU/ml (R Sackstein et al, Nature Medicine 14:181-187 (2008))) in each case in Hank's balanced salt solution (HBSS) without divalent cations containing 10 mM HEPES, 0.1% human serum albumin and 1 mM GDP-fucose (Sigma) for 60 min at 37° C., whereas control cells (buffer-treated) were treated in the same buffer without FTVII or without FTVI (cell viability was assessed routinely by dual laser flow cytometry using propidium iodide and annexin V staining; cell viability was consistently greater than 80% at 24 hours following exofucosylation with either FTVI or FTVII). Mice were then injected intravascularly with either buffer-treated (BT) Tregs or with exofucosylated Tregs at a dose of $2.5 \times 10^5$ cells/mouse. Mice were then followed clinically and mouse weights were monitored for 50 days post-initial PBMC injection. Data as shown in Figures reveal that FTVII treatment of human Tregs induces expression of E-selectin ligands, including HCELL. Injection of exofucosylated autologously-derived Tregs into mice with xenogeneic GVHD (induced by prior administration of autologous PBMCs) results in dampening of GVHD, as evidenced by reversal of weight loss; exofucosylated Tregs are 3-fold more potent in reversing GVHD than are unfucosylated Tregs. See FIGS. 31-34.

Example 5

Alpha(1,3)-Fucosyltransferase Treatment of MSC and of Human Blood Leukocytes Induces L-Selectin Ligand Activity on the Cells as Assessed by Stamper-Woodruff Lymphocyte Adherence Assay The Stamper Woodruff lymphocyte adherence assay is the conventional tool to assess L-selectin ligand activity (R. Sackstein, Immunol. Rev. 230: 140-163 (2009)). This assay, which was devised in the mid-1970s to evaluate the molecular basis of lymphocyte binding to lymph node high endothelial venules, measures the capacity of L-selectin—as natively expressed on the surface of a live lymphocyte—to attach to its cognate ligand(s) expressed on the surface of a relevant cell. The assay is performed under rotatory shear conditions, thereby placing a discrete biophysical restriction on the binding interaction: only the most potent L-selectin ligands (presented on the surface of cells attached to glass) will support adherence of L-selectin displayed on the rotating suspension of lymphocytes. Indeed, the only L-selectin ligands that are robust enough to support L-selectin-mediated binding of lymphocytes in this assay are HCELL and the "endothelial" L-selectin ligands displayed on lymph node high endothelial venules (collectively, these L-selectin ligands are called "addressins") (R. Sackstein, Immunol. Rev. 230: 140-163 (2009)).

To assess the expression of L-selectin ligand activity induced by α(1,3)-exofucosylation, the Stamper-Woodruff was performed on cytospin preparations of native cells, buffer-treated cells, and α(1,3)-exofucosylated cells. Briefly, lymphocyte suspensions prepared fresh from human blood ($10^7$/ml lymphocytes in RPMI 1640 medium) were overlaid onto glass slides containing preparations of relevant cells placed on the slides by cytocentrifugation. Slides were placed on a rotating platform for incubation under shear (80 rpm) at 4° C. for 30 minutes. Slides were then rinsed in PBS to remove nonadherent lymphocytes, fixed in 3% glutaraldehyde, and stained with methyl green-thionin. Slides were examined for lymphocyte adherence to cytocentrifuged cells by light microscopy. L-selectin ligand activity was measured by counting the number of lymphocytes adherent to a confluent area of cytocentrifuged cells, using an ocular grid under 250× magnification. The cytocentrifuged cells that have adherent lymphcytes are scored, and the percentage of such cells within the total lawn of cytocentrifuged cells is quantified (as shown on Key in Table 1).

TABLE 1

Results of Stamper-Woodruff Assay
(L-selectin binding activity of cells)

| Type of Cell | L-SELECTIN LIGAND ACTIVITY | | |
|---|---|---|---|
| | Native cells | Buffer-treated cells | α(1,3)-exofucosylated cells |
| Human MSC | 0 | 0 | ++++ |
| Human CD4 T cell | + | + | ++++ |
| Human CD8 T cell | 0 | 0 | ++ |
| Human B cell | 0 | 0 | + |
| Human Treg cell | 0 | 0 | +++ |
| Human Monocyte | + | + | ++++ |
| Human Dendritic Cell | + | + | ++++ |

KEY:
0 <10% of cells bind L-selectin⁺ lymphocytes
+ 10-30% of cells bind L-selectin⁺ lymphocytes
++ 30-50% of cells bind L-selectin⁺ lymphocytes
+++ 50-70% of cells bind L-selectin⁺ lymphocytes
++++ >70% of cells bind L-selectin⁺ lymphocytes As shown in Table 1, native MSCs have no L-selectin binding activity, but α(1,3)-exofucosylation of MSCs induces profound L-selectin binding activity, with L-selectin-mediated lymphocyte binding observed on essentially all exofucosylated cells. Human CD4 T cells, human monocytes, and human dendritic cells each display modest L-selectin binding activity, but these cells support robust L-mediated lymphocyte adherence following α(1,3)-exofucosylation. Human Tregs, B cells and CD8 cells do not natively possess L-selectin ligand activity, but each cell type can be induced to bind L-selectin by α(1,3)-exofucosylation, with exofucosylated Tregs showing marked increases in L-selectin adherence. Thus, L-selectin binding is enhanced on essentially all human leukocytes following α(1,3)-exofucosylation, and, in particular, L-selectin ligand activity can be profoundly induced on human MSC, CD4 T cells, monocytes, dendritic cells and Tregs by α(1,3)-exofucosylation. In each case, this L-selectin binding activity is a reflection of enforced HCELL expression, and is commensurate with results of HCELL expression on these cells as exhibited by western blot data staining for sLex/E-Ig as displayed in FIGS. 25, 28A-28C, 30A-30E, and 33.

Example 6

HCELL Expression on Murine MSC Licenses Pancreatotropism and Confers Durable Reversal of Autoimmune Diabetes in NOD Mice Introduction Despite significant advances in the pharmacotherapy of glycemia control, type 1 diabetes (T1D) is still associated with significant morbidity and mortality, and it continues to pose a major public health burden demanding innovative treatment strategies[1, 2]. Cell-based immunomodulatory therapy has emerged as a promising approach in the treatment of T1D[3]. Because of their immunomodulatory properties, safety profile, easy acquisition, and robust ex vivo expansion, mesenchymal stem cells (MSCs) have become the most rapidly growing cell therapy for the treatment of various refractory immune-mediated diseases including T1D[4-7]. In preclinical models using NOD mice, we and others have recently reported that systemically-administered MSCs have utility in dampening autoimmune diabetes[8-13]. However, the benefits of MSC therapy in reversal of hyperglycemia were temporary, highlighting a pressing need to develop strategies to improve the effectiveness of MSC-based therapy for T1D[6].

The efficacy of immunomodulatory cell therapy is closely related to the ability of the infused cells to traffic to the inflamed tissue[14, 15]. For some organs (e.g., the heart), direct (local) injection of cells into the affected site can achieve requisite colonization for physiologic benefit[16]. However, for treatment of T1D, the vascular route of cell delivery is mandated, as direct injection of cells into the pancreatic parenchyma would trigger release of proteases and other enzymes that could induce profound, life-threatening pancreatic inflammation. The migration of blood-borne cells into tissues is initiated by tethering/rolling adhesive interactions on target tissue endothelium. The most potent mediators of these binding interactions are the selectins, a family of three $Ca^{++}$-dependent lectins (E-, P- and L-selectin, also known as CD62E, CD62P, and CD62L, respectively) that bind to sialofucosylated glycan determinants expressed on their respective ligands[17]. Importantly, within the microvasculature at all inflammatory sites, the endothelial selectin, E-selectin, is inducibly expressed in response to inflammatory cytokines such as TNF-α[17,18]. E-selectin binds to membrane glycoproteins and/or glycolipids on circulating cells that prototypically display the sialofucosylated tetrasaccharide known as "sialylated Lewis X" (sLex). However, MSCs do not natively express E-selectin ligands[19]. This deficit in trafficking limits the engraftment of MSCs in inflamed peripheral tissues following intravenous administration[17,20], constraining the utility of MSC-based therapeutics. Accordingly, we sought to investigate whether MSC trafficking to inflamed pancreas could be licensed via cell surface glycan modification to enforce E-selectin ligand expression, and whether this would impact MSC therapeutic effect(s) in new onset autoimmune diabetes in NOD mice. Our findings provide new insights on the biology of MSC effects in diabetes, highlighting a unique and prominent role for enforced expression of the E-selectin ligand HCELL in enhancing the capacity of murine MSCs to reverse hyperglycemia in diabetic NOD mice.

Materials and Methods

Mice

C57BL/6, B6.129(Cg)-Cd44$^{tm1Hbg}$/J (CD44$^{-/-}$ on CD57BL/6 genetic background; CD44-knock out ("CD44-KO")), BALB/c, and NOD mice were purchased from Jackson Laboratories and were housed and/or bred in a pathogen-free environment at the Harvard Medical School Facilities for Animal Care and Housing. Experiments requiring the use of mice were approved by the Institutional Animal Care and Use Committee.

MSC Culture

Bone marrow MSCs were derived as described previously [9, 10]. In brief, isolated marrow cells from C57BL/6 (wild-type) or from CD44-KO mice were flask-seeded in culture medium consisting of Dulbecco's Modified Eagle Medium with 10% fetal bovine serum (Lonza), 10 ng/ml fibroblast growth factor (PeproTech), 100 U/ml penicillin and 100 ug/ml streptomycin (Gibco). MSCs in culture passage 4 to 6 were used for experiments.

MSC Characterization and Differentiation

MSCs were characterized by flow cytometry using anti-mouse antibodies (all from eBioscience) directed to cell surface markers Sca1, CD44, CD73, CD45, CD29, and CD105, together with relevant isotype controls. Recombinant mouse E-selectin (CD62E)-human Fc chimera was purchased from R&D Systems. MSCs were tested for their differentiation capacity into various mesodermal lineages as previously described [21, 22]. Briefly, chondrogenic differentiation of MSCs was induced with ascorbic acid (50 µg/ml) and TGFβ1 (1 ng/ml) in culture medium. After 3 weeks of culture, plates were washed with PBS, fixed with 4% paraformaldehyde, and stained with 0.05% alcian blue for light microscopic visualization of cartilage. Osteogenic differentiation was induced with ascorbic acid (50 µg/ml), sodium β-glycerophosphate (10 mM), and dexamethasone (10 nM) in culture medium. Two weeks later, plates were washed, fixed with 4% paraformaldehyde, and stained with 2% alizarin red for visualization of characteristic calcium deposits. Adipogenic differentiation was induced by the addition of dexamethasone (100 nM) and insulin (6 ng/ml) in F12 medium supplemented with 1% fetal calf serum, 1% glutamine, 1% penicillin-streptomycin. Cells were fixed in 4% parafomaldehyde and stained with 0.3% Oil Red solution in 60% isopropanol to assess lipid-laden vacuoles.

MSC Exofucosylation

MSCs in suspension ($10 \times 10^6$ per 200 ul reaction) were treated for 90 min at 37° C. with 60 mU/mL fucosyltransferase VI (FTVI) in reaction buffer consisting of $Ca^{2+}$- and $Mg^{2+}$-free Hanks Balanced Salt Solution (HBSS) containing 20 mM HEPES, 0.1% human serum albumin and 1 mM GDP-fucose ("FTVI-modified MSC"), or with reaction buffer alone (unmodified MSC). Following treatment, MSCs were washed with HBSS containing 0.2% HSA and 20 mM HEPES. Cell viability was assessed by trypan blue exclusion and propidium iodide staining (consistently >85% viability 24 hours post-detachment and treatment). FTVI modification was assessed by flow cytometry. FTVI enzyme was provided by Dr. Roland Wohlgemuth (Sigma Chemical Corporation).

Western Blot Analysis

FTVI-modified and unmodified MSC lysates were prepared by incubation with 2% Nonidet P-40 (NP-40) in Buffer A (150 mM NaCl, 50 mM Tris-HCl, pH 7.4, 20 mg/mL phenylmethylsulfonyl fluoride, 0.02% sodium azide, and protease inhibitor cocktail tablet (Roche Molecular Biochemicals). All Western blots of whole cell lysates or of immunoprecipitated protein were performed under reducing conditions on 7.5% SDS-PAGE gels as described previously [19]. The amount of lysate in each lane was normalized to cell number for each Western blot performed. Blots were visualized with chemiluminescence using Lumi-Light Western Blotting Substrate (Roche).

Flow Cytometry and Immunoprecipitation Studies

Flow cytometry was performed as described previously [19]. For more details please refer to the Supplementary Methods section.

Parallel Plate Flow Chamber Adhesion Assay

A dynamic flow adhesion assay was performed using a parallel plate flow chamber (250 µm channel depth×5.0 mm channel width), to assess E-selectin mediated MSC binding over stimulated human umbilical vein endothelial cells (HUVEC) as previously described [19]. For more details, please refer to the Supplementary Methods section.

Transduction of MSCs with hGH Viral Vector

MSCs were transduced with the lentivirus containing hGH plasmid construct as described previously[21]. Levels of hGH were measured by enzyme-linked immunosorbent assay (Roche Diagnostics) in MSC supernatants and in serum of injected animals.

Transduction of MSCs with GFP Viral Vector

MSCs were transduced with a retrovirus plasmid containing GFP (GFP-MSC) as described previously[21]. Transduced MSC were assessed for perinuclear expression of GFP by fluorescent microscopy. In a complementary approach to the use of GFP-MSCs to assess homing, MSCs (non-GFP-transduced) were labeled with the fluorescent dye CFSE.

Immunofluorescence

Pancreata were embedded in Tissue Tek OCT, frozen and sectioned in a cryomicrotome. Immunofluorescence images were acquired using a Nikon E-1000 epifluorescence microscope (×400 total magnification). For more details on specific staining, please refer to the Supplementary Methods section.

Mitogen-Stimulation CD3/CD28 T Cell Proliferation Assay

T cell proliferation assay using anti-CD3 and anti-CD28 stimulation was used to assess effects of FTVI modification on immunomodulatory capacity of MSCs. Briefly, $1 \times 10^5$ NOD splenocytes were stimulated with purified mouse anti-CD3e and anti-CD28 (each at 1 µg per well, eBioscience) for 72 hours in RPMI media (Lonza), supplemented with 10% fetal bovine serum (Gemini 310-Products), 1% penicillin streptomycin (Lonza) and 1% glutamine (Lonza), in the presence of a titrating concentration ($5 \times 10^2$ $5 \times 10^4$) of irradiated (3000 rad) unmodified and FTVI-modified MSCs. In the last 12 hours of the 72 hour incubation period, cells were pulsed with 1 µCi of tritiated thymidine, and lymphocyte proliferation ($^3$H-thymidine incorporation) was measured by scintillation counting. Results are reported as an average of triplicate samples (mean cpm±SEM).

Reversal of New-Onset Hyperglycemia Studies in NOD Mice

Unmodified and FTVI-modified MSCs ($0.5 \times 10^6$ cells in 200 ul) were injected intravenously via tail vein without anesthesia into female NOD mice on the second day of hyperglycemia (>250 mg glucose/dL), and at 7 days and 30 days following onset of hyperglycemia. To assess effect of MSC administration on hyperglycemia, blood was obtained via tail vein and glucose measured as described previously [9, 10].

Statistics

Data from experimental assays and immunohistological experiments were analyzed using student t-test and Mann Whitney tests. Survival data were assessed using Kaplan-Meyer analysis. To perform the analysis and to generate graphs, Prism software was used (GraphPad Software, Inc., San Diego, Calif.). P value <0.05 was considered significant. Data represent mean±SEM.

Supplementary Methods

Flow Cytometry and Immunoprecipitation Studies

Flow cytometry was performed as described previously[19] using biotinylated mAb HECA452 (anti-human cutaneous lymphocyte antigen, which recognizes sLex; Rat IgM (BioLegend)), and anti-mouse CD44 mAb (KM114; Rat IgG1), purified anti-mouse CD44 mAb (IM7; Rat IgG2b), and phycoerythrin (PE)-labeled streptavidin (all obtained from BD Pharmingen). For western blotting, MSC lysates were incubated with anti-CD44 immunoprecipitating antibodies (KM114/IM7) or with appropriate isotype controls and then collected with Protein G-agarose (Invitrogen). Immunoprecipitates were washed extensively using Buffer A containing 2% NP-40, 1% SDS, and then subjected to SDS-PAGE, transferred to polyvinylidene difluoride membrane, and immunostained with HECA452 or anti-mouse CD44 antibodies (KM114/IM7), followed by incubation with appropriate HRP-conjugated secondary antibodies for visualization by chemiluminescence using Lumi-Light Western Blotting Substrate (Roche).

Parallel Plate Flow Chamber Adhesion Assay

Confluent HUVECs were stimulated for 6 h with TNF-α (40 ng/ml) to up-regulate E-selectin expression. Wild-type (WT) and CD44KO MSC were harvested with 0.005% Trypsin/EDTA, and were either FTVI modified or treated with buffer alone (control) for 90 minutes at 37° C. MSC were then resuspended at $10^6$ cells/ml in Hanks' Balanced Salt Solution supplemented with 1 mM calcium chloride, 1 mM magnesium chloride, 5 mM HEPES, and 1 mg/ml BSA. MSC were perfused over the HUVEC monolayer at 0.5 dynes/cm$^2$, and then subjected to shear stress levels of 1.0, 2.0, 5.0, 10.0, 20.0, and 30.0 dynes/cm$^2$ at 3-minute intervals. MSC that interacted with HUVEC (cells that rolled in the field of view or rolled into it within a 10 second time frame) were viewed at the center of the chamber, minimum of 6 fields of view at each shear stress level. As controls to assess specificity of E-selectin binding to stimulated HUVEC, FTVI-modified MSC were treated with sialidase from *Vibrio cholerae* (0.1 U/ml; Roche) to cleave terminal sialic acid from sLex, and adherence was also assessed in presence of function-blocking anti-human E-selectin mAb (10 ug/ml) (BD Pharmingen).

Immunofluorescence

Tissues were cryostat-sectioned at 10 um thickness and fixed on slides in cold acetone for 5 min. After drying, sections were blocked with 1% BSA and incubated in primary antibody overnight. Sections were washed 3× in Tris-buffered Saline (TBS) and incubated with secondary antibody for one hour. E-selectin (CD62E) staining was performed using primary rat anti-mouse CD62E (R&D Systems, 1:100), and secondary PE-conjugated goat anti-rat IgG (Southern Biotech, 1:500). Isotype-matched rat mAb was used as a staining control. CD31 staining was performed using rat anti-mouse CD31 (Biocare, 1:200) and secondary PE-conjugated goat anti-rat IgG (Southern Biotech, 1:500). Assessment of CD31 and E-selectin co-localization was performed on sequential sections. Insulin staining was undertaken using purified guinea pig anti-insulin (Dako, 1:5) and APC conjugated donkey anti-guinea Pig IgG (H+L) (Jackson Immunoresearch, 1:200). HECA452 mAb (Rat anti-CLA IgM mAb (Biolegend, 1:200)) and FITC conjugated mouse anti-rat IgM (Biolegend, 1:500) were used to detect FTVI-modified MSC within tissue sections. Sections were overlaid with mounting media alone or, when indicated, with mounting media containing DAPI (Vector Labs), cover-slipped, and then visualized by immunofluorescence microscopy.

Results

Expression and Functional Analysis of FTVI-Modified MSC

Figure 7:
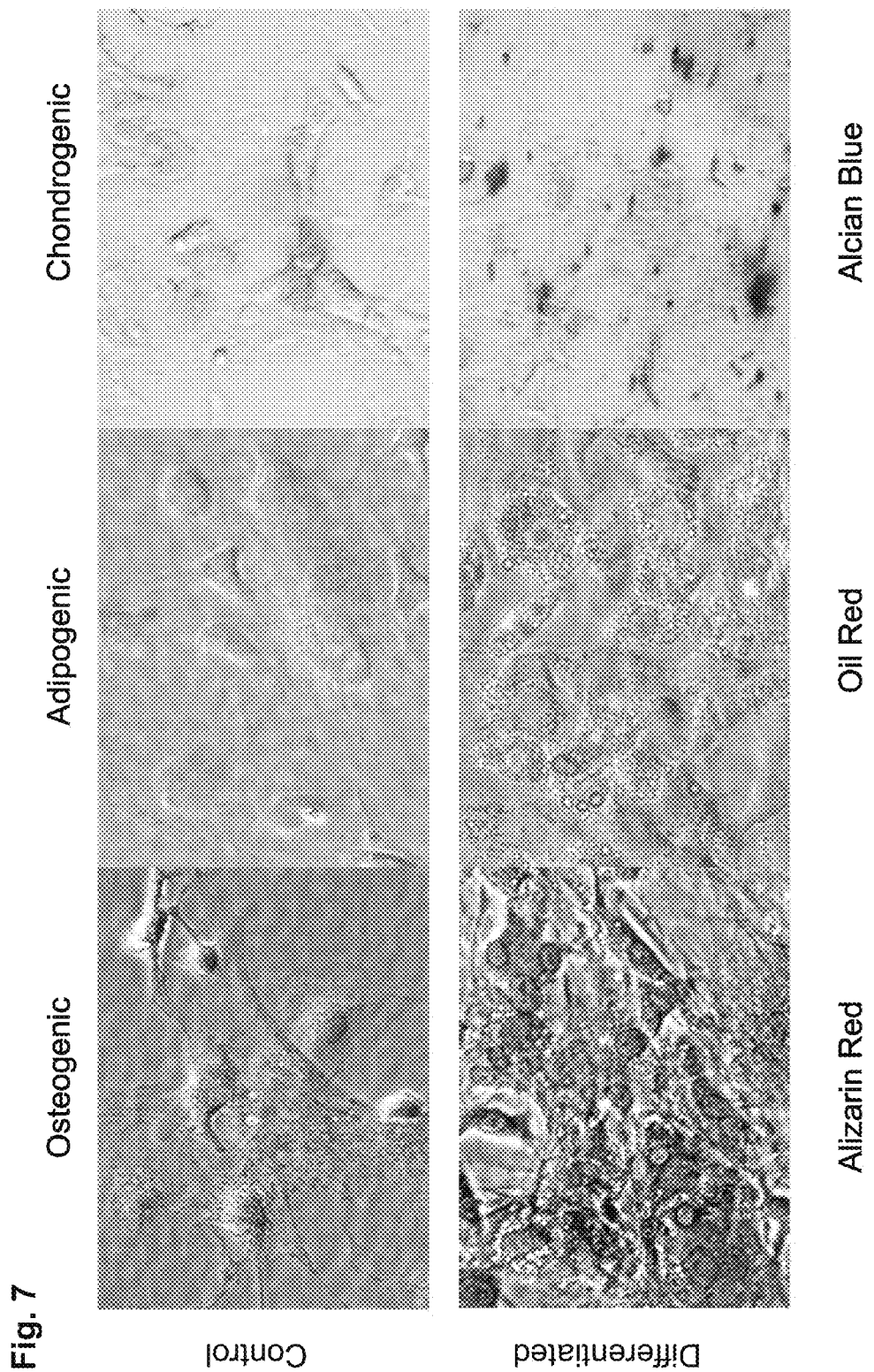
FIG. 7. Characterization of mouse bone marrow derived MSCs. MSCs were differentiated into osteocytes, adipocytes and chondrocytes (×200 magnification).

Bone marrow-derived MSCs from C57BL/6 mice, ("wild-type"), a diabetes-resistant strain, and from CD44-KO mice (CD44$^{-/-}$ on C57BL/6 background) showed characteristic small spindle fibroblast-like pattern and could be differentiated into mesodermal cell types (FIG. 7). MSCs expressed cell surface markers characteristics of MSCs (FIG. 1A). MSCs did not natively express E-selectin ligands, as shown by absence of reactivity with mAb HECA 452 (which recognizes canonical sialofucosylated E-selectin binding determinants (such as sialylated Lewis X (sLe$^x$)) and by absence of binding to E-selectin-Ig chimera (E-Ig) that serves as a probe for E-selectin ligand activity (FIG. 1B).

A prior study of human MSCs showed that cell surface glycoengineering (i.e., Glycosyltransferase-Programmed Stereosubstitution (GPS)) using the α-(1,3)-fucosyltransferase VI (FTVI) induces E-selectin adherence via conversion of native membrane CD44 into the molecule known as Hematopoietic Cell E-/L-selectin Ligand (HCELL), a fucosylated sialyllactosaminyl glycovariant of CD44 that potently binds E-selectin[19]. To determine whether cell surface exofucosylation could program E-selectin ligand activity on murine MSCs, cells were treated with FTVI using reaction conditions that were optimized to preserve cell viability. FTVI modification of MSCs markedly induced staining with mAb HECA452, as well as binding with a murine E-selectin-Ig chimera (mE-Ig) (FIG. 1B). Notably, protease digestions of MSCs prior to FTVI modification markedly reduced mE-Ig reactivity, indicating that glycoproteins, not glycolipids, were predominant carriers of E-selectin binding determinants (FIG. 1B). Following exofucosylation of mouse MSC, western blot of whole cell lysates (FIG. 1C) and of immunoprecipitated CD44 (FIG. 1D) revealed that the principal membrane glycoprotein decorated with the sialofucosylations recognized by E-Ig and HECA-452 was the "standard" (i.e., containing no splice variant exons) form of CD44 (~100 kDa). These data indicate that FTVI modification converts murine MSC surface CD44 into HCELL.

FTVI-Modified Mouse MSCs have Increased Binding to E-selectin Under Physiologic Shear Stress Conditions To assess the capacity of FTVI-modified mouse MSCs to bind E-selectin under physiologic shear stress conditions, we performed parallel plate flow chamber assays of both unmodified and FTVI-modified MSCs. To this end, HUVEC monolayers were first stimulated with TNF-α to upregulate E-selectin expression. As shown in FIG. 2, FTVI-modification enabled MSC adhesion to HUVEC at shear stress levels of 0.5 dynes/cm$^2$ to as much as 20 dynes/cm$^2$. In flow chamber studies, MSC adherence to stimulated HUVEC was strictly dependent on E-selectin receptor/ligand interactions as incubation of HUVEC with function-blocking E-selectin mAb and sialidase treatment of MSCs (to eliminate sLe$^x$ display) each profoundly reduced adhesion of FTVI-modified MSCs, to levels similar to that of unmodified MSCs (FIG. 2). Altogether, these findings indicate that FTVI modification of murine MSC induces potent E-selectin binding activity, capable of sustaining E-selectin adherence at hemodynamic shear stress levels well beyond those typical of post-capillary venules[17].

Figure 3A:
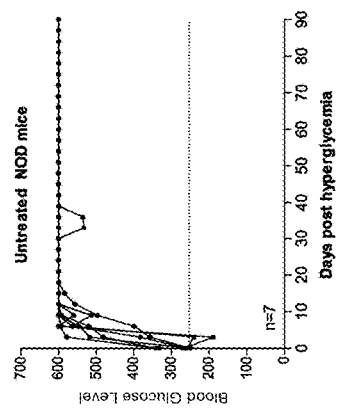
FIGS. 3A-3C. Effects of intravenous administration of unmodified and FTVI-modified MSC on hyperglycemia in new onset diabetic NOD mice.
Figure 3B:
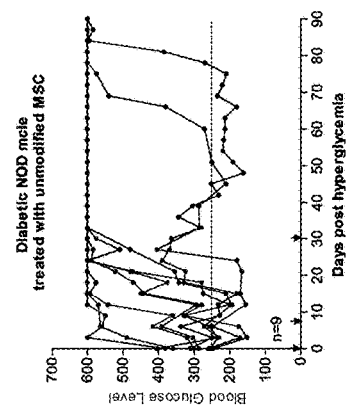
Figure 3C:
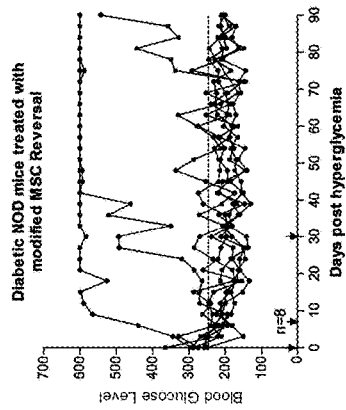

Systemically-Administered FTVI-modified MSCs Potently Reverse New Onset Hyperglycemia in NOD Mice To assess whether FTVI-modification affected the capacity of MSCs to modulate diabetes in NOD mice, new onset diabetic NOD mice either received no cells (untreated control), or received 5×10$^5$ FTVI-modified or 5×10$^5$ unmodified C57BL/6 MSCs intravenously (via tail vein) on day 2 of hyperglycemia (glucose >250 mg/dL), followed by intravenous injections at days 7 and 30 after onset of hyperglycemia. As shown in FIG. 3A, untreated NOD mice showed a rapid increase in their blood glucose levels and, with exception of one animal, died within a few weeks of the onset of hyperglycemia. As compared to the administration of unmodified MSCs (FIG. 3B), which resulted in a temporary reversal of autoimmune diabetes (i.e., 3 of 9 mice were normoglycemic at 3 weeks, 2 of 9 animals were normoglycemic at 6 weeks, and all animals were hyperglycemic by 12 weeks), the infusion of FTVI-modified MSCs robustly and durably reversed hyperglycemia (FIG. 3C). Strikingly, 7 out of 8 mice were normoglycemic for 3 weeks, 6 of 8 mice remained normoglycemic for 6 weeks, and 5 of 8 mice were free of diabetes for upwards of 12 weeks following initial treatment (FIG. 3C). While the majority of the mice in the unmodified and FTVI-modified MSC group which had blood glucose levels above 600 mg/dl survived up to 90 days, only one (out of 7 mice) in the untreated group (i.e., receiving no MSCs) survived 90 days.

E-Selectin Expression and MSC Localization in the Pancreas of NOD Mice

To examine the effect of FTVI-modification on MSC trafficking to the pancreas, we first assessed the expression of E-selectin within microvasculature of the pancreas of 14-week-old NOD mice using immunofluorescence microscopy. Peri-islet microvessels are reported to be the primary site of inflammatory cell trafficking which results in insulitis [23, 24]. There was no E-selectin expression in pancreata of diabetic-resistant mice (FIG. 4A), whereas peri-islet microvessels of the pancreas of NOD mice expressed E-selectin (FIG. 4B), which co-localized with CD31 staining in sequential sections (FIGS. 4C-4D). Infiltration of T-cells into the diabetic islet margins was confirmed by CD3 staining of NOD pancreata during diabetic onset (FIG. 4E). To assess pancreatic infiltration of systemically administered FTVI-modified MSCs in NOD mice, we stained frozen sections of pancreata with antibody HECA452. As shown in FIGS. 4F-4G, HECA452$^+$ MSCs were observed in the peri-islet area within the vicinity of E-selectin-expressing microvasculature 1 day after transplantation, colonizing (E-selectin-expressing) perivascular regions and (L-selectin-expressing) areas of T cell infiltrates. To assess the extent of homing of FTVI-modified and unmodified MSCs after systemic administration, GFP-transduced FTVI-modified and unmodified MSCs were intravenously injected into NOD mice, and their pancreata, pancreatic and mesenteric lymph nodes and spleen were harvested at day 4 post-injection, sectioned, and assessed for presence of MSCs by fluorescence microscopy. FTVI-modified MSCs showed 3-fold higher infiltration of pancreas as compared to unmodified MSCs, whereas no difference in pancreatic infiltrates of infused FTVI-modified and unmodified MSC were seen in diabetes-resistant BALB/c mice (FIG. 4H). However, no difference was noted in the extent of homing of FTVI-modified and unmodified MSCs into lymphoid tissues of treated NOD mice.

Figure 5A:
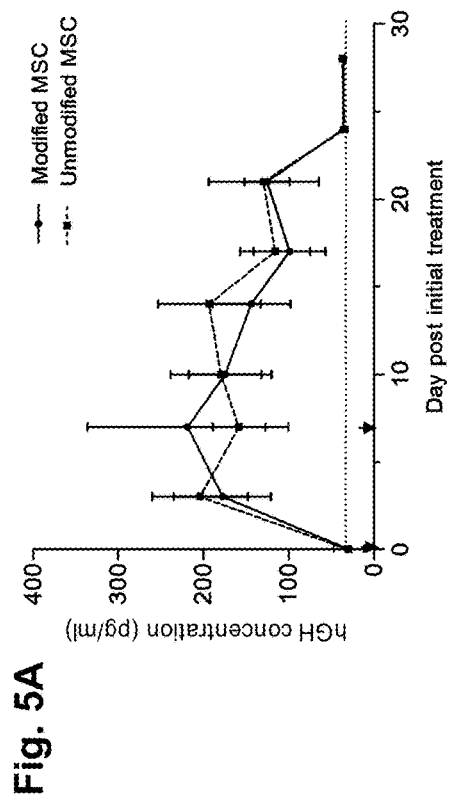
FIGS. 5A-5B. FTVI-modification of MSCs does not affect cell survival or immunosuppressive capacity.
Figure 5B:
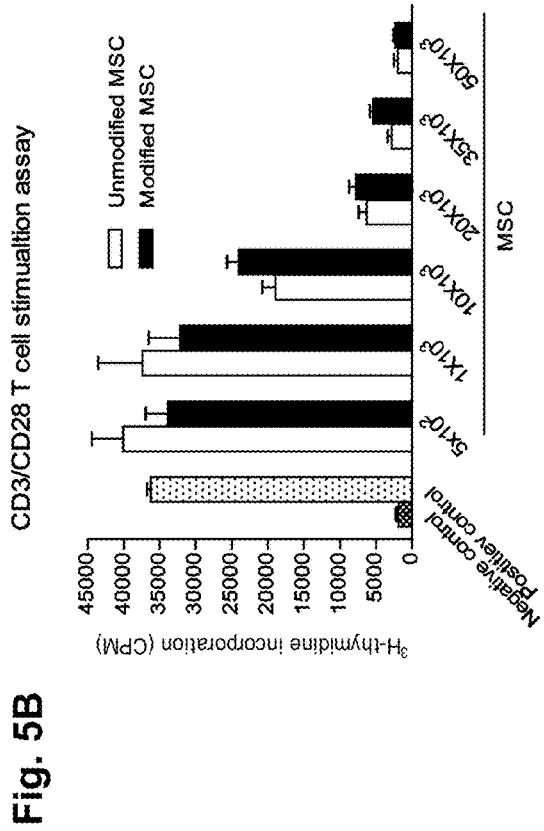

Exofucosylation has No Effect on MSC Immunosuppressive Capacity or on In Vivo Survival We have previously reported that measuring human growth hormone (hGH) produced by hGH-transduced MSCs is a sensitive method to ascertain longevity of administered MSCs[21]. To assess if the enhanced reversal of hyperglycemia of administered FTVI-modified MSCs was consequent to a survival advantage, 5×10$^5$ of hGH-transduced FTVI-modified and unmodified MSCs were injected into NOD mice at day 2 and 7 following onset of hyperglycemia, and serum hGH was measured at various timepoints post-injection. As shown in FIG. 5A, there was no difference in the pattern of hGH production, indicating that FTVI modification did not affect MSC persistence in vivo. To evaluate whether exofucosylation modifies MSC immunomodulatory capabilities, we performed co-culture T cell suppression assays. T cell proliferation was equally dampened by FTVI-modified and unmodified MSCs (FIG. 5B), indicating that exofucosylation does not impart additional immunomodulation properties on MSCs.

Figure 8:
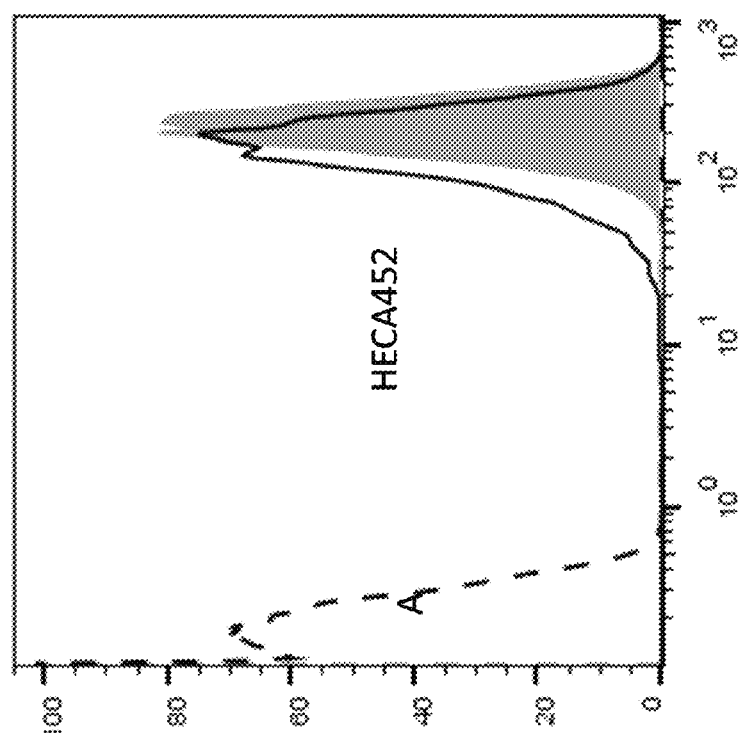
FIG. 8. FTVI modification of $CD44^{-/-}$ MSCs results in similar increase in HECA452 reactivity as wild-type (WT) MSCs. Unmodified MSC (dotted line) show no reactivity with HECA452, while FTVI-modified MSC (solid line) and FTVI-modified CD44 KO MSC (filled grey) showed similar levels of staining with HECA452, indicating that exofucosylation creates sialofucosylated epitopes on alternative (i.e., non-CD44) scaffolds in CD44 KO MSC.

Absence of MSC CD44 Expression Abrogates the Anti-diabetic Effect of FTVI-modified MSC To examine whether CD44 expression is requisite for the enhanced anti-diabetic potency of FTVI-modified MSCs, we generated MSCs from CD44 KO mice (CD44$^{-/-}$ on C57BL/6 genetic background). With exception of CD44, MSCs generated from marrow of CD44 KO mice showed identical levels of cell surface adhesion molecules. By flow cytometry, exofucosylated CD44 KO MSCs showed HECA452-reactivity equivalent to that of exofucosylated wild-type MSCs (FIG. 8), indicating that sialofucosylated determinants were created on alternative (i.e., non-CD44) scaffolds. To assess whether administration of CD44 KO MSCs conferred anti-diabetic activity, 5×10$^5$ cells each of FTVI-modified and unmodified CD44 KO and of C57BL/6 wild-type MSCs were injected into new-onset diabetic NOD mice at days 2, 7 and 30 post-hyperglycemia onset. Compared to wild-type MSCs, CD44 deficiency of MSCs resulted in a significant impairment in their anti-diabetic effect, as demonstrated by failure in reversing autoimmune diabetes in 5 out 6 mice receiving unmodified CD44 KO MSCs, and in 6 out 7 mice receiving FTVI-modified CD44 KO MSCs (FIG. 6A and FIG. 6B, respectively). Following injection in NOD mice, CFSE-labeled FTVI-modified and unmodified CD44 KO MSCs showed no difference in trafficking to pancreata (FIG. 6C), with levels similar to that observed for wild-type MSCs (FIG. 4H). MSC suppressive capacity in vitro was not abrogated by lack of MSC CD44 expression nor by exofucosylation of CD44 KO MSCs (FIG. 6D), suggesting that the absence of euglycemic effect(s) of administered FTVI-treated CD44$^{-/-}$ MSCs is not attributable to inherent deficits in immunoregulation. Notably, the finding that exofucosylation renders expression of cell surface sialofucosylations recognizable by HECA452 on CD44 KO MSCs yet such cells do not realize intended biologic outcomes in diabetic NOD mice clearly highlights the importance of biochemical studies (e.g., western blot analysis)—beyond just simple flow cytometry studies to evaluate induced E-Ig and HECA452 immunoreactivity—in defining/predicting the biologic impact of enforced selectin binding engendered by cell surface glycan engineering.

Discussion

Because of their immunomodulatory properties, safety profile, and robust expansion ex vivo, MSCs have become the focus of several human trials to treat various refractory immune-mediated diseases including T1D[6]. MSCs have been found to suppress insulitis and autoimmune diabetes via multifaceted immunomodulatory effects on pathogenic components critical to elaboration of T1D[25, 26]. These effects include the capacity to modulate expression of inflammatory vs. regulatory cytokines thereby promoting expansion of regulatory DC and T cells, and MSC expression of negative costimulatory molecules (e.g., PDL-1) which can directly inhibit autoreactive T cells [8-10,13]. Hence, MSC therapy has great potential to be an exciting and unique strategy for T1D treatment. Nevertheless, there is a pressing need for studies to improve the efficacy MSC-based therapy in T1D[6].

In prior studies, we observed that intravenous administration of fully allogenic MSCs was associated with a transient reversal of hyperglycemia in diabetic NOD mice [9]. We hypothesized that a proximate hurdle in realizing a more robust anti-diabetic effect might be the relative paucity of MSC homing to inflamed pancreas. Here, we sought to assess whether systemic administration of MSCs with enhanced homing capacity via enforced HCELL expression would influence reversal of diabetes in the NOD model. To this end, we utilized the C57BL/6 strain as the allogenic source of MSCs since the CD44 KO phenotype was available on this genetic background. We focused on metabolic control as the primary end-point for assessing the efficacy of MSC therapy, as we had previously examined the immune mechanisms mediating anti-diabetic effects of MSC [9, 10].

In contrast to other studies which characteristically assess the effects of anti-diabetic interventions for relatively short time periods (typically <30 days), in this study the effects of MSC on reversal of autoimmune diabetes were assessed over a prolonged observation period (90 days). Our data here indicate that conversion of native membrane CD44 into HCELL by cell surface α-(1,3)-exofucosylation ("FTVI-modification") confers high efficiency mouse MSC binding to E-selectin. We observed E-selectin expression in the peri-islet area of pancreata of NOD mice with insulitis, but not in pancreata of diabetic-resistant mice. Consistent with these findings, we did not observe differences in the level of homing of injected allogenic C57BL/6 FTVI-modified and unmodified MSCs into pancreata of diabetic-resistant mice (BALB/c hosts), but, compared with unmodified MSCs, there was heightened pancreatic infiltration of systemically administered C57BL/6 (allogenic) FTVI-modified MSCs in diabetic NOD mice, with concomitant durable reversal of diabetes. Notably, we did not observe differences in infiltration of lymphoid tissues between animals receiving FTVI-modified and unmodified MSCs, but there was marked increase in lodgement/engraftment of cells within the perivascular regions of E-selectin-expressing microvessels and within clusters of leukocytes. Collectively, these data draw attention to a primary role of MSC pancreatic colonization in suppressing autoimmune diabetes, but do not exclude the potential contribution of extrapancreatic effects of MSCs.

Compared to the anti-diabetic effects observed using intravenously administered fully allogenic unmodified MSCs in this study and in prior studies [9], the marked improvement in T1D reversal using fully allogeneic FTVI-modified (HCELL) MSCs observed here does not appear to be attributable to an enhanced immunosuppressive capacity of the glycoengineered MSC itself or to in vivo survival advantage endowed by glycoengineering of MSCs. In a prior study, we observed improved anti-diabetic effects in NOD mice following intravenous administration of semi-allogeneic MSCs obtained from NOR mice [10], likely a reflection of decreased rejection of the semi-allogeneic MSCs yielding improved in vivo tissue colonization/persistence of cells. However, in clinical applications, it would be advantageous to employ strategies to augment potency of fully allogeneic-source MSCs, especially as manufacturing and regulatory issues support the use of "off-the-shelf" (i.e., culture-expanded, pooled) allogeneic MSC products. The finding that exofucosylated CD44 KO MSCs lack the capacity to induce durable reversal of hyperglycemia, despite evident creation of FTVI-dependent surface sialofucosylated determinants detectable by HEC452 reactivity, indicates that E-selectin binding determinants displayed expressly on the CD44 scaffold (i.e., elaboration of HCELL) are required to achieve potent anti-diabetic effects. This may be related to a key role for HCELL expression to attain requisite tissue homing and extravasation [27] and/or could reflect a requirement for HCELL/CD44 expression to achieve appropriate lodgment in relevant microenvironmental sites [28]. A role for in situ tissue lodgment to achieve MSC effect(s) has been highlighted by studies of MSC co-transplantation with islet allografts engendering immunoprivileged zones [29-31]. In this regard, the observed localization of HCELL+ MSCs within islet perivascular areas and within islet leukocyte infiltrates highlights an operative role for HCELL in licensing immunomodulation: since E-selectin is expressed within endothelial beds of the affected tissue and leukocytes characteristically express L-selectin, expression of HCELL, a potent E-selectin and L-selectin ligand, serves to promote tissue lodgement expressly within the microenvironments of most intense immunoreactivity. While further studies of the immunomodulatory effects of MSC in vivo are warranted, the data here highlight the potential of enhanced pancreatotropism via systemic administration of HCELL+ MSCs in the therapy of T1D. More broadly, the fact that E-selectin is upregulated by cytokines such as TNF and IL-1 within endothelial beds at all inflammatory sites [17,18] offers the opportunity to exploit enforced MSC HCELL expression to improve the efficacy of MSC-based therapy for a wide variety of inflammatory conditions.

References-Example 6

1. Bresson D, von Herrath M. Immunotherapy for the prevention and treatment of type 1 diabetes: optimizing the path from bench to bedside. Diabetes Care. 2009; 32:1753-1768.
2. Ludvigsson J, Krisky D, Casas R et al. GAD65 antigen therapy in recently diagnosed type 1 diabetes mellitus. N Engl J Med. 2012; 366:433-442.
3. Bonifacio E. Immunotherapy in type 1 diabetes: a shorter but more winding road? Diabetes. 2012; 61:2214-2215.
4. Prockop D J, Brenner M, Fibbe W E et al. Defining the risks of mesenchymal stromal cell therapy. Cytotherapy. 2010; 12:576-578.
5. Dazzi F, van Laar J M, Cope A et al. Cell therapy for autoimmune diseases. Arthritis Res Ther. 2007; 9:206.
6. Abdi R, Fiorina P, Adra C N et al. Immunomodulation by mesenchymal stem cells: a potential therapeutic strategy for type 1 diabetes. Diabetes. 2008; 57:1759-1767.
7. Tyndall A, Houssiau F A. Mesenchymal stem cells in the treatment of autoimmune diseases. Ann Rheum Dis. 2010; 69:1413-1414.
8. Madec A M, Mallone R, Afonso G et al. Mesenchymal stem cells protect NOD mice from diabetes by inducing regulatory T cells. Diabetologia. 2009; 52:1391-1399.
9. Fiorina P, Jurewicz M, Augello A et al. Immunomodulatory function of bone marrow-derived mesenchymal stem cells in experimental autoimmune type 1 diabetes. J Immunol. 2009; 183:993-1004.
10. Jurewicz M, Yang S, Augello A et al. Congenic mesenchymal stem cell therapy reverses hyperglycemia in experimental type 1 diabetes. Diabetes. 2010; 59:3139-3147.
11. Bassi E J, Moraes-Vieira P M, Moreira-Sa C S et al. Immune regulatory properties of allogeneic adipose-derived mesenchymal stem cells in the treatment of experimental autoimmune diabetes. Diabetes. 2012; 61:2534-2545.
12. Kota D J, Wiggins L L, Yoon N et al. TSG-6 produced by hMSCs delays the onset of autoimmune diabetes by suppressing Th1 development and enhancing tolerogenicity. Diabetes. 2013; 62:2048-2058.
13. Borg D J, Weigelt M, Wilhelm C et al. Mesenchymal stromal cells improve transplanted islet survival and islet function in a syngeneic mouse model. Diabetologia. 2014; 57:522-531.
14. Lee R H, Seo M J, Reger R L et al. Multipotent stromal cells from human marrow home to and promote repair of pancreatic islets and renal glomeruli in diabetic NOD/scid mice. Proc Natl Acad Sci USA. 2006; 103:17438-17443.
15. Montane J, Bischoff L, Soukhatcheva G et al. Prevention of murine autoimmune diabetes by CCL22-mediated Treg recruitment to the pancreatic islets. J Clin Invest. 2011; 121:3024-3028.

16. Amado L C, Saliaris A P, Schuleri K H et al. Cardiac repair with intramyocardial injection of allogeneic mesenchymal stem cells after myocardial infarction. Proc Natl Acad Sci USA. 2005; 102:11474-11479.

17. Sackstein R. Glycosyltransferase-programmed stereosubstitution (GPS) to create HCELL: engineering a roadmap for cell migration. Immunol Rev. 2009; 230:51-74.

18. Bevilacqua M P, Stengelin S, Gimbrone M A Jr, Seed B. Endothelial leukocyte adhesion molecule 1: an inducible receptor for neutrophils related to complement regulatory proteins and lectins. Science. 1989; 243:1160-5.

19. Sackstein R, Merzaban J S, Cain D W et al. Ex vivo glycan engineering of CD44 programs human multipotent mesenchymal stromal cell trafficking to bone. Nat Med. 2008; 14:181-187.

20. Kang S K, Shin I S, Ko M S et al. Journey of mesenchymal stem cells for homing: strategies to enhance efficacy and safety of stem cell therapy. Stem Cells Int. 2012; Article ID 342968.

21. El Haddad N, Heathcote D, Moore R et al. Mesenchymal stem cells express serine protease inhibitor to evade the host immune response. Blood. 2011; 117:1176-1183.

22. Lee R H, Kim B, Choi I et al. Characterization and expression analysis of mesenchymal stem cells from human bone marrow and adipose tissue. Cell Physiol Biochem. 2004; 14:311-324.

23. Stranford S, Ruddle N H. Follicular dendritic cells, conduits, lymphatic vessels, and high endothelial venules in tertiary lymphoid organs: Parallels with lymph node stroma. Front Immunol. 2012; 3:350.

24. Korpos E, Kadri N, Kappelhoff R et al. The peri-islet basement membrane, a barrier to infiltrating leukocytes in type 1 diabetes in mouse and human. Diabetes. 2013; 62:531-542.

25. Dazzi F, Lopes L, Weng L. Mesenchymal stromal cells: a key player in 'innate tolerance'? Immunology. 2012; 137:206-213.

26. Uccelli A, Moretta L, Pistoia V. Mesenchymal stem cells in health and disease. Nat Rev Immunol. 2008; 8:726-36.

27. Thankamony S P, Sackstein R. Enforced hematopoietic cell E- and L-selectin ligand (HCELL) expression primes transendothelial migration of human mesenchymal stem cells. Proc Natl Acad Sci USA. 2011; 108:2258-2263.

28. Zhu H, Mitsuhashi N, Klein A et al. The role of the hyaluronan receptor CD44 in mesenchymal stem cell migration in the extracellular matrix. Stem Cells. 2006; 24:928-935.

29. Ding Y, Xu D, Feng G et al. Mesenchymal stem cells prevent the rejection of fully allogenic islet grafts by the immunosuppressive activity of matrix metalloproteinase-2 and -9. Diabetes. 2009; 58:1797-1806.

30. Berman D M, Willman M A, Han D et al. Mesenchymal stem cells enhance allogeneic islet engraftment in nonhuman primates. Diabetes. 2010; 59:2558-2568.

31. Yeung T Y, Seeberger K L, Kin T et al. Human mesenchymal stem cells protect human islets from pro-inflammatory cytokines. PLoS ONE. 2012; 7:e38189.

Example 7

Cell Surface Glycan Engineering of Neural Stem Cells Augments Neurotropism and Improves Recovery in a Murine Model of Multiple Sclerosis Introduction Nature has developed an extremely efficient mechanism to deliver circulating cells to sites of inflammation and injury. This process is controlled by a highly ordered cascade of molecular interactions (Butcher, E. C. 1991; Sackstein, R. 2005; Springer, T. A. 1994). The first essential event in cell recruitment involves shear-resistant adhesion of flowing cells on the endothelial surface, a process most efficiently mediated by selectins, a family of three $Ca^{2+}$ dependent lectins (comprised of E-, P-, and L-selectin), binding to their respective counter-receptors. These interactions initially tether the cell to the vessel wall and, in the context of vascular shear flow, cause the cell to roll along the endothelial surface at velocities below that of the prevailing hemodynamic stream (Step 1). This process facilitates engagement of specific cell-borne chemokine receptors to pertinent chemokines present in the perivascular areas, thereby triggering inside-out signal transduction events leading to increased adhesiveness of integrin family members (Step 2). Adhesive interactions between the activated cell integrins and their cognate endothelial cell counter-receptors then leads to arrest of rolling and firm adhesion of the cell to the vessel wall (Step 3), and, ultimately, transendothelial migration (extravasation, Step 4).

In multiple sclerosis (MS), and in its animal model, experimental autoimmune encephalomyelitis (EAE), recruitment of immunologic effectors is mediated by the upregulation of the vascular selectins, E- and P-selectin. E- and P-selectin are expressed on brain endothelium after in vivo activation with LPS or TNF-α, however, in murine EAE, P-selectin is expressed only transiently (Piccio, L., Rossi, B., et al. 2002). Notably, E-selectin is expressed throughout the inflammatory period with a patchy distribution at sites where vessels branch, suggesting the existence of preferential recruitment areas (Piccio, L., Rossi, B., et al. 2002). E-selectin is also characteristically found in vessels from acute plaques in MS patients (Lee, S. J. and Benveniste, E. N. 1999; Washington, R., Burton, J., et al. 1994). These findings suggest that E-selectin plays a dominant role in the recruitment of circulating cells to the brain in inflammatory diseases.

All three selectins bind to specialized carbohydrate determinants, comprised of sialofucosylations containing an α(2,3)-linked sialic acid substitution on galactose, and an α(1,3)-linked fucose modification on N-acetylglucosamine, prototypically displayed as the terminal tetrasaccharide sialyl Lewis X (sLe$^x$) (Polley, M. J., Phillips, M. L., et al. 1991; Sackstein, R. 2005). This structure, also known as "CD15s", may be displayed on either a protein scaffold (i.e., a glycoprotein) or a lipid scaffold (i.e., a glycolipid), and is recognized by mAb such as CSLEX-1 and HECA-452 (Alon, R., Feizi, T., et al. 1995; Dimitroff, C. J., Lee, J. Y., et al. 2001; Fuhlbrigge, R. C., Kieffer, J. D., et al. 1997; Gadhoum, S. Z. and Sackstein, R. 2008; Merzaban, J. S., Burdick, M. M., et al. 2011). Although additional structural modifications principally involving sulfation increase binding affinity of P- and L-selectin to sLe$^x$, no such modifications are needed for optimal binding of E-selectin (Leppanen, A., White, S. P., et al. 2000; Rosen, S. D. 2004).

Neural stem cell (NSC)-based therapy has generated great hope for halting and/or reversing disease progression in CNS inflammatory and/or degenerative diseases (Ben-Hur, T., Einstein, O., et al. 2003; Einstein, O., Fainstein, N., et al. 2007; Einstein, O., Grigoriadis, N., et al. 2006; Imitola, J., Raddassi, K., et al. 2004; Lee, S. T., Chu, K., et al. 2008; Pluchino, S., Quattrini, A., et al. 2003; Pluchino, S., Zanotti, L., et al. 2005; Ziv, Y., Avidan, H., et al. 2006). It is well known that NSCs express Step 2 and Step 3/4 effectors, such as CXCR4 (Bezzi, P., Domercq, M., et al. 2001; Flax, J. D., Aurora, S., et al. 1998; Imitola, J., Raddassi, K., et al. 2004) and VLA-4 (Pluchino, S., Zanotti, L., et al. 2005; Rampon, C., Weiss, N., et al. 2008), respectively, but there are no data on whether NSCs natively express Step 1 effectors. Accordingly, we examined expression of Step 1 effectors on mouse NSCs, and found that these cells are conspicuously devoid of Step 1 effectors, in particular, E-selectin ligands. Using the EAE model, we analyzed whether enforced E-selectin ligand activity via cell surface glycan engineering would impact migration of administered NSCs and, more importantly, the therapeutic effect(s) of administered cells. To this end, we utilized a technology called glycosyltransferase-programmed stereosubstitution (GPS) to create relevant selectin-binding glycan determinants on the cell surface (Sackstein, R., Merzaban, J. S., et al. 2008). We report here that GPS enforces expression of E-selectin ligands on NSCs by modifying glycans of two neural stem cell membrane glycoproteins, CD44 and of NCAM, creating the E-selectin ligands HCELL (Hematopoietic Cell E-/L-selectin Ligand) and NCAM-E, respectively. Glycoengineering of NSC E-selectin ligand activity resulted in increased neurotropism and yielded improved clinical outcome in EAE in absence of detectable long-term engraftment, indicating that these tissue-specific stem cells engendered a restorative effect, not a direct regenerative effect. Importantly, this neurorestorative effect is not a universal property of adult stem cells, as administration of GPS-engineered mouse hematopoietic stem/progenitor cells (HSPC) did not improve EAE clinical course. These findings have profound clinical implications in providing the first direct evidence that cell surface glycoengineering to create effectors of cell migration can improve the efficacy of stem cell-based therapeutics, and also provide new perspectives on the use of NSCs in the treatment of neuroinflammatory diseases.

Results

Expression of Molecular Effectors of Cell Migration on Neural Stem Cells

Figure 9A:
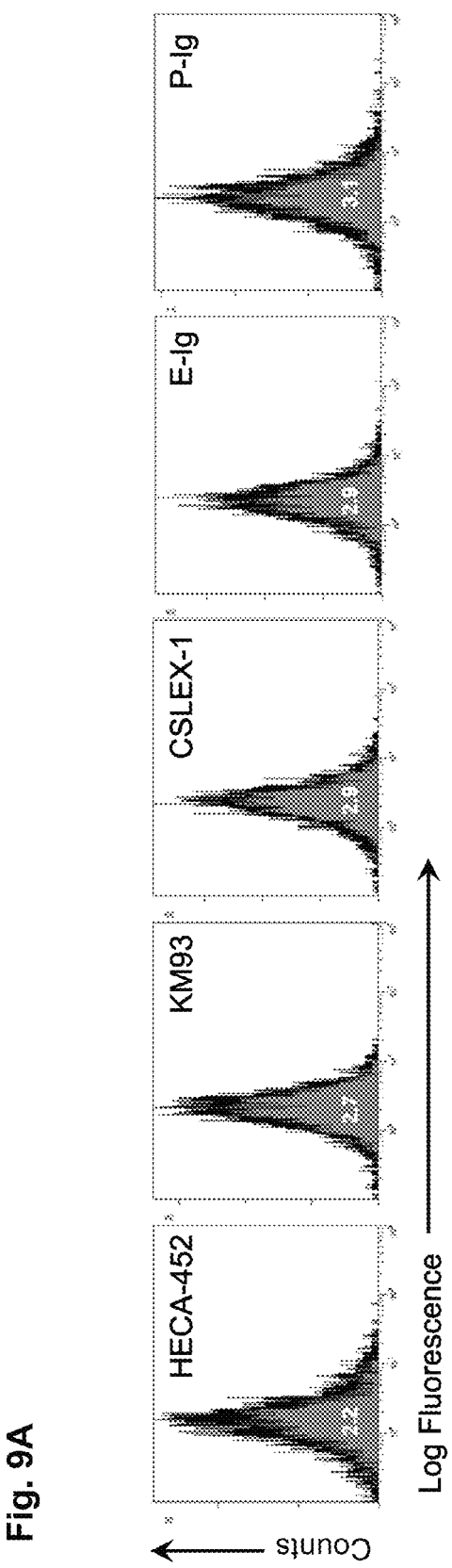
FIGS. 9A-9B: Neural stem cells (NSCs) lack E-selectin ligands but express a number of other cell surface adhesion molecules.
Figure 9B:
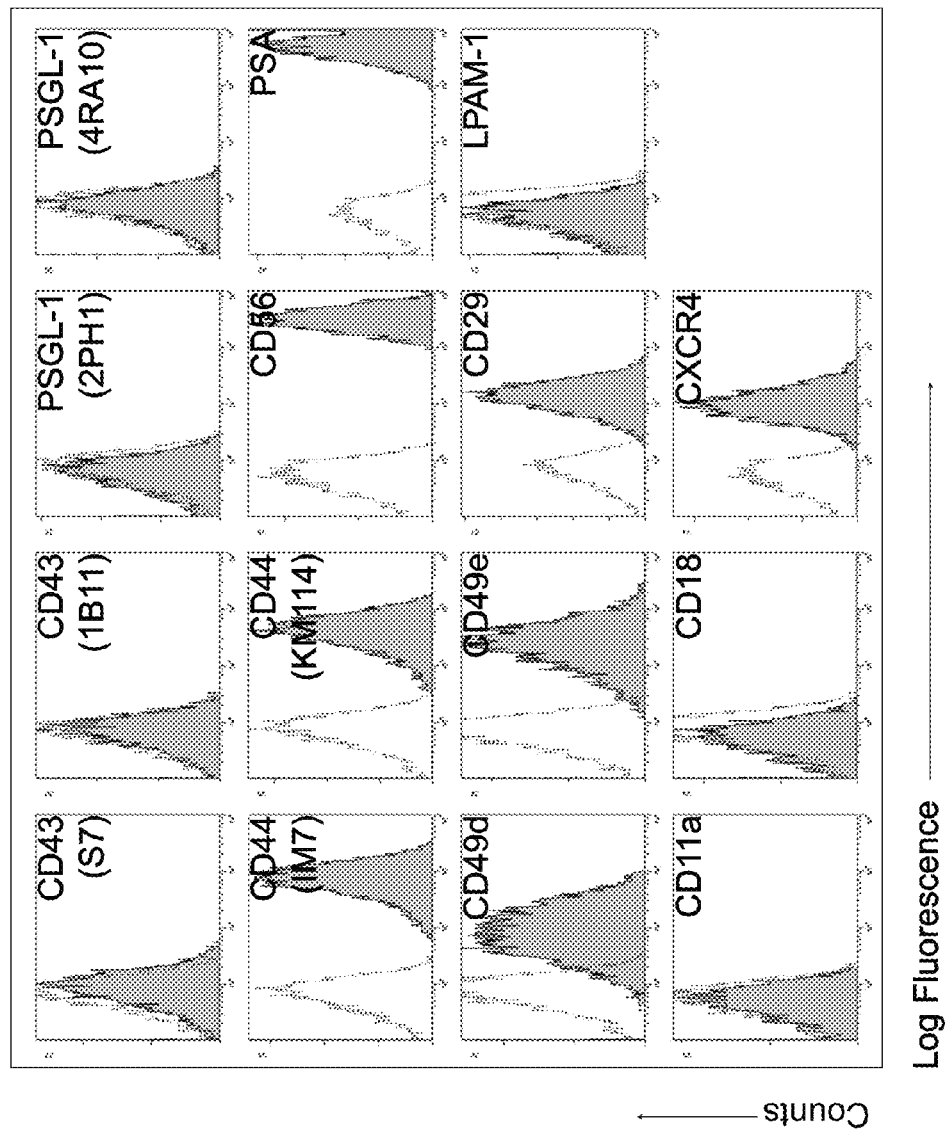
Figure 15:
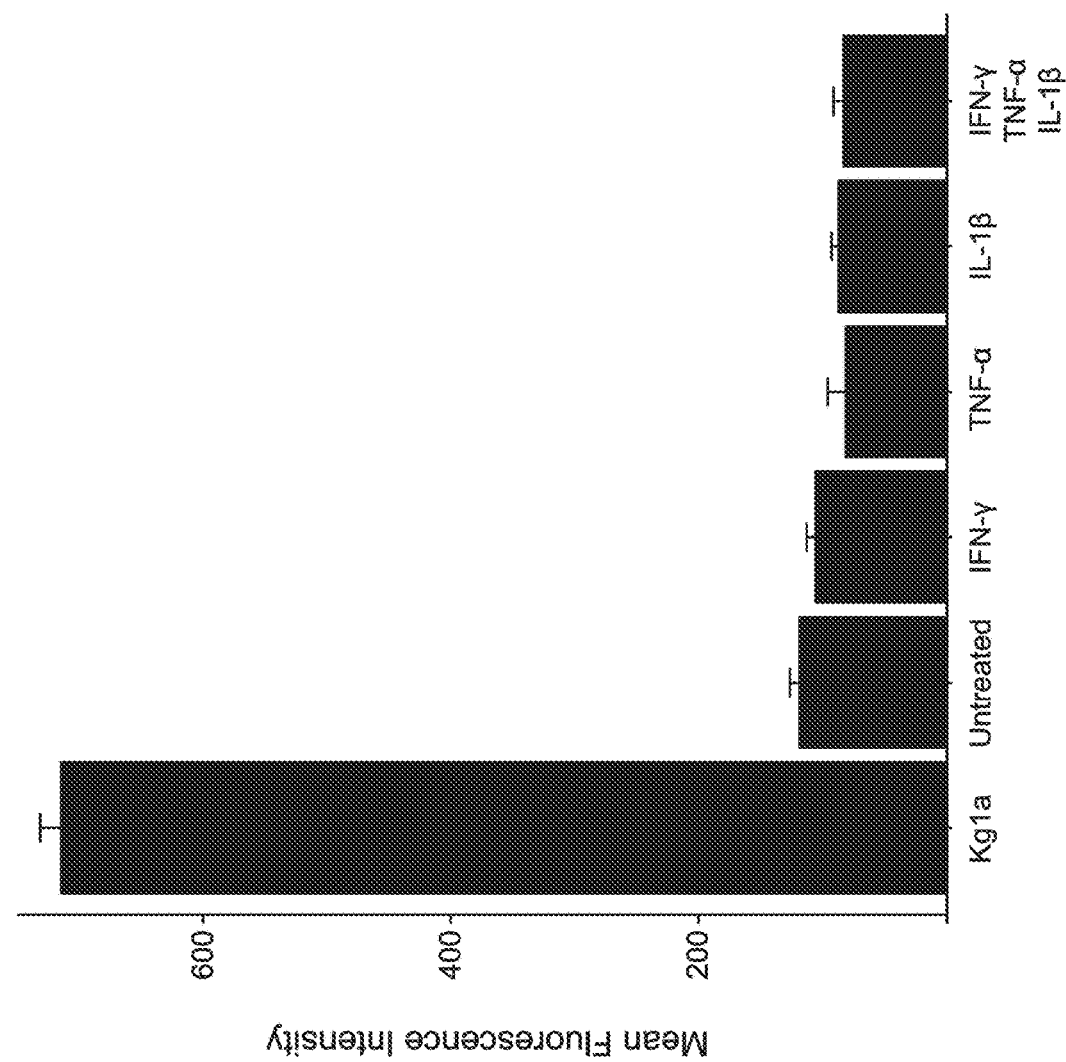
FIG. 15: Inflammatory cytokine treatment does not induce selectin ligand expression on mouse NSCs. NSCs were stimulated with 10 ng/ml of TNFα, 10 ng/ml IL-1β, 10 ng/ml IFNγ independently or in combination (all at 10 ng/ml). At 24 h, NSCs were harvested and analyzed by flow cytometry for E-selectin binding. Controls included untreated NSCs and Kg1a cells (positive control for E-selectin binding).

To analyze expression of molecular effectors of Step 1, Step 2 and Step 3/4 of cell migration, flow cytometry was performed on primary cultures of mouse NSCs. NSCs were devoid of reactivity with E-selectin-Ig chimera (E-Ig) and P-selectin-Ig chimera (P-Ig), indicating absence of E- and P-selectin ligands (FIG. 9A) even in the presence of inflammatory mediators (FIG. 15); they also did not stain with mAb CSLEX1, KM93, or HECA452 (each of which identify sLe$^x$). NSCs expressed CD44 and the integrins VLA-4 (CD49d/CD29) and VLA-5 (CD49e/CD29), as well as the chemokine receptor CXCR4; this pattern of NSC marker expression has been observed by others (Back, S. A., Tuohy, T. M., et al. 2005; Campos, L. S., Decker, L., et al. 2006; Campos, L. S., Leone, D. P., et al. 2004; Imitola, J., Raddassi, K., et al. 2004; Ji, J. F., He, B. P., et al. 2004; Leone, D. P., Relvas, J. B., et al. 2005; Pluchino, S., Quattrini, A., et al. 2003; Pluchino, S., Zanotti, L., et al. 2005) (FIG. 9B). The NSCs also characteristically expressed Neural Cell Adhesion Molecule (NCAM) in addition to the well-described polysialic acid (PSA) (Vitry, S., Avellana-Adalid, V., et al. 2001) (FIG. 9B). NSCs did not express PSGL-1, CD43, LFA-1 (lacking both CD11a ($\alpha_1$) and CD18 ($\beta_2$) chains), and LPAM-1 ($\alpha_4\beta_7$) (FIG. 9B). These results indicate that NSCs are deficient in expression of Step 1 effectors of the multistep cascade of cell transmigration, yet express chemokine receptors and relevant integrin effectors that mediate Steps 2-4 in extravasation and that are also involved in their mobilization in the developing brain via radial migration (Imitola, J., Comabella, M., et al. 2004).

GPS Enforces E-selectin Ligand Activity on Neural Stem Cells

Figure 10A:
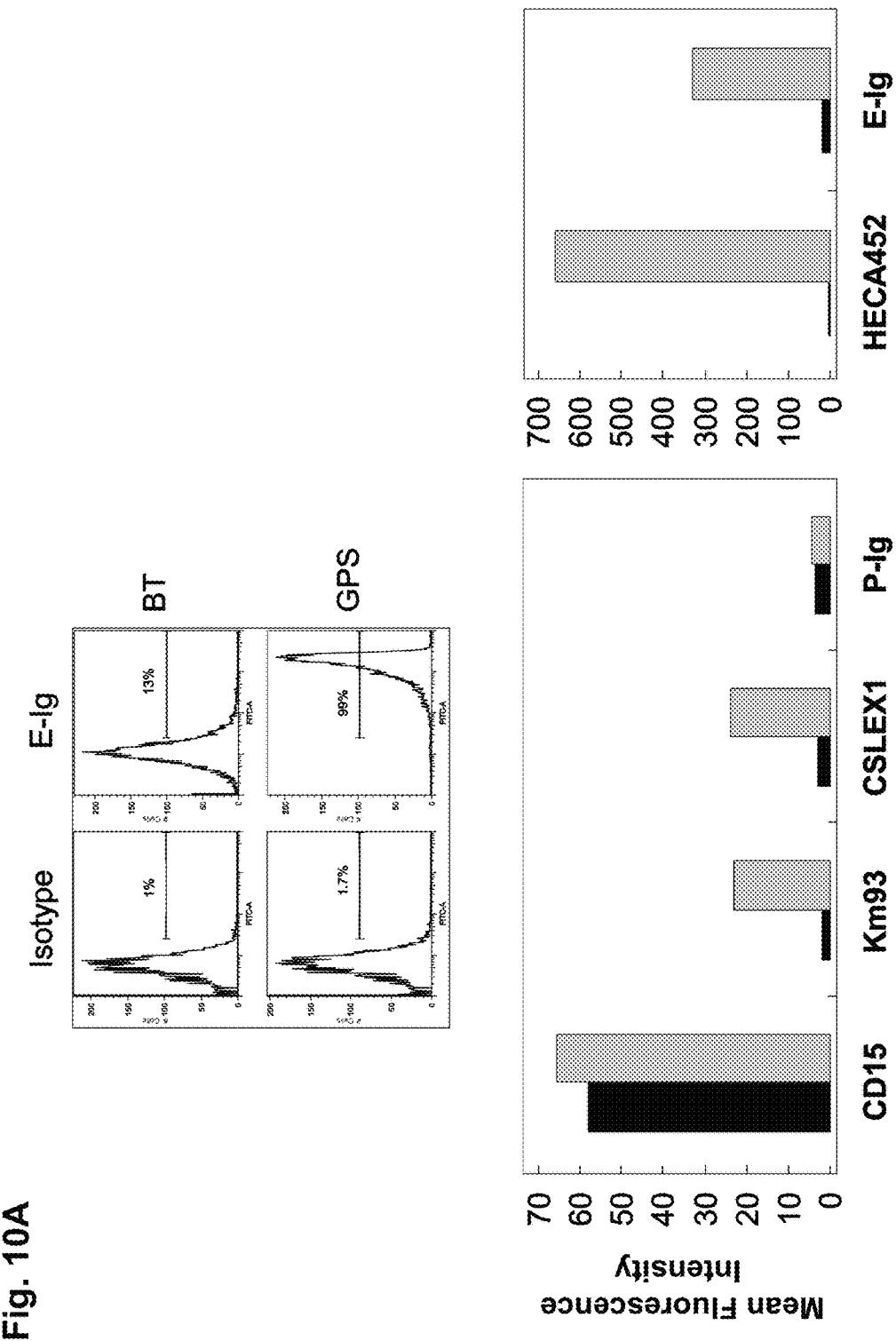
FIGS. 10A-10C: GPS treatment (i.e., α(1,3)-exofucosylation via FTVI treatment) of NSCs generates sialofucosylations mainly on glycoproteins, some of which are glycophosphatidylinositol (GPI)-linked.
Figure 10B:
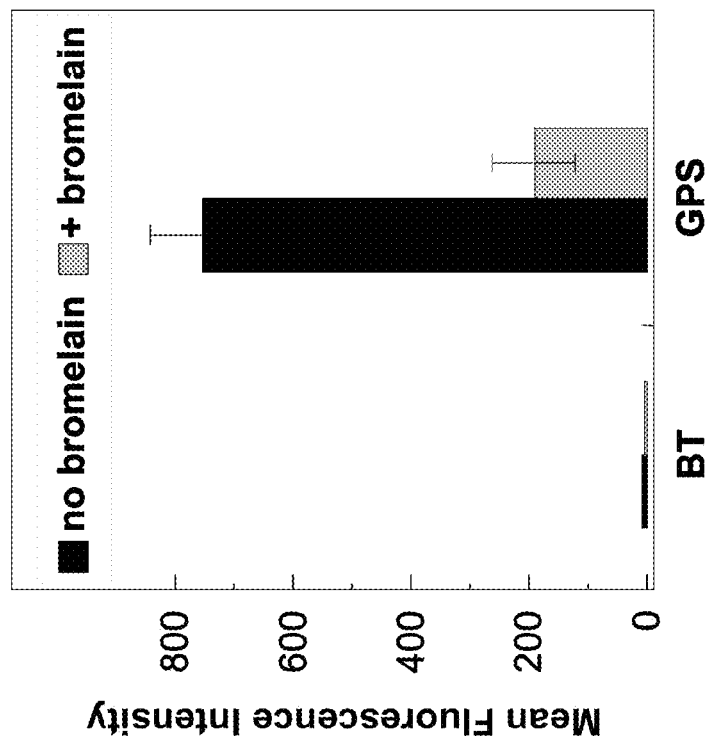

CD44, a molecule involved in migration of NSCs (Deboux, C., Ladraa, S., et al. 2013) and brain cancer stem cells (Fu, J., Yang, Q. Y., et al. 2013), is strongly expressed among NSCs in culture (FIG. 9B). However, the finding that NSC lack E-selectin binding (FIG. 9A) indicates that these cells do not natively express the E-selectin binding glycoform of CD44 known as HCELL (Dimitroff, C. J., Lee, J. Y., et al. 2000; Dimitroff, C. J., Lee, J. Y., et al. 2001; Sackstein, R. 2004). We thus sought to determine whether a non-genetic manipulation using glycosyltransferase-programmed stereosubstitution (GPS) of CD44 glycans would enforce HCELL expression (Sackstein, R., Merzaban, J. S., et al. 2008). To this end, we treated NSCs with the $\alpha(1,3)$-linkage-specific fucosyltransferase, fucosyltransferase VI (FTVI). This enzyme specifically places a fucose onto a terminal type 2-lactosamine unit; if that lactosamine is capped with an $\alpha(2,3)$-linked sialic acid, sLe$^x$ is created. Following FTVI treatment of NSCs (GPS-NSC), reactivity with mAbs CSLEX1, KM93 and HECA452 was induced, consistent with strong expression of sLe$^x$ epitopes (FIG. 10A), with associated E-Ig binding (FIG. 10A) but without induction of P-Ig binding (FIG. 10A). Notably, expression of CD15 (also known as SSEA-1 or Le$^x$) is high in NSCs (FIG. 10A), and although FTVI can fucosylate unsialylated terminal lactosamines thereby yielding CD15 (SSEA-1), the expression of CD15 was unchanged following enforced fucosylation (FIG. 10A). Altogether, these data indicate that $\alpha(1,3)$-exofucosylation only occurred on sialylated lactosaminyl glycans. Bromelain digestion of NSCs prior to GPS treatment markedly reduced HECA452 reactivity (FIG. 10B), demonstrating that glycoproteins, not glycolipids, were the predominant carriers of sialofucosylated determinants. Treatment of GPS-NSCs with phosphatidylinositol phospholipase C (PI-PLC) resulted in a modest but significant decrease in the HECA452 signal by FACS (FIG. 10C), indicating that a minor population of sLe$^x$-decorated glycoproteins are glycophosphatidyl (GPI)-linked.

Figure 10C:
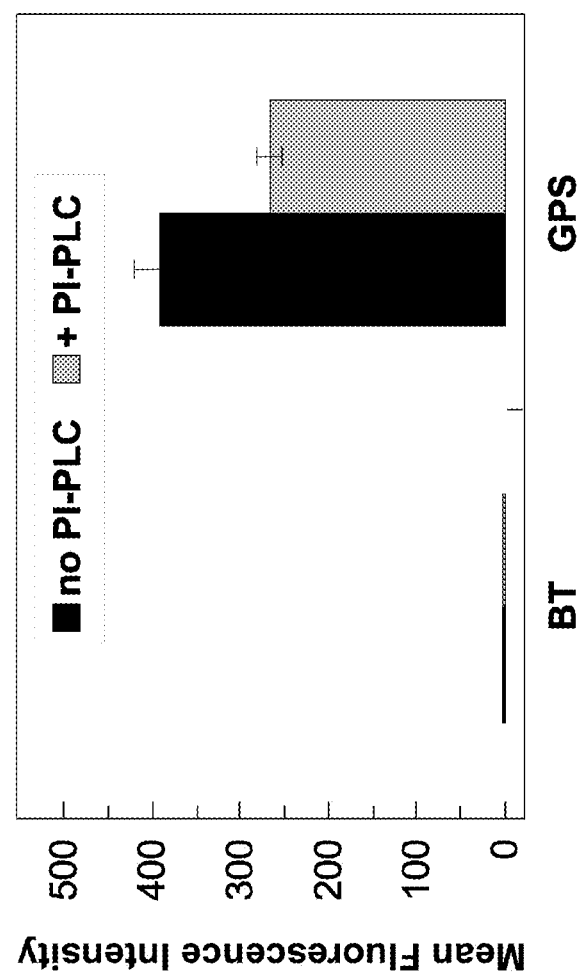
Figure 11A:
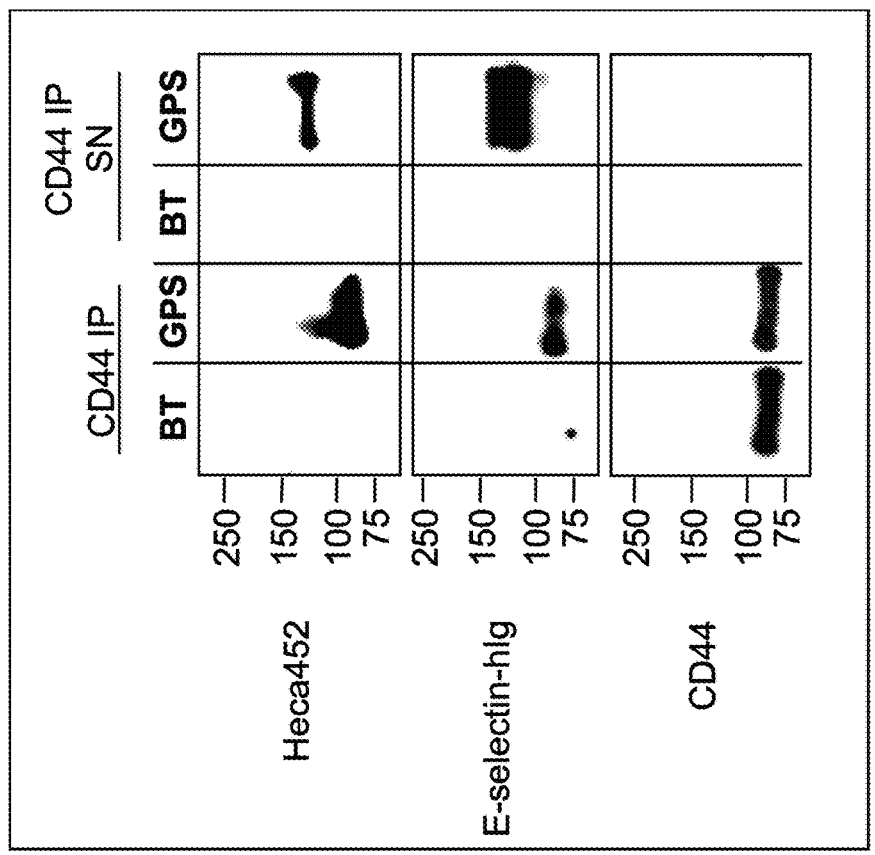
FIGS. 11A-11C: GPS treatment of NSCs creates transient E-selectin ligands at 100, 120 and 140-kDa which correspond to HCELL and N-CAM-E.
Figure 11B:
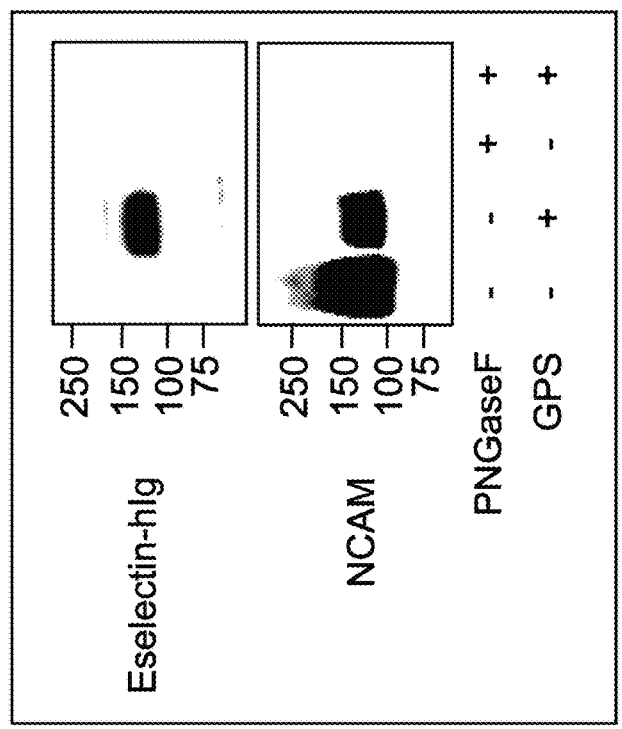
Figure 16C:
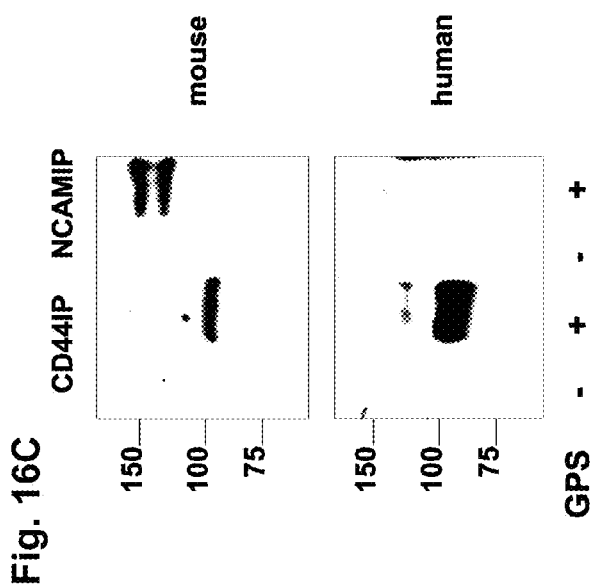
FIGS. 16A-16C: HCELL is the only E-selectin ligand created by GPS treatment in one (exemplary) human NSC line (CC-2599).
Figure 16A:
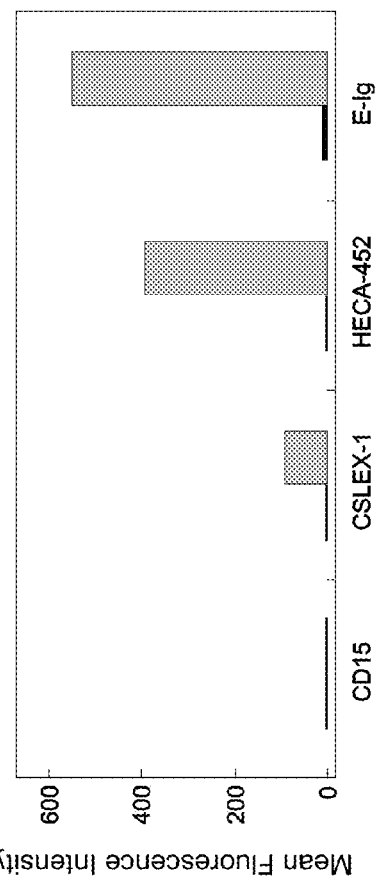
Figure 16B:
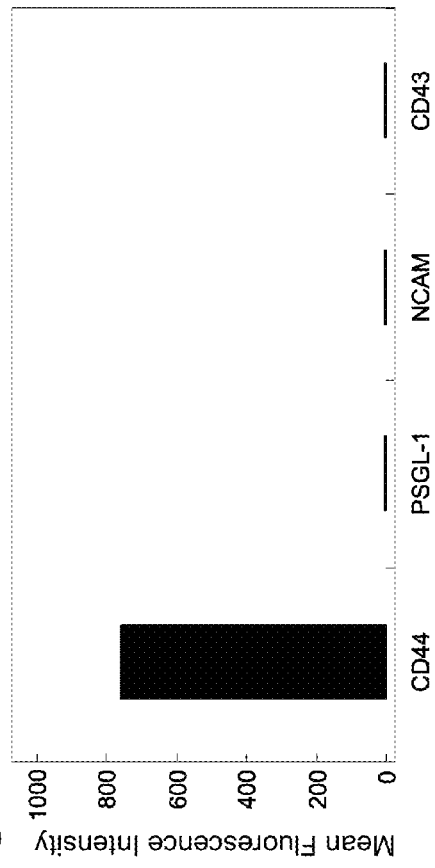

Western blot of cell lysates and of immunoprecipitated CD44 from GPS-NSCs revealed that one of the glycoproteins decorated with the essential sialofucosylations recognized by HECA452 was the standard, unspliced, form of CD44 (~100 kDa; FIG. 11A), and CD44 also reacted with E-Ig (FIG. 11A). However, following exhaustive immunoprecipitation of CD44, other candidate glycoprotein E-selectin ligand(s) were identified by evidence of reactivity with E-Ig and HECA452 in the residual supernatant fraction. Two bands were apparent at ~120 and ~140 kDa. Based on the molecular weight profile of these bands (FIG. 11A) and the partial PI-PLC sensitivity of E-selectin binding (FIG. 10C), a characteristic of the 120 kDa form of NCAM (Gascon, E., Vutskits, L., et al. 2007; Maness, P. F. and Schachner, M. 2007; Rutishauser, U. 2008), we speculated that NCAM could be serving as an additional E-selectin ligand. We thus performed immunoprecipitation with a pan-NCAM mAb, and observed that the residual bands persisting after exhaustive immunoprecipitation of CD44 were indeed those of NCAM (FIG. 11B). To determine if the relevant sialofucosylations on NCAM were displayed on N-glycans, we tested E-Ig reactivity on western blot of lysates of GPS-NSCs following digestion with N-glycosidase F (FIG. 11A); no evident staining with E-Ig following digestion was observed, indicBing that the relevant E-selectin binding determinant(s) are displayed on N-glycans. The contribution of the GPI-anchored form of NCAM-E to overall sLe$^x$ expression after enforced fucosylation of NSC is modest, as shown by a small decrease in HECA452 signal (and E-Ig signal—data not shown) following PI-PLC treatment (FIG. 10C). Therefore, enforced α(1,3)-fucosylation of murine NSCs created HCELL as well as a unique E-selectin ligand reactive form of the neural precursor molecule NCAM, which we named "NCAM-E". Interestingly, human NSCs (CC-2599) only express HCELL and not NCAM-E following GPS treatment (FIGS. 16A-16C).

Figure 11C:
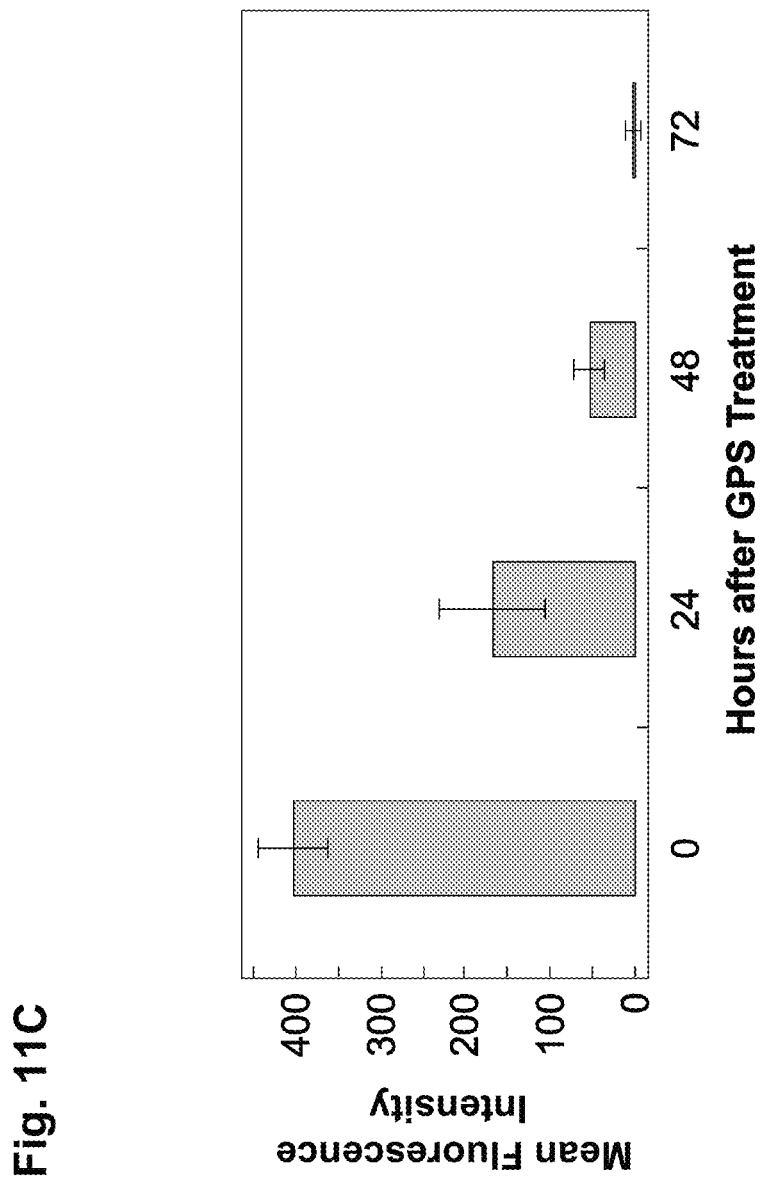
Figure 17:
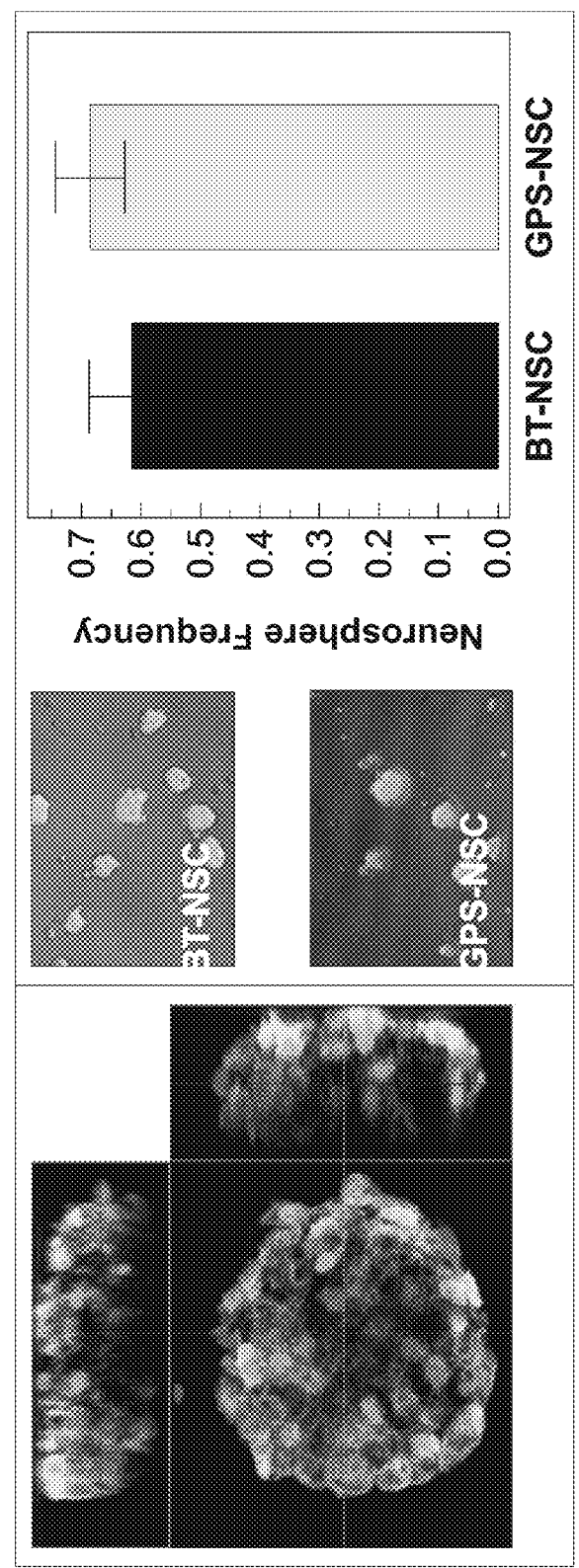
FIG. 17: GPS treatment does not affect of the ability of NSCs to form neurospheres. 200 viable GFP+ NSCs were plated per well in a 96 well plate immediately following GPS treatment for 7 days. The resulting neurospheres were counted and neurosphere frequency was calculated as the number of neurospheres divided by number of cells plated. There was no statistically significant difference in the density of neurospheres or the number of neurospheres formed between BT-NSCs and GPS-NSCs. A representative image of the GFP+ neurospheres used for these experiments is shown where the red fluorescence indicates Nestin expression and the green fluorescence indicates GFP. Note that BT- and GPS-GFP+ NSCs were both able to form neurospheres equally. This figure is related to FIGS. 11A-11C.
Figure 18B:
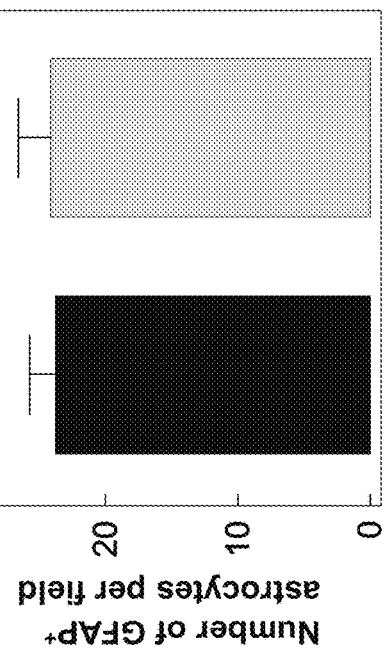
FIGS. 18A-18D: GPS treatment does not affect the differentiation capacity of NSCs into neurons (FIG. 18A), astrocytes (FIGS. 18B, 18D) or oligodendrocyte precursors (FIGS. 18C, 18D). $1 \times 10^5$ BT- and GPS-NSC were cultured in the appropriate differentiation media and after 120 hours, numbers of MAP-2+ neurons (FIG. 18A), GFAP+ astrocytes (FIGS. 18B, 18D), and NG2+ oligodendrocytes (FIG. 18C) were counted per 20× vision field. There was no statistically significant difference between the ability of BT and GPS-NSCs to differentiate along these three lineages (p=0.1).
Figure 18C:
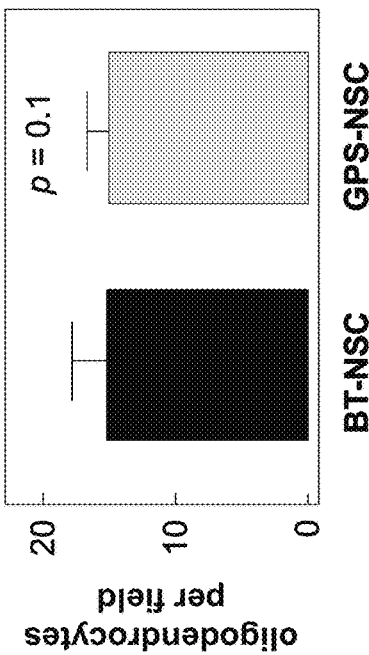
Figure 18A:
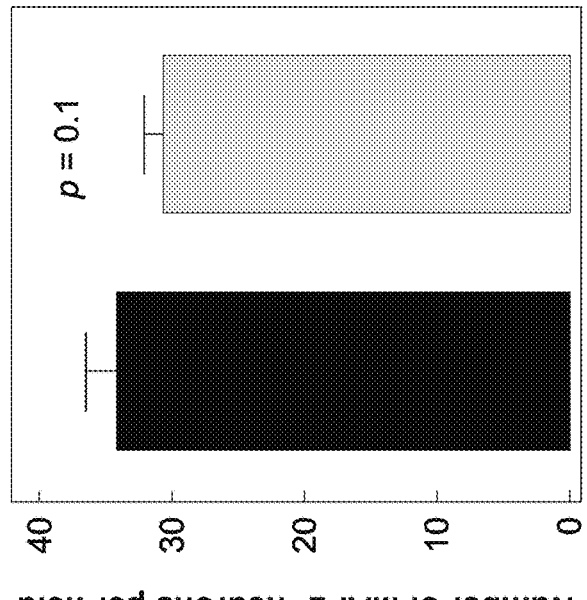
Figure 18D:
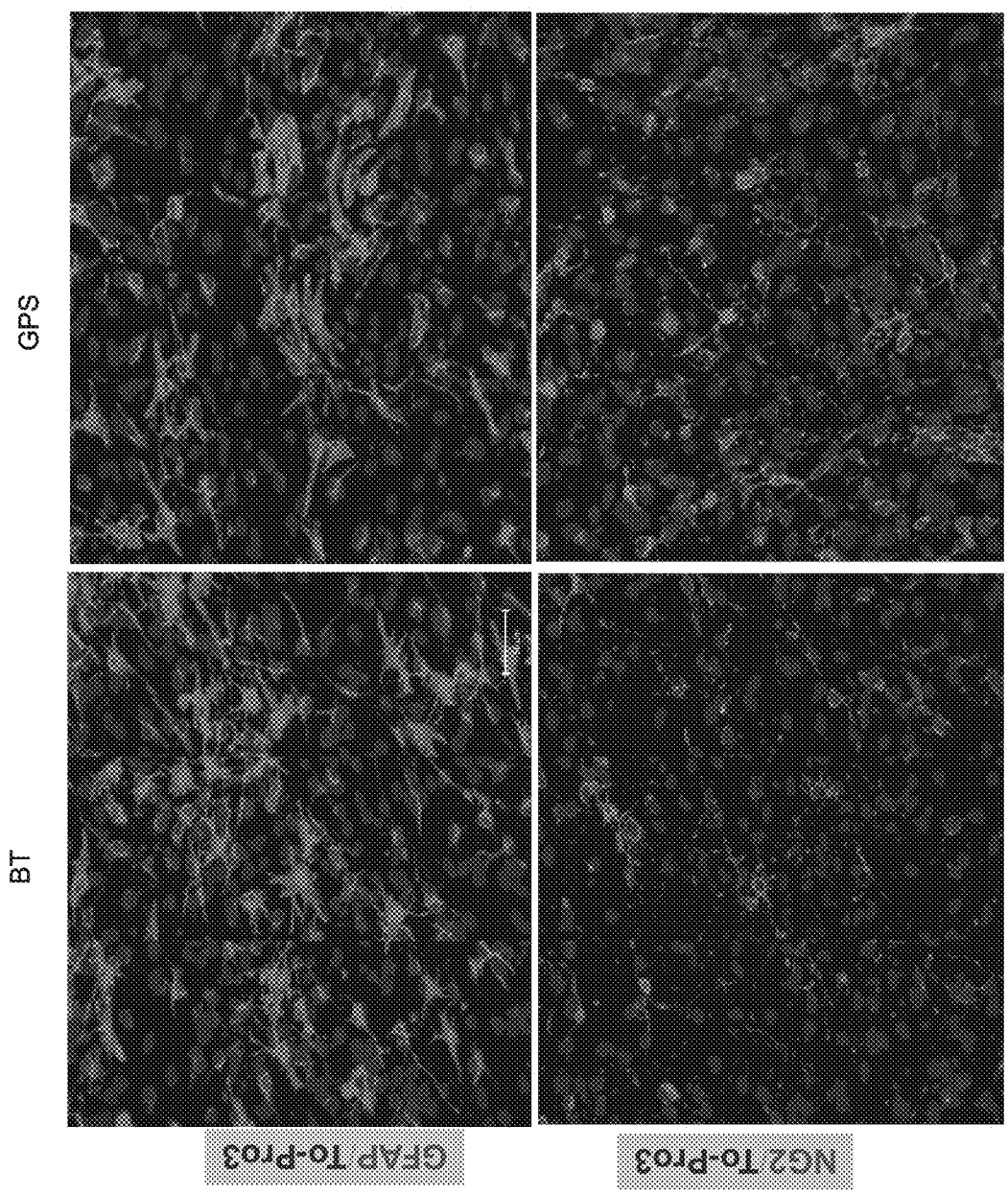

To assess the stability of GPS-engineered E-selectin ligand activity on NSCs, we measured E-Ig reactivity by flow cytometry at 24 h intervals following enforced exofucosylation. E-selectin ligand activity was stable for up to 24 h, subsequently declining to undetectable levels by 72 h, presumably due to turnover of surface protein (FIG. 11C). NSC viability (FIG. 17) was unaffected by enforced exofucosylation and there were no differences in the number or proliferation of neurospheres in clonogenic assays or in differentiation of NSCs (FIGS. 18A-18D). Thus, there were no evident phenotypic differences induced by GPS treatment of NSCs, except for creation of E-selectin ligands.

Figure 19A:
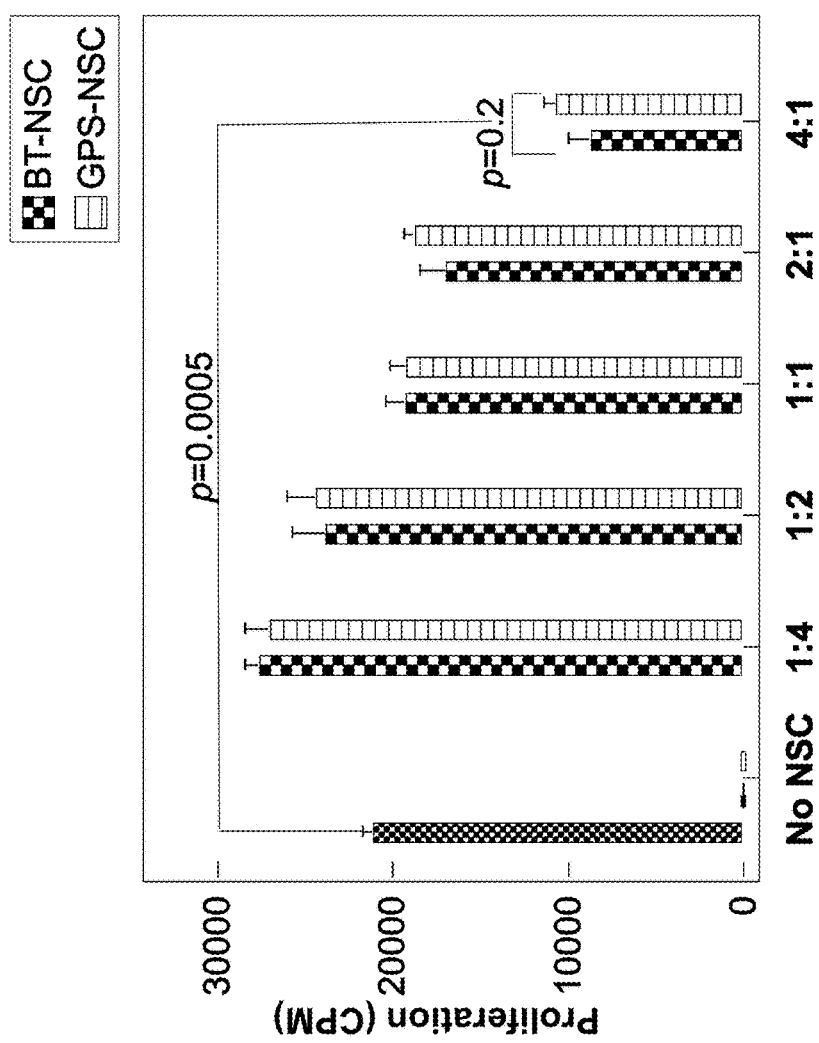
FIGS. 19A-19C: GPS treatment does not affect the immunomodulation function of NSCs in vitro. Direct in vitro suppressive effects of NSCs on lymph node cells (LNCs) were measured by coculturing irradiated NSCs with LNCs isolated from naïve C57BL/6 mice. Both irradiated BT-NSC and GPS-NSC suppressed $^3$H-thymidine incorporation (FIG. 19A) into LNCs in response to concanavalin A (ConA) in a dose-dependent manner and also suppress inflammatory cytokine production (FIG. 19B) as measured by ELISA to an equal degree; the ratios correspond to numbers of NSCs to numbers of LNCs (1:4, 1:2, 1:1, 2:1, and 4:1). Note that by increasing the ratio of NSC:LNC compared to LNC alone (first bar), the amount of $^3$H-thymidine incorporation decreased significantly (p=0.0005). Also note that there was no statistically significant difference between the ability of BT-NSC and GPS-NSC to inhibit proliferation (p=0.2).
Figure 19B:
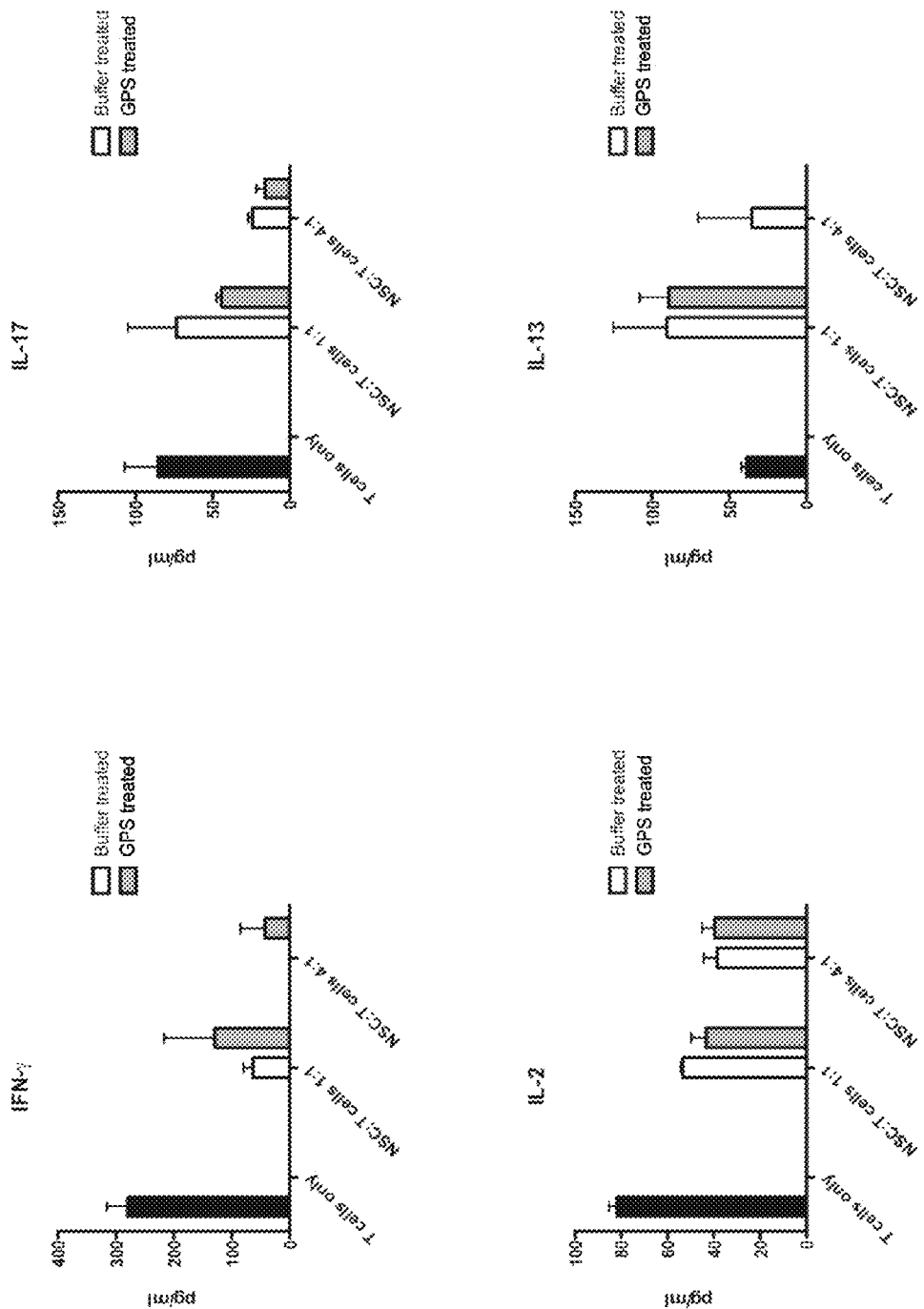
Figure 19C:
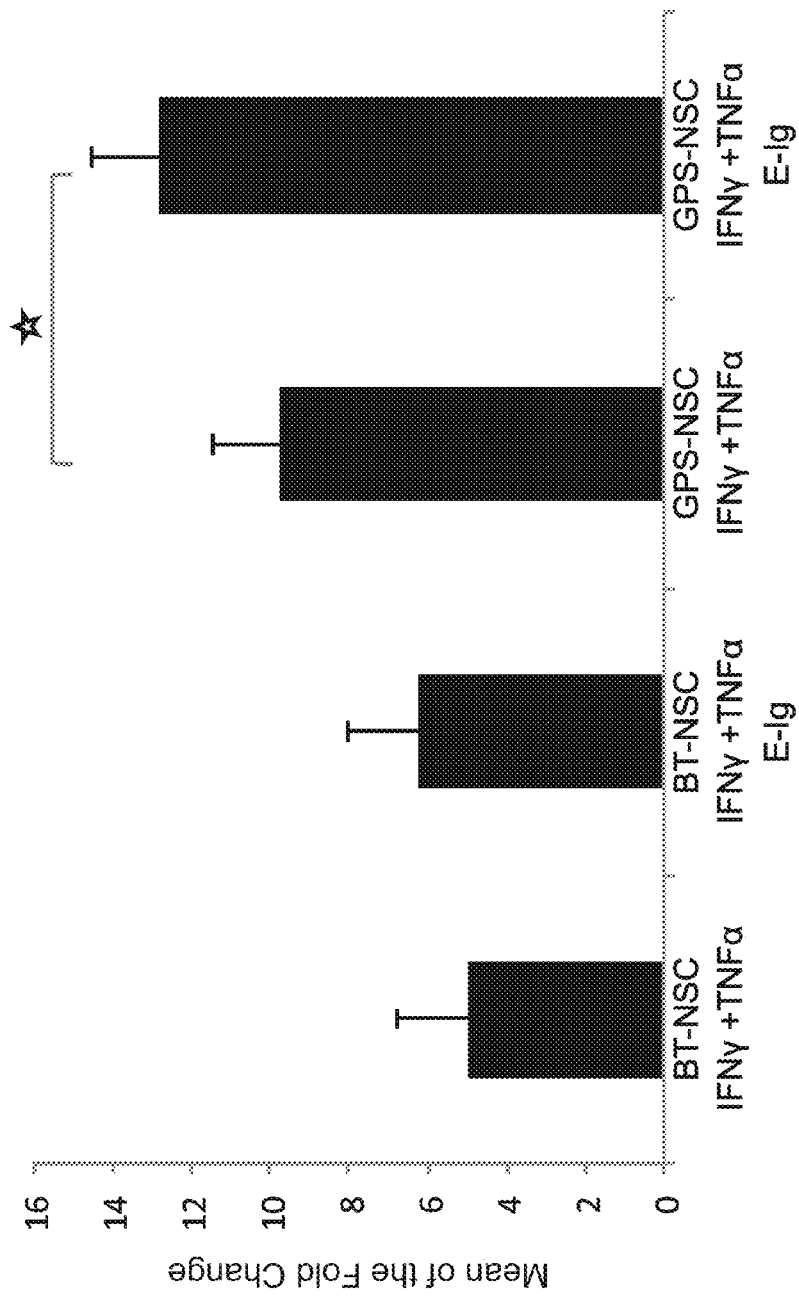

NSCs have been shown to inhibit the proliferation T cells in vitro (Einstein, O., Fainstein, N., et al. 2007; Einstein, O., Grigoriadis, N., et al. 2006; Martino, G. and Pluchino, S. 2006), and, in particular, to dampen mitogenic responses of T cells in vitro. To assess whether this immunoregulatory function of NSCs is affected by enforced E-selectin ligand activity, we examined the ability of GPS-NSCs and control buffer-treated NSCs (BT-NSCs) to suppress the proliferation of lymph node cells in response to Con A activation. As displayed in FIGS. 19A-19C, both GPS- and BT-NSCs were able to decrease T cell proliferation as well as suppress the level of inflammatory cytokine production equally, suggesting that there is no immunomodulatory advantage or disadvantage provided by the GPS treatment itself on NSCs. Interestingly, we also observed equal release of leukemia inhibitory factor (LIF) from NSCs upon inflammatory cytokine treatment for both BT- and GPS-NSCs that was enhanced upon binding of GPS-treated cells to E-Ig (FIG. 19C). Thus, enforced exofucosylation of NSCs induced transient E-selectin ligand activity without undesirable effects on NSC phenotype or function as determined by in vitro studies.

GPS-NSCs Display Robust Physiological Rolling Interactions with E-selectin

Figure 12A:
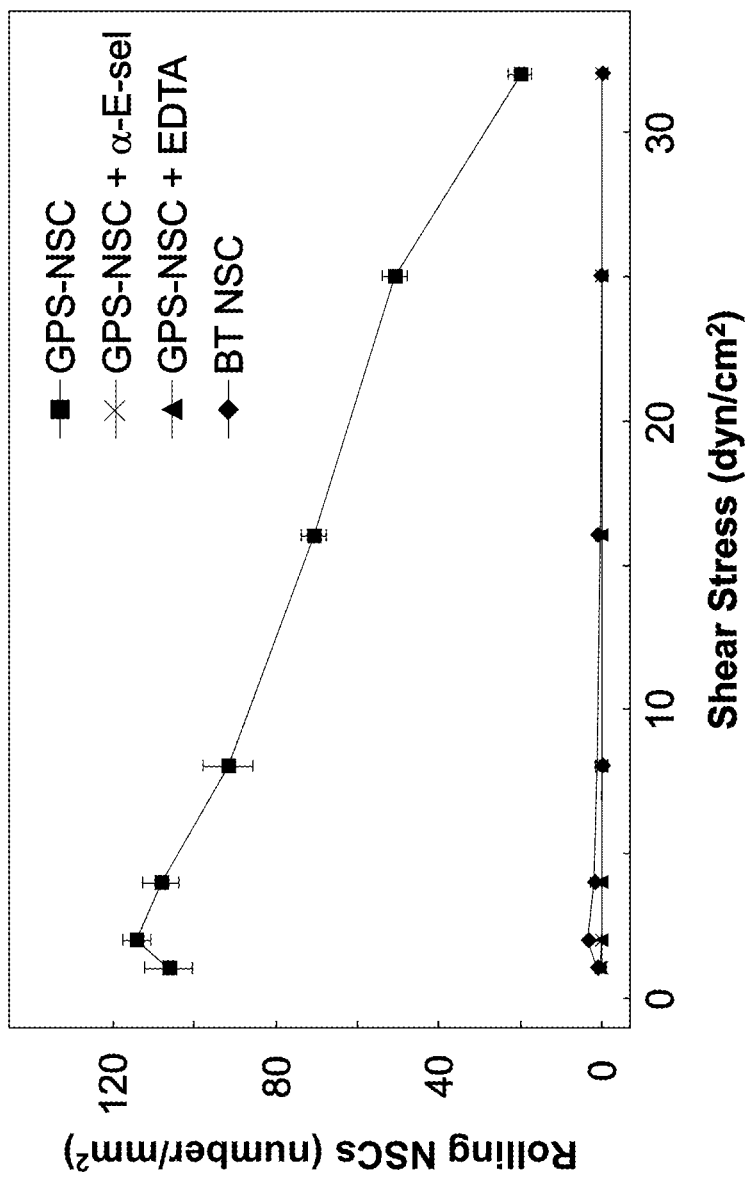
FIGS. 12A-12B: GPS-NSCs have markedly enhanced shear-resistant adhesive interactions with endothelial E-selectin under defined shear stress conditions.
Figure 12B:
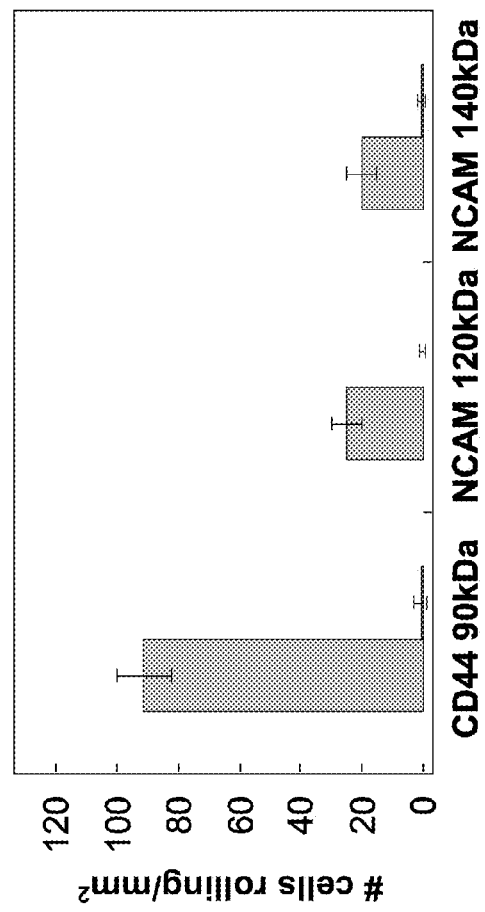

To analyze the potency of E-selectin ligand activity of GPS-NSCs under physiologic blood flow conditions, parallel plate flow chamber studies were performed using human umbilical vein endothelial cells (HUVEC) stimulated by cytokines (IL-1β and TNF-α) to express E-selectin. As shown in FIG. 12A, GPS-NSCs exhibited prominent E-selectin ligand activity that was completely abrogated in the presence of EDTA or by the use of a blocking anti-E-selectin mAb. Significant shear-resistant rolling interactions were observed within usual post-capillary venular shear levels (1-4 dynes/cm$^2$), and persisted over 20 dynes/cm$^2$ (FIG. 12A). To analyze which of the glycan-engineered E-selectin ligands, HCELL or NCAM-E, is the more potent E-selectin ligand on NSCs, we used the blot-rolling assay. (Fuhlbrigge, R. C., King, S. L., et al. 2002) This technique permits the detection of shear-dependent selectin ligand interactions on membrane proteins resolved by SDS-PAGE, thus allowing the evaluation of the individual contribution of HCELL and NCAM-E to the E-selectin ligand activity of GPS-NSC. Accordingly, to evaluate the respective E-selectin binding properties, E-selectin transfected CHO cells (CHO-E) were perfused over HECA-452 immunostained blots of GPS-NSC lysates. As illustrated in FIG. 12B, more CHO-E cells interacted and adhered to HCELL compared to either the 120 kD or the 140 kD forms of NCAM-E. CHO-E cells suspended in flow medium containing 5 mM EDTA had negligible adhesion to any regions of the blot, confirming $Ca^{2+}$-dependent binding consistent with selectin ligand activity.

GPS-NSCs Exhibit Increased Homing and Tissue Infiltration in Vivo in EAE

Figure 13A:
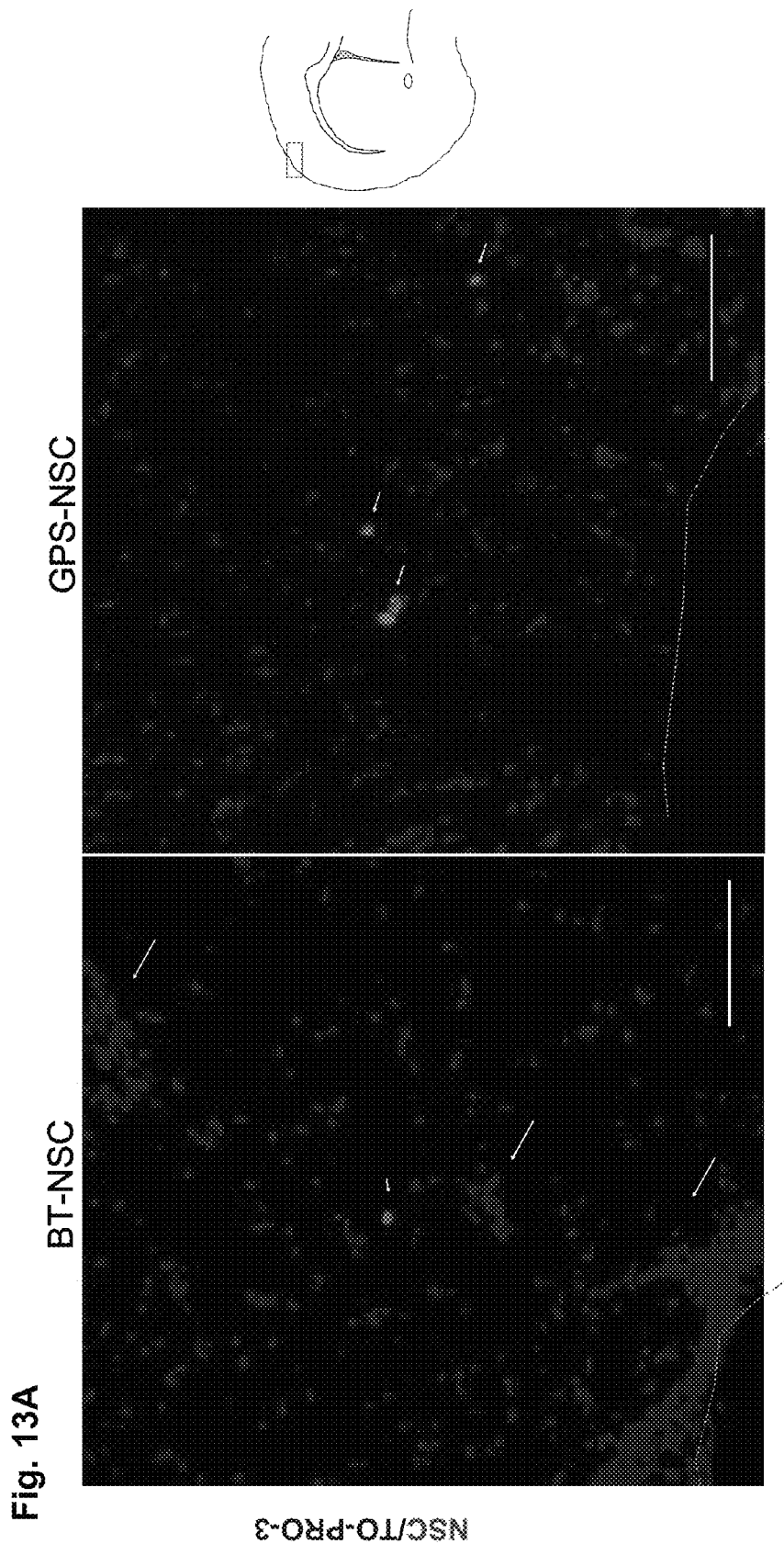
Figure 20B:
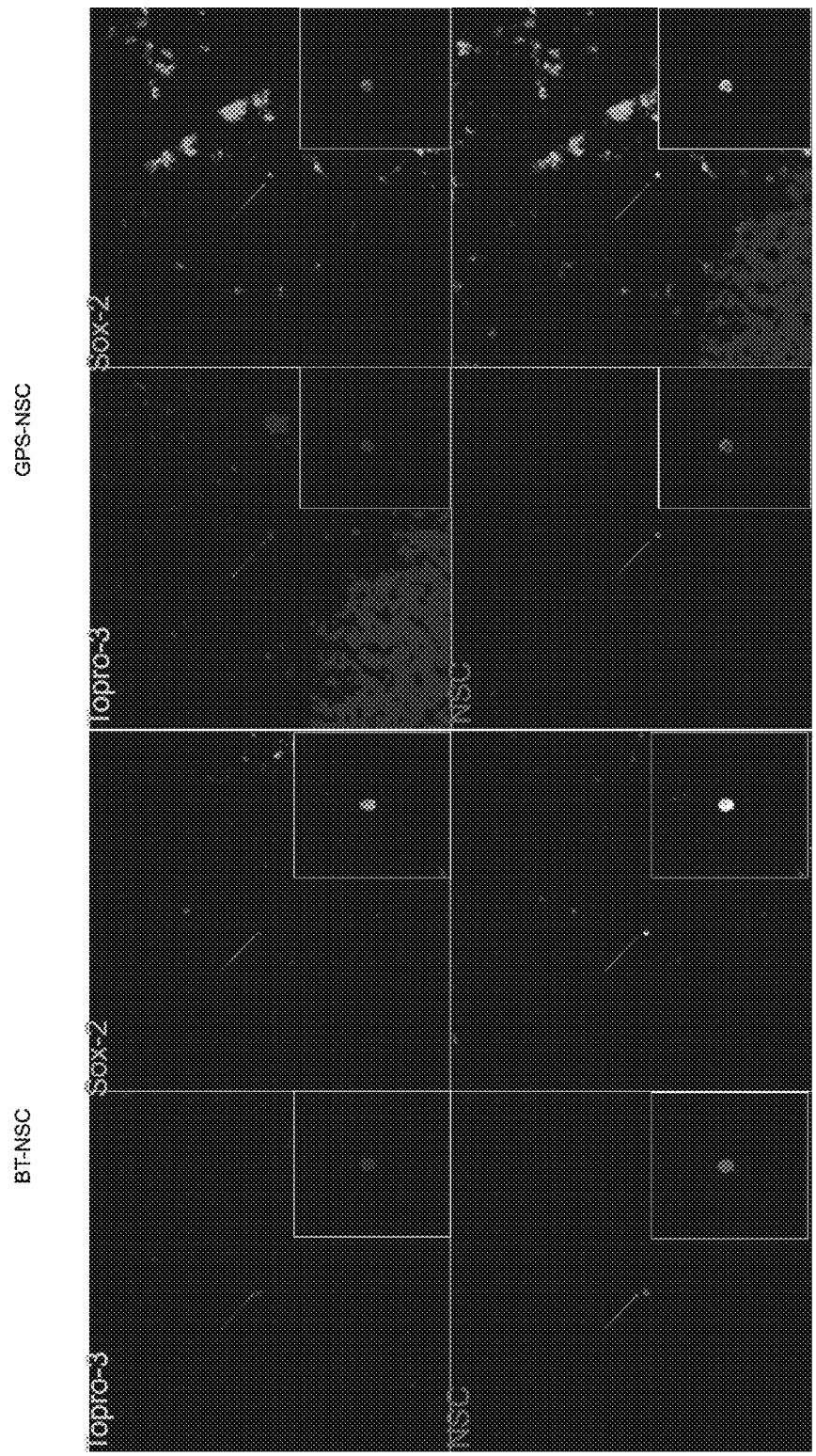

To assess whether injected NSCs infiltrated the CNS parenchyma, we performed confocal microscopy studies. To this end, GPS-NSCs and BT-NSCs were labeled with PKH26 dye and were injected intravenously into MOG-induced chronic EAE mice in two separate i.v. injections: before disease onset (day 9 post-immunization (PI)) and at the onset of the disease (day 13 PI). These days were chosen based on prior studies of E-selectin expression on brain endothelium in EAE (Piccio, L., Rossi, B., et al. 2002). Lumbar-sacral spinal cords and brains were harvested 4 days (day 17 PI) after the second NSC injection. Confocal analysis of the brain demonstrated both higher amounts of GPS-NSCs (FIG. 13A) and localization outside of Flk-1$^+$ vessels in the brain (FIGS. 20A-20B). Further, parallel analysis of the spinal cord (FIGS. 13B-13D), where the majority of pathology occurs in EAE, demonstrated two-fold greater numbers of extravascular GPS-NSCs infiltrates over BT-NSCs infiltrates by day 17 PI (FIG. 13D). These data indicate that GPS-NSCs infiltrate the CNS parenchyma significantly more effectively than BT-NSCs in both the brain and the spinal cord. To further confirm our confocal data, we studied the effect of GPS-engineered E-selectin ligand activity on short-term homing of NSCs in vivo. NSCs were stained using a fluorochrome tracking dye, CFSA-SE (carboxyfluorescein diacetate succinimidyl ester) and adoptively transferred into C57BL/6 mice on day 9 and day 13 PI with MOG as described in Materials and Methods. Within 16 h after the second cell injection, we observed that GPS-NSCs accumulated in the brain, spleen and liver three- to five-fold more efficiently than BT-NSCs (FIG. 13E). The relative advantage of GPS-NSCs in infiltrating the brain, spleen and liver reflected a true difference in trafficking, and not simply the preferential expansion of these cells in situ, as their average CFDA-SE fluorescence was not reduced relative to BT-NSCs (data not shown). Indeed of those cells that migrated to the spleen, it is evident that there are close interactions of NSCs with CD4$^+$ T cells (FIG. 13F). Injected cells also accumulated in lungs, but without difference between GPS- and BT-NSC, likely a reflection of steric trapping in pulmonary microvessels (FIG. 13E). Thus, the sLe$^x$ structure formed on NSCs following GPS-treatment licenses migration of these cells into these organs, and highlights the critical role of the E-selectin ligand activity in driving tissue-specific migration of NSCs in vivo.

Figure 14A:
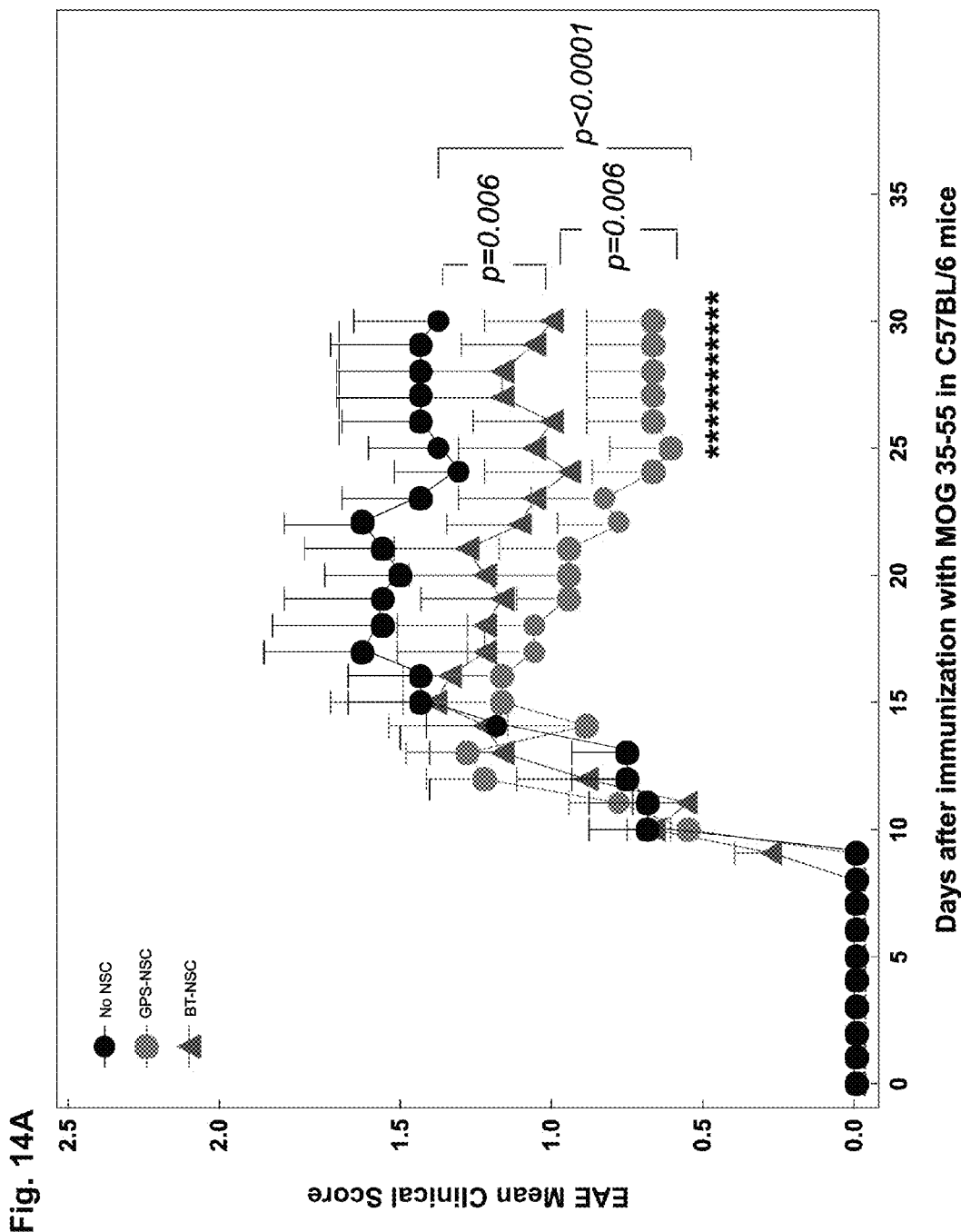
Figure 14B:
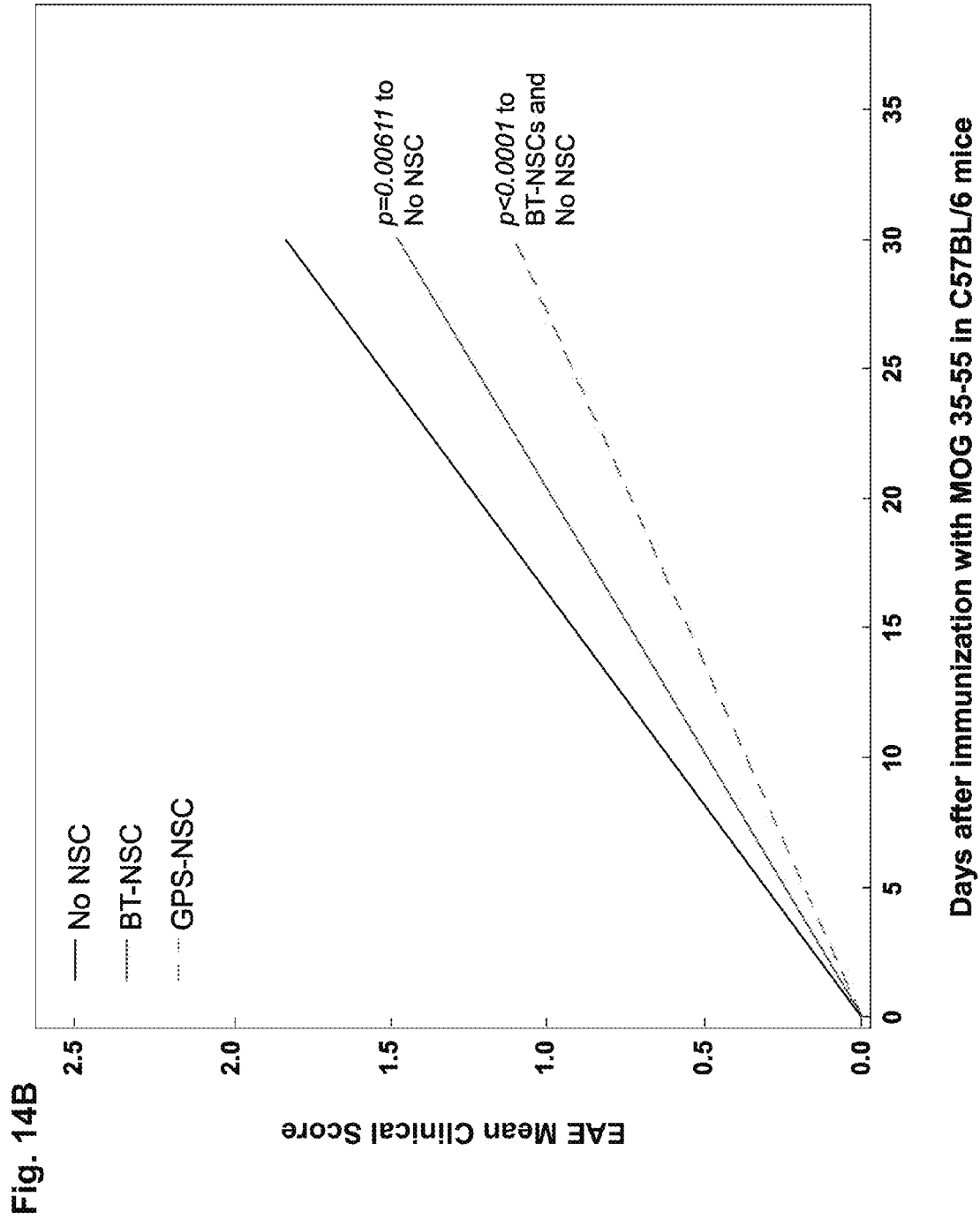

GPS-NSCs Increased Homing Translates into Amelioration of Neuropathology by Enhanced Endogenous Indirect Neuroregeneration in EAE To address whether improved tissue homing of NSC had an enhanced therapeutic effect, we monitored the neurologic status of C57BL/6 mice receiving NSC injections following MOG-induced chronic EAE and analyzed clinical parameters as well as tissue restoration and pathology. Neural precursors were administered in two separate i.v. injections on day 9 PI and on day 13 PI. Five groups of EAE mice were tested: (1) GPS-NSCs; (2) BT-NSCs; (3) HBSS (sham; i.e. no cells); (4) BT-HSPC; and (5) GPS-HSPC. The clinical score was evaluated daily in individual mice in a blind fashion (FIG. 14A), and the linear regression of cumulative burden of disease was calculated (FIG. 14B and Table 2).

TABLE 2

EAE features in C57BL/6 mice treated i.v. GPS treated NSCs.

| Treatment | Route of cell administration | No. of mice | Disease onset (days p.i) | Maximum clinical score | Cumulative disease score (0-20 p.i) | Cumulative disease score (21-30 p.i) |
|---|---|---|---|---|---|---|
| No NSC | — | 30 | 13.22 ± 0.6 | 2.2 ± 0.4 | 15.75 ± 0.6 | 14.9 ± 2.4 |
| NSCs BT | i.v | 30 | 12 ± 0.6 | 2.1 ± 0.3 | 12.3 ± 0.9 | 10.9 ± 2 |
| NSCs-GPS | i.v | 30 | 12.2 ± 0.5 | 1.8 ± 0.1$^{ns}$ | 10.8 ± 1.4$^{ns}$ | 7.1 ± 1.5* |

*$p < 0.05$ ANOVA multiple comparisons.

Figure 21A:
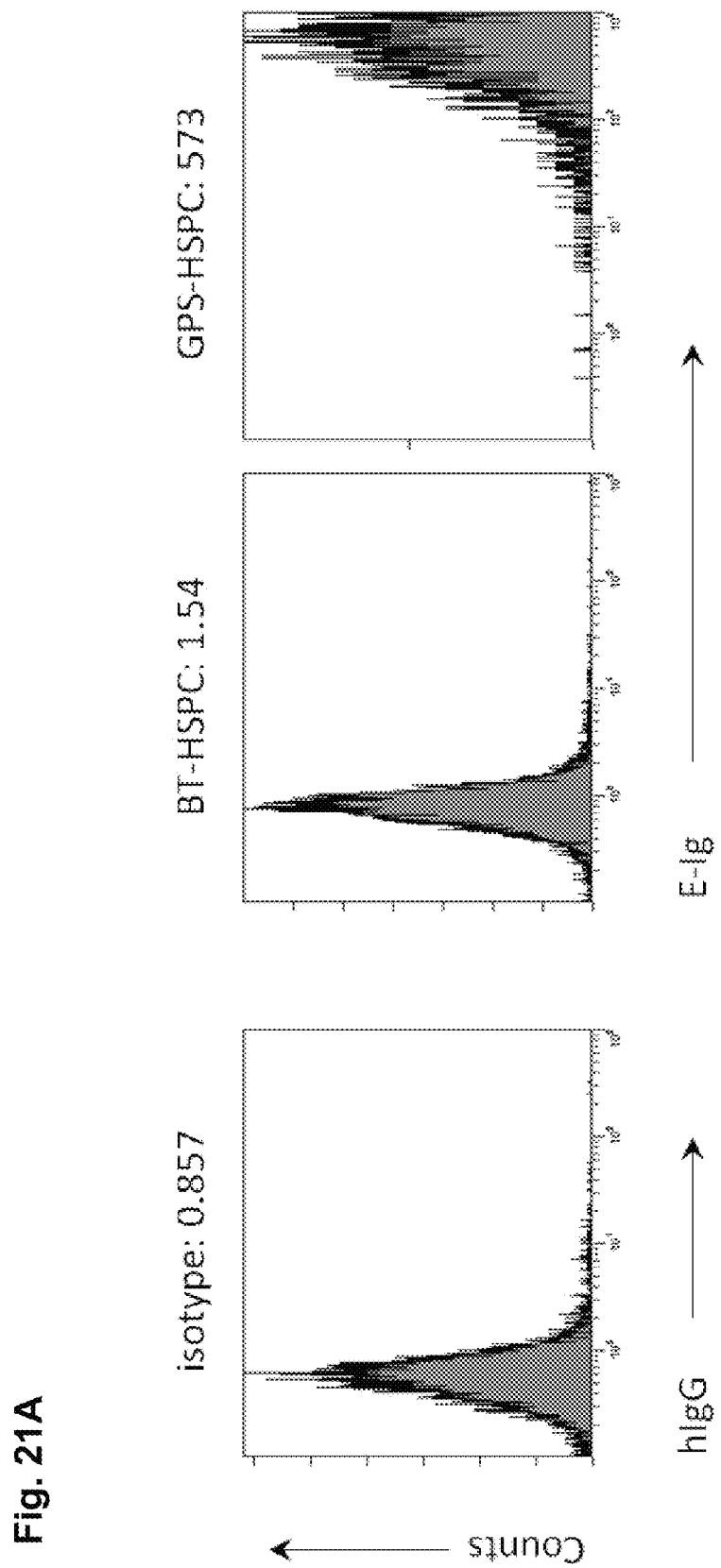
FIGS. 21A-21C: GPS treatment generates robust E-selectin ligand activity on mouse HSPCs but this does not translate into amelioration of EAE.
Figure 21B:
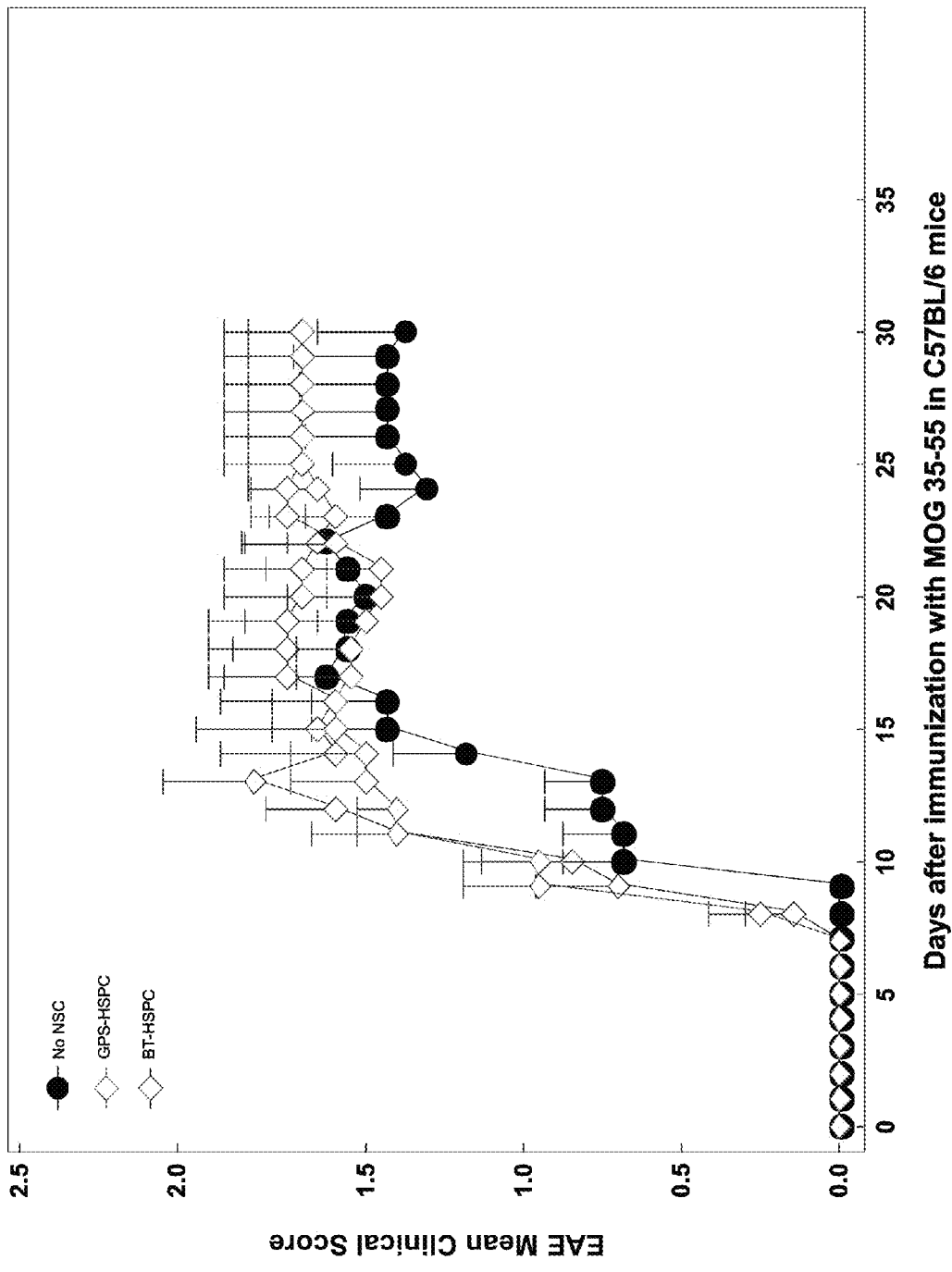
Figure 21C:
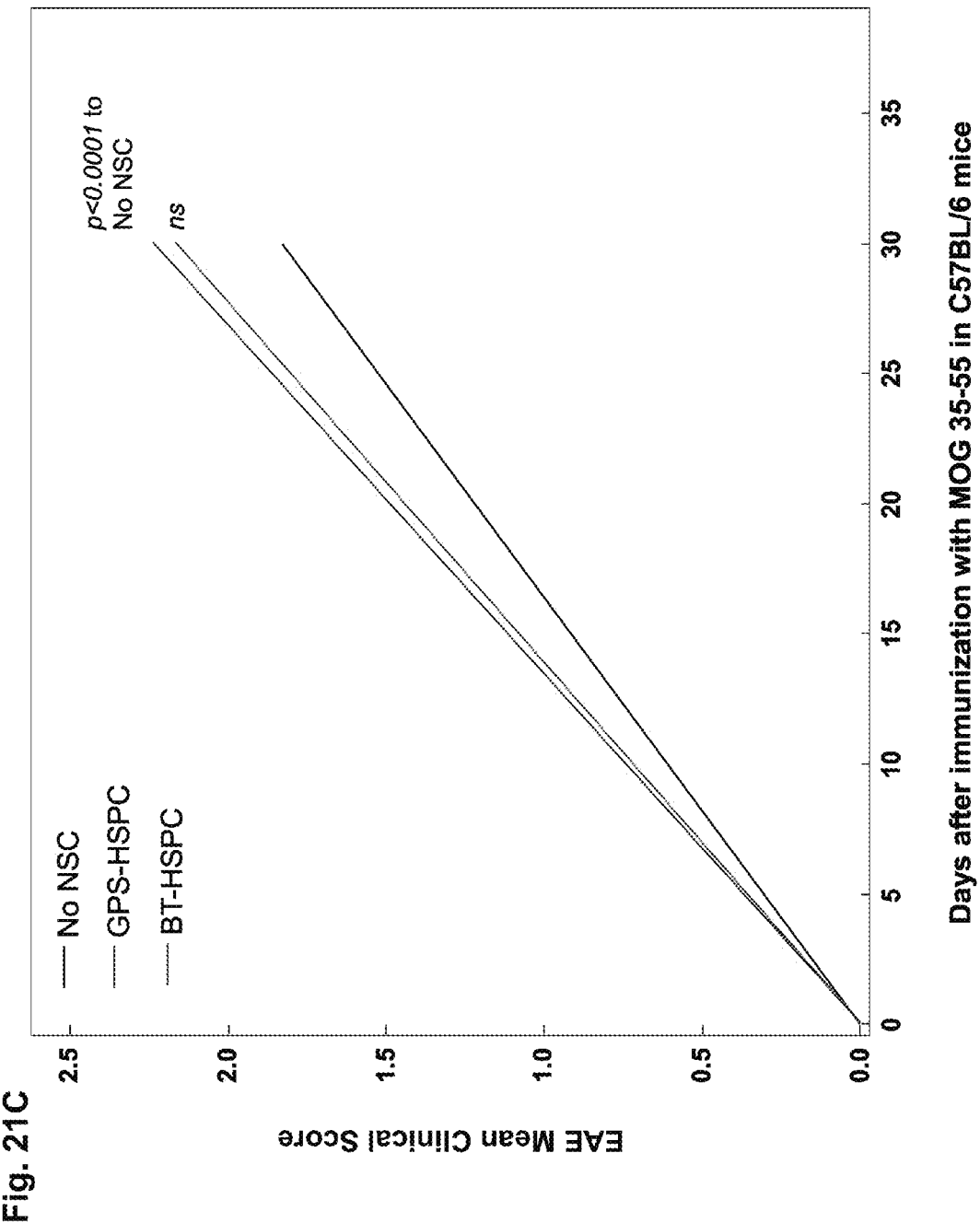

The injection of control NSCs (BT-NSC) attenuated the clinical severity of EAE compared to HSPC and sham treated animals (p=0.006). However, i.v. injection of GPS-NSCs (n=30) showed a more significantly improved clinical score compared to BT-NSCs (n=30; p=0.006), GPS-HSPC (n=30; p<0.0001), BT-HSPC (n=30; p<0.0001), and sham (n=30; p<0.0001) treated animals. It is important to note that this amelioration of disease severity is specific to NSCs, since neither the injection of GPS-HSPC (which display markedly increased E-selectin ligand activity, see FIG. 21A (Merzaban, J. S., Burdick, M. M., et al. 2011)) or the injection of BT-HSPC showed an improvement in the clinical score of MOG-induced animals compared to control animals (FIGS. 21B-21C and Table 3).

TABLE 3

EAE clinical features in C57BL/6 mice injected with i.v. GPS treated HSPCs.

| Treatment | Route of cell administration | No. of mice | Disease onset (days p.i) | Maximum clinical score | Cumulative disease score (0-20 p.i) | Cumulative disease score (21-30 p.i) |
|---|---|---|---|---|---|---|
| No Cells | — | 30 | 13.22 ± 0.6 | 2.2 ± 0.4 | 15.75 ± 0.6 | 14.9 ± 2.4 |
| BT-HSPC | i.v | 30 | 10 ± 0.7 | 2.1 ± 0.2 | 17.2 ± 1* | 16.7 ± 1* |
| GPS-HSPC | i.v | 30 | 9.5 ± 0.4 | 2.5 ± 0.6 | 18.3 ± 2.2** | 16.8 ± 1.7* |

*$p < 0.05$ ANOVA multiple comparisons.

Indeed, injection of either GPS- or BT-HSPCs showed a trend towards worsened clinical outcomes indicating that the observed salutary effects of NSC infusion are not a general property of adult stem cells.

Figure 14C:
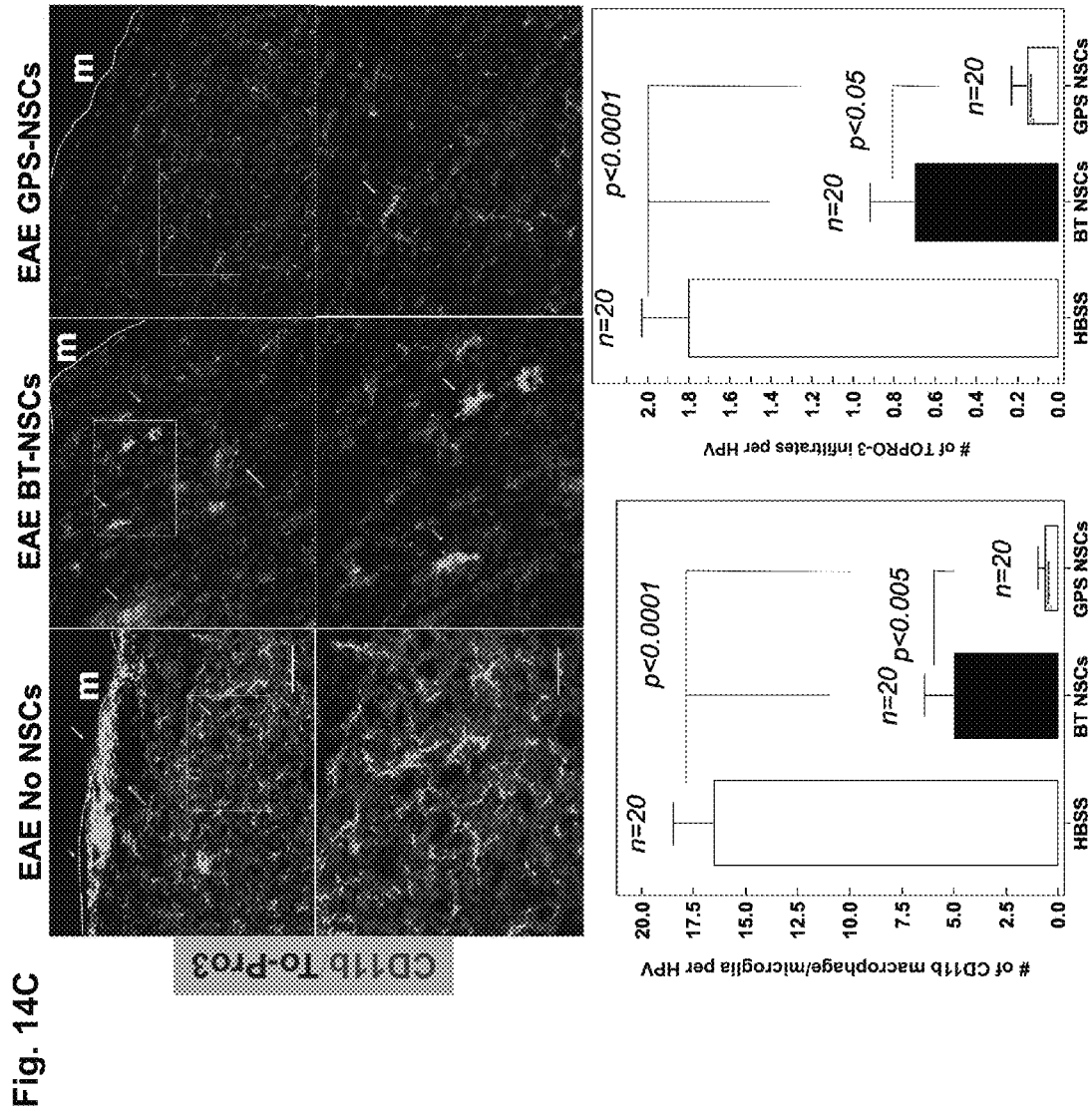
Figure 14E:
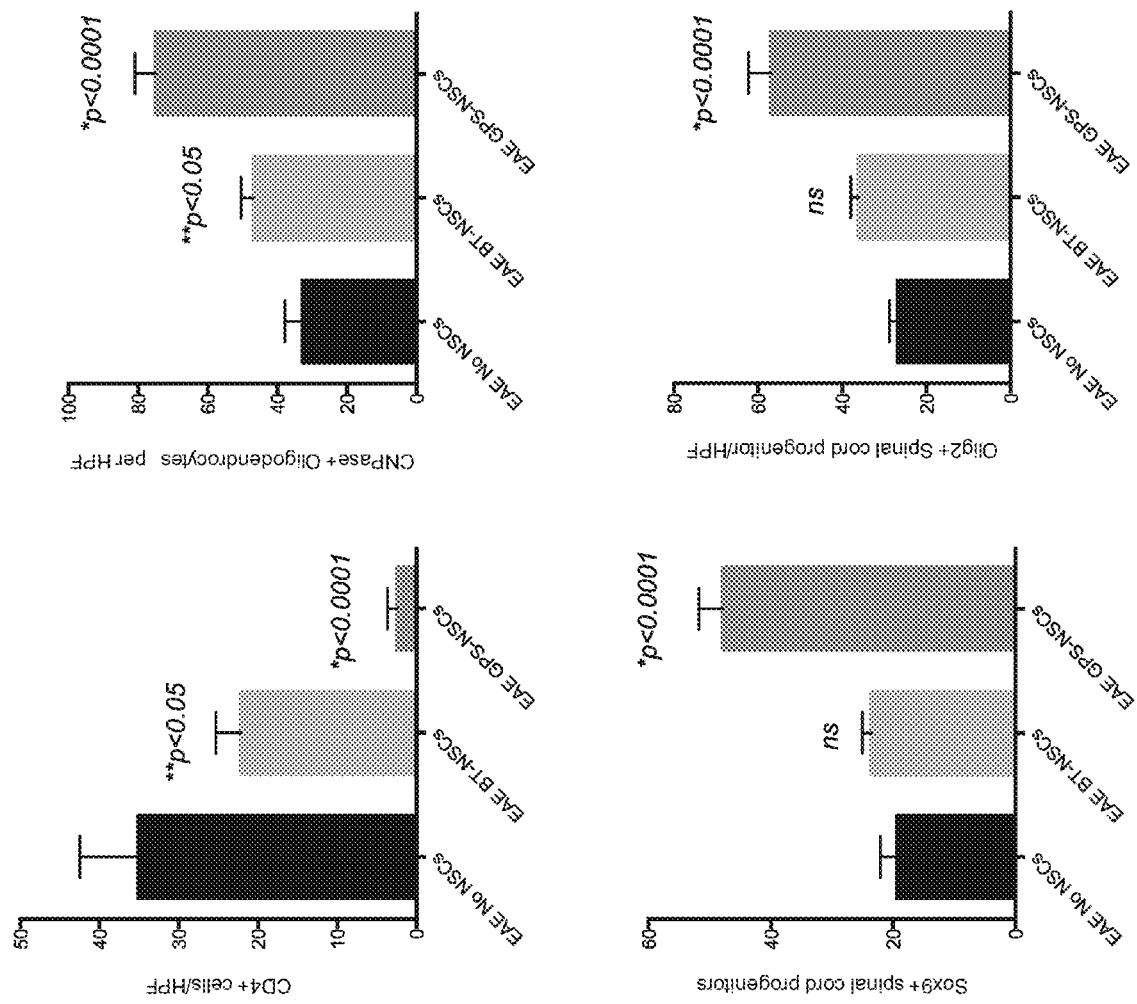
Figure 14F:
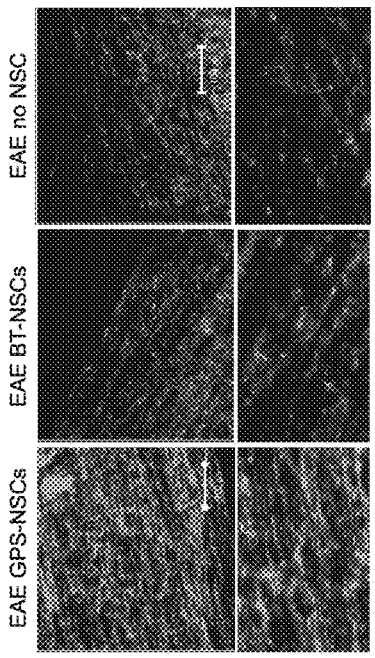
Figure 14G:
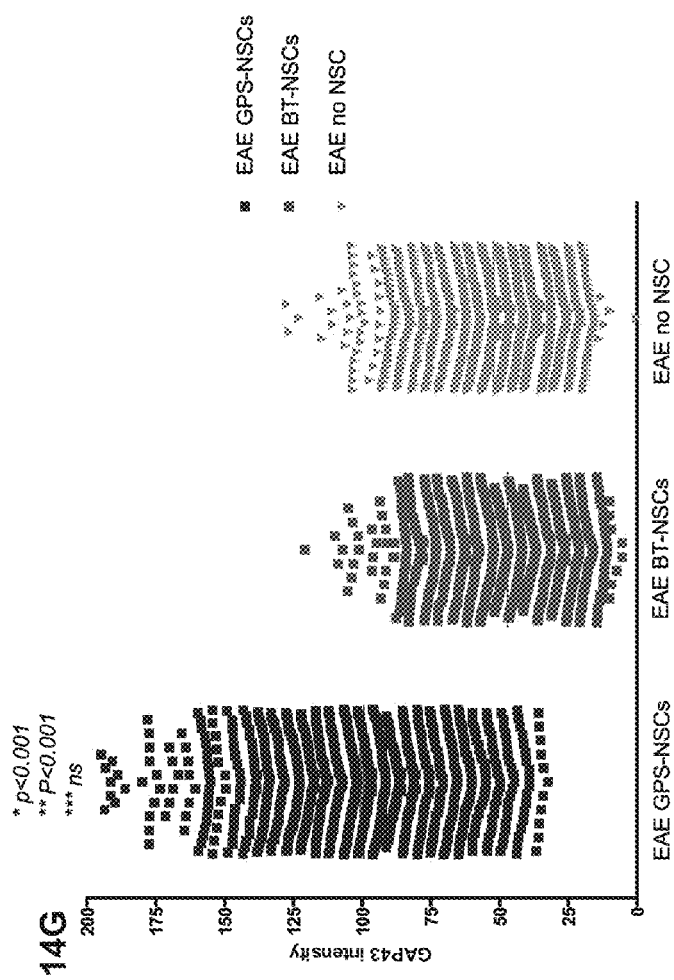

Notably, examination of the neuropathology at day 30 after EAE induction showed statistically significant differences in several parameters of inflammation and neuroregeneration in mice that received GPS-NSC compared to BT-NSC and sham treated animals (FIG. 14C). To determine the impact of NSC injections on the neuropathology of EAE, we evaluated a number of different markers. First, to assess the extent of inflammation, we stained sections of spinal cord from each study group of mice for CD11b, a marker that identifies infiltrating macrophages and microglia. Animals with EAE that received HBSS buffer alone displayed high levels of staining for CD11 b, with cells exhibiting increased numbers of membrane processes, morphologic evidence of an activated phenotype (FIG. 14C). The numbers of CD11 b-stained cells were significantly decreased in mice that received BT-NSCs (p<0.0001), and notably, these levels were even further decreased in animals injected with GPS-NSCs (p<0.005 compared to BT-NSCs). Importantly, the macrophage/microglia displayed decreased CD11b staining and more discrete membrane processes indicative of decreased activation (FIG. 14C). In addition, quantification of brain CD4+ T cells in the different treatment groups revealed a significant decrease of infiltrating T cells in animals given GPS-NSCs (FIGS. 14D-14E). To assess neuroregeneration, we stained sections of spinal cord for the markers GAP-43 and SMI-32 (FIGS. 14F-14I). In animals injected with GPS-NSCs, there was increased expression of GAP-43, a molecule associated with axon integrity and regeneration, compared to that in mice that received either BT-NSCs or HBSS buffer alone (FIGS. 14F-14G). Conversely, a specific reduction in the expression of SMI-32, a marker of axonal degeneration, was observed in animals that received GPS-NSCs compared to mice receiving either BT-NSCs or HBSS buffer (FIGS. 14H-14I). These data support the notion that the improved clinical effects afforded by GPS-NSCs over BT-NSCs are secondary to increased lesional migration of tissue-specific NSC yielding enhanced neuroprotection.

Figure 22:
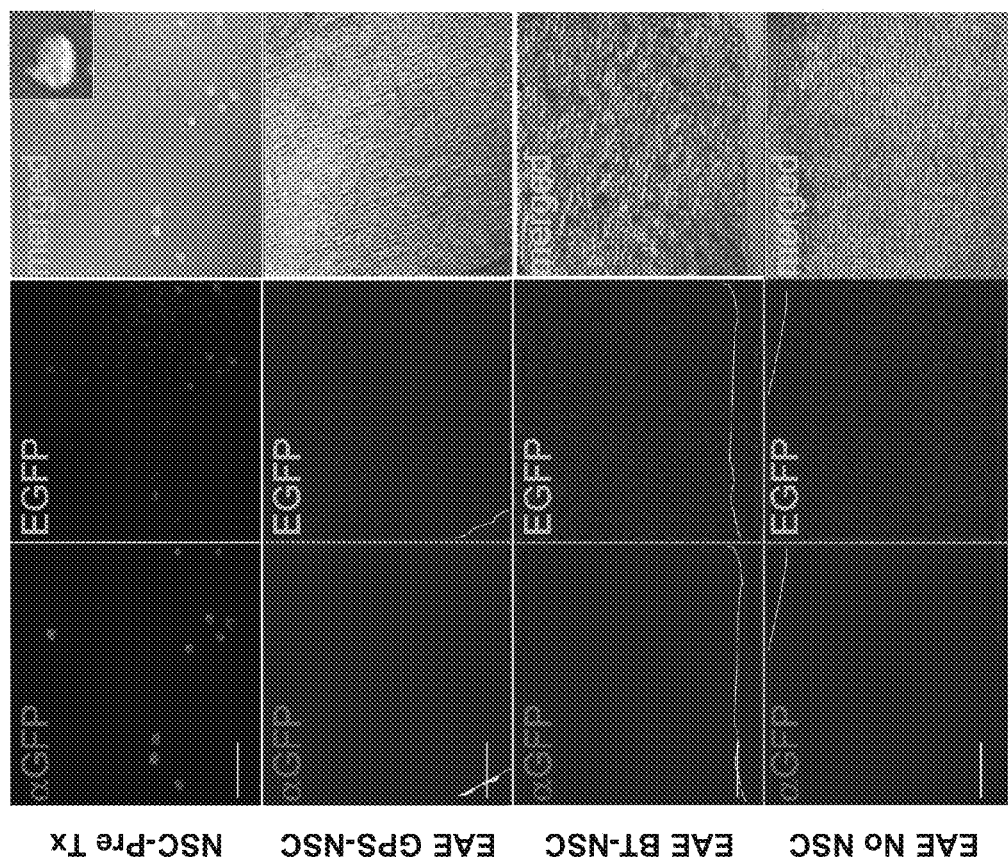
FIG. 22: No evidence of GFP signal was observed at Day 30 PI from either BT- or GPS-NSCs injected into EAE mice. C57BL/6 Mice were sacrificed 30 days after immunization with MOG 35-55 (on day 0) and subsequent injection with $1 \times 10^6$ buffer-treated NSCs (BT-NSC), GPS-treated NSCs (GPS-NSC) or sham-treated mice (No NSC) on day 9 and day 13 and immunohistochemistry for GFP+ cells was performed. At 30 days PI GFP+ cells were not identified in sections of relevant study groups, even when antibodies against GFP (red) were compared to endogenous GFP signal (EGFP; green). Cultured NSCs before injection were used as a positive control (NSC-Pre Tx) and showed a robust GFP signal. Scale bar, 50 μm. This figure is related to FIGS. 14A-14H.

To further assess whether observed effects of GPS-NSCs reflect increased neuroregeneration, we stained for markers associated with oligodendrogenesis and mature oligodendrocytes, including CNPase, Olig-2, and SOX9. We observed a statistically significant enhancement in the number of Olig-2, SOX9 and CNPase cells in animals that received GPS-NSCs compared to BT-NSCs or sham control (FIGS. 14D-14E). Although there was evidence of injected NSCs at day 17 PI (SOX-2+ cells; FIGS. 20A-20B), we did not observe persistent colonization by NSC (tagged with GFP) at 30 days PI (FIG. 22) in any of the injection groups, suggesting that the mechanism of NSC neuroprotection associated with improved homing does not necessitate the continued presence, nor differentiation towards neural lineage cells, of administered NSCs. Altogether, these data indicate that the treatment of mice with GPS-NSCs enhanced the delivery of NSCs to the CNS and provided neurorestoration via an indirect neuroregenerative effect, not through direct neuroregeneration (i.e., cell replacement).

Discussion

MS is a chronic, demyelinating disease of the CNS characterized by multifocal inflammatory lesions yielding gradual destruction of the myelin sheath, leading to axonal injury and loss (Imitola, J., Chitnis, T., et al. 2006). Stem cell-based therapeutics offers the promise of repair of damaged/inflamed tissue by replacing affected cells (direct regeneration) and/or by production of supportive/trophic factors in the milieu that evoke tissue restoration by endogenous cells (indirect regeneration). In the case of disseminated neurologic diseases like MS, use of tissue-specific NSCs could prove clinically useful in achieving CNS recovery, but a proximate hurdle to accomplishing this goal is to deliver adequate numbers of cells to sites of neural injury. Prior studies have shown a benefit of transplanted NSCs in experimental models of stroke, spinal cord trauma and MS (Ben-Hur, T., Einstein, O., et al. 2003; Einstein, O., Fainstein, N., et al. 2007; Einstein, O., Grigoriadis, N., et al. 2006; Imitola, J., Raddassi, K., et al. 2004; Lee, S. T., Chu, K., et al. 2008; Pluchino, S., Quattrini, A., et al. 2003; Pluchino, S., Zanotti, L., et al. 2005; Ziv, Y., Avidan, H., et al. 2006). Direct injection into the affected site was used as route of delivery in these studies, however, in order to attain appropriate colonization of NSC within affected tissue(s) in multifocal CNS diseases, the vascular route of delivery is required as local administration (i.e., in situ injection) is impractical given the diffuse nature of disease and associated anatomic constraints. To date, there have been no studies to evaluate the expression of molecular effectors of cell migration on NSCs, and, more importantly, no studies to address how optimizing expression of such effectors could enhance NSC neurotropism.

Our studies reveal that NSCs express relevant Step 2-4 effectors, but are conspicuously deficient in Step 1 effectors: (1) they do not natively express ligands for E-selectin or P-selectin (even when grown in the presence of inflammatory cytokines (FIG. 15)); (2) they lack expression of the glycan sLe$^x$, which is the canonical selectin binding determinant; and (3) they do not express the glycoprotein PSGL-1, a selectin ligand on myelin-specific Th1 cells that has been reported to mediate trafficking to the brain (Piccio, L., Rossi, B., et al. 2005; Piccio, L., Rossi, B., et al. 2002). Importantly, expression of endothelial selectins, especially E-selectin, has been implicated in recruitment of immunologic effectors in MS and EAE (Lee, S. J. and Benveniste, E. N. 1999; Piccio, L., Rossi, B., et al. 2002). Thus, we sought here to assess whether glycan engineering of NSC to enforce expression of E-selectin ligands would enhance systemic delivery of the cells and, in consequence, have biologic effects in an MS model.

The dataset here show that cultured NSC express two well-characterized neural cell surface molecules, CD44 and NCAM (Back, S. A., Tuohy, T. M., et al. 2005; Pluchino, S., Quattrini, A., et al. 2003). Strikingly, exofucosylation of mouse NSCs yielded high expression of sLe$^x$ determinants prominently on these glycoproteins, programming conversion of CD44 into the potent E-selectin ligand HCELL (Dimitroff, C. J., Lee, J. Y., et al. 2000; Dimitroff, C. J., Lee, J. Y., et al. 2001) and also inducing expression of two sialofucosylated glycoforms of NCAM of ~120 kDa and ~140 kDa, which we designate "NCAM-E". Blot rolling assays revealed that HCELL is the principal E-selectin ligand expressed on GPS-NSCs (FIG. 12B). These findings are corroborated by results of flow cytometry following the removal of NCAM-E by PI-PLC digestion, showing considerable retention of NSC sLe$^x$ expression and E-Ig reactivity (FIG. 10C).

NCAM, a member of the immunoglobulin superfamily, is expressed on both neurons and glia, and is conventionally viewed as a mediator of cell-cell interactions establishing a physical anchorage of cells to their environment. Post-translational glycan modifications consisting of α-2,8-linked polysialic acid (PSA) on the NCAM protein core provides unique properties in neural migration (Gascon, E., Vutskits, L., et al. 2007; Maness, P. F. and Schachner, M. 2007; Rutishauser, U. 2008) and PSA-NCAM appears to play a crucial role in mediating precursor cell migration in the brain (Glaser, T., Brose, C., et al. 2007; Lavdas, A. A., Franceschini, I., et al. 2006; Zhang, H., Vutskits, L., et al. 2004). Our data now provide the first evidence that NCAM displays relevant terminal α-(2,3)-sialyllactosaminyl glycans that can serve as acceptors for exofucosylation to create sLe$^x$ determinants. Following cell surface glycoengineering of NSCs, PSA expression levels did not change and the induced E-selectin ligand activity is not permanent, as there was complete loss of sLe$^x$ expression within 72 hours of enforced fucosylation (FIGS. 11A-11C). Thus, subsequent to extravasation, temporal reversion to native NCAM should occur, and infiltrating NSCs would then be capable of undergoing endogenous NCAM-mediated intraparenchymal CNS migration. Notably, though murine NSC express NCAM bearing α-(2,3)-sialyllactosaminyl glycans, our studies of human NSCs (CC-2599) indicate that these cells only express HCELL and not NCAM-E following exofucosylation (FIG. 15); thus, human NSC may express relevant sialolactosaminyl glycans that serve as acceptors for enforced fucosylation only on CD44. These species differences should be considered when interpreting xenograft studies where human NSCs are used in rodent systems (Goncharova, V., Das, S., et al. 2014).

The induction of E-selectin ligand activity has profound implications for cell trafficking, serving to direct cell migration to endothelial beds that express E-selectin. As shown by others, we observed that NSCs display the chemokine receptor CXCR4 and the integrin VLA-4 (see FIGS. 9A-9B). It has been shown that expression of CXCR4 on human NSCs (Bezzi, P., Domercq, M., et al. 2001; Flax, J. D., Aurora, S., et al. 1998; Imitola, J., Raddassi, K., et al. 2004) promotes migration in vivo toward CNS injury wherein local astrocytes and endothelium up-regulate the cognate ligand stromal cell-derived factor 1α (SDF-1α, also known as CXCL12) (Imitola, J., Raddassi, K., et al. 2004). These observations define CXCR4 as a prominent Step 2 effector in promoting NSC homing to CNS injury. The corresponding endothelial receptor for VLA-4, VCAM-1, is also upregulated in the inflammatory response of the brain to injury (Justicia, C., Martin, A., et al. 2006). The VLA-4/VCAM-1 axis has similarly been shown to play a critical role in migration of NSC, in that only NSCs that constitutively express VLA-4, in addition to CXCR4, were able to accumulate around inflamed CNS microvessels in affected lesions in EAE (Pluchino, S., Zanotti, L., et al. 2005). A recent xenograft study suggests that integrins may play a role as step 1 mediators of migration on human NSCs in a rat stroke model suggesting that selectin interactions are not necessary in this model system (Goncharova, V., Das, S., et al. 2014). Although further work is warranted, the varying role(s) of integrins as mediators of Step 1 interactions could reflect differences in the inflammatory model used, the host animal system, the permeability of vessels, the expression of endothelial adhesion molecules at that site of inflammation, the presence of soluble adhesion molecules at the site, and the physical properties of the vessel that dictate the flow rate (i.e. diameter of vessel) (Berlin, C., Bargatze, R. F., et al. 1995; Ding, Z. M., Babensee, J. E., et al. 1999; Zarbock, A., Kempf, T., et al. 2012; Zarbock, A., Lowell, C. A., et al. 2007). In any case, expression of E-selectin ligands as Step 1 effectors on NSCs would serve to complement the constitutive expression of CXCR4 and VLA-4, thereby optimizing the recruitment of NSC to inflammatory sites. Accordingly, though we observed that intravenously administered (non-modified) BT-NSCs can infiltrate the brain of EAE mice (FIG. 13E), enforced E-selectin ligand expression by glycoengineering yielded markedly increased migration of NSCs to the brain. This increased neurotropism was associated with markedly diminished CNS inflammation (FIGS. 14A-14I). Moreover, as shown in FIGS. 13A-13F, NSC accumulation in the CNS parenchyma was two-fold higher among GPS-NSCs than BT-NSCs by day 17 post-injection, indicating that enforced expression of Step 1 effectors promotes extravasation.

In addition to enhanced neurotropism, short-term homing data also revealed a significantly higher accumulation of GPS-NSCs in the spleen and liver than in BT-NSCs (FIG. 13E). These findings are consistent with results of a study reporting that systemically administered NSCs tend to accumulate in the brains of mice with EAE, and also in the spleen and the liver (Politi, L. S., Bacigaluppi, M., et al. 2007). E-selectin expression in the spleen has been described in humans, non-human primates and rodents (Alam, H. B., Sun, L., et al. 2000; Drake, T. A., Cheng, J., et al. 1993; Redl, H., Dinges, H. P., et al. 1991; Schweitzer, K. M., Drager, A. M., et al. 1996), and is upregulated by pro-inflammatory cytokines that are characteristically expressed in CNS inflammatory conditions (Emamgholipour, S., Eshaghi, S. M., et al. 2013; Weishaupt, A., Jander, S., et al. 2000); indeed, conjugation of $sLe^x$ to polymers has been shown to markedly enhance the accumulation of such polymers within the spleen (Horie, K., Sakagami, M., et al. 2000; Horie, K., Sakagami, M., et al. 2004), providing direct evidence that $sLe^x$ expression promotes splenic delivery. It has been reported that infiltration of the spleen by NSCs dampens production of inflammatory cytokines by resident spleen cells (e.g., macrophages) resulting in anti-inflammatory effects (Lee, S. T., Chu, K., et al. 2008). Other studies have reported that intravascularly administered NSCs provide peripheral immunosuppression (Einstein, O., Fainstein, N., et al. 2007; Einstein, O., Grigoriadis, N., et al. 2006) or local immunomodulation that restrains CNS injury, rather than by enhancing neuroregeneration (Martino, G. and Pluchino, S. 2006; Pluchino, S., Zanotti, L., et al. 2009; Wang, L., Shi, J., et al. 2009). Thus, the observed increased splenic homing by enforced expression of E-selectin ligand activity on NSCs could be contributory to neuroprotection via immunomodulation by virtue of increased tissue ratio of NSCs to immune cells. This notion is supported by our in vitro data showing that although GPS-NSCs did not confer an immunomodulatory advantage compared to that observed with control NSCs, as the ratio of input NSCs to splenocytes is increased, T cell proliferation decreases (FIG. 19A).

Previous studies of cell surface exoglycosylation had utilized human mesenchymal stem cells in a xenotransplant model and did not address the therapeutic impact on tissue injury, i.e., whether glycoengineered stem cells would home to a site of inflammation and whether such cells would have desired regenerative and/or tissue-protective effect(s). Though enhanced recruitment of NSCs to the CNS was observed following infusion of GPS-NSCs, there was no commensurate increase in long-term engraftment of NSCs. Thus, though enhanced CNS infiltration was achieved by exploiting physiologic cell migration (i.e., in a non-invasive fashion that would preserve CNS tissue microenvironmental architecture), we did not observe that administered NSCs differentiated into progeny that regenerate functional CNS tissue in situ (i.e., through direct regeneration). In fact, we observed that administration of GPS-NSCs improved the ability of endogenous neuronal progenitors to become oligodendroglia (FIGS. 14D-14E). Our findings thus do not support the paradigm of direct neuroregeneration, but instead suggest that the predominant role of NSCs in CNS tissue repair is via trophic effects that support repair by endogenous cells (Caplan, A. I. 2009; Hess, D. C. and Borlongan, C. V. 2008; Laterza, C., Merlini, A., et al. 2013; Phinney, D. G. and Prockop, D. J. 2007), thus yielding neurorestoration (i.e., through indirect neuroregeneration). Consistent with this notion, undifferentiated NSCs have been reported to significantly reduce scar formation and increase survival and function of endogenous glial and neuronal progenitors through the secretion of neurotrophins such as LIF (Laterza, C., Merlini, A., et al. 2013). In addition, NSCs support the formation of injury-induced growth niches through the expression of molecules such as BMP-4 and Noggin (Imitola, J., Raddassi, K., et al. 2004; Pluchino, S., Zanotti, L., et al. 2005) that trigger indirect neuroregeneration by endogenous cells.

Figure 23:
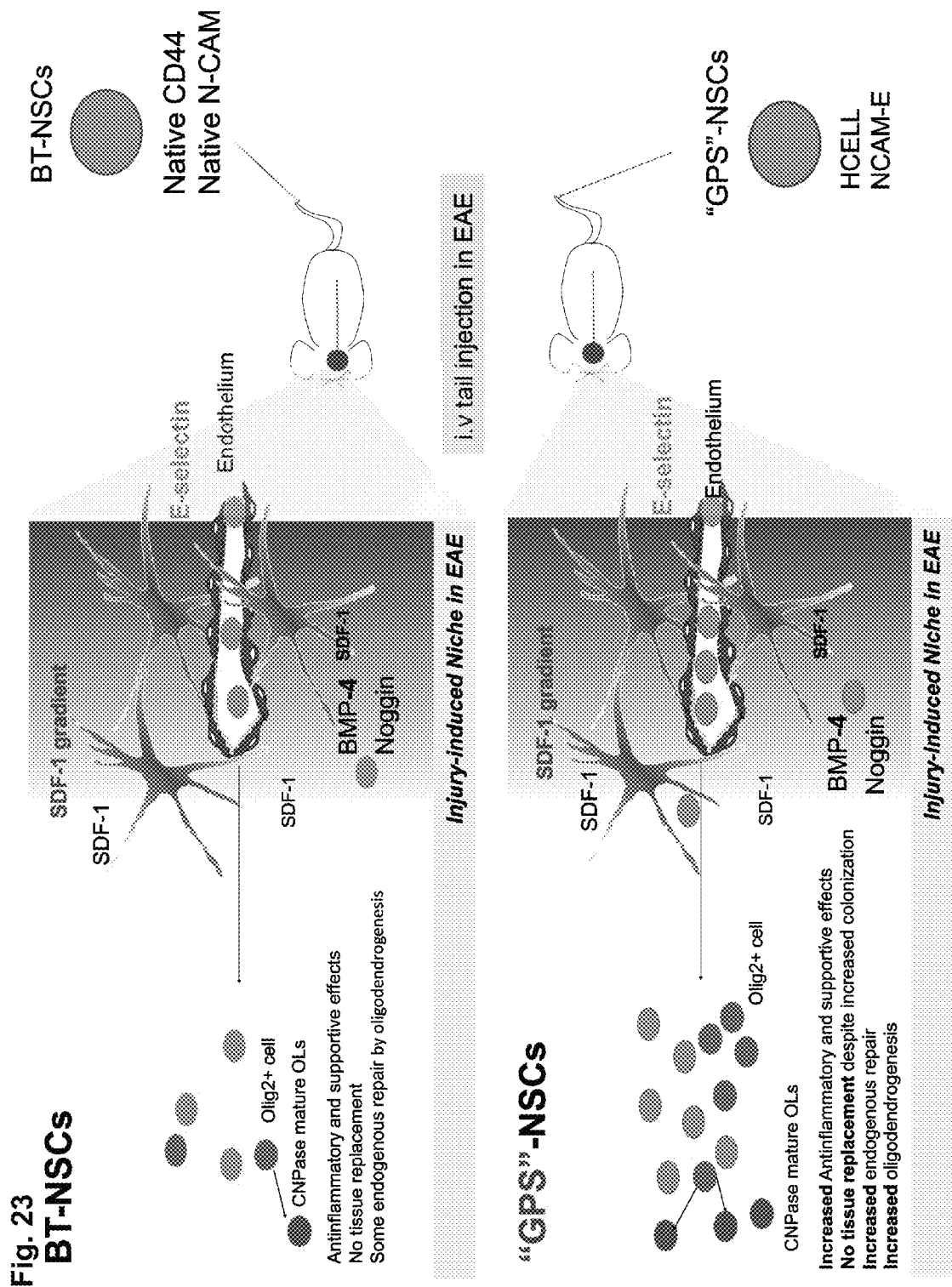
FIG. 23: Model of neurorestoration afforded by GPS treatment of native-NSCs surface proteins, CD44 and NCAM, creating novel step 1 effectors, HCELL and NCAM-E, that efficiently bind endothelial E-selectin in EAE mice. As a result of injury, endothelial cells and glia may produce injury signals (e.g., SDF-1α and E-selectin) that direct GPS-NSCs toward the injury-induced niches in higher number than in control mice. Despite the increased number of NSCs recruited, instead of cell replacement, NSCs offer local modulation of immunity and endogenous regeneration of CNS by increasing the number of SOX-9+/Olig-2+ oligodendroglia. This subsequently leads to more mature oligodendroglial cells (CNPase+), less axonal loss, and more axonal regeneration. Niche molecules secreted by primitive neural stem cells may promote some of the effects provided by their increased colonization.

Collectively, our data support a mechanism in which glycan engineering of NSC to enforce expression of E-selectin ligands heightens tissue colonization, mediating immunomodulation and tissue repair without necessitating persistent/long-term engraftment of administered NSCs. Notably, despite enhanced E-selectin ligand activity, infusion of GPS-HSPC did not improve the course of EAE (indeed, injection of HSPC worsens disease, see FIGS. 21A-21B and Table 3), indicating that the observed neuroprotective effects of GPS-NSCs are not a general property of adult stem cells and are due to neurorestorative effects inherent to NSC. Consistent with this finding of adult stem cell-specific biologic effect(s), human HSPCs have been found to elicit strong host immune rejection in a mouse model of congenital corneal disease while other adult stem cells such as mesenchymal stem cells suppress the host immune response (Liu, H., Zhang, J., et al. 2010). Though further studies on the molecular mechanism(s) mediating the observed neuroprotection by NSCs are warranted, our results indicate that cell surface glycan engineering did not change the self-renewal capacity, differentiation potential or alter the innate immunomodulatory capacity of neural stem cells. Collectively, the data presented here lead us to propose a model (FIG. 23) whereby enforced E-selectin ligand expression via exofucosylation of the surface of NSCs yields increased tissue recruitment at CNS inflammatory sites, thereby enhancing payload delivery of NSC trophic factors where they are needed. Because E-selectin expression is markedly upregulated at endothelial beds at all sites of inflammation in humans, our findings have profound translational implications for future clinical trials exploiting cell surface glycan engineering to improve the efficacy of stem cell therapeutics for MS as well as other devastating multifocal inflammatory diseases.

Materials and Methods

Ethics Statement: All mouse experiments were performed in accordance with the NIH guidelines for the care and use of animals and under approval of the Institutional Animal Care and Use Committees of Harvard Medical School. The following are the specifics related to using mice these experiments. Justification for use: EAE is a valuable model for the human disease multiple sclerosis. There are no mathematical models, computer simulations or in vitro systems that can substitute for the in vivo disease. Many of the treatments available for MS and other autoimmune diseases were first tested and their mechanisms investigated in EAE. MOG induced EAE in C57/BL6 mice is valuable because of the availability of many knockout and transgenic mice on that background. Veterinary care: Mice are handled and cared for according to federal, institutional, and AAALAC guidelines. Procedures to minimize adverse effects: After immunization, animals are examined daily.

Those affected by EAE develop a floppy tail (grade1), partial hind limbs (grade2), complete hind limb paralysis (grade 3), quadriparesis (grade 4), moribund or animal death (grade 5). Most animals have a grade 0 to 3, and, rarely, animals reach grade 4 and in such cases euthanasia is performed. When animals are affected by EAE, they are provided with gel packs to ensure access to fluids and are provided with access to food within the cage. Euthanasia is performed by CO2 inhalation administered according to institutional guidelines.

Reagents: The following antibodies were purchased from BD Pharmingen: function blocking mouse anti-human E-selectin (68-5H11; IgG1), rat anti-human CLA (HECA-452; IgM), mouse anti-human sLe$^x$ (CSLEX-1; IgM), mouse anti-human CD15 (IgM), rat anti-mouse PSGL-1 (2PH1 and 4RA10; IgG1), mouse anti-human PSGL-1 (KPL-1; IgG1), rat anti-mouse CD44 (KM114 and IM7; IgG1), mouse anti-human CD44 (515; IgG1), rat anti-mouse CD43 (S7; IgG2a), mouse anti-human CD43 (1G10; IgG1), mouse anti-(mouse anti-adult and embryonic pan N-Cam) CD56 (NCAM13; IgG2b), mouse anti-human CD56 (NCAM16.2; IgG2b), rat anti-human CXCR4 (2B11; IgG2b), mouse anti-human CXCR4 (12G5; IgG2a), rat anti-mouse CD18 (GAME-46; IgG1), rat anti-mouse CD29 (KM16; IgG2a), rat anti-mouse CD49d (9C10; IgG2b), rat anti-mouse CD11a (2D7; IgG2a), rat anti-mouse CD11b (M1/70; IgG2b), rat anti-mouse CD49e (MFRS; IgG2a), mouse IgG1,κ isotype, mouse IgG2a isotype, mouse IgM isotype, rat IgG isotype, rat IgM isotype, and human IgG$_1$ isotype. The following secondary antibodies were also purchased from BD Pharmingen: PE Streptavidin, biotin anti-rat IgM, and goat anti-mouse Ig-HRP. The following secondary antibodies were purchased from Southern Biotech.: rabbit anti-human IgG-biotin, goat anti-mouse IgM-PE, goat anti-rat IgG-PE, goat anti-mouse Ig-biotin, goat anti-rat Ig-HRP, and goat anti-human Ig-HRP. Recombinant mouse E-selectin/human Ig chimera (E-Ig) and recombinant mouse P-selectin/human Ig chimera (P-Ig) were from R&D. Mouse anti-human sLe$^x$ (KM93; IgM) was purchased from Calbiochem. Rat anti-mouse CD43 (1B11; IgG2a) was purchased from Biolegend. Rat anti-mouse LPAM-1 (DATK32; IgG2a) and mouse anti-SMI32 (SMI-32; IgG1) were purchased from Abcam. Mouse anti-human CD15 (80H5; IgM) was purchased from Coulter-Immunotech. PNGase F was purchased from New England Biolabs. PI-PLC, Bromelain, Soybean Trypsin Inhibitor, DNase, mouse anti-Map2 (HM-2; IgG1) were purchased from Sigma. Mouse-anti GFP (B2, IgG$_{2a}$) was purchased from Santa Cruz Biotechnology, Inc (Santa Cruz, Calif.). To-pro3 was purchased from Invitrogen. Mouse anti-human polysialic acid (PSA; IgG2a) was a kind gift from Dr. Nicholas Stamatos. Fucosyltransferase VI (FTVI) enzyme was a gift of Dr. Roland Wohlgemuth (Sigma-Aldrich).

Cells: Mouse NSCs were isolated and cultured as described (Imitola, J., Comabella, M., et al. 2004; Imitola, J., Raddassi, K., et al. 2004) previously. Briefly, a suspension of dissociated NSCs ($5 \times 10^5$ cells per ml), isolated from the telencephalic VZ of murine embryonic day 12, were cultured in 98% DMEM/F12 (GIBCO), 1% N2 supplement (GIBCO), 1% penicillin/streptomycin (GIBCO) 8 mg/ml heparin (Sigma), 10 ng/ml leukemia inhibiting factor (LIF, Chemicon), 20 ng/ml bFGF (Calbiochem) in uncoated 25-cm$^2$ flasks (Falcon) at 37° C. in 5% CO$_2$. NSCs were used after second passage for most experiments. Single cell suspension of neural stem cells was achieved by mechanical dissociation of the neurospheres in Versene (Life Technologies).

For isolation of mouse HSPC, bone marrow was harvested from the femur and tibia of C57BL/6 mice and single cell suspensions were made. Red blood cells were lysed using red blood cell lysing buffer (Sigma). Cells were then washed and filtered through a 100 μm cell strainer (BD Falcon) prior to lineage depletion using the Lineage Cell Depletion Kit from Miltenyi Biotec. Cell preparations were depleted using the autoMACS™ Separator (Miltenyi Biotec.). Following depletion, the cells were then positively selected for c-kit using CD117 MicroBeads (Miltenyi Biotec.). The resulting Lineage$^{neg}$-kit$^{POS}$ population (referred to as HSPC) was used for in vivo EAE mouse studies.

Chinese hamster ovary cells transfected with full-length E-selectin (CHO-E) and were maintained as described previously (Dimitroff, C. J., Lee, J. Y., et al. 2001). The human βFGF-dependent NSC cell line, CC-2599, was cultured as previously described (Imitola, J., Raddassi, K., et al. 2004) and used for data presented in FIGS. 16A-16C.

GPS-Treatment, PI-PLC and Bromelain Reactions: The procedure for GPS treatment of murine NSCs was as previously described for MSCs (Sackstein, R., Merzaban, J. S., et al. 2008). Briefly, neurospheres were first harvested and dissociated into single cells by incubating with PBS/EDTA (0.02%) for 15 min at 37° C. Cells were then washed with HBSS, counted, and resuspended in 60 mU/ml FTVI in HBSS (without Ca$^{2+}$ or Mg$^{2+}$) containing 20 mM HEPES, 0.1% human serum albumin and 1 mM GDP-fucose for 40 min at 37° C. PI-PLC reactions were performed at 37° C. using 0.1 U/ml for 1 hr. Bromelain reactions were performed at 37° C. in HBSS+2% BSA+0.1% bromelain for 1 hr.

Flow Cytometry: Aliquots of cells ($2 \times 10^5$ cells) were washed with PBS/2% FBS and incubated with primary mAbs or with isotype control mAbs (either unconjugated or fluorochrome conjugated). The cells were washed in PBS/2% FBS and, for indirect immunofluorescence, incubated with appropriate secondary fluorochrome-conjugated anti-isotype antibodies. After washing cells, FITC or PE fluorescence intensity was determined using a Cytomics FC 500 MPL flow cytometer (Beckman Coulter Inc., Fullerton, Calif.).

Immunoprecipitation Studies: Cell lysates of BT-NSC or GPS-NSC were incubated with immunoprecipitating antibodies or with appropriate isotype controls and then incubated with Protein G-agarose. Immunoprecipitates were washed extensively using Buffer A containing 2% NP-40, 1% SDS. In some experiments, immunoprecipitates were treated with N-glycosidase F (New England Biolabs) as previously described (Dimitroff, C. J., Lee, J. Y., et al. 2001). For Western blot analysis, all immunoprecipitates were diluted in reducing sample buffer, boiled, then subjected to SDS-PAGE, transferred to PVDF membrane, and immunostained with HECA-452 or E-Ig.

Western Blot Analysis: BT- and GPS-NSCs were lysed using 2% NP-40 in Buffer A (150 mM NaCl, 50 mM Tris-HCl, pH 7.4, 1 mM EDTA, 20 μg/ml PMSF, 0.02% sodium azide; and protease inhibitor cocktail tablet (Roche Molecular Biochemicals)). Western blots of quantified protein lysates or of immunoprecipitated protein were performed under reducing conditions as described previously (Dimitroff, C. J., Lee, J. Y., et al. 2001). Blots were visualized with chemiluminescence using Lumi-Light Western Blotting Substrate (Roche).

Parallel Plate Flow Chamber Adhesion Assays: E-selectin binding capacity of BT-NSCs and GPS-NSCs was compared using the parallel plate flow chamber assay (Glycotech; Gaithersburg, Md.). NSCs ($0.5 \times 10^6$ cells/ml, suspended in HBSS/10 mM HEPES/2 mM CaCl$_2$ solution) were drawn over confluent HUVEC monolayers. Initially, the NSCs were allowed to contact the HUVEC monolayer at a shear stress of 0.5 dyne/cm$^2$, subsequently the flow rate was adjusted to exert shear stress ranging from 0.5 to 30 dynes/cm$^2$. The number of BT- or GPS-NSCs adherent to the HUVEC monolayer were quantified in the final 15 sec interval at shear stress of 0.5, 1, 2, 5, 10, 20 and 30 dyne/cm$^2$. Each assay was performed at least 3 times and the values averaged. Control assays were performed by adding 5 mM EDTA to the assay buffer to chelate Ca$^{2+}$ required for selectin binding or treating HUVEC with function-blocking anti-human E-selectin mAb at 37° C. for 15 min. prior to use in adhesion assays.

Blot Rolling Assay: The blot rolling assay has been described previously (Dimitroff, C. J., Lee, J. Y., et al. 2000; Fuhlbrigge, R. C., King, S. L., et al. 2002; Sackstein, R. and Fuhlbrigge, R. 2006) and here was used to detect selectin-binding activity of NSC membrane proteins resolved by SDS-PAGE. Western blots of NSC membrane preparations were stained with anti-CLA (HECA-452) and rendered translucent by immersion in DMEM with 10% glycerol. CHO-E cells were resuspended (5×10$^6$/mL) in DMEM containing 2 mM CaCl$_2$ and 10% glycerol. The blots were placed under a parallel plate flow chamber, and CHO-E cells were perfused at a physiologically relevant shear stress of 1.0 dyne/cm$^2$, an adjustment in the volumetric flow rate was made to account for the increase in viscosity due to the presence of 10% glycerol in the flow medium. Molecular weight markers were used as guides to aid placement of the flow chamber over stained bands of interest. The number of interacting cells per square millimeter was tabulated as a function of the molecular weight region and compiled into an adhesion histogram. Nonspecific adhesion was assessed by perfusing CHO-E cell suspensions containing 5 mM EDTA in the flow medium.

Immunization for EAE-Induction and Neural Stem Cells Injection: NSCs or bone marrow HSPC (Lineage$^{neg}$C-kit$^{POS}$) were either treated with GPS or not and 1×10$^6$ cells were injected into the tail vein of C57BL/6 mice on day 9 and day 13 after immunization (PI) with MOG 35-55 (subcutaneously in the flanks; see details in Supplementary Material). EAE was scored in a blinded fashion; the investigator was not involved in the injections and was not aware of the composition of the groups. Details of the grading scale used are outlined in the Supplementary Material. BT-NSC, GPS-NSCs, BT-HSPCs or GPS-HSPCs were injected as a cell suspension into the tail-vein of EAE mice in a volume of 0.2 ml of HBSS. Sham treated mice (No NSCs) injected with HBSS alone were used as a negative control.

Short-term Homing Studies: BT-NSCs and GPS-NSCs were labelled with 5 mM CFDA-SE (Invitrogen) for 5 min at room temperature in RPMI containing 10% FBS and injected intravenously into MOG-treated C57BL6 mice on day 9 and day 13 post-immunization (PI). Two million NSCs in a volume of 0.2 mL of HBSS were injected into each mouse on each day. HBSS buffer alone was used to determine background signals. BT-NSCs and GPS-NSCs were also injected into animals that were not immunized with MOG and used to standardize the signals observed in each tissue assayed. Sixteen hours after the second NSC transfer, mice were sacrificed and perfused with 1×PBS without Ca$^{2+}$ and Mg$^{2+}$. The brain, spinal cord, lymph nodes, spleen, liver and lung were isolated. The brain and spinal cord were homogenized. Resulting pellets were resuspended in 0.25% Trypsin-EDTA (Invitrogen) and incubated at 37° C. for 10 minutes. The digestion process was stopped using DMEM containing 0.01% SBTI, 0.001% DNase and 0.075% BSA. The lymph nodes, spleen and liver were mechanically dissociated and the resulting single-cell suspensions were assessed for frequencies of CFDA-SE positive cells by flow cytometry in the FL1 channel. Flow cytometric data was analyzed and expressed as percent of CFDA-SE-positive events detected in 200,000 cells scanned within a narrow gate that is set to include NSC. This gate was determined based on mixing cultured NSCs with suspensions of cells isolated from each tissue tested (brain, spinal cord, lymph node, spleen, liver and lung).

Analysis of NSC Migration to CNS: BT-NSCs, GPS-NSCs were labelled with PKH26 dye (Invitrogen) and injected intravenously into MOG-treated C57BL6 mice on day 9 and day 13 post-immunization (PI). One million NSCs in a volume of 0.2 mL of HBSS were injected into each mouse on each day. HBSS buffer alone was used to determine background signals. Four days after the second NSC transfer, mice were sacrificed and perfused with 1×PBS without Ca$^{2+}$ and Mg$^{2+}$ and lumbar-sacral spinal cords were harvested. The spinal cord was chosen because in the B6 model, the CNS lesions in the forebrain are very variable in size and location compared with the spinal cords, which possess a more predictable location (lumbosacral region) and also more exuberant pathology (Chitnis, T., Najafian, N., et al. 2001; Rasmussen, S., Wang, Y., et al. 2007; Wang, Y., Imitola, J., et al. 2008). For FACS analysis, the spinal cords were then homogenized and the resulting pellets were resuspended in 0.25% Trypsin-EDTA (Invitrogen) and incubated at 37° C. for 10 minutes. The digestion process was stopped using DMEM containing 0.01% SBTI, 0.001% DNase and 0.075% BSA. For histology analysis, the brain and spinal cord were snap-frozen in liquid nitrogen and stored in −80° C. until sectioning. The cryostat sections (20 μm) of lumbar-sacral spinal cord or anterior, middle and posterior brain were fixed with 4% paraformaldehyde for 15 minutes and then stained with antibodies of interest, Blood vessels were visualized by anti-Flk-1 (VEGFR2, Sigma) and NSCs were stained with either anti-sox-2 (Millipore) or visualized by PKH26 dye in red. The spinal cords were then homogenized and the resulting pellets were resuspended in 0.25% Trypsin-EDTA (Invitrogen) and incubated at 37° C. for 10 minutes. The digestion process was stopped using DMEM containing 0.01% SBTI, 0.001% DNase and 0.075% BSA. Blood vessels were visualized by Flk-1 (VEGFR2) staining.

Immunization for EAE-induction and NSC/HSPC Injection: NSCs or HSPC (Lineage$^{neg}$C-kit$^{POS}$) were either treated with GPS or not and 1×10$^6$ cells were injected into the tail vein of C57BL/6 mice on day 9 and day 13 after immunized (PI) with MOG 35-55. MOG 35-55 (M-E-V-G-W-Y-R-S-P-F-S-R-O-V-H-L-Y-R-N-G-K) corresponding to mouse sequence is synthesized by QCB Inc. Division of BioSource International (Hopkinton, Mass.), and purified to >99% by HPLC. Mice are immunized subcutaneously in the flanks with 150-200 μg of MOG peptide in 0.1 ml PBS and 0.1 ml CFA containing 0.4 mg *Mycobacterium Tuberculosis* (H37Ra, Difco, Detroit, Mich.) and injected intraperitoneally with 200 ng Pertussis toxin (List Laboratories, Campbell, Calif.) on the day of immunization and 2 days later. EAE was scored in a blinded fashion; the investigator was not involved in the injections and was not aware of the composition of the groups. The following grade was used: grade 1, limp tail or isolated weakness of gait without limp tail; grade 2, partial hind leg paralysis; grade 3, total hind leg or partial hind and front leg paralysis; grade 4, total hind leg and partial front leg paralysis; grade 5, moribund or dead animal. BT-NSC, GPS-NSCs, BT-HSPCs, GPS-HSPCs were injected as a cell suspension into the tail-vein of EAE mice in a volume of 0.2 ml of HBSS. Sham treated mice (No NSCs) injected with HBSS alone were used as a negative control.

Immunohistologic Staining: Mice were perfused with 50 ml normal saline before sacrificing to remove any intravascular PBMCs. For confocal imaging animals were perfused intracardially with 10 ml of 4% paraformaldehyde in PBS. The brain and spinal cord were removed and embedded in OCT., quick frozen in liquid nitrogen and kept at −70° C. until sectioning. Cryostat sections (10 µm) of spinal cords were fixed with acetone or 4% paraformaldehyde and then labelled with the antibody of interest. Isotype-matched Ig and omission of the primary antibody served as negative controls. Each specimen was evaluated at a minimum of three different levels of sectioning. The entire tissue section (a longitudinal spinal cord section) was evaluated for a given cellular marker at 40× magnification. The number of cells staining positive for the given markers were counted in ten 40× (high power fields) fields per section. The results for one section were totaled, and the results between sections were averaged.

Staining for Confocal Microscopy: Paraformaldehyde fixed sections (40 µm) were washed in PBS, blocked in PBS containing 4% goat serum, 0.3% BSA, and 0.3% triton and subsequently incubated with primary antibodies overnight and secondary antibodies for 2 h in blocking solution. We used highly cross-adsorbed secondary antibodies to avoid cross-reactivity (Alexa 488 and Alexa 594). Confocal microscopy was performed using a Zeiss Laser Scanning Microscope 3D analysis software (Zeiss, Thornwood, N.Y.) with a multitrack acquisition protocol to avoid potential overlapping of the two fluorochromes.

Effects of GPS Treatment on NSC Differentiation, Self-Renewal Capacity and Immunosuppressive Effects In Vitro: The procedure for GPS treatment of murine NSCs was as previously described for MSCs (Sackstein, R., Merzaban, J. S., et al. 2008). BT- and GPS-NSCs were compared in vitro for their capacity to self-renew, form neurospheres, differentiate into MAP2$^+$ neurons, and inhibit the proliferation of ConA activated lymph node cells. NSC differentiation and self-renewal capacity: Neurospheres initially cultured in FGF/EGF containing media were plated on poly-D-lysine (PDL)-coated glass coverslips allowed to proliferate then harvested and treated for an hour with buffer (control) or enzymatic treatment with FTVI (60mU/mL), subsequently the resulting BT-NSCs and GPS-NSCs were plated at clonal density of 20 cells per µl and allowed to proliferate as neurospheres for 96 hours to 5 days. Neurosphere imaging was captured with an Axiovision microscope (NY). For neuronal, astrocyte, and oligodendrocyte differentiation, dissociated neurospheres were plated on PL-coated glass coverslips in a 24 well plate and cultured without FGF/EGF but in the presence of neurobasal medium containing 1% Glutamax, 1% Antibiotic/Antimycotic and 2% B27-Supplement. Fresh media was added every other day until day 5, and the cells were then subjected to immunofluorescence staining with MAP2 (neurons), GFAP (astrocytes), and NG2 (oligodendrocyte precursors). MAP2$^+$, GFAP$^+$, and NG2$^+$ cells were counted using standard stereological technique by an investigator blinded to the treatments. Cocultures of Neural Stem Cells and Lymph Node Cells: Lymph nodes were isolated from naïve C57BL/6 mice. Lymph node cells (LNC) were cultured as single-cell suspensions in a 96 well plate at 2×10$^5$ cells per well, as previously described (Einstein, O., Fainstein, N., et al. 2007). Culture medium consisted of RPMI-1640 supplemented with 10% fetal bovine serum, L-glutamine, sodium pyruvate, non-essential amino acid, 2-mercaptoethanol, HEPES and antibiotics (BioWhittaker) with 2.5 µg/ml concanavalin A (ConA, Sigma) or without. Neurospheres were dissociated and were first either treated with GPS or not (BT) and subsequently irradiated with 3,000 Rad. Following irradiation the dissociated NSCs were then added directly to the LNC culture medium at different ratios with ConA stimulated LNCs. The ratios tested of numbers of NSCs to numbers of LNCs were: 1:4, 1:2, 1:1, 2:1, and 4:1. The cells were then cultured for 48 hours before adding thymidine. Thymidine incorporation assays were performed 16 hours later.

Assessment of E-Selectin Ligands Following Treatment of NSCs with Inflammatory Cytokines: 1.5×10$^6$ cells/well were seeded in a 6 well plate containing 3 ml proliferation medium per well and stimulated with either 10 ng/ml of TNFα (R&D; 410-TRNC), 10 ng/ml IL-1β (R&D; 401-ML), 10 ng/ml IFNγ (R&D; 485-MI) independently or in combination (all three at 10 ng/ml). After 24 h and 48 h, the neurospheres were harvested by centrifugation and stained with E-Ig for flow cytometric analysis.

Measurement of LIF mRNA: 1×10$^6$ mouse embryonic NSCs were treated for 24 hours with or without inflammatory cytokines (IFN-Y at 10 ng/ml and TNF-α at 15 ng/ml). Total RNA was then extracted using Trizol reagent and the quality of the extracted RNA was measured using Agilent 2200 Tab station system. cDNA synthesis was done using high capacity cDNA reverse transcription kit (Applied Biosystems) and a Random Hexamer. mRNA level was measured using RT-PCR and the fold change in gene expression was calculated using $2^{-\Delta\Delta CT}$ method. The forward primer sequence for the LIF gene was CCTACCTGCGTCT-TACTCCATCA and the reverse primer was CCCCAAAGGCTCAATGGTT (Sigma). The relative expression of LIF mRNA was assayed relative to GAPDH housekeeping gene in which TGCACCACCAACTGCT-TAGC was used as a forward primer and GGCATGGACT-GTGGTCATGAG as reverse primer.

Analysis of NSC Migration to CNS: BT-NSCs, GPS-NSCs were labeled with PKH26 dye (Invitrogen) and injected intravenously into MOG-treated C57BL6 mice on day 9 and day 13 post-immunization (PI). One million NSCs were injected into each mouse on each day. HBSS buffer alone was used to determine background signals. Either 24 hours or 4 days after the second NSC transfer, mice were sacrificed, perfused, and lumbar-sacral spinal cords were harvested. The spinal cord was chosen because in the B6 model, the CNS lesions in the forebrain are very variable in size and location compared with the spinal cords, which possess a more predictable location (lumbosacral region) and also more exuberant pathology (Chitnis, T., Najafian, N., et al. 2001; Rasmussen, S., Wang, Y., et al. 2007; Wang, Y., Imitola, J., et al. 2008). For flow cytometric analysis, the spinal cords were then homogenized and the resulting pellets were resuspended in 0.25% Trypsin-EDTA and incubated at 37° C. for 10 minutes. The digestion process was stopped using DMEM containing 0.01% SBTI, 0.001% DNase and 0.075% BSA. For histology analysis, the brain and spinal cord were snap-frozen in liquid nitrogen and stored in −80° C. until sectioning. The cryostat sections (20 µm) of lumbar-sacral spinal cord or anterior, middle and posterior brain were fixed and then stained with antibodies of interest. Blood vessels were visualized by anti-Flk-1 (VEGFR2) and NSCs were stained with either anti-SOX-2 or visualized by PKH26 dye in red. For neuropathology analysis, cell quantification was performed by stereological analysis of animals in different groups. Spinal cords and brain were sectioned and every third section of the cervical and lumbosacral region was stained, cell quantification was performed in high power magnification of 3-5 sections. LSM 510 Confocal microscope with motorized stage was used to stereologically calculate the intensity of staining, and total cell numbers/per high power magnification.

Statistical Analysis—Data are expressed as the mean±SEM. Statistical significance of differences between means was determined by two-way ANOVA. If means were shown to be significantly different, multiple comparisons were performed post-hoc by the Turkey t-test. Statistical significance was defined as $p<0.05$.

REFERENCES

Example 7

Alam H B, Sun L, Ruff P, Austin B, Burris D, Rhee P. 2000. E- and P-selectin expression depends on the resuscitation fluid used in hemorrhaged rats. *The Journal of surgical research*, 94:145-152.

Alon R, Feizi T, Yuen C T, Fuhlbrigge R C, Springer T A. 1995. Glycolipid ligands for selectins support leukocyte tethering and rolling under physiologic flow conditions. *Journal of immunology*, 154:5356-5366.

Back S A, Tuohy T M, Chen H, Wallingford N, Craig A, Struve J, Luo N L, Banine F, Liu Y, Chang A, et al. 2005. Hyaluronan accumulates in demyelinated lesions and inhibits oligodendrocyte progenitor maturation. *Nature medicine*, 11:966-972.

Ben-Hur T, Einstein O, Mizrachi-Kol R, Ben-Menachem O, Reinhartz E, Karussis D, Abramsky O. 2003. Transplanted multipotential neural precursor cells migrate into the inflamed white matter in response to experimental autoimmune encephalomyelitis. *Glia*, 41:73-80.

Berlin C, Bargatze R F, Campbell J J, von Andrian U H, Szabo M C, Hasslen S R, Nelson R D, Berg E L, Erlandsen S L, Butcher E C. 1995. alpha 4 integrins mediate lymphocyte attachment and rolling under physiologic flow. *Cell*, 80:413-422.

Bezzi P, Domercq M, Brambilla L, Galli R, Schols D, De Clercq E, Vescovi A, Bagetta G, Kollias G, Meldolesi J, et al. 2001. CXCR4-activated astrocyte glutamate release via TNFalpha: amplification by microglia triggers neurotoxicity. *Nat Neurosci*, 4:702-710.

Butcher E C. 1991. Leukocyte-endothelial cell recognition: three (or more) steps to specificity and diversity. *Cell*, 67:1033-1036.

Campos L S, Decker L, Taylor V, Skarnes W. 2006. Notch, epidermal growth factor receptor, and beta1-integrin pathways are coordinated in neural stem cells. *J Biol Chem*, 281:5300-5309.

Campos L S, Leone D P, Relvas J B, Brakebusch C, Fassler R, Suter U, ffrench-Constant C. 2004. Beta1 integrins activate a MAPK signalling pathway in neural stem cells that contributes to their maintenance. *Development*, 131:3433-3444.

Caplan A I. 2009. Why are MSCs therapeutic? New data: new insight. *The Journal of pathology*, 217:318-324.

Chitnis T, Najafian N, Abdallah K A, Dong V, Yagita H, Sayegh M H, Khoury S J. 2001. CD28-independent induction of experimental autoimmune encephalomyelitis. *J Clin Invest*, 107:575-583.

Deboux C, Ladraa S, Cazaubon S, Ghribi-Mallah S, Weiss N, Chaverot N, Couraud P O, Baron-Van Evercooren A. 2013. Overexpression of CD44 in neural precursor cells improves trans-endothelial migration and facilitates their invasion of perivascular tissues in vivo. *PloS one*, 8:e57430.

Dimitroff C J, Lee J Y, Fuhlbrigge R C, Sackstein R. 2000. A distinct glycoform of CD44 is an L-selectin ligand on human hematopoietic cells. *Proc Natl Acad Sci USA*, 97:13841-13846.

Dimitroff C J, Lee J Y, Rafii S, Fuhlbrigge R C, Sackstein R. 2001. CD44 is a major E-selectin ligand on human hematopoietic progenitor cells. *J Cell Biol*, 153:1277-1286.

Ding Z M, Babensee J E, Simon S I, Lu H, Perrard J L, Bullard D C, Dai X Y, Bromley S K, Dustin M L, Entman M L, et al. 1999. Relative contribution of LFA-1 and Mac-1 to neutrophil adhesion and migration. *Journal of immunology*, 163:5029-5038.

Drake T A, Cheng J, Chang A, Taylor F B, Jr. 1993. Expression of tissue factor, thrombomodulin, and E-selectin in baboons with lethal *Escherichia coli* sepsis. *The American journal of pathology*, 142:1458-1470.

Einstein O, Fainstein N, Vaknin I, Mizrachi-Kol R, Reihartz E, Grigoriadis N, Lavon I, Baniyash M, Lassmann H, Ben-Hur T. 2007. Neural precursors attenuate autoimmune encephalomyelitis by peripheral immunosuppression. *Annals of neurology*, 61:209-218.

Einstein O, Grigoriadis N, Mizrachi-Kol R, Reinhartz E, Polyzoidou E, Lavon I, Milonas I, Karussis D, Abramsky O, Ben-Hur T. 2006. Transplanted neural precursor cells reduce brain inflammation to attenuate chronic experimental autoimmune encephalomyelitis. *Experimental neurology*, 198: 275-284.

Emamgholipour S, Eshaghi S M, Hossein-nezhad A, Mirzaei K, Maghbooli Z, Sahraian M A. 2013. Adipocytokine profile, cytokine levels and foxp3 expression in multiple sclerosis: a possible link to susceptibility and clinical course of disease. *PloS one*, 8:e76555.

Flax J D, Aurora S, Yang C, Simonin C, Wills A M, Billinghurst L L, Jendoubi M, Sidman R L, Wolfe J H, Kim S U, et al. 1998. Engraftable human neural stem cells respond to developmental cues, replace neurons, and express foreign genes. *Nat Biotechnol*, 16:1033-1039.

Fu J, Yang Q Y, Sai K, Chen F R, Pang J C, Ng H K, Kwan A L, Chen Z P. 2013. TGM2 inhibition attenuates ID1 expression in CD44-high glioma-initiating cells. *Neuro-oncology*, 15:1353-1365.

Fuhlbrigge R C, Kieffer J D, Armerding D, Kupper T S. 1997. Cutaneous lymphocyte antigen is a specialized form of PSGL-1 expressed on skin-homing T cells. *Nature*, 389: 978-981.

Fuhlbrigge R C, King S L, Dimitroff C J, Kupper T S, Sackstein R. 2002. Direct real-time observation of E- and P-selectin-mediated rolling on cutaneous lymphocyte-associated antigen immobilized on Western blots. *Journal of immunology*, 168:5645-5651.

Gadhoum S Z, Sackstein R. 2008. CD15 expression in human myeloid cell differentiation is regulated by sialidase activity. *Nat Chem Biol*, 4:751-757.

Gascon E, Vutskits L, Kiss J Z. 2007. Polysialic acid-neural cell adhesion molecule in brain plasticity: from synapses to integration of new neurons. *Brain Res Rev*, 56:101-118.

Glaser T, Brose C, Franceschini I, Hamann K, Smorodchenko A, Zipp F, Dubois-Dalcq M, Brustle O. 2007. Neural cell adhesion molecule polysialylation enhances the sensitivity of embryonic stem cell-derived neural precursors to migration guidance cues. *Stem cells*, 25:3016-3025.

Goncharova V, Das S, Niles W, Schraufstatter I, Wong A K, Povaly T, Wakeman D, Miller L, Snyder E Y, Khaldoyanidi S K. 2014. Homing of neural stem cells from the venous compartment into a brain infarct does not involve conventional interactions with vascular endothelium. *Stem cells translational medicine*, 3:229-240.

Hess D C, Borlongan C V. 2008. Stem cells and neurological diseases. *Cell proliferation*, 41 Suppl 1:94-114.

Horie K, Sakagami M, Kuramochi K, Ito T, Hamana H. 2000. Effect of the sialyl Lewis X (SLe(x)) moiety on splenic accumulation of SLe(x)-carboxymethylpullulan conjugate. *Microbiology and immunology*, 44:401-404.

Horie K, Sakagami M, Masuda K, Notoya M, Hamana H, Yoshikawa T, Hirano K. 2004. Sialyl Lewis X-carboxymethylpullulan conjugate: a novel homing device to spleen and lymph nodes. *Biological & pharmaceutical bulletin*, 27:1275-1280.

Imitola J, Chitnis T, Khoury S J. 2006. Insights into the molecular pathogenesis of progression in multiple sclerosis: potential implications for future therapies. *Arch Neurol*, 63:25-33.

Imitola J, Comabella M, Chandraker A K, Dangond F, Sayegh M H, Snyder E Y, Khoury S J. 2004. Neural stem/progenitor cells express costimulatory molecules that are differentially regulated by inflammatory and apoptotic stimuli. *The American journal of pathology*, 164:1615-1625.

Imitola J, Cote D, Rasmussen S, Xie X S, Liu Y, Chitnis T, Sidman R L, Lin C P, Khoury S J. 2011. Multimodal coherent anti-Stokes Raman scattering microscopy reveals microglia-associated myelin and axonal dysfunction in multiple sclerosis-like lesions in mice. *Journal of biomedical optics*, 16:021109.

Imitola J, Raddassi K, Park K I, Mueller F J, Nieto M, Teng Y D, Frenkel D, Li J, Sidman R L, Walsh C A, et al. 2004. Directed migration of neural stem cells to sites of CNS injury by the stromal cell-derived factor 1 alpha/CXC chemokine receptor 4 pathway. *Proc Natl Acad Sci USA*, 101:18117-18122.

Ji J F, He B P, Dheen S T, Tay S S. 2004. Expression of chemokine receptors CXCR4, CCR2, CCR5 and CX3CR1 in neural progenitor cells isolated from the subventricular zone of the adult rat brain. *Neuroscience letters*, 355:236-240.

Justicia C, Martin A, Rojas S, Gironella M, Cervera A, Panes J, Chamorro A, Planas A M. 2006. Anti-VCAM-1 antibodies did not protect against ischemic damage either in rats or in mice. *J Cereb Blood Flow Metab*, 26:421-432.

Laterza C, Merlini A, De Feo D, Ruffini F, Menon R, Onorati M, Fredrickx E, Muzio L, Lombardo A, Comi G, et al. 2013. iPSC-derived neural precursors exert a neuroprotective role in immune-mediated demyelination via the secretion of LIF. *Nature communications*, 4:2597.

Lavdas A A, Franceschini I, Dubois-Dalcq M, Matsas R. 2006. Schwann cells genetically engineered to express PSA show enhanced migratory potential without impairment of their myelinating ability in vitro. *Glia*, 53:868-878.

Lee S J, Benveniste E N. 1999. Adhesion molecule expression and regulation on cells of the central nervous system. *Journal of neuroimmunology*, 98:77-88.

Lee S T, Chu K, Jung K H, Kim S J, Kim D H, Kang K M, Hong N H, Kim J H, Ban J J, Park H K, et al. 2008. Anti-inflammatory mechanism of intravascular neural stem cell transplantation in haemorrhagic stroke. *Brain: a journal of neurology*, 131:616-629.

Leone D P, Relvas J B, Campos L S, Hemmi S, Brakebusch C, Fassler R, Ffrench-Constant C, Suter U. 2005. Regulation of neural progenitor proliferation and survival by beta1 integrins. *J Cell Sci*, 118:2589-2599.

Leppanen A, White S P, Helin J, McEver R P, Cummings R D. 2000. Binding of glycosulfopeptides to P-selectin requires stereospecific contributions of individual tyrosine sulfate and sugar residues. *J Biol Chem*, 275:39569-39578.

Liu H, Zhang J, Liu C Y, Wang I J, Sieber M, Chang J, Jester J V, Kao W W. 2010. Cell therapy of congenital corneal diseases with umbilical mesenchymal stem cells: lumican null mice. *PloS one*, 5:e10707.

Maness P F, Schachner M. 2007. Neural recognition molecules of the immunoglobulin superfamily: signaling transducers of axon guidance and neuronal migration. *Nat Neurosci*, 10:19-26.

Martino G, Pluchino S. 2006. The therapeutic potential of neural stem cells. *Nat Rev Neurosci*, 7:395-406.

Merzaban J S, Burdick M M, Gadhoum S Z, Dagia N M, Chu J T, Fuhlbrigge R C, Sackstein R. 2011. Analysis of glycoprotein E-selectin ligands on human and mouse marrow cells enriched for hematopoietic stem/progenitor cells. *Blood*, 118:1774-1783.

Phinney D G, Prockop D J. 2007. Concise review: mesenchymal stem/multipotent stromal cells: the state of transdifferentiation and modes of tissue repair—current views. *Stem cells* (Dayton, Ohio), 25:2896-2902.

Piccio L, Rossi B, Colantonio L, Grenningloh R, Gho A, Ottoboni L, Homeister J W, Scarpini E, Martinello M, Laudanna C, et al. 2005. Efficient recruitment of lymphocytes in inflamed brain venules requires expression of cutaneous lymphocyte antigen and fucosyltransferase-VII. *J Immunol*, 174:5805-5813.

Piccio L, Rossi B, Scarpini E, Laudanna C, Giagulli C, Issekutz A C, Vestweber D, Butcher E C, Constantin G. 2002. Molecular mechanisms involved in lymphocyte recruitment in inflamed brain microvessels: critical roles for P-selectin glycoprotein ligand-1 and heterotrimeric G(i)-linked receptors. *Journal of immunology*, 168:1940-1949.

Pluchino S, Quattrini A, Brambilla E, Gritti A, Salani G, Dina G, Galli R, Del Carro U, Amadio S, Bergami A, et al. 2003. Injection of adult neurospheres induces recovery in a chronic model of multiple sclerosis. *Nature*, 422:688-694.

Pluchino S, Zanotti L, Brini E, Ferrari S, Martino G. 2009. Regeneration and repair in multiple sclerosis: the role of cell transplantation. *Neuroscience letters*, 456:101-106.

Pluchino S, Zanotti L, Rossi B, Brambilla E, Ottoboni L, Salani G, Martinello M, Cattalini A, Bergami A, Furlan R, et al. 2005. Neurosphere-derived multipotent precursors promote neuroprotection by an immunomodulatory mechanism. *Nature*, 436:266-271.

Politi L S, Bacigaluppi M, Brambilla E, Cadioli M, Falini A, Comi G, Scotti G, Martino G, Pluchino S. 2007. Magnetic-resonance-based tracking and quantification of intravenously injected neural stem cell accumulation in the brains of mice with experimental multiple sclerosis. *Stem cells*, 25:2583-2592.

Polley M J, Phillips M L, Wayner E, Nudelman E, Singhal A K, Hakomori S, Paulson J C. 1991. CD62 and endothelial cell-leukocyte adhesion molecule 1 (ELAM-1) recognize the same carbohydrate ligand, sialyl-Lewis x. *Proc Natl Acad Sci USA*, 88:6224-6228.

Rampon C, Weiss N, Deboux C, Chaverot N, Miller F, Buchet D, Tricoire-Leignel H, Cazaubon S, Baron-Van Evercooren A, Couraud P O. 2008. Molecular mechanism of systemic delivery of neural precursor cells to the brain: assembly of brain endothelial apical cups and control of transmigration by CD44. *Stem cells*, 26:1673-1682.

Rasmussen S, Wang Y, Kivisakk P, Bronson R T, Meyer M, Imitola J, Khoury S J. 2007. Persistent activation of microglia is associated with neuronal dysfunction of callosal projecting pathways and multiple sclerosis-like lesions in relapsing—remitting experimental autoimmune encephalomyelitis. *Brain*, 130:2816-2829.

Redl H, Dinges H P, Buurman W A, van der Linden C J, Pober J S, Cotran R S, Schlag G. 1991. Expression of endothelial leukocyte adhesion molecule-1 in septic but not traumatic/hypovolemic shock in the baboon. *The American journal of pathology*, 139:461-466.

Rosen S D. 2004. Ligands for L-selectin: homing, inflammation, and beyond. *Annu Rev Immunol*, 22:129-156.

Rutishauser U. 2008. Polysialic acid in the plasticity of the developing and adult vertebrate nervous system. *Nat Rev Neurosci*, 9:26-35.

Sackstein R. 2004. The bone marrow is akin to skin: HCELL and the biology of hematopoietic stem cell homing. *J Invest Dermatol*, 122:1061-1069.

Sackstein R. 2005. The lymphocyte homing receptors: gatekeepers of the multistep paradigm. *Curr Opin Hematol*, 12:444-450.

Sackstein R, Fuhlbrigge R. 2006. The blot rolling assay: a method for identifying adhesion molecules mediating binding under shear conditions. *Methods in molecular biology*, 341:217-226.

Sackstein R, Merzaban J S, Cain D W, Dagia N M, Spencer J A, Lin C P, Wohlgemuth R. 2008. Ex vivo glycan engineering of CD44 programs human multipotent mesenchymal stromal cell trafficking to bone. *Nature medicine*, 14:181-187.

Schweitzer K M, Drager A M, van der Valk P, Thijsen S F, Zevenbergen A, Theijsmeijer A P, van der Schoot C E, Langenhuijsen M M. 1996. Constitutive expression of E-selectin and vascular cell adhesion molecule-1 on endothelial cells of hematopoietic tissues. *The American journal of pathology*, 148:165-175.

Springer T A. 1994. Traffic signals for lymphocyte recirculation and leukocyte emigration: the multistep paradigm. *Cell*, 76:301-314.

Vitry S, Avellana-Adalid V, Lachapelle F, Evercooren A B. 2001. Migration and multipotentiality of PSA-NCAM+ neural precursors transplanted in the developing brain. *Molecular and cellular neurosciences*, 17:983-1000.

Wang L, Shi J, van Ginkel F W, Lan L, Niemeyer G, Martin D R, Snyder E Y, Cox N R. 2009. Neural stem/progenitor cells modulate immune responses by suppressing T lymphocytes with nitric oxide and prostaglandin E2. *Experimental neurology*, 216:177-183.

Wang Y, Imitola J, Rasmussen S, O'Connor K C, Khoury S J. 2008. Paradoxal dysregulation of the neural stem cell pathway sonic hedgehog-Gli1 in autoimmune encephalomyelitis and multiple sclerosis. *Annals of neurology*, 64:417-427.

Washington R, Burton J, Todd R F, 3rd, Newman W, Dragovic L, Dore-Duffy P. 1994. Expression of immunologically relevant endothelial cell activation antigens on isolated central nervous system microvessels from patients with multiple sclerosis. *Annals of neurology*, 35:89-97.

Weishaupt A, Jander S, Bruck W, Kuhlmann T, Stienekemeier M, Hartung T, Toyka K V, Stoll G, Gold R. 2000. Molecular mechanisms of high-dose antigen therapy in experimental autoimmune encephalomyelitis: rapid induction of Th1-type cytokines and inducible nitric oxide synthase. *Journal of immunology*, 165:7157-7163.

Zarbock A, Kempf T, Wollert K C, Vestweber D. 2012. Leukocyte integrin activation and deactivation: novel mechanisms of balancing inflammation. *Journal of molecular medicine*, 90:353-359.

Zarbock A, Lowell C A, Ley K. 2007. Spleen tyrosine kinase Syk is necessary for E-selectin-induced alpha(L)beta(2) integrin-mediated rolling on intercellular adhesion molecule-1. *Immunity*, 26:773-783.

Zhang H, Vutskits L, Calaora V, Durbec P, Kiss J Z. 2004. A role for the polysialic acid-neural cell adhesion molecule in PDGF-induced chemotaxis of oligodendrocyte precursor cells. *J Cell Sci*, 117:93-103.

Ziv Y, Avidan H, Pluchino S, Martino G, Schwartz M. 2006. Synergy between immune cells and adult neural stem/progenitor cells promotes functional recovery from spinal cord injury. *Proceedings of the National Academy of Sciences of the United States of America*, 103:13174-13179.

What is claimed is:

1. A method of enhancing pancreatic infiltration of intravenously administered mesenchymal stem cells (MSCs) in a subject having type 1 diabetes, the method comprising:
   administering to the subject a population of MSCs modified, ex vivo, with at least one glycosyltransferase effective to increase expression of an Hematopoietic Cell E-/L-selectin Ligand (HCELL), the population expressing the HCELL at a level that exceeds the level of expression of a native population of the MSCs,
   wherein said cell administration occurs coincident with E-selectin expression on endothelial cells within the pancreatic tissue of the subject and/or coincident with accumulation of leukocytes within the pancreatic tissue of the subject;
   wherein the administering enhances the pancreatic infiltration of the intravenously administered MSCs relative to that of the unmodified MSCs and provides an anti-diabetic effect to the subject.

2. The method of claim 1, wherein said cell administration occurs coincident with E-selectin expression on endothelial cells and infiltrates of leukocytes bearing L-selectin within the target tissue.

3. The method of claim 1, wherein an immunomodulatory effect is achieved by colonization of the MSCs in the pacreatic tissue of the subject.

4. The method of claim 1, wherein the subject is a human, non-human primate, mouse, rat, dog, cat, horse, or cow.

5. The method of claim 1, wherein the subject is a human patient.

* * * * *